(12) United States Patent
Janganati et al.

(10) Patent No.: US 9,908,892 B2
(45) Date of Patent: *Mar. 6, 2018

(54) MELAMPOMAGNOLIDE B DERIVATIVES

(71) Applicants: Venumadhav Janganati, Little Rock, AR (US); Narsimha Reddy Penthala, Little Rock, AR (US); Peter A. Crooks, Little Rock, AR (US); Craig T. Jordan, Rochester, NY (US)

(72) Inventors: Venumadhav Janganati, Little Rock, AR (US); Narsimha Reddy Penthala, Little Rock, AR (US); Peter A. Crooks, Little Rock, AR (US); Craig T. Jordan, Rochester, NY (US)

(73) Assignee: BIOVENTURES, LLC, Little Rock, AR (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/254,849

(22) Filed: Sep. 1, 2016

(65) Prior Publication Data

US 2016/0368929 A1 Dec. 22, 2016

Related U.S. Application Data

(62) Division of application No. 14/537,389, filed on Nov. 10, 2014, now Pat. No. 9,469,650.

(60) Provisional application No. 61/901,714, filed on Nov. 8, 2013.

(51) Int. Cl.
C07D 493/04 (2006.01)

(52) U.S. Cl.
CPC ................................. C07D 493/04 (2013.01)

(58) Field of Classification Search
CPC .................................................... C07D 493/04
See application file for complete search history.

(56) References Cited

U.S. PATENT DOCUMENTS

| | | | |
|---|---|---|---|
| 4,241,046 A | 12/1980 | Papahadjopoulos | |
| 4,394,448 A | 7/1983 | Szoka et al. | |
| 4,529,561 A | 7/1985 | Hunt et al. | |
| 4,755,388 A | 7/1988 | Heath et al. | |
| 4,828,837 A | 5/1989 | Uster et al. | |
| 4,925,661 A | 5/1990 | Huang | |
| 4,954,345 A | 9/1990 | Mueller | |
| 4,957,735 A | 9/1990 | Huang | |
| 5,043,164 A | 8/1991 | Huang et al. | |
| 5,064,655 A | 11/1991 | Uster et al. | |
| 5,077,211 A | 12/1991 | Yarosh | |
| 5,264,618 A | 11/1993 | Felgner et al. | |
| 7,312,242 B2 | 12/2007 | Crooks et al. | |
| 7,678,904 B2 | 3/2010 | Crooks et al. | |
| 8,884,027 B2 | 11/2014 | Crooks et al. | |
| 9,469,650 B2 | 10/2016 | Janganati et al. | |
| 9,487,536 B2 | 11/2016 | Bommagani et al. | |
| 2007/0015161 A1 | 1/2007 | Echeverri et al. | |
| 2007/0111203 A1 | 5/2007 | Cao et al. | |
| 2009/0312298 A1 | 12/2009 | Bamber et al. | |
| 2011/0092762 A1 | 4/2011 | Wong et al. | |
| 2012/0122943 A1 | 5/2012 | Crooks et al. | |
| 2014/0045821 A1 | 2/2014 | Wipf et al. | |
| 2015/0133444 A1 | 5/2015 | Janganati et al. | |
| 2015/0203508 A1 | 7/2015 | Bommagani et al. | |
| 2016/0077084 A1 | 3/2016 | MacNicol et al. | |
| 2016/0083397 A1 | 3/2016 | Penthala et al. | |
| 2016/0368928 A1 | 12/2016 | Bommagani et al. | |

FOREIGN PATENT DOCUMENTS

| | | |
|---|---|---|
| EP | 2125859 B1 | 5/2013 |
| WO | 2008022104 A1 | 2/2008 |
| WO | 2012145678 A1 | 10/2012 |
| WO | 2013019561 A1 | 2/2013 |
| WO | 2014172607 A1 | 10/2014 |
| WO | 2014172608 A2 | 10/2014 |
| WO | 2016090166 A1 | 6/2016 |

OTHER PUBLICATIONS https://www.oncolink.org/cancers (2017).*
Acton E. et al., "Anticancer Specificity of Some Ellipticinium Salts against Human Brain Tumors in Vitro," J. Med. Chem., 1994, pp. 2185-2189, vol. 37.
Bork, P. et al., "Sesquiterpene lactone containing Mexican Indian medicinal plants and pure sesquiterpene lactones as potent inhibitors of transcription factor NF-kB," FEBS Letters, 1997, pp. 85-90, vol. 402, Federation of European Biochemical Societies.
Boyd, M. et al., "Some Practical Considerations and Applications of the National Cancer Institute In Vitro Anticancer Drug Discovery Screen," Drug Development Research, 1995, 13 pgs., vol. 34.
Brouwers, L. et al., "Network Neighbors of Drug Targets Contribute to Drug Side-Effect Similarity," PloS ONE, Jul. 2011, pp. 1-7, vol. 6, Issue 7, No. 222187.
Cha, H. et al., "Evoluntionarily Repurposed Networks Reveal the Well-Known Antifungal Drug Thiabendazole to Be a Novel Vascular Disrupting Agent," PLOS Biol., Aug. 2012, pp. 1-13, vol. 10, Issue 8, No. e1001379.
Dai, Y. et al., "The NF (Nuclear factor)-kB inhibitor parthenolide interacts with histone deacetylase inhibitors to induce MKK7/JNK1-dependent apoptosis in human acute myeloid leukaemia cells," British Journal of Haematology, Aug. 4, 2010, pp. 70-83, vol. 151, Blackwell Publishing Ltd.
De Groot, F. et al., "Synthesis and Biological Evaluation of 2'-Carbamate-Linked and 2'-Carbonate-Linked Prodrugs of Paclitaxel: Selective Activation by the Tumor-Associated Protease Plasmin," J. Med. Chem., 2000, pp. 3093-3102, vol. 43.
Dell'Agli, M. et al., "Inhibition of NF-kB and metalloproteinase-9 expression and secretion by parthenolide derivatives," Bioorganic & Medicinal Chemistry Letters, 2009, pp. 1858-1860, vol. 19, Elsevier Ltd.

(Continued)

Primary Examiner — Shirley V Gembeh
(74) Attorney, Agent, or Firm — Polsinelli PC

(57) ABSTRACT

The present disclosure provides derivatives of melampomagnolide B (MMB), including carbonates, carbamates, and thiocarbamates. The derivatives may be synthesized via an MMB triazole intermediate. These derivatives are useful for treating cancer in humans.

7 Claims, 9 Drawing Sheets
(8 of 9 Drawing Sheet(s) Filed in Color)

(56) References Cited

OTHER PUBLICATIONS

Deschler, B. et al., "Acute Myeloid Leukemia: Epidemiology and Etiology," Cancer, Nov. 1, 2006, pp. 2099-2107, vol. 107, No. 9, Wiley Interscience.

Deshpande, A. et al., "Insulin Induction of Xenopus laevis Oocyte Maturation Is Inhibited by Monoclonal Antibody against p21 ras Proteins," Mol. Cell. Biol., Mar. 1987, pp. 1285-1288, vol. 7, No. 3.

El-Feraly, F., "Melampolides from Magnolia Grandiflora," Phytochemistry, 1984, pp. 2372-2374, vol. 23, No. 10, Pergamon Press Ltd., Great Britain.

Estey, E. et al., "Acute myeloid leukaemia," Lancet, Nov. 25, 2006, pp. 1894-1907, vol. 368.

Ghantous, A. et al., "What made sesquiterpene lactones reach cancer clinical trials?", Drug Discovery Today, Aug. 2010, pp. 668-678, vol. 15, Nos. 15/16, Elsevier Ltd.

Gopal, Y.N. et al., "Parthenolide Specifically Depletes Histone Deacetylase 1 Protein and Induces Cell Death through Ataxia Telangiectasia Mutated," Chemistry & Biology, Jul. 2007, pp. 813-823, vol. 14, Elsevier Ltd.

Guzman, M. et al., "The sesquiterpene lactone parthenolide induces apoptosis of human acute myelogenous leukemia stem and progenitor cells," Blood, Jun. 1, 2005, pp. 4163-4169, vol. 105, No. 11.

Guzman, M. et al., "Feverfew: weeding out the root of leukaemia," Expert Opin. Biol. Ther., 2005, pp. 1147-1152, vol. 5, No. 9, Ashley Publications Ltd.

Guzman, M. et al., "An orally bioavailable pathenolide analog selectively eradicates acute myelogenous leukemia stem and progenitor cells," Blood, Dec. 15, 2007, pp. 4427-4435, vol. 110, No. 13.

Hall, I. et al., "Anti-Inflammatory Activity of Sesquiterpene Lactones and Related Compounds," J. Pharmaceutical Sciences, May 1979, pp. 537-542, vol. 68, No. 5.

Han, C. et al., "Semisynthetic Derivatives of Sesquiterpene Lactones by Palladium-Catalyzed Arylation of the alpha-Methylene-gamma-lactone Substructure," J. Org. Chem., 2009, pp. 7176-7179, vol. 74.

Hassane, D. et al., "Chemical genomic screening reveals synergism between parthenolide and inhibitors of the PI-3 kinase and mTOR pathways," Blood, Dec. 23, 2010, pp. 5983-5990, vol. 116, No. 26.

Hehner, S. et al., "Sesquiterpene Lactones Specifically Inhibit Activation of NF-kB by Preventing the Degradation of IkB-alpha and IkB-beta," J. Biol. Chem., 1998, pp. 1288-1297, vol. 273, No. 3.

Heptinstall, S. et al., "Inhibition of Platelet Behaviour by Feverfew: a Mechanism of Action Involving Sulphydryl Groups," Folia Haematol., 1988, pp. 447-449, vol. 115, No. 4.

Hewamana, S. et al., "The NF-kB subunit Rel A is associated with in vitro survival and clinical disease progression in chronic lymphocytic leukemia and represents a promising therapeutic target," Blood, May 1, 2008, pp. 4681-4689, vol. 111, No. 9.

International Search Report and Written Opinion dated Feb. 5, 2016 from related Patent Application No. PCT/US2015/063792; 10 pgs.

International Search Report and Written Opinion dated Nov. 7, 2014 from related Patent Application No. PCT/US2014/034605; 11 pgs.

International Search Report and Written Opinion dated Sep. 12, 2014 from related Patent Application No. PCT/US2014/034604; 9 pgs.

Kim, Y. et al., "Resistance of cholangiocarcinoma cells to parthenolide-induced apoptosis by the excretory-secretory products of Clonorchis sinensis," Parasitol. Res., 2009, pp. 1011-1016, vol. 104, Springer.

Kim, Y. et al., "Myeloperoxidase Expression as a Potential Determinant of Parthenolide-Induced Apoptosis in Leukemia Bulk and Leukemia Stem Cells," JPET, 2010, pp. 389-400, vol. 335, No. 2.

Knight, D., "Feverfew: Chemistry and Biological Activity," Natural Products Reports, 1995, pp. 271-276.

Kolev, J. et al., "Discovery of potent parthenolide-based antileukemic agents enabled by late-stage P450-mediated C—H functionalization," NIH Public Access, Author Manuscript, 2015, pp. 1-22, published in final edited form as: ACS Chem. Biol., Jan. 17, 2014, pp. 164-173, vol. 9, No. 1.

Lowenberg, B. et al., "Mitoxantrone Versus Daunorubicin in Induction-Consolidation Chemotherapy—The Value of Low-Dose Cytarabine for Maintenance of Remission, and an Assessment of Prognostic Factors in Acute Myeloid Leukemia in the Elderly: Final Report of the Leukemia Cooperative Group of the European Organization for the Research and Treatment of Cancer and the Dutch-Belgian Hemato-Oncology Cooperative Hovon Group Randomized Phase III Study AML-9," J. Clin. Oncol., 1998, pp. 872-881, vol. 16, No. 3.

Macias, F. et al., "Potential Allelopathic Activity of Several Sesquiterpene Lactone Models," Phytochemistry, 1992, pp. 1969-1977, vol. 31, No. 6, Pergamon Press Ltd., Great Britain.

Mood, K. et al., "Contribution of JNK, Mek, Mos and PI-3K signaling to GVBD in Xenopus oocytes," Cellular Signaling, 2004, pp. 631-642, vol. 16, Elsevier Inc.

Nasim, S. et al., "Antileukemic activity of aminoparthenolide analogs," Bioorg. Med. Chem. Lett., 2008, pp. 3870-3873, vol. 18, Elsevier Ltd.

Nasim, S. et al., "Melampomagnolide B: A new antileukemic sesquiterpene," Bioorg. Med. Chem., 2011, pp. 1515-1519, vol. 19, Elsevier Ltd.

Neelakantan, S. et al., "Aminoparthenolides as novel anti-leukemic agents: Discovery of the NF-kB inhibitor, DMAPT (LC-1)," Bioorg. Med. Chem. Lett., 2009, pp. 4346-4349, vol. 19, Elsevier Ltd.

Notice of Allowance dated Jun. 7, 2016 from related U.S. Appl. No. 14/537,389; 9 pgs.

Notice of Allowance dated Jun. 8, 2016 from related U.S. Appl. No. 14/676,537; 8 pgs.

Nozaki, S. et al., "Repression of GADD153/CHOP by NF-kB: a possible cellular defense against endoplasmic reticulum stress-induced cell death," Oncogene, 2001, pp. 2178-2185, vol. 20, Nature Publishing Group.

Office Action dated Mar. 11, 2016 from related U.S. Appl. No. 14/537,389; 8 pgs.

Office Action dated Oct. 5, 2015 from related U.S. Appl. No. 14/537,389; 10 pgs.

Office Action dated Feb. 8, 2016 from related U.S. Appl. No. 14/676,537; 19 pgs.

Office Action dated Jan. 25, 2017 from related U.S. Appl. No. 14/785,196; 20 pgs.

Office Action dated Jul. 29, 2016 from related U.S. Appl. No. 14/785,196; 12 pgs.

Office action dated Feb. 13, 2017 from related U.S. Appl. No. 14/785,183; 12 pgs.

Office Action dated Jun. 9, 2016 from related U.S. Appl. No. 14/785,183; 18 pgs.

Oka, D. et al., "Sesquiterpene lactone parthenolide suppresses tumor growth in a xenograft model of renal cell carcinoma by inhibiting the activation of NF-kB," Int. J. Cancer, 2007, pp. 2576-2581, vol. 120, Wiley-Liss, Inc.

Okada, I. et al., "Stabilization of Actin Filaments Prevents Germinal Vesicle Breakdown and Affects Microtubule Organization in Xenopus Oocytes," Cytoskeleton, May 2012, pp. 312-323, vol. 69, Wiley Periodicals, Inc.

Papke, R. et al., "The pharmacological activity of nicotine and nornicotine on nAChRs subtypes: relevance to nicotine dependence and drug discovery," J. Neurochem., 2007, pp. 160-167, vol. 101.

Pei, S. et al., "Targeting Aberrant Glutathione Metabolism to Eradicate Human Acute Myelogenous Leukemia Cells," J. Biol. Chem., Nov. 22, 2013, pp. 33542-33558, vol. 288, No. 47.

International Search Report and Written Opinion dated Apr. 25, 2017 from related International Patent Application No. PCT/US2017/015376; 13 pgs.

Cotarca, L. et al., "Bis(trichloromethyl) Carbonate in Organic Synthesis," Synthesis, Jan. 1, 1996, pp. 553-576, vol. 996, No. 5, Georg Thieme Verlag KG.

Penthala, N. et al., "Heck products of parthenolide and melampomagnolide-B as anticancer modulators that modify cell cycle progression," European Journal of Medicinal Chemistry, 2014, pp. 517-525, vol. 85, Elsevier Masson SAS.

(56) References Cited

OTHER PUBLICATIONS

Pfaffenrath, V. et al., "The efficacy and safety of *Tanacetum parthenium* (feverfew) in migraine prophylaxis—a double-blind, multicentre, randomized placebo-controlled dose-response study," Cephalalgia, 2002, pp. 523-532, vol. 22, Blackwell Science Ltd., London.
Pubchem, Compound Summary for CID 44255396, Nov. 16, 2009; 3 pgs.
Ralstin, M. et al., "Parthenolide Cooperates with NS398 to Inhibit Growth of Human Hepatocellular Carcinoma Cells through Effects on Apoptosis and G0-G1 Cell Cycle Arrest," Mol. Cancer Res., Jun. 2006, pp. 387-399, vol. 4, No. 6.
Restriction Requirement with Notice of References Cited dated Oct. 6, 2015 from related U.S. Appl. No. 14/676,537; 11 pgs.
Riganti, C. et al., "Artemisinin induces doxorubicin resistance in human colon cancer cells via calcium-dependent activation of HIF-1alpha and P-glycoprotein overexpression," British Journal of Pharmacology, 2009, pp. 1054-1066, vol. 156.
Saadane, A. et al., "Parthenolide inhibits ERK and AP-1 which are dysregulated and contribute to excessive IL-8 expression and secretion in cystic fibrosis cells," J. Inflammation, 2011, pp. 1-15, vol. 8, No. 26, BioMed Central.
Sharma, G. et al., "Synthesis and Structure of alpha/delta-Hybrid Peptides—Access to Novel Helix Patterns in Foldamers," Chem. Eur. J., 2009, pp. 5552-5566, vol. 15, Wiley-VCH Verlag GmbH & Co. KgaA, Weinheim.
Sharma, G. et al., "Theoretical and Experimental Studies on alpha/E-Hybrid Peptides: Design of a 14/12-Helix from Peptides with Alternating (S)—C-Linked Carbo-E-amino Acid [(S)—E-Caa(x)] and L-Ala," J. Org. Chem., 2009, pp. 6703-6713, vol. 74, No. 17.
Skalska, J. et al., "Modulation of Cell Surface Protein Free Thiols: A Potential Novel Mechanism of Action of the Sesquiterpene Lactone Parthenolide," PLoS ONE, Dec. 2009, pp. 1-8, vol. 4, Issue 12, No. e8115.
Staab, H., "New Methods of Preparative Organic Chemistry IV. Syntheses Using Heterocyclic Amides (Azolides)," Angew. Chem. Internat. Edit., 1962, pp. 351-367, vol. 1, No. 7.
Sugimoto, H. et al., "Activation of Dithiocarbamate by 2-Halothiazolium Salts," J. Org. Chem., 1988, pp. 2263-2267, vol. 53, No. 10.
Sweeney, C. et al., "Nuclear Factor-kB Is Constitutively Activated in Prostate Cancer In vitro and Is Overexpressed in Prostatic Intraepithelial Neoplasia and Adenocarcinoma of the Prostate," Clin. Cancer Res., Aug. 15, 2004, pp. 5501-5507, vol. 10.
Tazzari, P. et al., "Multidrug resistance-associated protein 1 expression is under the control of the phosphoinositide 3 kinase/Akt signal transduction network in human acute myelogenous leukemia blasts," Leukemia, 2007, pp. 427-438, vol. 21, Nature Publishing Group.

Wen, J. et al., "Oxidative Stress-mediated Apoptosis. The Anticancer Effect of the Sesquiterpene Lactone Parthenolide," J. Biol. Chem., 2002, pp. 38954-38964, vol. 277, No. 41.
Wheeler, G. et al., "Xenopus: An Ideal System for Chemical Genetics," Genesis, 2012, pp. 207-218, vol. 50, Wiley Periodicals, Inc.
Won, Y-K. et al., "Parthenolide sensitizes ultraviolet (UV)-B-induced apoptosis via protein kinase C-dependent pathways," Carcinogenesis, 2005, pp. 2149-2156, vol. 26, No. 12, Oxford University Press.
Woods, J. et al., "Fluorinated Amino-Derivatives of the Sesquiterpene Lactone, Parthenolide, as 19F NMR Probes in Deuterium-Free Environments," J. Med. Chem., 2011, pp. 7934-7941, vol. 54, ACS Publications.
Yip-Schneider, M. et al., "Parthenolide and sulindac cooperate to mediate growth suppression and inhibit the nuclear factor-kB pathway in pancreatic carcinoma cells," Mol. Cancer Ther., Apr. 2005, pp. 587-594, vol. 4, No. 4.
Zhu, T. et al., "Differential Recognition of ACE Inhibitors in Xenopus Laevis Oocytes Expressing Rat PEPT1 and PEPT2," Pharmaceutical Res., 2000, pp. 526-532, vol. 17, No. 5, Plenum Publishing Corporation.
Deshpande, A. et al., "In vitro Induction of Germinal Vesicle Breakdown in Xenopus laevis Oocytes in Melittin," Differentiation, 1982, pp. 127-132, vol. 21, Springer-Verlag.
Guo, Y., "The Role of Aven in Cell Cycle Regulation," Dissertation, Department of Pharmacology and Cancer Biology, Duke University, Aug. 13, 2008, pp. 1-147, (166 total pgs.), ProQuest, LLC.
Kodadek, T. et al., "Optimized protocols for the isolation of specific protein-binding peptides or peptoids from combinatorial libraries displayed on beads," Mol. BioSyst., 2006, pp. 25-35, vol. 2, The Royal Society of Chemistry.
Office Action dated Jun. 1, 2017 from related U.S. Appl. No. 14/785,196; 17 pgs.
Moumou, M. et al., "Access to new sequiterpenoids by catalytic acid rearrangement of 9alpha-hydroxyparthenolide," Tetrahedron Lett., 2012, pp. 3000-3003, vol. 53, Elsevier Ltd.
Neukirch, H. et al., "Transannular Cyclization in Cyclodecenes: The Case Study of Melampolides," Eur. J. Org. Chem., 2003, pp. 3969-3975, Wiley-VCH Verlag GmbH & Co. KGaA, Weinheim.
Office Action dated Aug. 9, 2017 from related U.S. Appl. No. 15/251,889; 16 pgs.
Office Action dated Oct. 18, 2017 from related U.S. Appl. No. 14/785,196; 16 pgs.
Zhai, J. et al., "Biomimetic Semisynthesis of Arglabin from Parthenolide," J. Org. Chem., 2012, pp. 7103-7107, vol. 77, American Chemical Society.
Zhang, Q. et al., "Guaianolide Sesquiterpene Lactones, a Source to Discover Agents That Selectively Inhibit Acute Myelogenous Leukemia Stem and Progenitor Cells," J. Med. Chem., 2012, pp. 8757-8769, vol. 55, American Chemical Society.

* cited by examiner

MELAMPOMAGNOLIDE B DERIVATIVES

CROSS REFERENCE TO RELATED APPLICATIONS

This application is a divisional of U.S. Ser. No. 14/537,389, filed Nov. 10, 2014, which claims the benefit of U.S. provisional application No. 61/901,714, filed Nov. 8, 2013, the disclosures of which are hereby incorporated by reference in their entirety.

GOVERNMENTAL RIGHTS

This invention was made with government support under Grant No. CA158275 awarded by the National Institutes of Health (NIH). The government has certain rights to the invention.

FIELD OF THE INVENTION

This disclosure generally relates to a series of melampomagnolide B (MMB) derivatives, including carbamate, thiocarbamate and carbonate derivatives of MMB. These compounds exhibit potent anticancer activity.

BACKGROUND OF THE INVENTION

Parthenolide (PTL), an abundant sesquiterpene lactone found in the medicinal herb feverfew (*Tanacetum parthenium*), has undergone intense pharmacological research, especially for its antileukemic properties. Initial biomechanistic studies of PTL and its derivatives indicate that the compound promotes apoptosis by inhibiting the NF-kB transcription factor complex, thereby downregulating anti-apoptotic genes under NF-kB control. PTL and its derivatives may also interfere with glutathione function, specifically glutathione's ability to sequester reactive oxygen species. In culture, PTL induces robust apoptosis of primary acute myeloid leukemia (AML) cells in culture. To overcome poor water-solubility, PTL may be derivatized with an alkylamino, which can convert into water-soluble salts. A series of fluorinated amino derivatives of PTL exhibit activity in antiproliferative assays in HL-60 (human promyelocytic leukemia) cells. PTL has also been the source of several antileukemic compounds arising from chemical modification of the PTL molecule.

Melampomagnolide B (MMB), a melampolide originally isolated from *Magnolia grandiflora*, is an antileukemic sesquiterpene with properties similar to those of PTL. MMB has been synthesized via selenium oxide oxidation of the C10 methyl group of PTL, resulting in a concomitant conversion of the geometry of the C9-C10 double bond from trans to the cis geometry. MMB contains a primary OH group, providing a point of attachment for derivatives with increased water solubility, bioavailability, and tissue targeting. Phase 1 clinical data from dimethylaminoparthenolide (DMAPT), a synthetic aminoparthenolide derivative, indicated improved bioavailability and longer in vivo half-lifes for PTL and MMB derivatives with increased water solubility.

SUMMARY OF THE INVENTION

Briefly, therefore, one aspect of the present disclosure encompasses compounds comprising Formula (I) or (II):

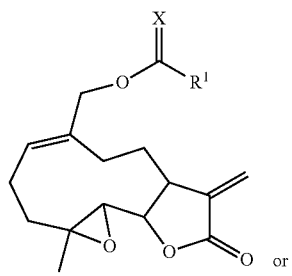

(I)

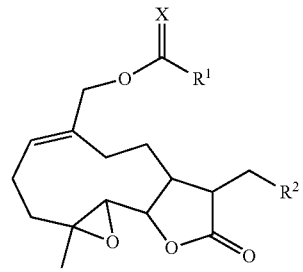

(II)

wherein:

X is O or S;

$R^1$ and $R^2$ are independently selected from the group consisting of —$NR^3R^4$, —$OR^3$, —O-alkyl-$NR^3R^4$, —$SR^3$, —S-alkyl-$NR^3R^4$, alkyl-C(O)$NR^3R^4$, and -alkyl-$R^5$;

$R^3$ is selected from the group consisting of hydrocarbyl, substituted hydrocarbyl, and $R^5$;

$R^4$ is selected from the group consisting of hydrogen, hydrocarbyl, and substituted hydrocarbyl;

$R^5$ is an optionally substituted nitrogen-containing heterocyclic ring;

one or more of $R^3$ and $R^4$ may form part of a ring or ring system chosen from the group consisting of heterocyclic, substituted heterocyclic, and combinations thereof; and when $R^4$ is hydrogen, $R^3$ is selected from the group consisting of alkyl, $R^5$, and substituted hydrocarbyl having at least one hydroxyl or $R^5$.

Another aspect of the disclosure provides a process for preparing a compound comprising Formula (I) or (II). The process comprises (a) contacting a compound comprising Formula (III) with a triazole reagent to form a compound comprising Formula (IV). The process continues with (b) contacting the compound of Formula (IV) with a compound comprising formula $R^1$—H to form a compound comprising Formula (I). The process is according to the following reaction scheme:

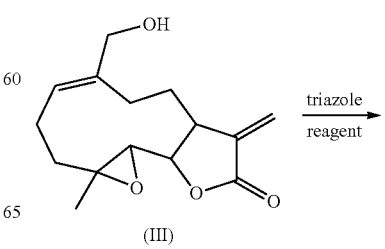

(III)

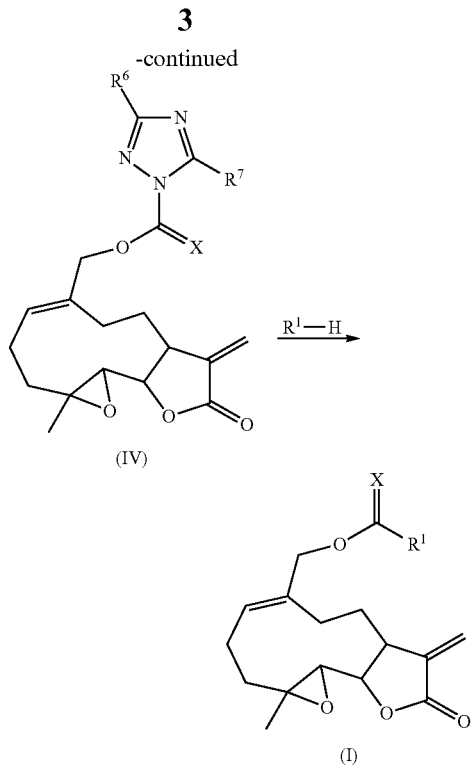

wherein:

X is O or S;

R$^1$ is selected from the group consisting of —NR$^3$R$^4$, —OR$^3$, —O-alkyl-NR$^3$R$^4$, —SR$^3$, —S-alkyl-NR$^3$R$^4$, alkyl-C(O)NR$^3$R$^4$, -alkyl-C(O)R$^5$, and -alkyl-R$^5$;

R$^3$ is selected from the group consisting of hydrocarbyl, substituted hydrocarbyl, and R$^5$;

R$^4$, R$^6$, and R$^7$ are independently selected from the group consisting of hydrogen, hydrocarbyl, and substituted hydrocarbyl;

R$^5$ is an optionally substituted nitrogen-containing heterocyclic ring;

one or more of R$^3$ and R$^4$ may form part of a ring or ring system chosen from the group consisting of heterocyclic, substituted heterocyclic, and combinations thereof; and when R$^4$ is hydrogen, R$^3$ is selected from the group consisting of alkyl, R$^5$, and substituted hydrocarbyl having at least one hydroxyl or R$^5$.

Yet another aspect of the disclosure provides a method for inhibiting growth of a cancer cell. The method comprises contacting the cancer cell with an amount of a compound comprising Formula (I) or (II), or a salt thereof, effective to inhibit growth of the cancer cell.

Other features and iterations of the invention are described in more detail below.

BRIEF DESCRIPTION OF THE FIGURES

The application file contains at least one drawing executed in color. Copies of this patent application publication with color drawing(s) will be provided by the Office upon request and payment of the necessary fee.

DETAILED DESCRIPTION OF THE INVENTION

Figure 1:
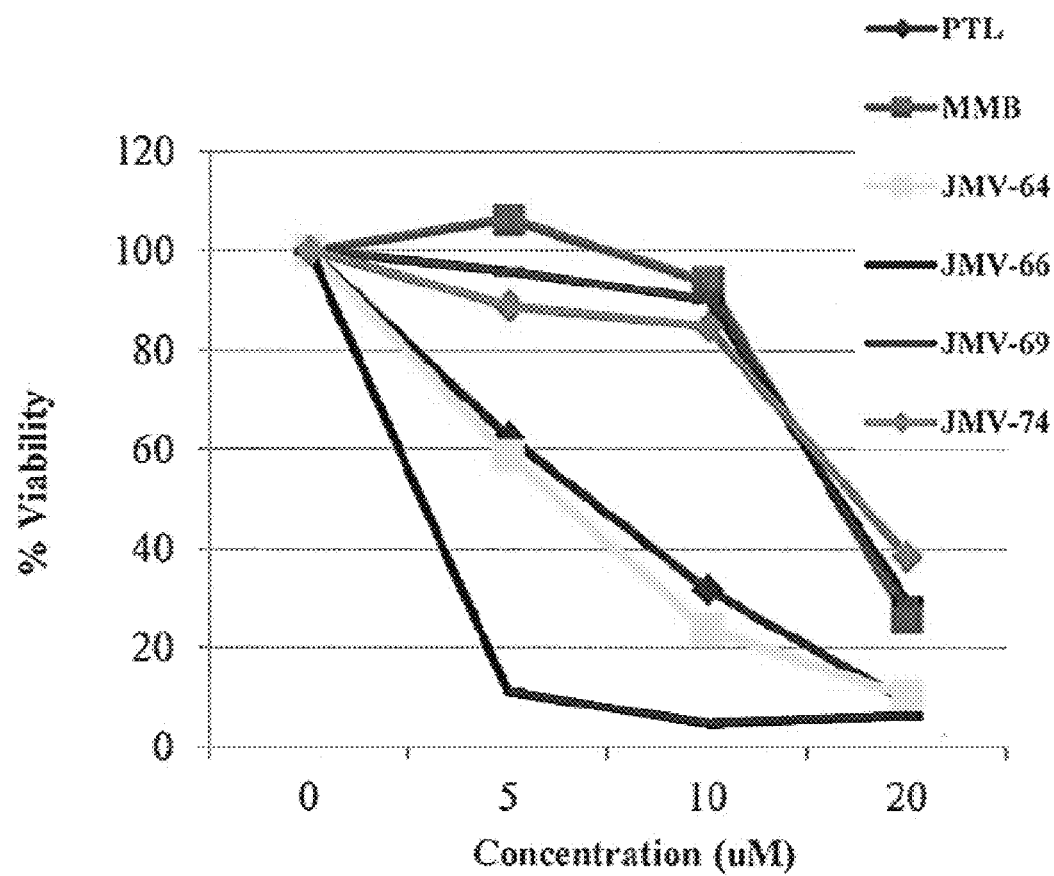
FIG. 1 shows the antileukemic activity of PTL, MMB, JMV 64, JMV 66, JMV 69, and JMV 74 against the AML 052308 cell line as a function of concentration (μM) and percentage of cell viability.
Figure 2:
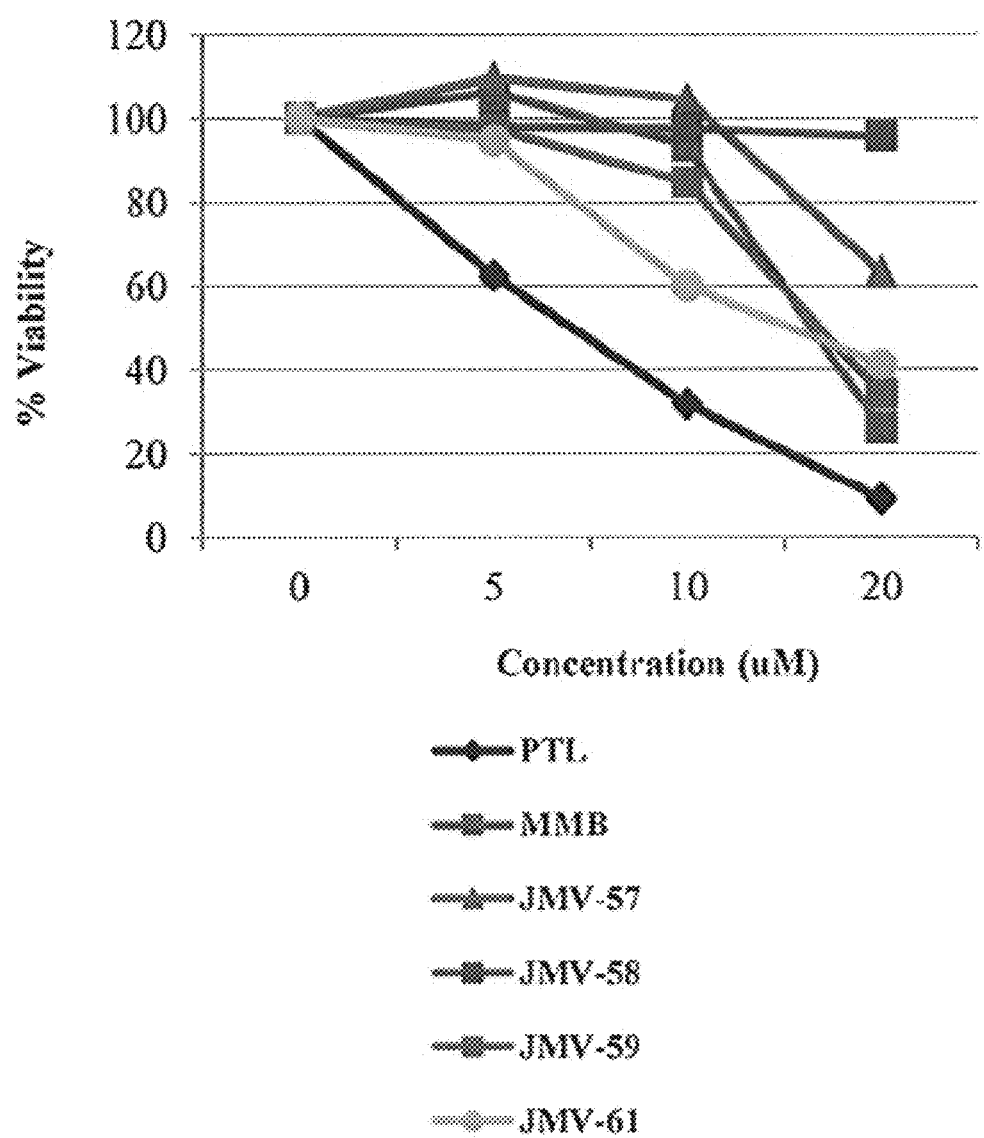
FIG. 2 shows the antileukemic activity of PTL, MMB, JMV 57, JMV 58, JMV 59, and JMV 61 against the AML 052308 cell line as a function of concentration (μM) and percentage of cell viability.
Figure 3:
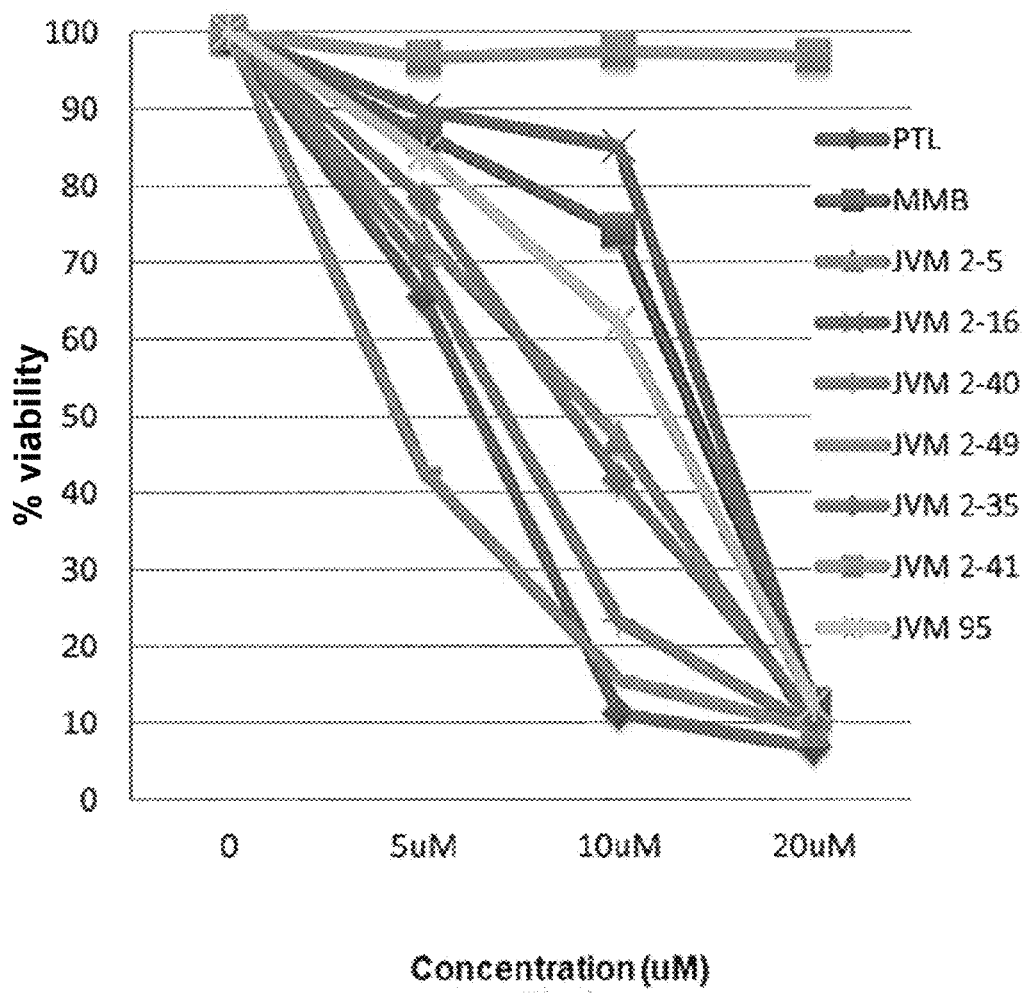
FIG. 3 shows the 24-hour M9's percentage of live cells relative to untreated cells for PTL, MMB, JMV 2-5, JMV 2-16, JMV 2-40, JMV 2-49, JVM 2-35, JVM 2-41, and JVM 95 as a function of concentration (μM).
Figure 4:
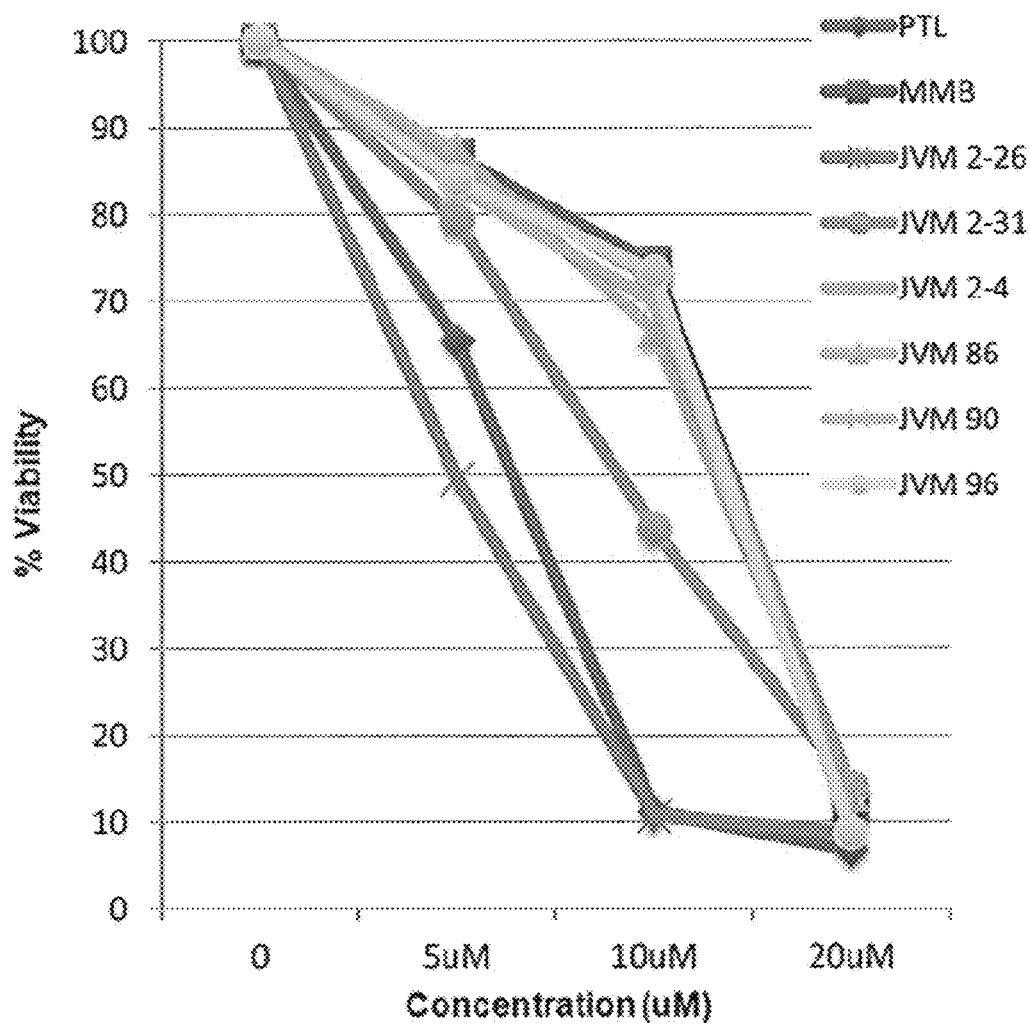
FIG. 4 shows the 24-hour M9's percentage of live cells relative to untreated cells for PTL, MMB, JMV 2-26, JMV 2-31, JMV 2-4, JMV 86, JVM 90, and JVM 96 as a function of concentration (μM).
Figure 5:
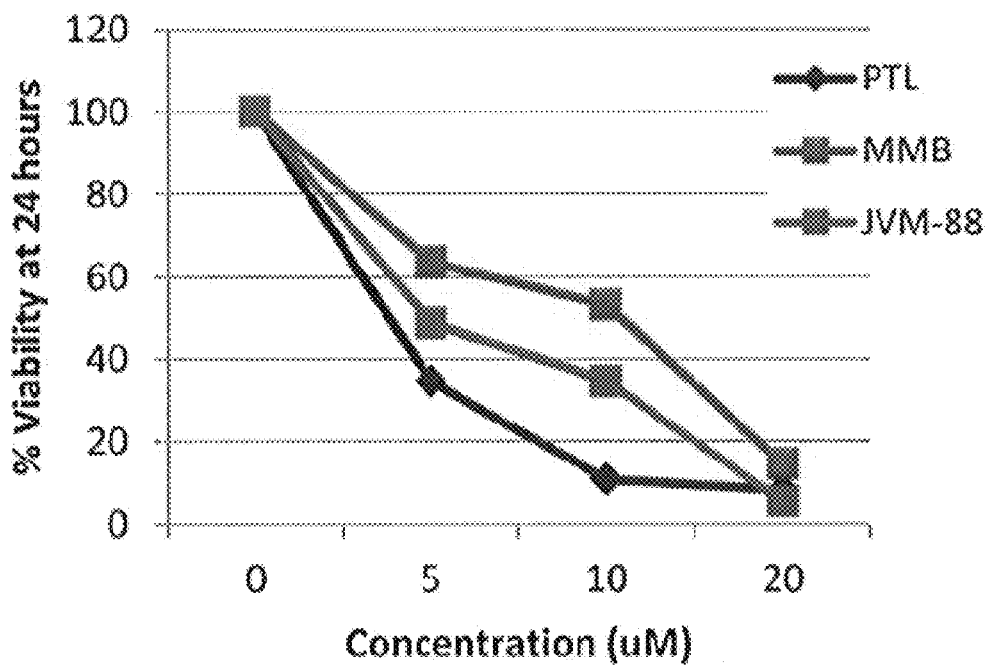
FIG. 5 shows the antileukemic activity of PTL, MMB, and JMV 88 against the M9 ENL cell line as a function of concentration (μM) and percentage of cell viability at 24 hours.
Figure 6:
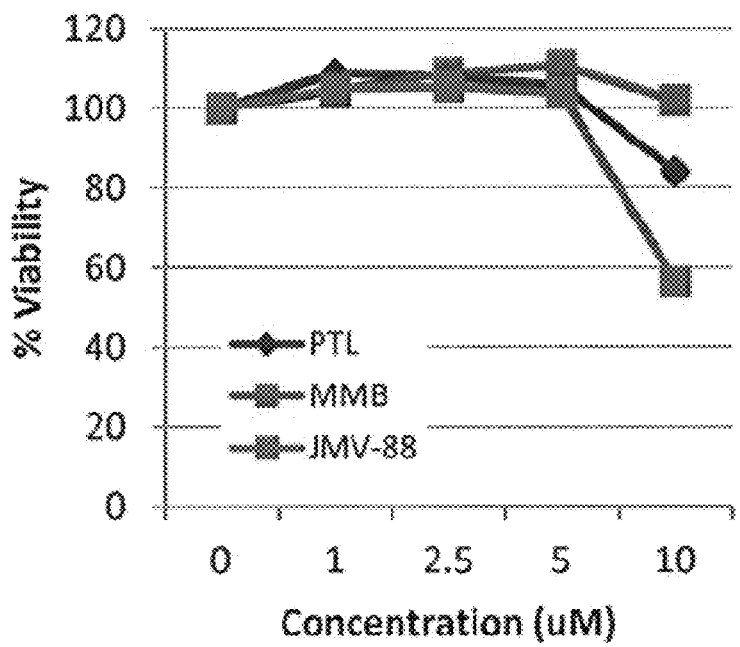
FIG. 6 shows the antileukemic activity of PTL, MMB, and JMV 88 against the AML 123009 cell line as a function of concentration (μM) and percentage of cell viability.
Figure 7:
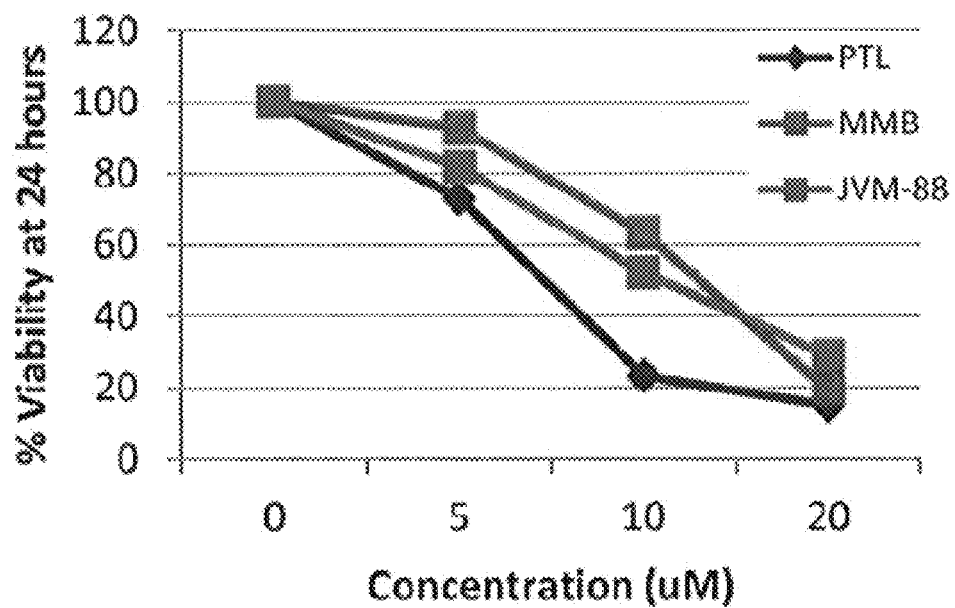
FIG. 7 shows the antileukemic activity of PTL, MMB, and JMV 88 against the AML 100510 cell line as a function of concentration (μM) and percentage of cell viability at 24 hours.

Provided herein are carbamate, thiocarbamate, and carbonate conjugates of MMB, which may be synthesized via an intermediate prepared by reacting MMB with carbonylditriazole to afford MMB triazole (JVM 2-16, Example 10). This triazole intermediate may be reacted with various heterocyclic amines, including, for example, imidazole, morpholine, piperidine, pyrrolidine, triazole, and pyridine, to afford the corresponding carbamate conjugate. To prepare carbonate conjugates of MMB, MMB triazole may be reacted with hydroxyl-containing compounds, including methanol, ethanol, N,N-dimethylethanolamine, morpholinoethanol, and piperidinopropanol. A thiocarbamate conjugate (JVM-66, Example 6) may be synthesized by reacting MMB with thiocarbonyldiimidazole. Also provided herein are carbamate and carbonate conjugates of MMB, which may be synthesized via an intermediate prepared by reacting MMB with p-nitrophenylchloroformate to afford an ester of MMB. This ester derivative may be reacted with various heterocyclic amines, including, for example, imidazole, morpholine, piperidine, pyrrolidine, triazole, and pyridine, or hydroxyl-containing compounds, including methanol, ethanol, N,N-dimethylethanolamine, morpholinoethanol, and piperidinopropanol to afford the corresponding carbamate or carbonate conjugate.

These compounds were tested for anticancer activity against primary and non-primary AML cell lines and various solid tumor cell lines. Several compounds were efficient anticancer agents against the AML cell lines and various solid tumor cell lines.

In general, the compounds detailed herein include compounds comprising a melampomagnolide B (MMB) structure as diagrammed below. For the purposes of illustration, the ring atoms of MMB are numbered as shown below:

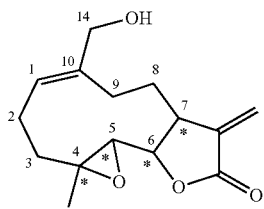 [SMILES: C=C1C(=O)OC2C1CC/C(CO)=C\CCC1(C)OC21]

MMB compounds have asymmetric centers. In particular, the MMB compounds may have at least four chiral carbons (designated by asterisks in the diagram above); namely, C4, C5, C6, and C7.

I. Compounds Comprising Formula (I) or (II)

Provided herein are a compound comprising Formula (I) or (II):

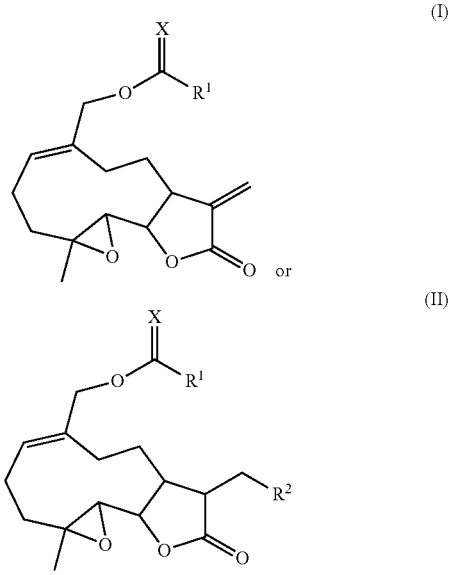

wherein:
X is O or S;
$R^1$ and $R^2$ are independently selected from the group consisting of —$NR^3R^4$, —$OR^3$, —O-alkyl-$NR^3R^4$, —$SR^3$, —S-alkyl-$NR^3R^4$, alkyl-C(O)$NR^3R^4$, and -alkyl-$R^5$;
$R^3$ is selected from the group consisting of hydrocarbyl, substituted hydrocarbyl, and $R^5$;
$R^4$ is selected from the group consisting of hydrogen, hydrocarbyl, and substituted hydrocarbyl;
$R^5$ is an optionally substituted nitrogen-containing heterocyclic ring;
 one or more of $R^3$ and $R^4$ may form part of a ring or ring system chosen from the group consisting of heterocyclic, substituted heterocyclic, and combinations thereof; and
when $R^4$ is hydrogen, $R^3$ is selected from the group consisting of alkyl, $R^5$, and substituted hydrocarbyl having at least one hydroxyl or $R^5$.

In an exemplary embodiment of a compound comprising Formula (I), X is O; $R^1$ is $NR^3R^4$; and $R^3$, $R^4$ and $R^5$ are as described above.

In some embodiments, $R^1$ and $R^2$ may be selected from the group consisting of alkoxy, alkylamino, dialkylamino, dialkylaminoalkoxy, heterocyclylalkoxy, hydroxyalkylamino, heterocyclylamino, and heterocyclylalkylamino. In some exemplary embodiments, $R^1$ and $R^2$ may be selected from the group consisting of methylamino, dimethylamino, hydroxyhexylamino, hydroxyethylamino, pyrrolyl, pyrrolidinyl, pyridinyl, piperidinyl, pyrazinyl, piperazinyl, pyrimidinyl, imidazolyl, triazolyl, hydroxypiperdinyl, difluoropiperdinyl, triazolylamino, methylthiotriazolylamino, morpholinyl, morpholinylethylamino, pyridinylmethylamino, piperdinylethylamino, pyridinylethylamino, morpholinylpropylamino, imidiazolylpropylamino, methoxy, dimethylaminoethoxy, piperdinylpropoxy, piperdinylethoxy, pyrrolidinylethoxy, morpholinylethyoxy, piperidinylethoxyhydroxyethylthio, and piperdinylethyl. In other exemplary embodiments, $R^1$ and $R^2$ may be independently selected from the group consisting of imidazolylpropylaminocarbonylethylcarbonyl, difluoropiperinylcarbonylethylcarbonyl, methylthiotriazolylaminocarbonylethylcarbonyl, chloropyridinylmethylaminocarbonylethylcarbonyl, methylpiperdinylcarbonylethylcarbonyl, and methylpiperazinylcarbonylethylcarbonyl. In a particular embodiment, $R^1$ may be $R^5$, and $R^2$ may be dialkylamino. In still other embodiments, one or more $R^1$, $R^2$, $R^3$, $R^4$, or $R^5$ may be substituted with at least one selected from the group consisting of methyl, ethyl, propyl, cyano, $C_1$-$C_3$-alkylamino, carboxyl, hydroxyl, trifluoromethyl, thio, alkylthio, and halogen.

(a) Downstream Applications

In some embodiments, the compound comprising Formula (I) or (II) may be converted into a pharmaceutically acceptable salt. "Pharmaceutically acceptable salts" are salts commonly used to form alkali metal salts and to form addition salts of free acids or free bases. The nature of the salt may vary, provided that it is pharmaceutically acceptable.

Suitable pharmaceutically acceptable acid addition salts of compounds comprising Formula (I) or (II) may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, hydroxybutyric, salicylic, galactaric and galacturonic acid. Suitable pharmaceutically acceptable base addition salts include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine-(N-methylglucamine) and procaine. All of these salts may be prepared by conventional means from the corresponding compound by reacting, for example, the appropriate acid or base with the any compound comprising Formula (I) or (II).

(b) Stereochemistry

The compounds comprising Formulas (I) and (II) may independently have an optical activity of (−) or (+). In particular, the configuration of C4, C5, C6, and C7, respectively, may be RRRR, RRSR, RRRS, RRSS, RSRR, RSSR, RSRS, RSSS, SRRR, SRSR, SRRS, SRSS, SSRR, SSSR, SSRS, or SSSS. The configuration of C4, C5, C6, and C7 may be as shown in Formulas (Ia) and (IIa):

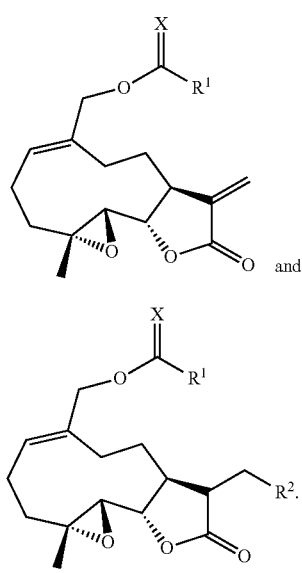

II. Processes for Preparing Compounds Comprising Formula (I) or (II)

In particular, provided herein are processes for preparing a compound comprising Formula (I) or (II). In general, the process comprises contacting MMB with an appropriate reagent to form a compound comprising Formula (I) or (II).

In an aspect, provided herein are processes for preparing a compound comprising Formula (I) or (II). The process comprises (a) contacting MMB with a triazole reagent to form a triazole intermediate. The process continues with (b) contacting the triazole intermediate with a compound comprising formula $R^1$—H to form a compound comprising Formula (I) or (II).

In another aspect, provided herein are processes for preparing a carbamate or carbonate compound comprising Formula (I). The process comprises (a) contacting MMB with p-nitrophenylchloroformate to form an ester derivative of MMB. The process continues with (b) contacting the ester derivative of MMB with a compound comprising formula $R^1$—H to form a compound comprising Formula (I).

In still another aspect, provided herein are processes for preparing an amide compound comprising Formula (I). The process comprises (a) contacting MMB with an acid anhydride to form a carboxylic acid derivative. The process continues with (b) contacting the carboxylic acid derivative with a compound comprising formula $R^1$—H to form a compound comprising Formula (I).

(a) Carbamate and Carbonate Derivatives of MMB Via a Triazole Intermediate

Carbamate derivatives may be synthesized using, for example, phosgene, acid chlorides, carbamoyl chloride, or 1,1-carbonyldiimidazole (CDI). In some embodiments, CDI may form a carbamate ester on MMB. CDI advantageously provides easy handling, low expense, and relatively low toxicity. In particular embodiments, imidazole carboxylic esters may be formed by reaction of CDI with MMB. In this reaction imidazole, while a byproduct, also participated in an unexpected Michael addition reaction with the MMB exocyclic double bond of the carbamate product (Scheme 1).

Scheme 1. Synthesis of imidazole carbamate derivative of MMB

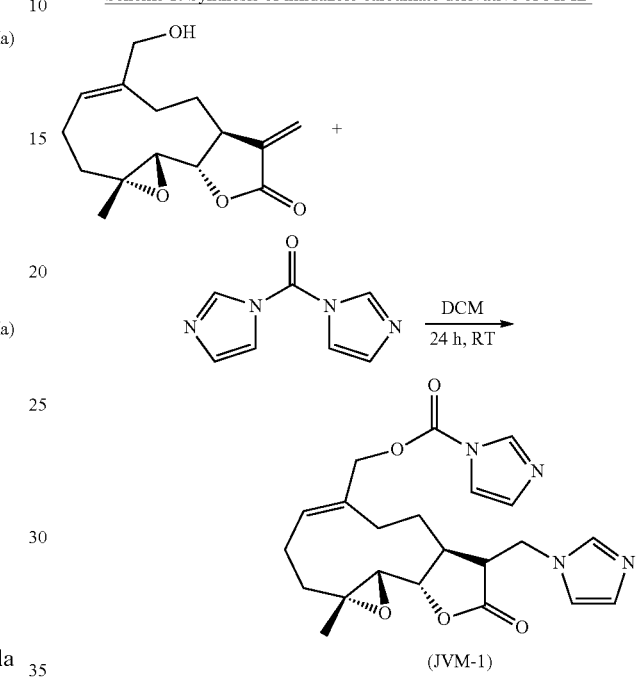

Thiocarbamate derivatives of MMB may be formed by reacting MMB with thiocarbonyl diimidazole dissolved in dichloromethane. If the reaction is maintained for 3-4 h, the major product was the Michael adduct JVM 66A. If the reaction is run for a shorter time (e.g., 1 hour), the thiocarbamate (JVM 66) was the major product (Scheme 2). A detailed synthesis of JVM 66 is provided below at Example 6.

Scheme 2. Synthesis of thiocarbamate derivatives of MMB

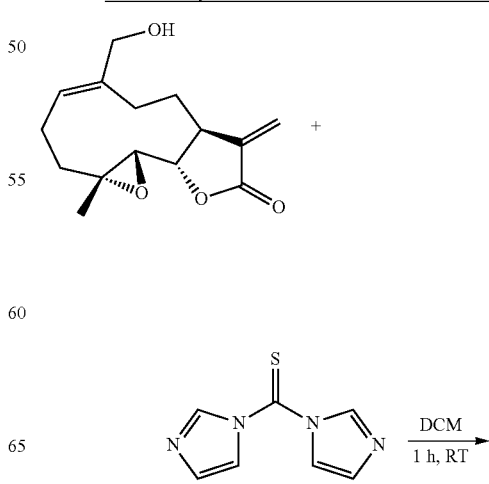

-continued

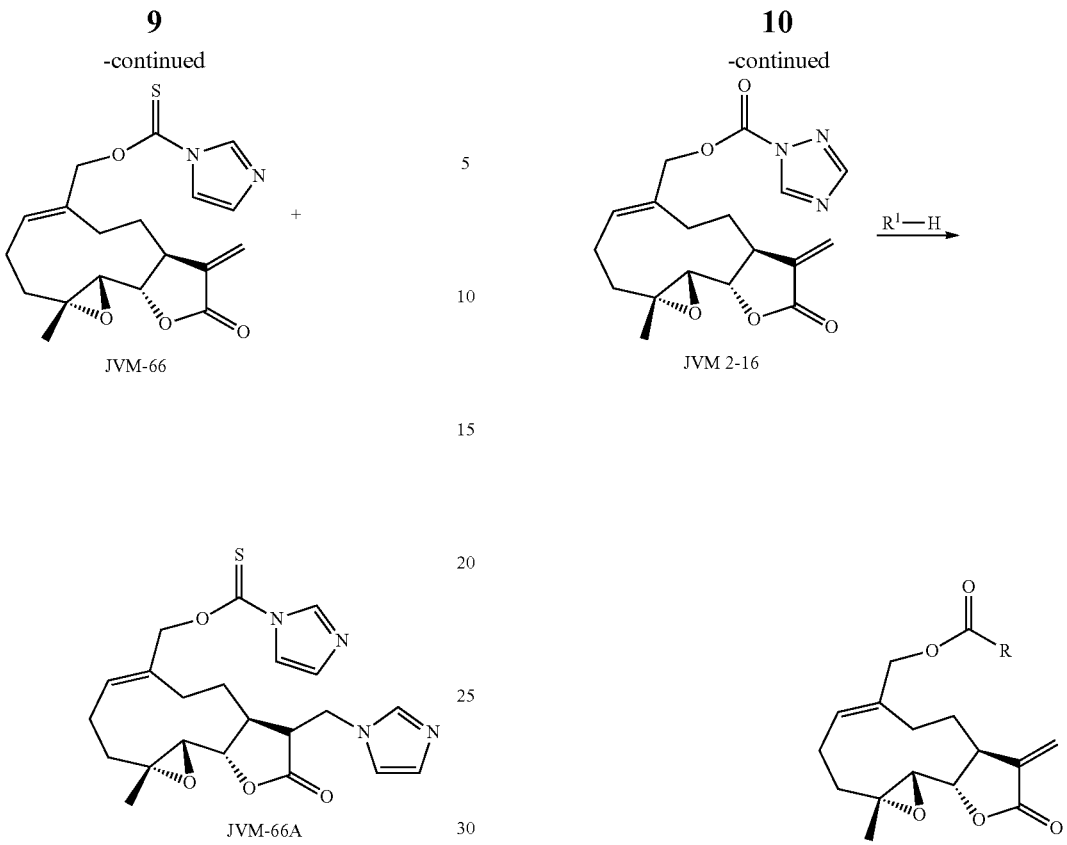

The triazole derivative of MMB (JVM 2-16) was prepared by reacting MMB with carbonylditriazole (CTD) dissolved in dichloromethane. The triazole byproduct does not participate in a Michael addition reaction because triazole has only weak nucleophilic properties. The triazole intermediate (JVM 2-16) reacted with various heterocyclic amines and alcohols to form a variety of carbamate and carbonate derivatives (Scheme 3). A detailed synthesis of JVM 2-16 is provided below at Example 10.

Scheme 3. Synthesis of carbamate and carbonate derivatives of MMB

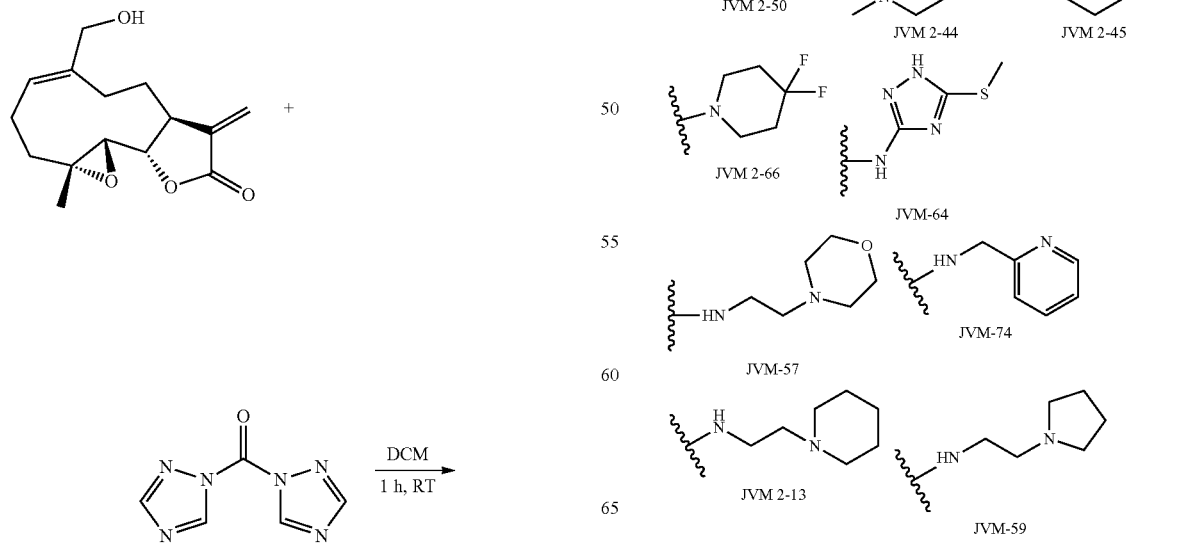

-continued

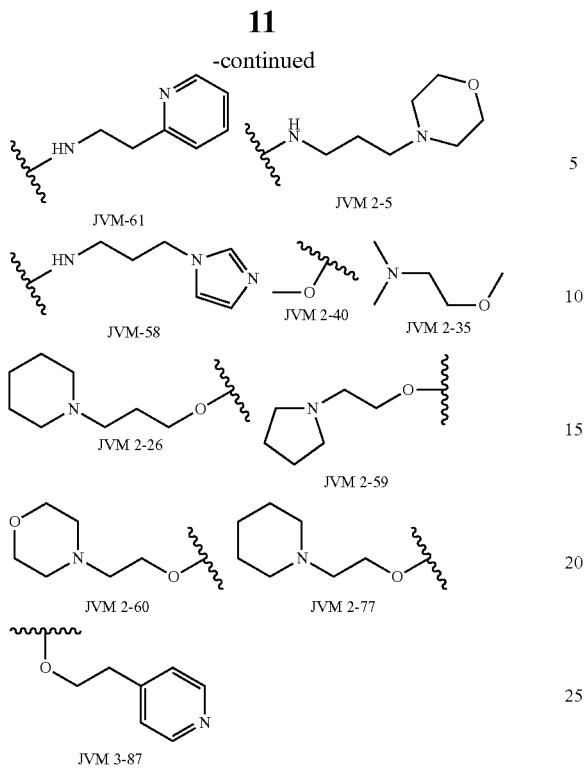

In still other embodiments, the triazole intermediate (JVM 2-16) may be reacted with mercaptoethanol in the presence of triethylamine to afford JVM 2-41. A detailed synthesis of JVM 2-41 is provided below at Example 15.

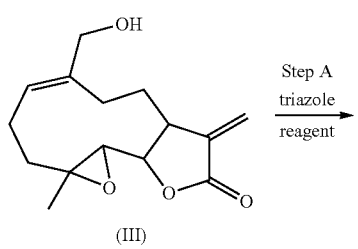

In particular, provided herein are processes for preparing a compound comprising Formula (I) or (II). The process comprises (a) contacting a compound comprising Formula (III) with a triazole reagent to form a compound comprising Formula (IV). The process continues with (b) contacting the compound of Formula (IV) with a compound comprising formula $R^1$—H to form a compound comprising Formula (I) or (II). This process is illustrated according to the following reaction scheme:

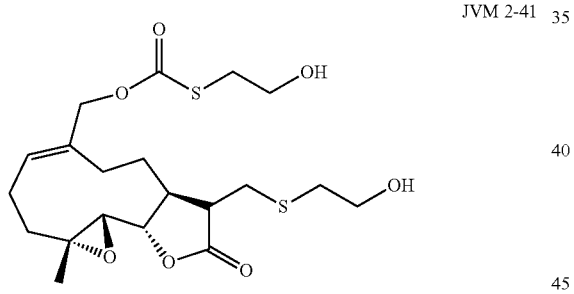

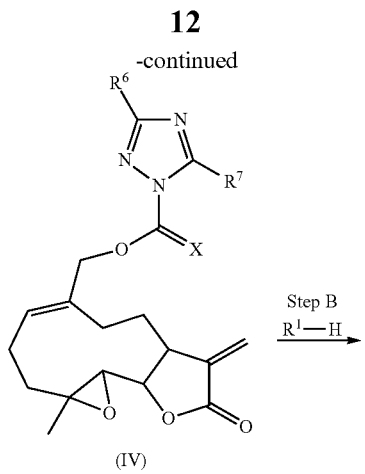

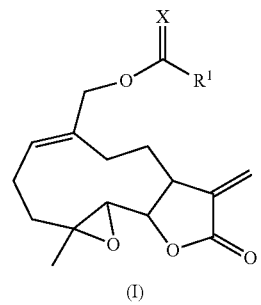

wherein:

X is O or S;

$R^1$ is selected from the group consisting of —$NR^3R^4$, —$OR^3$, —O-alkyl-$NR^3R^4$, —$SR^3$, —S-alkyl-$NR^3R^4$, alkyl-C(O)$NR^3R^4$, and -alkyl-$R^5$;

$R^3$ is selected from the group consisting of hydrocarbyl, substituted hydrocarbyl, and $R^5$;

$R^4$, $R^6$, and $R^7$ are independently selected from the group consisting of hydrogen, hydrocarbyl, and substituted hydrocarbyl;

$R^5$ is an optionally substituted nitrogen-containing heterocyclic ring;

one or more of $R^3$ and $R^4$ may form part of a ring or ring system chosen from the group consisting of heterocyclic, substituted heterocyclic, and combinations thereof; and when $R^4$ is hydrogen, $R^3$ is selected from the group consisting of alkyl, $R^5$, and substituted hydrocarbyl having at least one hydroxyl or $R^5$.

(i) Step (a)—Reaction Mixture

Step (a) of the process comprises contacting a compound comprising Formula (III) with a triazole reagent to form a compound comprising Formula (IV). The process commences with the formation of a reaction mixture comprising the compound comprising Formula (III), which is detailed above, the triazole reagent, and optionally a solvent system.

The triazole reagent may be any compound which reacts with a hydroxyl group to provide a triazolyl carbamate, such as a compound comprising Formula (IV). Non-limiting examples of suitable triazole reagents include carbonylditriazole (such as 1,1'-carbonyl-di-(1,2,4-triazole) and thiocarbonylditriazole. Another possible synthetic approach to the synthesis of the imidazole carbamate analog of MMB is by utilizing carbonyldiimidazole as a reagent instead of carbonylditriazole.

The amounts of triazole reagent that are contacted with the compound comprising Formula (III) may vary. In general, the mole to mole ratio of the compound comprising Formula (III) to triazole agent may range from about 1:0.2 to about 1:15. In certain embodiments, the mole to mole ratio of the compound comprising Formula (III) to the triazole reagent may range from about 1:0.2 to about 1:0.7, from about 1:0.7 to about 1:1.5, from about 1:1.5 to about 1:2.5, from about 1:2.5 to about 1:5, from about 1:5 to about 1:10, or from about 1:10 to about 1:15. In certain embodiments, the mole to mole ratio of the compound comprising Formula (III) to the triazole reagent may range from about 1:0.7 to about 1:3.

The reaction is generally conducted in the presence of a solvent or solvent system. The solvent may be a polar aprotic solvent, a polar protic solvent, or a nonpolar solvent. Non-limiting examples of suitable polar aprotic solvents include acetone, acetonitrile, diethoxymethane, N,N-dimethylformamide (DMF), dimethyl sulfoxide (DMSO), N,N-dimethylpropanamide (or dimethylpropionamide; DMP), 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl)ether, N,N-dimethylacetamide (DMA), N-methyl-2-pyrrolidinone (NMP), 1,4-dioxane, ethyl formate, formamide, hexachloroacetone, hexamethylphosphoramide, methyl acetate, N-methylacetamide, N-methylformamide, methylene chloride (dichloromethane, DCM), chloroform, methoxyethane, morpholine, nitrobenzene, nitromethane, propionitrile, pyridine, sulfolane, tetramethylurea, tetrahydrofuran (THF), 2-methyl tetrahydrofuran, tetrahydropyran, trichloromethane, and combinations thereof. Non-limiting examples of suitable polar protic solvents include water; alcohols such as methanol, ethanol, isopropanol, n-propanol, isobutanol, n-butanol, s-butanol, t-butanol, and the like; diols such as propylene glycol; organic acids such as formic acid, acetic acid, and so forth; amides such as formamide, acetamide, and the like; and combinations of any of the above. Representative nonpolar solvents include, but are not limited to, alkane and substituted alkane solvents (including cycloalkanes), aromatic hydrocarbons, esters, ethers, ketones, and combinations thereof. Specific polar aprotic solvents that may be employed include, for example, dichloromethane, chloroform, and combinations thereof.

In general, the volume to mass ratio of the solvent to the compound comprising Formula (III) ranges from about 1:1 to about 100:1. In various embodiments, the volume to mass ratio of the solvent to the compound comprising Formula (III) may range from about 1:1 to about 5:1, from about 5:1 to about 10:1, from about 10:1 to about 20:1, from about 20:1 to about 30:1, from about 30:1 to about 40:1, from about 40:1 to about 50:1, from about 50:1 to about 60:1, from about 60:1 to about 70:1, from about 70:1 to about 80:1, from about 80:1 to about 90:1, or from about 90:1 to about 100:1. In exemplary embodiments, the volume to mass ratio of the solvent to the compound comprising Formula (III) may range from about 20:1 to about 30:1.

(ii) Step (a)—Reaction Conditions

In general, the reaction is conducted at a temperature that ranges from about 0° C. to about 50° C. In various embodiments, the reaction may be conducted at a temperature from about 0° C. to about 10° C., from about 10° C. to about 20° C., from about 20° C. to about 30° C., from about 30° C. to about 40° C., or from about 40° C. to about 50° C. In certain embodiments, the reaction may be conducted at a temperature of about 25° C. The reaction generally is conducted in an inert atmosphere (e.g., under nitrogen or argon) and under ambient pressure.

Typically, the reaction is allowed to proceed for a sufficient period of time until the reaction is complete, as determined by chromatography (e.g., TLC, HPLC) or another suitable method. In this context, a "completed reaction" generally means that the reaction mixture contains a significantly diminished amount of the compound comprising Formula (III), and a significantly increased amount of the compound comprising Formula (IV) compared to the amounts of each present at the beginning of the reaction. Typically, the amount of the compound comprising Formula (III) remaining in the reaction mixture after the reaction is complete may be less than about 3%, or less than about 1%. In general, the reaction may proceed for about 5 minutes to about 48 hours. Typically, the duration of the reaction is longer at lower reaction temperatures. In certain embodiments, the reaction may be allowed to proceed for about a period of time ranging from about 5 minutes to about 10 minutes, from about 10 minutes to about 15 minutes, from about 15 minutes to about 30 minutes, from about 30 minutes to about 1 hour, about 1 hour to about 3 hours, from about 3 hours to about 6 hours, from about 6 hours to about 12 hours, from about 12 hours to about 18 hours, from about 18 hours to about 24 hours, from about 24 hours to about 36 hours, or from about 36 hours to about 48 hours. In certain embodiments, the reaction may be allowed to proceed about 5 minutes to about 15 minutes. In other embodiments, the reaction may be allowed to proceed about 45 minutes to about 75 minutes. In still other embodiments, the reaction may be allowed to proceed about 18 hours to about 36 hours.

Generally, the compound comprising Formula (IV) is not isolated and step (b) of the process proceeds in the same reaction pot or reactor. In some embodiments, the compound comprising Formula (IV) may be isolated from the reaction mixture using techniques known to those of skill in the art. Non-limiting examples of suitable techniques include precipitation, extraction, evaporation, distillation, chromatography, and crystallization.

The yield of the compound comprising Formula (IV) can and will vary. Typically, the yield of the compound comprising Formula (IV) may be at least about 40%. In one embodiment, the yield of the compound comprising Formula (IV) may range from about 40% to about 60%. In another embodiment, the yield of the compound comprising Formula (IV) may range from about 60% to about 80%. In a further embodiment, the yield of the compound comprising Formula (IV) may range from about 80% to about 90%. In still another embodiment, the yield of the compound comprising Formula (IV) may be greater than about 90%, or greater than about 95%.

(iii) Step (b)—Reaction Mixture

Step (b) of the process continues with (b) contacting the compound of Formula (IV) with a compound comprising formula $R^1$—H to form a compound comprising Formula (I). The process commences with the formation of a reaction mixture comprising the compound comprising Formula (IV), which is detailed above, a compound comprising the formula $R^1$—H, and optionally a solvent system.

In some embodiments, the compound comprising formula $R^1$—H may be selected from the group consisting of imidazole, benzimidazole, morpholine, piperidine, pyrrole, pyrrolidine, triazole, tetrazole, piperazine, pyridine, pyrazoloimidazole, methanol, ethanol, N,N-dimethylethanolamine, morpholinoethanol, and piperidinopropanol.

The amounts of the compound comprising formula $R^1$—H that are contacted with the compound comprising Formula (IV) may vary. In general, the mole to mole ratio of the compound comprising Formula (IV) to the compound comprising formula $R^1$—H may range from about 1:0.2 to about 1:15. In certain embodiments, the mole to mole ratio of the compound comprising Formula (IV) to the compound comprising formula $R^1$—H may range from about 1:0.2 to about 1:0.7, from about 1:0.7 to about 1:1.5, from about 1:1.5 to about 1:2.5, from about 1:2.5 to about 1:5, from about 1:5 to about 1:10, or from about 1:10 to about 1:15. In certain embodiments, the mole to mole ratio of the compound comprising Formula (IV) to the compound comprising formula $R^1$—H may range from about 1:0.7 to about 1:3.

Contact with the compound comprising formula $R^1$—H generally is conducted in the presence of a solvent or solvent system. Suitable solvents are detailed above in Section II(a)(i). In exemplary embodiments, the solvent may be dichloromethane, chloroform, or combinations thereof. In general, the volume to mass ratio of the solvent to the compound comprising Formula (IV) ranges from about 1:1 to about 100:1. In various embodiments, the volume to mass ratio of the solvent to the compound comprising Formula (IV) may range from about 1:1 to about 5:1, from about 5:1 to about 10:1, from about 10:1 to about 20:1, from about 20:1 to about 30:1, from about 30:1 to about 40:1, from about 40:1 to about 50:1, from about 50:1 to about 60:1, from about 60:1 to about 70:1, from about 70:1 to about 80:1, from about 80:1 to about 90:1, or from about 90:1 to about 100:1. In exemplary embodiments, the volume to mass ratio of the solvent to the compound comprising Formula (IV) may range from about 20:1 to about 30:1.

(iv) Step (b)—Reaction Conditions

In general, the reaction is conducted at a temperature that ranges from about 0° C. to about 50° C. In various embodiments, the reaction may be conducted at a temperature from about 0° C. to about 10° C., from about 10° C. to about 20° C., from about 20° C. to about 30° C., from about 30° C. to about 40° C., or from about 40° C. to about 50° C. In certain embodiments, the reaction may be conducted at a temperature of about 25° C. The reaction generally is conducted in an inert atmosphere (e.g., under nitrogen or argon) and under ambient pressure.

Typically, the reaction is allowed to proceed for a sufficient period of time until the reaction is complete, as determined by chromatography (e.g., TLC, HPLC) or another suitable method. Typically, the amount of the compound comprising Formula (IV) remaining in the reaction mixture after the reaction is complete may be less than about 3%, or less than about 1%. In general, the reaction may proceed for about 5 minutes to about 48 hours. Typically, the duration of the reaction is longer at lower reaction temperatures. In certain embodiments, the reaction may be allowed to proceed for about a period of time ranging from about 5 minutes to about 10 minutes, from about 10 minutes to about 15 minutes, from about 15 minutes to about 30 minutes, from about 30 minutes to about 1 hour, about 1 hour to about 3 hours, from about 3 hours to about 6 hours, from about 6 hours to about 12 hours, from about 12 hours to about 18 hours, from about 18 hours to about 24 hours, from about 24 hours to about 36 hours, or from about 36 hours to about 48 hours. In certain embodiments, the reaction may be allowed to proceed about 20 minutes to about 40 minutes. In other embodiments, the reaction may be allowed to proceed about 8 hours to about 12 hours.

The yield of the compound comprising Formula (I) or (II) can and will vary. Typically, the yield of the compound comprising Formula (I) or (II) may be at least about 40%. In one embodiment, the yield of the compound comprising Formula (I) or (II) may range from about 40% to about 60%. In another embodiment, the yield of the compound comprising Formula (I) or (II) may range from about 60% to about 80%. In a further embodiment, the yield of the compound comprising Formula (I) or (II) may range from about 80% to about 90%. In still another embodiment, the yield of the compound comprising Formula (I) or (II) may be greater than about 90%, or greater than about 95%.

(b) Carbamate and Carbonate Derivatives of MMB Via an Ester Derivative

In still yet other embodiments, MMB (3) may be reacted with p-nitrophenylchloroformate (4) in the presence of triethylamine to from the p-nitrophenyloxycarbonyl ester of MMB (5). The p-nitrophenyloxycarbonyl ester of MMB may then be reacted with various primary and secondary heterocyclic amines to afford carbamate analogs of MMB (6) (Scheme 4).

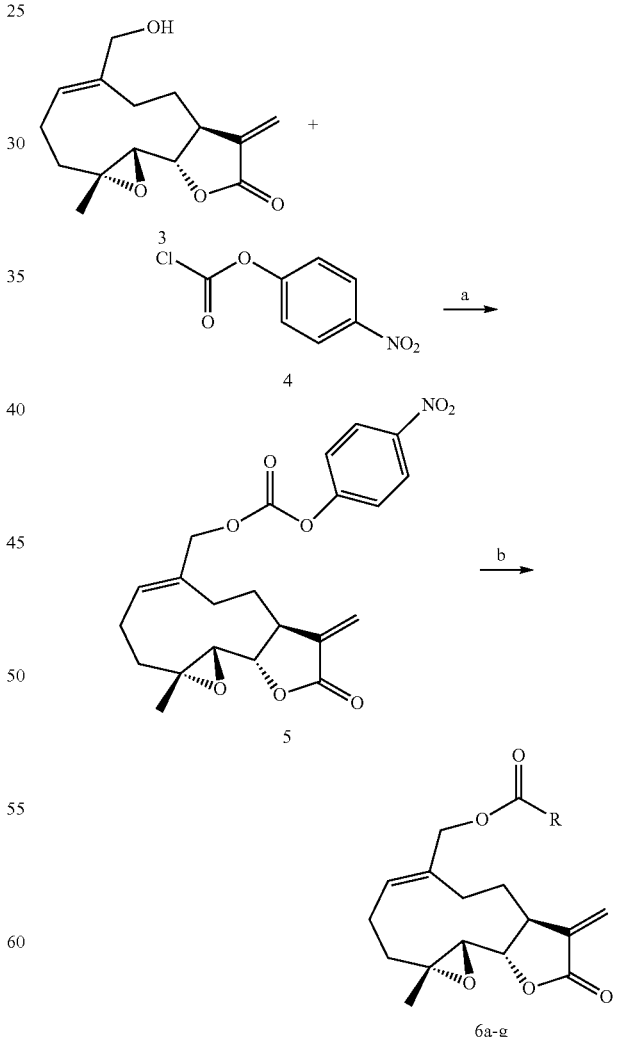

Scheme 4. Synthesis of carbamoylated MMB analogs 6a-6g: Reagents and conditions: (a) CH$_2$Cl$_2$, triethylamine, rt, 24 h; (b) CH$_2$Cl$_2$, heterocyclic amines, rt, 5-12 h.

In particular, provided herein are processes for preparing a carbamate or carbonate compound comprising Formula (I). The process comprises (a) contacting MMB (2) with p-nitrophenylchloroformate to form an ester derivative of MMB (e.g. (5)). The process continues with (b) contacting the ester derivative of MMB with a compound comprising formula $R^1$—H to form a compound comprising Formula (I).

(i) Step (a)—Reaction Mixture

Step (a) of the process comprises contacting MMB with p-nitrophenylchloroformate to form an ester derivative of MMB (e.g. (5)). The process commences with the formation of a reaction mixture comprising MMB, which is detailed above, p-nitrophenylchloroformate, and optionally a solvent system.

The amounts of p-nitrophenylchloroformate that are contacted with MMB may vary. In general, the mole to mole ratio of MMB to p-nitrophenylchloroformate may range from about 1:0.2 to about 1:15. In certain embodiments, the mole to mole ratio of MMB to p-nitrophenylchloroformate may range from about 1:0.2 to about 1:0.7, from about 1:0.7 to about 1:1.5, from about 1:1.5 to about 1:2.5, from about 1:2.5 to about 1:5, from about 1:5 to about 1:10, or from about 1:10 to about 1:15. In certain embodiments, the mole to mole ratio of MMB to p-nitrophenylchloroformate may range from about 1:0.7 to about 1:3. In an exemplary embodiment, the mole to mole ratio of MMB to p-nitrophenylchloroformate may be about 1:0.7.

The reaction is generally conducted in the presence of a solvent or solvent system. The solvent may be a polar aprotic solvent, a polar protic solvent, or a nonpolar solvent. Non-limiting examples of suitable polar aprotic solvents include acetone, acetonitrile, diethoxymethane, N,N-dimethylformamide (DMF), dimethyl sulfoxide (DMSO), N,N-dimethylpropanamide (or dimethylpropionamide; DMP), 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl)ether, N,N-dimethylacetamide (DMA), N-methyl-2-pyrrolidinone (NMP), 1,4-dioxane, ethyl formate, formamide, hexachloroacetone, hexamethylphosphoramide, methyl acetate, N-methylacetamide, N-methylformamide, methylene chloride (dichloromethane, DCM), chloroform, methoxyethane, morpholine, nitrobenzene, nitromethane, propionitrile, pyridine, sulfolane, tetramethylurea, tetrahydrofuran (THF), 2-methyl tetrahydrofuran, tetrahydropyran, trichloromethane, and combinations thereof. Non-limiting examples of suitable polar protic solvents include water; alcohols such as methanol, ethanol, isopropanol, n-propanol, isobutanol, n-butanol, s-butanol, t-butanol, and the like; diols such as propylene glycol; organic acids such as formic acid, acetic acid, and so forth; amides such as formamide, acetamide, and the like; and combinations of any of the above. Representative nonpolar solvents include, but are not limited to, alkane and substituted alkane solvents (including cycloalkanes), aromatic hydrocarbons, esters, ethers, ketones, and combinations thereof. Specific polar aprotic solvents that may be employed include, for example, dichloromethane, chloroform, and combinations thereof.

A proton acceptor is generally added to facilitate the reaction. The proton acceptor generally has a pKa greater than about 7, or from about 7 to about 13, or more specifically from about 9 to about 11. Representative proton acceptors may include, but are not limited to, borate salts (such as, for example, $NaBO_3$), di- and tri-basic phosphate salts, (such as, for example, $Na_2HPO_4$ and $NaPO_4$), bicarbonate salts, carbonate salts, hydroxides, alkoxides, (including methoxide, ethoxide, propoxide, butoxide, and pentoxide, including straight chain and branched), and organic proton acceptors, (such as, for example, pyridine, triethylamine, N-methylmorpholine, and N,N-dimethylaminopyridine), and mixtures thereof. In some embodiments, the proton acceptor may be stabilized by a suitable counterion such as lithium, potassium, sodium, calcium, magnesium, and the like. In a specific embodiment, the proton acceptor is triethylamine. The amount of proton acceptor included in the reaction can and will vary, but can be readily determined by a person of ordinary skill in the art.

In general, the volume to mass ratio of the solvent to MMB ranges from about 1:1 to about 100:1. In various embodiments, the volume to mass ratio of the solvent to MMB may range from about 1:1 to about 5:1, from about 5:1 to about 10:1, from about 10:1 to about 20:1, from about 20:1 to about 30:1, from about 30:1 to about 40:1, from about 40:1 to about 50:1, from about 50:1 to about 60:1, from about 60:1 to about 70:1, from about 70:1 to about 80:1, from about 80:1 to about 90:1, or from about 90:1 to about 100:1. In exemplary embodiments, the volume to mass ratio of the solvent to MMB may range from about 20:1 to about 30:1. In other exemplary embodiments, the volume to mass ratio of the solvent to MMB may range from about 10:1 to about 20:1.

(ii) Step (a)—Reaction Conditions

In general, the reaction is conducted at a temperature that ranges from about 0° C. to about 50° C. In various embodiments, the reaction may be conducted at a temperature from about 0° C. to about 10° C., from about 10° C. to about 20° C., from about 20° C. to about 30° C., from about 30° C. to about 40° C., or from about 40° C. to about 50° C. In certain embodiments, the reaction may be conducted at a temperature of about 25° C. The reaction generally is conducted in an inert atmosphere (e.g., under nitrogen or argon) and under ambient pressure.

Typically, the reaction is allowed to proceed for a sufficient period of time until the reaction is complete, as determined by chromatography (e.g., TLC, HPLC) or another suitable method. In this context, a "completed reaction" generally means that the reaction mixture contains a significantly diminished amount of MMB, and a significantly increased amount of the carboxylic acid derivative compared to the amounts of each present at the beginning of the reaction. Typically, the amount of MMB remaining in the reaction mixture after the reaction is complete may be less than about 3%, or less than about 1%. In general, the reaction may proceed for about 5 minutes to about 48 hours. Typically, the duration of the reaction is longer at lower reaction temperatures. In certain embodiments, the reaction may be allowed to proceed for about a period of time ranging from about 5 minutes to about 10 minutes, from about 10 minutes to about 15 minutes, from about 15 minutes to about 30 minutes, from about 30 minutes to about 1 hour, about 1 hour to about 3 hours, from about 3 hours to about 6 hours, from about 6 hours to about 12 hours, from about 12 hours to about 18 hours, from about 18 hours to about 24 hours, from about 24 hours to about 36 hours, or from about 36 hours to about 48 hours. In certain embodiments, the reaction may be allowed to proceed about 5 minutes to about 15 minutes. In other embodiments, the reaction may be allowed to proceed about 45 minutes to about 75 minutes. In still other embodiments, the reaction may be allowed to proceed about 18 hours to about 36 hours. In an exemplary embodiment, the reaction may be allowed to proceed about 24 hours.

Generally, the ester derivative is not isolated and step (b) of the process proceeds in the same reaction pot or reactor. In some embodiments, the ester derivative may be isolated from the reaction mixture using techniques known to those of skill in the art. Non-limiting examples of suitable techniques include precipitation, extraction, evaporation, distillation, chromatography, and crystallization.

The yield of the ester derivative can and will vary. Typically, the yield of the ester derivative may be at least about 40%. In one embodiment, the yield of the ester derivative may range from about 40% to about 60%. In another embodiment, the yield of the ester derivative may range from about 60% to about 80%. In a further embodiment, the yield of the ester derivative may range from about 80% to about 90%. In still another embodiment, the yield of the ester derivative may be greater than about 90%, or greater than about 95%.

(iii) Step (b)—Reaction Mixture

Step (b) of the process continues with (b) contacting the ester derivative with a compound comprising formula $R^1$—H to form a compound comprising Formula (I) or (II). The process commences with the formation of a reaction mixture comprising the ester derivative, which is detailed above, a compound comprising the formula $R^1$—H, and optionally a solvent system.

In some embodiments, the compound comprising formula $R^1$—H may be selected from the group consisting of imidazole, benzimidazole, morpholine, piperidine, pyrrole, pyrrolidine, triazole, tetrazole, piperazine, pyridine, pyrazoloimidazole, methanol, ethanol, N,N-dimethylethanolamine, morpholinoethanol, and piperidinopropanol.

The amounts of the compound comprising formula $R^1$—H that are contacted with the ester derivative may vary. In general, the mole to mole ratio of the ester derivative to the compound comprising formula $R^1$—H may range from about 1:0.2 to about 1:15. In certain embodiments, the mole to mole ratio of the ester derivative to the compound comprising formula $R^1$—H may range from about 1:0.2 to about 1:0.7, from about 1:0.7 to about 1:1.5, from about 1:1.5 to about 1:2.5, from about 1:2.5 to about 1:5, from about 1:5 to about 1:10, or from about 1:10 to about 1:15. In certain embodiments, the mole to mole ratio of the ester derivative to the compound comprising formula $R^1$—H may range from about 1:0.7 to about 1:3. In an exemplary, the mole to mole ratio of the ester derivative to the compound comprising formula $R^1$—H may be about 1:1.

Contact with the compound comprising formula $R^1$—H generally is conducted in the presence of a solvent or solvent system. Suitable solvents are detailed above in Section II(b)(i). In exemplary embodiments, the solvent may be dichloromethane, chloroform, or combinations thereof. In general, the volume to mass ratio of the solvent to the ester derivative ranges from about 1:1 to about 100:1. In various embodiments, the volume to mass ratio of the solvent to the ester derivative may range from about 1:1 to about 5:1, from about 5:1 to about 10:1, from about 10:1 to about 20:1, from about 20:1 to about 30:1, from about 30:1 to about 40:1, from about 40:1 to about 50:1, from about 50:1 to about 60:1, from about 60:1 to about 70:1, from about 70:1 to about 80:1, from about 80:1 to about 90:1, or from about 90:1 to about 100:1. In exemplary embodiments, the volume to mass ratio of the solvent to the ester derivative may range from about 20:1 to about 30:1. In another exemplary embodiment, the volume to mass ratio of the solvent to the ester derivative may range from about 10:1 to about 20:1.

(iv) Step (b)—Reaction Conditions

In general, the reaction is conducted at a temperature that ranges from about 0° C. to about 50° C. In various embodiments, the reaction may be conducted at a temperature from about 0° C. to about 10° C., from about 10° C. to about 20° C., from about 20° C. to about 30° C., from about 30° C. to about 40° C., or from about 40° C. to about 50° C. In certain embodiments, the reaction may be conducted at a temperature of about 25° C. The reaction generally is conducted in an inert atmosphere (e.g., under nitrogen or argon) and under ambient pressure.

Typically, the reaction is allowed to proceed for a sufficient period of time until the reaction is complete, as determined by chromatography (e.g., TLC, HPLC) or another suitable method. Typically, the amount of the ester derivative remaining in the reaction mixture after the reaction is complete may be less than about 3%, or less than about 1%. In general, the reaction may proceed for about 5 minutes to about 48 hours. Typically, the duration of the reaction is longer at lower reaction temperatures. In certain embodiments, the reaction may be allowed to proceed for about a period of time ranging from about 5 minutes to about 10 minutes, from about 10 minutes to about 15 minutes, from about 15 minutes to about 30 minutes, from about 30 minutes to about 1 hour, about 1 hour to about 3 hours, from about 3 hours to about 6 hours, from about 6 hours to about 12 hours, from about 12 hours to about 18 hours, from about 18 hours to about 24 hours, from about 24 hours to about 36 hours, or from about 36 hours to about 48 hours. In certain embodiments, the reaction may be allowed to proceed about 20 minutes to about 40 minutes. In other embodiments, the reaction may be allowed to proceed about 5 hours to about 18 hours. In exemplary embodiments, the reaction may be allowed to proceed about 5 hours to about 12 hours.

The yield of the compound comprising Formula (I) or (II) can and will vary. Typically, the yield of the compound comprising Formula (I) or (II) may be at least about 40%. In one embodiment, the yield of the compound comprising Formula (I) or (II) may range from about 40% to about 60%. In another embodiment, the yield of the compound comprising Formula (I) or (II) may range from about 60% to about 80%. In a further embodiment, the yield of the compound comprising Formula (I) or (II) may range from about 80% to about 90%. In still another embodiment, the yield of the compound comprising Formula (I) or (II) may be greater than about 90%, or greater than about 95%.

(c) Amide Derivatives of MMB

In other embodiments, MMB may be reacted with succinic anhydride in presence of triethylamine to afford a carboxylic acid derivative of MMB, JVM 67. The MMB carboxylic acid derivative may be reacted with heterocyclic amines to afford the corresponding amide derivatives of MMB (Scheme 5). A detailed synthesis of JVM 67 is provided below at Example 7.

Scheme 5. Synthesis of amide derivatives of MMB
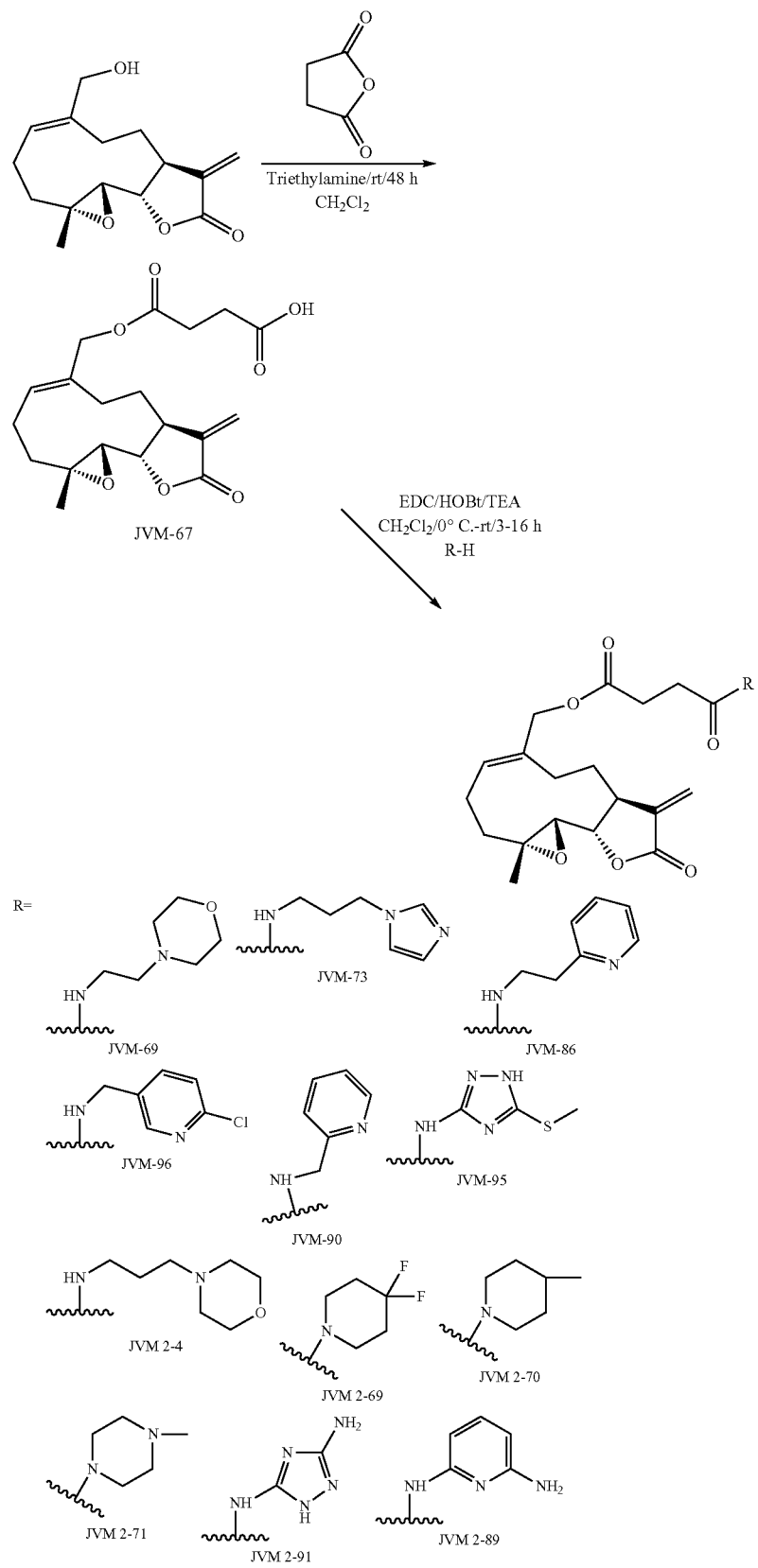

In particular, provided herein are processes for preparing an amide compound comprising Formula (I). The process comprises (a) contacting MMB with an acid anhydride to form a carboxylic acid derivative. The process continues with (b) contacting the carboxylic acid derivative with a compound comprising formula $R^1$—H to form a compound comprising Formula (I).

(i) Step (a)—Reaction Mixture

Step (a) of the process comprises contacting MMB with an acid anhydride to form a carboxylic acid derivative. The process commences with the formation of a reaction mixture comprising MMB, which is detailed above, the acid anhydride, and optionally a solvent system.

The acid anhydride may be any compound which reacts with a hydroxyl group to provide a carboxylic acid derivative. A suitable acid anhydride is a compound that has two acyl groups bonded to the same oxygen atom. In a preferred embodiment, the acid anhydride is a cyclic anhydride. Non-limiting examples of suitable acid anhydrides include succinic anhydride, maleic anhydride, itaconic anhydride, citraconic anhydride and 2-pentendioic anhydride. In an exemplary embodiment, the acid anhydride is succinic anhydride.

The amounts of acid anhydride that are contacted with MMB may vary. In general, the mole to mole ratio of MMB to acid anhydride may range from about 1:0.2 to about 1:15. In certain embodiments, the mole to mole ratio of MMB to acid anhydride may range from about 1:0.2 to about 1:0.7, from about 1:0.7 to about 1:1.5, from about 1:1.5 to about 1:2.5, from about 1:2.5 to about 1:5, from about 1:5 to about 1:10, or from about 1:10 to about 1:15. In certain embodiments, the mole to mole ratio of MMB to acid anhydride may range from about 1:0.7 to about 1:3. In an exemplary embodiment, the mole to mole ratio of MMB to acid anhydride may range from about 1:1.

The reaction is generally conducted in the presence of a solvent or solvent system. The solvent may be a polar aprotic solvent, a polar protic solvent, or a nonpolar solvent. Non-limiting examples of suitable polar aprotic solvents include acetone, acetonitrile, diethoxymethane, N,N-dimethylformamide (DMF), dimethyl sulfoxide (DMSO), N,N-dimethylpropanamide (or dimethylpropionamide; DMP), 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl)ether, N,N-dimethylacetamide (DMA), N-methyl-2-pyrrolidinone (NMP), 1,4-dioxane, ethyl formate, formamide, hexachloroacetone, hexamethylphosphoramide, methyl acetate, N-methylacetamide, N-methylformamide, methylene chloride (dichloromethane, DCM), chloroform, methoxyethane, morpholine, nitrobenzene, nitromethane, propionitrile, pyridine, sulfolane, tetramethylurea, tetrahydrofuran (THF), 2-methyl tetrahydrofuran, tetrahydropyran, trichloromethane, and combinations thereof. Non-limiting examples of suitable polar protic solvents include water; alcohols such as methanol, ethanol, isopropanol, n-propanol, isobutanol, n-butanol, s-butanol, t-butanol, and the like; diols such as propylene glycol; organic acids such as formic acid, acetic acid, and so forth; amides such as formamide, acetamide, and the like; and combinations of any of the above. Representative nonpolar solvents include, but are not limited to, alkane and substituted alkane solvents (including cycloalkanes), aromatic hydrocarbons, esters, ethers, ketones, and combinations thereof. Specific polar aprotic solvents that may be employed include, for example, dichloromethane, chloroform, and combinations thereof.

A proton acceptor is generally added to facilitate the reaction. The proton acceptor generally has a pKa greater than about 7, or from about 7 to about 13, or more specifically from about 9 to about 11. Representative proton acceptors may include, but are not limited to, borate salts (such as, for example, $NaBO_3$), di- and tri-basic phosphate salts, (such as, for example, $Na_2HPO_4$ and $NaPO_4$), bicarbonate salts, carbonate salts, hydroxides, alkoxides, (including methoxide, ethoxide, propoxide, butoxide, and pentoxide, including straight chain and branched), and organic proton acceptors, (such as, for example, pyridine, triethylamine, N-methylmorpholine, and N,N-dimethylaminopyridine), and mixtures thereof. In some embodiments, the proton acceptor may be stabilized by a suitable counterion such as lithium, potassium, sodium, calcium, magnesium, and the like. In a specific embodiment, the proton acceptor is triethylamine. The amount of proton acceptor included in the reaction can and will vary, but can be readily determined by a person of ordinary skill in the art.

In general, the volume to mass ratio of the solvent to MMB ranges from about 1:1 to about 100:1. In various embodiments, the volume to mass ratio of the solvent to MMB may range from about 1:1 to about 5:1, from about 5:1 to about 10:1, from about 10:1 to about 20:1, from about 20:1 to about 30:1, from about 30:1 to about 40:1, from about 40:1 to about 50:1, from about 50:1 to about 60:1, from about 60:1 to about 70:1, from about 70:1 to about 80:1, from about 80:1 to about 90:1, or from about 90:1 to about 100:1. In exemplary embodiments, the volume to mass ratio of the solvent to MMB may range from about 20:1 to about 30:1. In other exemplary embodiments, the volume to mass ratio of the solvent to MMB may range from about 10:1 to about 20:1.

(ii) Step (a)—Reaction Conditions

In general, the reaction is conducted at a temperature that ranges from about 0° C. to about 50° C. In various embodiments, the reaction may be conducted at a temperature from about 0° C. to about 10° C., from about 10° C. to about 20° C., from about 20° C. to about 30° C., from about 30° C. to about 40° C., or from about 40° C. to about 50° C. In certain embodiments, the reaction may be conducted at a temperature of about 25° C. The reaction generally is conducted in an inert atmosphere (e.g., under nitrogen or argon) and under ambient pressure.

Typically, the reaction is allowed to proceed for a sufficient period of time until the reaction is complete, as determined by chromatography (e.g., TLC, HPLC) or another suitable method. In this context, a "completed reaction" generally means that the reaction mixture contains a significantly diminished amount of MMB, and a significantly increased amount of the carboxylic acid derivative compared to the amounts of each present at the beginning of the reaction. Typically, the amount of MMB remaining in the reaction mixture after the reaction is complete may be less than about 3%, or less than about 1%. In general, the reaction may proceed for about 5 minutes to about 48 hours. Typically, the duration of the reaction is longer at lower reaction temperatures. In certain embodiments, the reaction may be allowed to proceed for about a period of time ranging from about 5 minutes to about 10 minutes, from about 10 minutes to about 15 minutes, from about 15 minutes to about 30 minutes, from about 30 minutes to about 1 hour, about 1 hour to about 3 hours, from about 3 hours to about 6 hours, from about 6 hours to about 12 hours, from about 12 hours to about 18 hours, from about 18 hours to about 24 hours, from about 24 hours to about 36 hours, or from about 36 hours to about 48 hours. In certain embodiments, the reaction may be allowed to proceed about 5 minutes to about 15 minutes. In other embodiments, the reaction may be allowed to proceed about 45 minutes to about 75 minutes. In still other embodiments, the reaction may be allowed to proceed about 36 hours to about 48 hours.

Generally, the carboxylic acid derivative is not isolated and step (b) of the process proceeds in the same reaction pot or reactor. In some embodiments, the carboxylic acid derivative may be isolated from the reaction mixture using techniques known to those of skill in the art. Non-limiting examples of suitable techniques include precipitation, extraction, evaporation, distillation, chromatography, and crystallization.

The yield of the carboxylic acid derivative can and will vary. Typically, the yield of the carboxylic acid derivative may be at least about 40%. In one embodiment, the yield of the carboxylic acid derivative may range from about 40% to about 60%. In another embodiment, the yield of the carboxylic acid derivative may range from about 60% to about 80%. In a further embodiment, the yield of the carboxylic acid derivative may range from about 80% to about 90%. In still another embodiment, the yield of the carboxylic acid derivative may be greater than about 90%, or greater than about 95%.

(iii) Step (b)—Reaction Mixture

Step (b) of the process continues with (b) contacting the carboxylic acid derivative with a compound comprising formula $R^1$—H to form a compound comprising Formula (I). The process commences with the formation of a reaction mixture comprising the carboxylic acid derivative, which is detailed above, a compound comprising the formula $R^1$—H, and optionally a solvent system.

In some embodiments, the compound comprising formula $R^1$—H may be selected from the group consisting of imidazole, benzimidazole, morpholine, piperidine, pyrrole, pyrrolidine, triazole, tetrazole, piperazine, pyridine, pyrazoloimidazole, methanol, ethanol, N,N-dimethylethanolamine, morpholinoethanol, and piperidinopropanol.

The amounts of the compound comprising formula $R^1$—H that are contacted with the carboxylic acid derivative may vary. In general, the mole to mole ratio of the carboxylic acid derivative to the compound comprising formula $R^1$—H may range from about 1:0.2 to about 1:15. In certain embodiments, the mole to mole ratio of the carboxylic acid derivative to the compound comprising formula $R^1$—H may range from about 1:0.2 to about 1:0.7, from about 1:0.7 to about 1:1.5, from about 1:1.5 to about 1:2.5, from about 1:2.5 to about 1:5, from about 1:5 to about 1:10, or from about 1:10 to about 1:15. In certain embodiments, the mole to mole ratio of the carboxylic acid derivative to the compound comprising formula $R^1$—H may range from about 1:0.7 to about 1:3.

Contact with the compound comprising formula $R^1$—H generally is conducted in the presence of a solvent or solvent system. Suitable solvents are detailed above in Section II(c)(i). In exemplary embodiments, the solvent may be dichloromethane, chloroform, or combinations thereof. Additionally, a proton acceptor is generally added to facilitate the reaction. Suitable proton acceptors are detailed above in Section II(c)(i). In a specific embodiment, the proton acceptor is triethylamine. Further, peptide coupling agents may also be added to the reaction. Non-limiting examples of suitable peptide coupling agents include EDC (1-Ethyl-3-(3-dimethylaminopropyl)carbodiimide)), HOBt (Hydroxybenzotriazole), DCC (N,N'-Dicyclohexylcarbodiimide), HATU ((1-[Bis(dimethylamino)methylene]-1H-1,2, 3-triazolo[4,5-b]pyridinium 3-oxid hexafluorophosphate)), HBTU (O-(Benzotriazol-1-yl)-N,N,N',N'-tetramethyluronium Hexafluorophosphate), and TBTU (O-(Benzotriazol-1-yl)-N,N,N',N'-tetramethyluronium tetrafluoroborate). In an exemplary embodiment, EDC (1-Ethyl-3-(3-dimethylaminopropyl)carbodiimide)) and HOBt (Hydroxybenzotriazole) are added to the reaction.

In general, the volume to mass ratio of the solvent to the carboxylic acid derivative ranges from about 1:1 to about 100:1. In various embodiments, the volume to mass ratio of the solvent to the carboxylic acid derivative may range from about 1:1 to about 5:1, from about 5:1 to about 10:1, from about 10:1 to about 20:1, from about 20:1 to about 30:1, from about 30:1 to about 40:1, from about 40:1 to about 50:1, from about 50:1 to about 60:1, from about 60:1 to about 70:1, from about 70:1 to about 80:1, from about 80:1 to about 90:1, or from about 90:1 to about 100:1. In exemplary embodiments, the volume to mass ratio of the solvent to the carboxylic acid derivative may range from about 20:1 to about 30:1. In another exemplary embodiment, the volume to mass ratio of the solvent to the carboxylic acid derivative may range from about 10:1 to about 20:1.

(iv) Step (b)—Reaction Conditions

In general, the reaction is conducted at a temperature that ranges from about 0° C. to about 50° C. In various embodiments, the reaction may be conducted at a temperature from about 0° C. to about 10° C., from about 10° C. to about 20° C., from about 20° C. to about 30° C., from about 30° C. to about 40° C., or from about 40° C. to about 50° C. In certain embodiments, the reaction may be conducted at a temperature of about 25° C. In other embodiments, the reaction may be conducted at a temperature from about 0° C. to about 25° C. The reaction generally is conducted in an inert atmosphere (e.g., under nitrogen or argon) and under ambient pressure.

Typically, the reaction is allowed to proceed for a sufficient period of time until the reaction is complete, as determined by chromatography (e.g., TLC, HPLC) or another suitable method. Typically, the amount of the carboxylic acid derivative remaining in the reaction mixture after the reaction is complete may be less than about 3%, or less than about 1%. In general, the reaction may proceed for about 5 minutes to about 48 hours. Typically, the duration of the reaction is longer at lower reaction temperatures. In certain embodiments, the reaction may be allowed to proceed for about a period of time ranging from about 5 minutes to about 10 minutes, from about 10 minutes to about 15 minutes, from about 15 minutes to about 30 minutes, from about 30 minutes to about 1 hour, about 1 hour to about 3 hours, from about 3 hours to about 6 hours, from about 6 hours to about 12 hours, from about 12 hours to about 18 hours, from about 18 hours to about 24 hours, from about 24 hours to about 36 hours, or from about 36 hours to about 48 hours. In certain embodiments, the reaction may be allowed to proceed about 3 hours to about 16 hours.

The yield of the compound comprising Formula (I) or (II) can and will vary. Typically, the yield of the compound comprising Formula (I) or (II) may be at least about 40%. In one embodiment, the yield of the compound comprising Formula (I) or (II) may range from about 40% to about 60%. In another embodiment, the yield of the compound comprising Formula (I) or (II) may range from about 60% to about 80%. In a further embodiment, the yield of the compound comprising Formula (I) or (II) may range from about 80% to about 90%. In still another embodiment, the yield of the compound comprising Formula (I) or (II) may be greater than about 90%, or greater than about 95%.

III. Compositions

The present disclosure also provides pharmaceutical compositions. The pharmaceutical composition comprises a compound comprising Formulas (I) or (II) which is detailed above in Section I, as an active ingredient and at least one pharmaceutically acceptable excipient.

The pharmaceutically acceptable excipient may be a diluent, a binder, a filler, a buffering agent, a pH modifying agent, a disintegrant, a dispersant, a preservative, a lubricant, taste-masking agent, a flavoring agent, or a coloring agent. The amount and types of excipients utilized to form pharmaceutical compositions may be selected according to known principles of pharmaceutical science.

In one embodiment, the excipient may be a diluent. The diluent may be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

In another embodiment, the excipient may be a binder. Suitable binders include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, polypeptides, oligopeptides, and combinations thereof.

In another embodiment, the excipient may be a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

In still another embodiment, the excipient may be a buffering agent. Representative examples of suitable buffering agents include, but are not limited to, phosphates, carbonates, citrates, tris buffers, and buffered saline salts (e.g., Tris buffered saline or phosphate buffered saline).

In various embodiments, the excipient may be a pH modifier. By way of non-limiting example, the pH modifying agent may be sodium carbonate, sodium bicarbonate, sodium citrate, citric acid, or phosphoric acid.

In a further embodiment, the excipient may be a disintegrant. The disintegrant may be non-effervescent or effervescent. Suitable examples of non-effervescent disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. Non-limiting examples of suitable effervescent disintegrants include sodium bicarbonate in combination with citric acid and sodium bicarbonate in combination with tartaric acid.

In yet another embodiment, the excipient may be a dispersant or dispersing enhancing agent. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

In another alternate embodiment, the excipient may be a preservative. Non-limiting examples of suitable preservatives include antioxidants, such as BHA, BHT, vitamin A, vitamin C, vitamin E, or retinyl palmitate, citric acid, sodium citrate; chelators such as EDTA or EGTA; and antimicrobials, such as parabens, chlorobutanol, or phenol.

In a further embodiment, the excipient may be a lubricant. Non-limiting examples of suitable lubricants include minerals such as talc or silica; and fats such as vegetable stearin, magnesium stearate or stearic acid.

In yet another embodiment, the excipient may be a taste-masking agent. Taste-masking materials include cellulose ethers; polyethylene glycols; polyvinyl alcohol; polyvinyl alcohol and polyethylene glycol copolymers; monoglycerides or triglycerides; acrylic polymers; mixtures of acrylic polymers with cellulose ethers; cellulose acetate phthalate; and combinations thereof.

In an alternate embodiment, the excipient may be a flavoring agent. Flavoring agents may be chosen from synthetic flavor oils and flavoring aromatics and/or natural oils, extracts from plants, leaves, flowers, fruits, and combinations thereof.

In still a further embodiment, the excipient may be a coloring agent. Suitable color additives include, but are not limited to, food, drug and cosmetic colors (FD&C), drug and cosmetic colors (D&C), or external drug and cosmetic colors (Ext. D&C).

The weight fraction of the excipient or combination of excipients in the composition may be about 99% or less, about 97% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

The composition can be formulated into various dosage forms and administered by a number of different means that will deliver a therapeutically effective amount of the active ingredient. Such compositions can be administered orally, parenterally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injection, or infusion techniques. Formulation of drugs is discussed in, for example, Gennaro, A. R., Remington's Pharmaceutical Sciences, Mack Publishing Co., Easton, Pa. ($18^{th}$ ed, 1995), and Liberman, H. A. and Lachman, L., Eds., Pharmaceutical Dosage Forms, Marcel Dekker Inc., New York, N.Y. (1980).

Solid dosage forms for oral administration include capsules, tablets, caplets, pills, powders, pellets, and granules. In such solid dosage forms, the active ingredient is ordinarily combined with one or more pharmaceutically acceptable excipients, examples of which are detailed above. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof.

For parenteral administration (including subcutaneous, intradermal, intravenous, intramuscular, and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil.

For topical (e.g., transdermal or transmucosal) administration, penetrants appropriate to the barrier to be permeated are generally included in the preparation. Transmucosal administration may be accomplished through the use of nasal sprays, aerosol sprays, tablets, or suppositories, and transdermal administration may be via ointments, salves, gels, patches, or creams as generally known in the art.

In certain embodiments, a composition comprising a compound of the invention is encapsulated in a suitable vehicle to either aid in the delivery of the compound to target cells, to increase the stability of the composition, or to minimize potential toxicity of the composition. As will be appreciated by a skilled artisan, a variety of vehicles are suitable for delivering a composition of the present invention. Non-limiting examples of suitable structured fluid delivery systems may include nanoparticles, liposomes, microemulsions, micelles, dendrimers and other phospholipid-containing systems. Methods of incorporating compositions into delivery vehicles are known in the art.

In one alternative embodiment, a liposome delivery vehicle may be utilized. Liposomes, depending upon the embodiment, are suitable for delivery of the compound of the invention in view of their structural and chemical properties. Generally speaking, liposomes are spherical vesicles with a phospholipid bilayer membrane. The lipid bilayer of a liposome may fuse with other bilayers (e.g., the cell membrane), thus delivering the contents of the liposome to cells. In this manner, the compound of the invention may be selectively delivered to a cell by encapsulation in a liposome that fuses with the targeted cell's membrane.

Liposomes may be comprised of a variety of different types of phosolipids having varying hydrocarbon chain lengths. Phospholipids generally comprise two fatty acids linked through glycerol phosphate to one of a variety of polar groups. Suitable phospholids include phosphatidic acid (PA), phosphatidylserine (PS), phosphatidylinositol (PI), phosphatidylglycerol (PG), diphosphatidylglycerol (DPG), phosphatidylcholine (PC), and phosphatidylethanolamine (PE). The fatty acid chains comprising the phospholipids may range from about 6 to about 26 carbon atoms in length, and the lipid chains may be saturated or unsaturated. Suitable fatty acid chains include (common name presented in parentheses) n-dodecanoate (laurate), n-tretradecanoate (myristate), n-hexadecanoate (palmitate), n-octadecanoate (stearate), n-eicosanoate (arachidate), n-docosanoate (behenate), n-tetracosanoate (lignocerate), cis-9-hexadecenoate (palmitoleate), cis-9-octadecanoate (oleate), cis,cis-9,12-octadecandienoate (linoleate), all cis-9, 12, 15-octadecatrienoate (linolenate), and all cis-5,8,11,14-eicosatetraenoate (arachidonate). The two fatty acid chains of a phospholipid may be identical or different. Acceptable phospholipids include dioleoyl PS, dioleoyl PC, distearoyl PS, distearoyl PC, dimyristoyl PS, dimyristoyl PC, dipalmitoyl PG, stearoyl, oleoyl PS, palmitoyl, linolenyl PS, and the like.

The phospholipids may come from any natural source, and, as such, may comprise a mixture of phospholipids. For example, egg yolk is rich in PC, PG, and PE, soy beans contains PC, PE, PI, and PA, and animal brain or spinal cord is enriched in PS. Phospholipids may come from synthetic sources too. Mixtures of phospholipids having a varied ratio of individual phospholipids may be used. Mixtures of different phospholipids may result in liposome compositions having advantageous activity or stability of activity properties. The above mentioned phospholipids may be mixed, in optimal ratios with cationic lipids, such as N-(1-(2,3-dioleolyoxy)propyl)-N,N,N-trimethyl ammonium chloride, 1,1'-dioctadecyl-3,3,3',3'-tetramethylindocarbocyanine perchloarate, 3,3'-deheptyloxacarbocyanine iodide, 1,1'-dedodecyl-3,3,3',3'-tetramethylindocarbocyanine perchloarate, 1,1'-dioleyl-3,3,3',3'-tetramethylindocarbocyanine methanesulfonate, N-4-(delinoleylaminostyryl)-N-methylpyridinium iodide, or 1,1-dilinoleyl-3,3,3',3'-tetramethylindocarbocyanine perchloarate.

Liposomes may optionally comprise sphingolipids, in which spingosine is the structural counterpart of glycerol and one of the one fatty acids of a phosphoglyceride, or cholesterol, a major component of animal cell membranes. Liposomes may optionally, contain pegylated lipids, which are lipids covalently linked to polymers of polyethylene glycol (PEG). PEGs may range in size from about 500 to about 10,000 daltons.

Liposomes may further comprise a suitable solvent. The solvent may be an organic solvent or an inorganic solvent. Suitable solvents include, but are not limited to, dimethylsulfoxide (DMSO), methylpyrrolidone, N-methylpyrrolidone, acetronitrile, alcohols, dimethylformamide, tetrahydrofuran, or combinations thereof.

Liposomes carrying the compound of the invention (i.e., having at least one methionine compound) may be prepared by any known method of preparing liposomes for drug delivery, such as, for example, detailed in U.S. Pat. Nos. 4,241,046, 4,394,448, 4,529,561, 4,755,388, 4,828,837, 4,925,661, 4,954,345, 4,957,735, 5,043,164, 5,064,655, 5,077,211 and 5,264,618, the disclosures of which are hereby incorporated by reference in their entirety. For example, liposomes may be prepared by sonicating lipids in an aqueous solution, solvent injection, lipid hydration, reverse evaporation, or freeze drying by repeated freezing and thawing. In a preferred embodiment the liposomes are formed by sonication. The liposomes may be multilamellar, which have many layers like an onion, or unilamellar. The liposomes may be large or small. Continued high-shear sonication tends to form smaller unilamellar liposomes.

As would be apparent to one of ordinary skill, all of the parameters that govern liposome formation may be varied. These parameters include, but are not limited to, temperature, pH, concentration of methionine compound, concentration and composition of lipid, concentration of multivalent cations, rate of mixing, presence of and concentration of solvent.

In another embodiment, a composition of the invention may be delivered to a cell as a microemulsion. Microemulsions are generally clear, thermodynamically stable solutions comprising an aqueous solution, a surfactant, and "oil." The "oil" in this case, is the supercritical fluid phase. The surfactant rests at the oil-water interface. Any of a variety of surfactants are suitable for use in microemulsion formulations including those described herein or otherwise known in the art. The aqueous microdomains suitable for use in the invention generally will have characteristic structural dimensions from about 5 nm to about 100 nm. Aggregates of this size are poor scatterers of visible light and hence, these solutions are optically clear. As will be appreciated by a skilled artisan, microemulsions can and will have a multitude of different microscopic structures including sphere, rod, or disc shaped aggregates. In one embodiment, the structure may be micelles, which are the simplest microemulsion structures that are generally spherical or cylindrical objects. Micelles are like drops of oil in water, and reverse micelles are like drops of water in oil. In an alternative embodiment, the microemulsion structure is the lamellae. It comprises consecutive layers of water and oil separated by layers of surfactant. The "oil" of microemulsions optimally comprises phospholipids. Any of the phospholipids detailed above for liposomes are suitable for embodiments directed to microemulsions. The composition of the invention may be encapsulated in a microemulsion by any method generally known in the art.

In yet another embodiment, a composition of the invention may be delivered in a dendritic macromolecule, or a dendrimer. Generally speaking, a dendrimer is a branched tree-like molecule, in which each branch is an interlinked chain of molecules that divides into two new branches (molecules) after a certain length. This branching continues until the branches (molecules) become so densely packed that the canopy forms a globe. Generally, the properties of dendrimers are determined by the functional groups at their surface. For example, hydrophilic end groups, such as carboxyl groups, would typically make a water-soluble dendrimer. Alternatively, phospholipids may be incorporated in the surface of a dendrimer to facilitate absorption across the skin. Any of the phospholipids detailed for use in liposome embodiments are suitable for use in dendrimer embodiments. Any method generally known in the art may be utilized to make dendrimers and to encapsulate compositions of the invention therein. For example, dendrimers may be produced by an iterative sequence of reaction steps, in which each additional iteration leads to a higher order dendrimer. Consequently, they have a regular, highly branched 3D structure, with nearly uniform size and shape. Furthermore, the final size of a dendrimer is typically controlled by the number of iterative steps used during synthesis. A variety of dendrimer sizes are suitable for use in the invention. Generally, the size of dendrimers may range from about 1 nm to about 100 nm.

IV. Methods for Inhibiting Cancer Cell Growth

A further aspect of the present disclosure provides a method for inhibiting growth of a cancer cell. Cancer cell growth includes cell proliferation and cell metastasis. The method comprises contacting the cancer cell with an effective amount of a compound comprising Formulas (I) or (II), or a pharmaceutically acceptable salt thereof, wherein the amount is effective to inhibit growth of the cancer cell. Compounds comprising Formulas (I) or (II) are detailed above in Section I. In some embodiments, the compound comprising Formulas (I) or (II) is used as part of a composition, examples of which are detailed above in Section III.

(a) Contacting the Cell

In some embodiments, the cancer cell may be in vitro. The cancer cell may be an established, commercially-available cancer cell line (e.g., American Type Culture Collection (ATCC), Manassas, Va.). The cancer cell line may be derived from a blood cancer or a solid tumor. The cancer cell line may be a human cell line or a mammalian cell line. In a specific embodiment, the cancer cell line may be derived from a blood cancer. In one exemplary embodiment, the cancer cell line may be derived from a leukemic cell. The leukemic cell may be an acute myeloid leukemia cell, a chronic myeloid leukemia cell, an acute lymphocytic leukemia cell, a chronic lymphocytic leukemia cell, a cutaneous T cell leukemia, or another type of leukemia cell. In some embodiments, the cancer cell line may be a leukemia cell line such as CCRF-CEM, HL-60(TB), K-562, MOLT-4, RPMI-8226, or SR. In a specific embodiment, the cancer cell line may be the leukemia cell line CCRF-CEM. In other embodiments, the cancer cell line may be a hematopoietic or lymphoid cell line. Non-limiting examples of hematopoietic or lymphoid cell lines include 380, 697, A3-KAW, A3/KAW, A4-Fuk, A4/Fuk, ALL-PO, ALL-SIL, AML-193, AMO-1, ARH-77, ATN-1, BALL-1, BC-3, BCP-1, BDCM, BE-13, BL-41, BL-70, BV-173, C8166, CA46, CCRF-CEM, CI-1, CMK, CMK-11-5, CMK-86, CML-T1, COLO 775, COLO-677, CTB-1, CTV-1, Daudi, DB, DEL, DG-75, DND-41, DOHH-2, EB1, EB2, EHEB, EJM, EM-2, EOL-1, EoL-1-cell, F-36P, GA-10, GA-10-Clone-4, GDM-1, GR-ST, GRANTA-519, H9, HAL-01, HD-MY-Z, HDLM-2, HEL, HEL 92.1.7, HH, HL-60, HPB-ALL, Hs 604.T, Hs 611.T, Hs 616.T, Hs 751.T, HT, HTK-, HuNS1, HuT 102, HuT 78, IM-9, J-RT3-T3-5, JeKo-1, JiyoyeP-2003, JJN-3, JK-1, JM1, JURKAT, JURL-MK1, JVM-2, JVM-3, K-562, K052, KARPAS-299, KARPAS-422, KARPAS-45, KARPAS-620, KASUMI-1, KASUMI-2, Kasumi-6, KCL-22, KE-37, KE-97, KG-1, KHM-1B, Ki-JK, KM-H2, KMM-1, KMOE-2, KMS-11, KMS-12-BM, KMS-12-PE, KMS-18, KMS-20, KMS-21BM, KMS-26, KMS-27, KMS-28BM, KMS-34, KO52, KOPN-8, KU812, KY821, KYO-1, L-1236, L-363, L-428, L-540, LAMA-84, LC4-1, Loucy, LOUCY, LP-1, M-07e, MC-CAR, MC116, ME-1, MEC-1, MEC-2, MEG-01, MHH-CALL-2, MHH-CALL-3, MHH-CALL-4, MHH-PREB-1, Mino, MJ, ML-2, MLMA, MM1-S, MN-60, MOLM-13, MOLM-16, MOLM-6, MOLP-2, MOLP-8, MOLT-13, MOLT-16, MOLT-4, MONO-MAC-1, MONO-MAC-6, MOTN-1, MUTZ-1, MUTZ-3, MUTZ-5, MV-4-11, NALM-1, NALM-19, NALM-6, NAMALWA, NB-4, NCI-H929, NCO2, NKM-1, NOMO-1, NU-DHL-1, NU-DUL-1, OCI-AML2, OCI-AML3, OCI-AML5, OCI-LY-19, OCI-LY10, OCI-LY3, OCI-M1, OPM-2, P12-ICHIKAWA, P30-OHK, P31-FUJ, P31/FUJ, P3HR-1, PCM6, PEER, PF-382, Pfeiffer, PL-21, Raji, Ramos-2G6-4C10, RCH-ACV, REC-1, Reh, REH, RI-1, RL, RPMI-8226, RPMI-8226, RPMI-8402, RS4-11, "RS4;11", SEM, Set-2, SIG-M5, SK-MM-2, SKM-1, SR, SR-786, ST486, SU-DHL-1, SU-DHL-10, SU-DHL-4, SU-DHL-5, SU-DHL-6, SU-DHL-8, SUP-B15, SUP-B8, SUP-HD1, SUP-M2, SUP-T1, SUP-T11, TALL-1, TF-1, THP-1, TO 175.T, Toledo, TUR, U-266, U-698-M, U-937, U266B1, UT-7, WSU-DLCL2, and WSU-NHL.

In another exemplary embodiment, the cancer cell line may be derived from a solid tumor cell. The solid tumor cell may be a non-small cell lung cancer, colon cancer, CNS cancer, melanoma cancer, ovarian cancer, renal cancer, prostate cancer, breast cancer, or another type of solid tumor cell. In some embodiments, the cancer cell line may be a non-small cell lung cancer cell line such as A549/ATCC, HOP-92, NCI-H226, NCI-H23, NCI-H322M, NCI-H460, or NCI-H522. In an exemplary embodiment, the cancer cell line may be a non-small cell lung cancer cell line such as HOP-92 or NCI-H522. In a specific embodiment, the cancer cell line may be the non-small cell lung cancer cell line HOP-92. In other embodiments, the cancer cell line may be a colon cancer cell line such as COLO 205, HCC-2998, HCT-116, HCT-15, HT29, KM12 or SW-620. In an exemplary embodiment, the cancer cell line may be a colon cancer cell line such as COLO 205, HCT-116 or SW-620. In different embodiments, the cancer cell line may be a CNS cancer cell line such as SF-268, SF-295, SF-539, SNB-19, SNB-75 or U251. In an exemplary embodiment, the cancer cell line may be a CNS cancer cell line such as SF-539 or SNB-75. In some other embodiments, the cancer cell line may be a melanoma cell line such as LOX IMVI, MALME-3M, M14, MDA-MB-435, SK-MEL-2, SK-MEL-28, SK-MEL-5, UACC-257, or UACC-62. In an exemplary embodiment, the cancer cell line may be a melanoma cell line such as LOX IMVI, MALME-3M, M14 or MDA-MB-435. In a specific embodiment, the cancer cell line may be the melanoma cell line MDA-MB-435. In still other embodiments, the cancer cell line may be an ovarian cancer cell line such as OVCAR-3, OVCAR-4, OVCAR-5, OVCAR-8, NCI/ADR-RES, IGROV1 or SK-OV-3. In an exemplary embodiment, the cancer cell line may be an ovarian cancer cell line such as IGROV1 or OVCAR-3. In some different embodiments, the cancer cell line may be a renal cancer cell line such as 786-0, A498, ACHN, CAKI-1, RXF 393, SN12C, TK-10, or UO-31. In an exemplary embodiment, the cancer cell line may be a renal cancer cell line such as ACHN, CAKI-1, RXF 393, or TK-10. In a specific embodiment, the cancer cell line may be the renal cancer cell line RXF 393. In other embodiments, the cancer cell line may be a prostate cancer cell line such as PC-3 or DU-145. In an exemplary embodiment, the cancer cell line may be a prostate cancer cell line such as DU-145. In some embodiments, the cancer cell line may be a breast cancer cell line such as MCF7, MDA-BM-231/ATCC, HS 578T, BT-549, T-47D, or MDA-MB-468. In an exemplary embodiment, the cancer cell line may be a breast cancer cell line such as MCF7, BG-549, T-47D, or MDA-MB-468. In a specific embodiment, the cancer cell line may be the breast cancer cell line MDA-MB-468.

In other embodiments, the cancer cell may be in vivo; i.e., the cell may be disposed in a subject. In such embodiments, the cancer cell is contacted with the compound comprising Formulas (I) or (II) by administering the compound comprising Formulas (I) or (II) to the subject. In some embodiments, the subject may be a human. In other embodiments, the subject may be a non-human animal. Non-limiting examples of non-human animals include companion animals (e.g., cats, dogs, horses, rabbits, gerbils), agricultural animals (e.g., cows, pigs, sheep, goats, fowl), research animals (e.g., rats, mice, rabbits, primates), and zoo animals (e.g., lions, tiger, elephants, and the like).

The cancer cell disposed in the subject may be a blood cancer cell (e.g., leukemia, lymphoma, myeloma) or a solid tumor cancer cell. The cancer may be primary or metastatic; early stage or late stage; and/or the tumor may be malignant or benign. Non-limiting cancers include bladder cancer, bone cancer, brain cancer, breast cancer, central nervous system cancer, cervical cancer, colon cancer, colorectal cancer, duodenal cancer, endometrial cancer, esophageal cancer, eye cancer, gallbladder cancer, germ cell cancer, kidney cancer, larynx cancer, leukemia, liver cancer, lymphoma, lung cancer, melanoma, mouth/throat cancer, ovarian cancer, pancreatic cancer, prostate cancer, skin cancer, testicular cancer, thyroid cancer, vaginal cancer, and drug resistant cancers. In one exemplary embodiment, the cancer cell may be a leukemia. The leukemia may be an acute lymphocytic (lymphoblastic) leukemia, a chronic lymphocytic leukemia, an acute myeloid leukemia, a chronic myeloid leukemia, a hairy cell leukemia, a T-cell prolymphocytic leukemia, a large granular lymphocytic leukemia, or an adult T-cell leukemia. In another exemplary embodiment, the cancer cell may be a solid tumor cancer cell selected from the group consisting of non-small cell lung cancer, colon cancer, CNS cancer, melanoma cancer, ovarian cancer, renal cancer, prostate cancer and breast cancer. In a specific embodiment, the cancer cell may be a solid tumor cancer cell selected from the group consisting of non-small cell lung cancer, melanoma cancer, renal cancer, and breast cancer.

The compound comprising Formulas (I) or (II) may be administered to the subject orally (as a solid or a liquid), parenterally (which includes intramuscular, intravenous, intradermal, intraperitoneal, and subcutaneous), or topically (which includes transmucosal and transdermal). An effective amount of the compound can be determined by a skilled practitioner in view of desired dosages and potential side effects of the compound.

The compound comprising Formulas (I) or (II) may be administered once or administered repeatedly to the subject. Repeated administrations may be at regular intervals of 2 hours, 6 hours, 12 hours, 24 hours, 2 days, 5 days, 7 days, 30 days, and so forth.

(b) Inhibiting Cancer Cell Growth

Following contact with an effective amount of the compound comprising Formulas (I) or (II) growth of the cancer cell is inhibited. Cell growth or proliferation can be measured in cells grown in vitro using standard cell viability or cell cytotoxicity assays (e.g., based on DNA content, cell permeability, etc.) in combination with cell counting methods (e.g., flow cytometry, optical density). Cell growth or proliferation can be measured in vivo using imaging procedures and/or molecular diagnostic indicators.

In an embodiment, contact with an effective amount of the compound comprising Formulas (I) or (II) selectively inhibits growth of cancer cells. As such, a compound comprising Formulas (I) or (II) does not appreciably kill non-cancer cells at the same concentration. Accordingly, more than 50% of non-cancer cells remain viable following contact with a compound comprising Formulas (I) or (II) at the same concentration. For example about 50%, about 55%, about 60%, about 65%, about 70%, about 75%, about 80%, about 85%, about 90%, about 95% or about 100% of non-cancer cells remain viable following contact with a compound comprising Formulas (I) or (II) at the same concentration. Or, 50%, 55%, 60%, 65%, 70%, 75%, 80%, 85%, 90%, 95% or 100% of non-cancer cells remain viable following contact with a compound comprising Formulas (I), (II), (III), (IV) or (V) at the same concentration.

In various embodiments, cancer cell growth may be inhibited about 0.5-fold, about 1-fold, about 2-fold, about 3-fold, about 4-fold, about 5-fold, about 8-fold, about 10-fold, or more than 10-fold relative to a reference value. In various other embodiments, cancer cell growth may be inhibited 0.5-fold, 1-fold, 2-fold, 3-fold, 4-fold, 5-fold, 8-fold, 10-fold, or more than 10-fold relative to a reference value. In other embodiments, cancer cell growth may be inhibited to such a degree that the cell undergoes cell death (via apoptosis or necrosis). Any suitable reference value known in the art may be used. For example, a suitable reference value may be cancer cell growth in a sample that has not been contacted with a compound comprising Formulas (I) or (II). In another example, a suitable reference value may be the baseline growth rate of the cells as determined by methods known in the art. In another example, a suitable reference value may be a measurement of the number of cancer cells in a reference sample obtained from the same subject. For example, when monitoring the effectiveness of a therapy or efficacy of a compound comprising Formulas (I) or (II), a reference sample may be a sample obtained from a subject before therapy or administration of the compound comprising Formulas (I) or (II) began.

(c) Optional Contact

In certain embodiments, the method may further comprise contacting the cell with at least one chemotherapeutic agent and/or a radiotherapeutic agent. The chemotherapeutic agent and/or radiotherapeutic agent may be administered concurrently or sequentially with the compound comprising Formulas (I) or (II).

The chemotherapeutic agent may be an alkylating agent, an anti-metabolite, an anti-tumor antibiotic, an anti-cytoskeletal agent, a topoisomerase inhibitor, an anti-hormonal agent, a targeted therapeutic agent, or a combination thereof. Non-limiting examples of suitable alkylating agents include altretamine, benzodopa, busulfan, carboplatin, carboquone, carmustine (BCNU), chlorambucil, chlornaphazine, cholophosphamide, chlorozotocin, cisplatin, cyclosphosphamide, dacarbazine (DTIC), estramustine, fotemustine, ifosfamide, improsulfan, lomustine (CCNU), mechlorethamine, mechlorethamine oxide hydrochloride, melphalan, meturedopa, nimustine, novembichin, phenesterine, piposulfan, prednimustine, ranimustine; temozolomide, thiotepa, triethylenemelamine, trietylenephosphoramide, triethylenethiophosphaoramide, trimethylolomelamine, trofosfamide, uracil mustard and uredopa. Suitable anti-metabolites include, but are not limited to aminopterin, ancitabine, azacitidine, 6-azauridine, capecitabine, carmofur (1-hexylcarbomoyl-5-fluorouracil), cladribine, cytarabine or cytosine arabinoside (Ara-C), dideoxyuridine, denopterin, doxifluridine, enocitabine, floxuridine, fludarabine, 5-fluorouracil, gemcetabine, hydroxyurea, leucovorin (folinic acid), 6-mercaptopurine, methotrexate, pemetrexed, pteropterin, thiamiprine, trimetrexate, and thioguanine. Non-limiting examples of suitable anti-tumor antibiotics include aclacinomysin, actinomycins, adriamycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mithramycin, mycophenolic acid, nogalamycin, olivomycins, peplomycin, plicamycin, potfiromycin, puromycin, quelamycin, rodorubicin, streptonigrin, streptozocin, tubercidin, valrubicin, ubenimex, zinostatin, and zorubicin. Non-limiting examples of suitable anti-cytoskeletal agents include colchicines, docetaxel, macromycin, paclitaxel, vinblastine, vincristine, vindesine, and vinorelbine. Suitable topoisomerase inhibitors include, but are not limited to, amsacrine, etoposide (VP-16), irinotecan, mitoxantrone, RFS 2000, teniposide, and topotecan. Non-limiting examples of suitable anti-hormonal agents such as aminoglutethimide, aromatase inhibiting 4(5)-imidazoles, bicalutamide, finasteride, flutamide, goserelin, 4-hydroxytamoxifen, keoxifene, leuprolide, LY117018, mitotane, nilutamide, onapristone, raloxifene, tamoxifen, toremifene, and trilostane. Examples of targeted therapeutic agents include, without limit, monoclonal antibodies such as alemtuzumab, epratuzumab, gemtuzumab, ibritumomab tiuxetan, rituximab, tositumomab, and trastuzumab; protein kinase inhibitors such as bevacizumab, cetuximab, dasatinib, erlotinib, gefitinib, imatinib, lapatinib, mubritinib, nilotinib, panitumumab, pazopanib, sorafenib, sunitinib, and vandetanib; angiogeneisis inhibitors such as angiostatin, endostatin, bevacizumab, genistein, interferon alpha, interleukin-2, interleukin-12, pazopanib, pegaptanib, ranibizumab, rapamycin, thalidomide; and growth inhibitory polypeptides such as erythropoietin, interleukins (e.g., IL-1, IL-2, IL-3, IL-6), leukemia inhibitory factor, interferons, thrombopoietin, TNF-α, CD30 ligand, 4-1BB ligand, and Apo-1 ligand. Also included are pharmaceutically acceptable salts, acids, or derivatives of any of the above listed agents. The mode of administration of the chemotherapeutic agent can and will vary depending upon the agent and the type of cancer. A skilled practitioner will be able to determine the appropriate dose of the chemotherapeutic agent.

The radiotherapeutic agent may include a radioisotope. Suitable radioisotopes include, without limit, Iodine-131, Iodine-125, Iodine-124, Lutecium-177, Phosphorous-132, Rhenium-186, Strontium-89, Yttrium-90, Iridium-192, and Samarium-153. Alternatively, the radiotherapeutic agent may include a high Z-element chosen from gold, silver, platinum, palladium, cobalt, iron, copper, tin, tantalum, vanadium, molybdenum, tungsten, osmium, iridium, rhenium, hafnium, thallium, lead, bismuth, gadolinium, dysprosium, holmium, and uranium. The appropriate dose of the radiotherapeutic agent may be determined by a skilled practitioner.

Definitions

The compounds described herein have asymmetric centers. Compounds of the present invention containing an asymmetrically substituted atom may be isolated in optically active or racemic form. All chiral, diastereomeric, racemic forms and all geometric isomeric forms of a structure are intended, unless the specific stereochemistry or isomeric form is specifically indicated.

The term "acyl," as used herein alone or as part of another group, denotes the moiety formed by removal of the hydroxy group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl, or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic conjugated planar ring or ring system comprising delocalized electrons. These aromatic groups are preferably monocyclic (e.g., furan or benzene), bicyclic, or tricyclic groups containing from 5 to 14 atoms in the ring portion. The term "aromatic" encompasses "aryl" groups defined below.

The terms "aryl" or "Ar" as used herein alone or as part of another group denote optionally substituted homocyclic aromatic groups, preferably monocyclic or bicyclic groups containing from 6 to 10 carbons in the ring portion, such as phenyl, biphenyl, naphthyl, substituted phenyl, substituted biphenyl, or substituted naphthyl.

The terms "carbocyclo" or "carbocyclic" as used herein alone or as part of another group denote optionally substituted, aromatic or non-aromatic, homocyclic ring or ring system in which all of the atoms in the ring are carbon, with preferably 5 or 6 carbon atoms in each ring. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "halogen" or "halo" as used herein alone or as part of another group refer to chlorine, bromine, fluorine, and iodine.

The term "heteroatom" refers to atoms other than carbon and hydrogen.

The term "heteroaromatic" as used herein alone or as part of another group denotes optionally substituted aromatic groups having at least one heteroatom in at least one ring, and preferably 5 or 6 atoms in each ring. The heteroaromatic group preferably has 1 or 2 oxygen atoms and/or 1 to 4 nitrogen atoms in the ring, and is bonded to the remainder of the molecule through a carbon. Exemplary groups include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl, and the like. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described above. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The term "oxygen-protecting group" as used herein denotes a group capable of protecting an oxygen atom (and hence, forming a protected hydroxyl group), wherein the protecting group may be removed, subsequent to the reaction for which protection is employed, without disturbing the remainder of the molecule. Exemplary oxygen protecting groups include ethers (e.g., allyl, triphenylmethyl (trityl or Tr), p-methoxybenzyl (PMB), p-methoxyphenyl (PMP)); acetals (e.g., methoxymethyl (MOM), β-methoxyethoxymethyl (MEM), tetrahydropyranyl (THP), ethoxy ethyl (EE), methylthiomethyl (MTM), 2-methoxy-2-propyl (MOP), 2-trimethylsilylethoxymethyl (SEM)); esters (e.g., benzoate (Bz), allyl carbonate, 2,2,2-trichloroethyl carbonate (Troc), 2-trimethylsilylethyl carbonate); silyl ethers (e.g., trimethylsilyl (TMS), triethylsilyl (TES), triisopropylsilyl (TIPS), triphenylsilyl (TPS), t-butyldimethylsilyl (TBDMS), t-butyldiphenylsilyl (TBDPS)) and the like. A variety of oxygen protecting groups and the synthesis thereof may be found in "Protective Groups in Organic Synthesis" by T. W. Greene and P. G. M. Wuts, $3^{rd}$ ed., John Wiley & Sons, 1999.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

Having described the invention in detail, it will be apparent that modifications and variations are possible without departing from the scope of the invention defined in the appended claims.

EXAMPLES

The following examples are included to demonstrate certain embodiments of the invention. It should be appreciated by those of skill in the art that the techniques disclosed in the examples represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth is to be interpreted as illustrative and not in a limiting sense.

Example 1. JVM 1

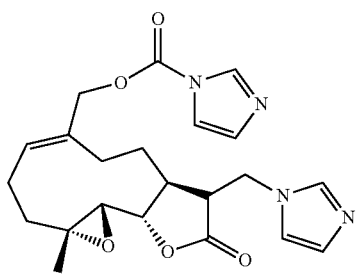

To a stirred solution of MMB (50 mg, 0.189 mmol) in dichloromethane, was added carbonyldiimidazole (46.02 mg, 0.284 mmol). The reaction mixture was stirred at ambient temperature for 24 hours. After completion of the reaction, the reaction mixture was diluted with chloroform (2 mL). The organic layer was washed with 10% citric acid solution (2 mL), dried over $Na_2SO_4$, and concentrated under reduced pressure. The residue was purified by column chromatography (silica gel eluted with 3% methanol in dichloromethane) to afford compound JVM 1 as an off-white solid (yield: 75%).

$^1$H-NMR (CDCl$_3$, 400 MHz) δ 8.13 (s, 1H), 7.68 (s, 1H), 7.42 (s, 1H), 7.09-7.05 (m, 3H), 5.72 (t, J=8 Hz, 1H), 4.94 (d, J=12 Hz, 1H), 4.55 (d, J=12.8 Hz, 2H), 4.36 (d, J=16 Hz, 1H), 3.902-3.856 (m, 1H), 2.79 (t, J=11.8 Hz, 1H), 2.60 (d, J=8 Hz, M), 2.44-1.91 (m, 8H), 1.83-1.74 (m, 1H), 1.66 (t, J=12 Hz, 1H), 1.52 (s, 1H), 1.07 (t, J=12 Hz, 1H); $^{13}$C NMR (CDCl$_3$, 100 MHz) δ 174.5, 148.7, 137.7, 137.0, 133.3, 132.7, 130.9, 130.6, 119.4, 117.1, 80.8, 69.8, 62.4, 59.9, 48.3, 43.7, 40.9, 36.2, 26.5, 23.8, 23.6, 17.8 ppm.

Example 2. JVM 57 (6d in Example 19)

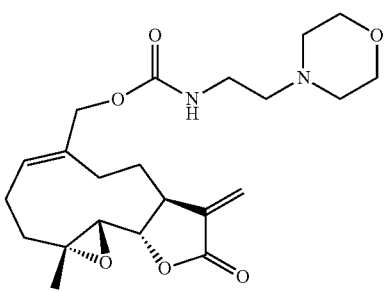 [SMILES: C=C1C(=O)O[C@H]2[C@H]1CC/C(COC(=O)NCCN1CCOCC1)=C\CC[C@@]1(C)O[C@@H]21]

4-(2-Aminoethyl)morpholine (25 mg, 0.19 mmol) in dichloromethane (2 mL) was added at 0° C. to the triazole intermediate of MMB (JVM 2-16) (70 mg, 0.19 mmol). The reaction mixture was stirred for 15 hours. Upon completion of the reaction, as determined by TLC, water was added to the reaction mixture and the resulting aqueous mixture was extracted with dichloromethane. The organic layer was washed with water followed by brine, dried over anhydrous $Na_2SO_4$, and concentrated to afford the crude product. The crude product was purified by column chromatography (silica gel eluted with 3% methanol in dichloromethane) to afford compound JVM 57 as a white solid (yield: 60%).

$^1$H NMR (CDCl$_3$, 400 MHz): δ 6.11 (d, J=3.6 Hz, 1H), 5.58 (t, J=8 Hz, 1H), 5.43 (d, J=2.8 Hz, 1H), 5.06 (s, 1H), 4.53 (d, J=12.4 Hz, 1H), 4.34 (d, J=12 Hz, 1H), 3.74 (t, J=8.8 Hz, 1H), 3.56 (s, 4H), 3.16 (t, J=5.2 Hz, 2H), 2.78-2.72 (m, 2H), 2.32 (s, 8H), 2.21-2.00 (m, 4H), 1.55 (t, J=10.4 Hz, 1H), 1.41 (s, 3H), 1.01 (t, J=12 Hz, 1H) ppm. $^{13}$C NMR (CDCl3, 100 MHz) δ 169.2, 155.9, 138.7, 135.4, 130.2, 120.0, 80.9, 67.0, 66.7, 63.1, 59.8, 57.2, 53.1, 42.5, 37.0, 36.5, 25.7, 24.4, 23.7, 17.8 ppm.

Example 3. JVM 59 (6b in Example 19)

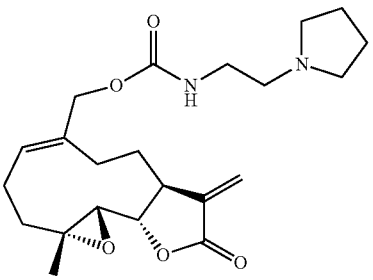 [SMILES: C=C1C(=O)O[C@H]2[C@H]1CC/C(COC(=O)NCCN1CCCC1)=C\CC[C@@]1(C)O[C@@H]21]

To the triazole intermediate of MMB (JVM 2-16) (70 mg, 0.19 mmol) in dichloromethane (2 mL) at 0° C. was added 1-(2-aminoethyl)pyrrolidine (21.6 mg, 0.19 mmol). The reaction mixture was stirred for 16 hours. Upon completion of the reaction, as determined by TLC, water was added to the reaction mixture and the aqueous mixture was extracted with dichloromethane. The organic layer was washed with water followed by brine, dried over anhydrous $Na_2SO_4$, and concentrated to afford the crude product. The crude product was purified by column chromatography (silica gel eluted with 5% methanol in dichloromethane) to afford compound JVM 59 as a white solid (yield: 55%).

$^1$H NMR (CDCl$_3$, 400 MHz): δ 6.22 (d, J=3.2 Hz, 1H), 5.65 (t, J=7 Hz, 1H), 5.55 (s, 1H), 4.62 (d, J=11.6 Hz, 1H), 4.47 (d, J=12.4 Hz, 1H), 3.82 (t, J=9.6 Hz, 1H), 3.35 (s, 2H), 2.90-2.83 (m, 2H), 2.70 (s, 4H), 2.42 (d, J=9.6 Hz, 2H), 2.38-2.13 (m, 7H) 1.84 (s, 4H), 1.66 (t, J=12 Hz, 1H), 1.52 (s, 3H), 1.13 (t, J=11.6 Hz, 1H) ppm. $^{13}$C NMR (CDCl3, 100 MHz) δ 169.3, 156.1, 138.6, 135.3, 129.8, 120.1, 80.9, 67.0, 63.1, 59.8, 55.1, 53.8, 42.5, 38.9, 36.5, 25.6, 24.3, 23.6, 23.2, 17.8 ppm.

Example 4. JVM 61 (6c in Example 19)

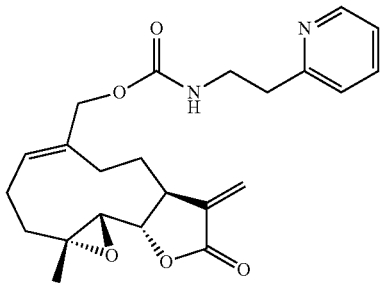 [SMILES: C=C1C(=O)O[C@H]2[C@H]1CC/C(COC(=O)NCCc1ccccn1)=C\CC[C@@]1(C)O[C@@H]21]

To the triazole intermediate of MMB (JVM 2-16) (70 mg, 0.19 mmol) in dichloromethane (2 mL), 2-ethylaminopyridine (23.18 mg, 0.19 mmol) was added at 0° C. The reaction mixture was stirred for 16 hours. Upon completion as determined by TLC, water was added to the reaction mixture and the aqueous mixture was extracted with dichloromethane. The organic layer was washed with water followed by brine, dried over anhydrous Na₂SO₄, and concentrated to afford the crude product. The crude product was purified by column chromatography (silica gel eluted with 5% methanol in dichloromethane) to afford compound JVM 61 as a white solid (yield: 65%).

$^1$H NMR (CDCl$_3$, 400 MHz): δ 8.50 (s, 1H), 7.62 (t, J=7.2 Hz, 1H), 7.15 (d, J=7.6 Hz, 2H), 6.19 (s, 1H), 5.64 (t, J=8 Hz, 1H), 5.56 (m, 2H), 4.62 (d, J=12.4 Hz, 1H), 4.44 (d, J=12.8 Hz, 1H), 3.84 (t, J=9.2 Hz, 1H), 3.60 (d, J=6 Hz, 2H), 2.99-2.82 (m, 4H), 2.41-2.12 (m, 5H), 1.75 (s, 1H), 1.64 (d, J=10.4 Hz, 1H), 1.52 (s, 3H), 1.07 (t, J=13.6 Hz, 1H). $^{13}$C NMR (CDCl$_3$, 100 MHz): δ 169.3, 159.1, 156.0, 149.1, 138.6, 136.6, 135.5, 129.9, 123.4, 121.6, 120.2, 81.0, 67.0, 63.2, 59.8, 42.5, 40.1, 37.1, 36.6, 25.8, 24.4, 23.7, 17.9 ppm.

Example 5. JVM 64 (6e in Example 19)

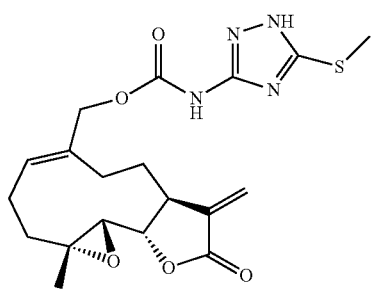 [SMILES: C=C1C(=O)O[C@H]2[C@H]1CC/C(COC(=O)Nc1n[nH]c(SC)n1)=C\CC[C@@]1(C)O[C@@H]21]

To the triazole intermediate of MMB (JVM 2-16) (70 mg, 0.19 mmol) in dichloromethane (2 mL), 5-(methylthio)-1H-1,2,4-triazol-3-amine (24.7 mg, 0.19 mmol) was added at 0° C. The reaction mixture was stirred for 8 hours. Upon completion as determined by TLC, water was added to the reaction mixture and the aqueous mixture was extracted with dichloromethane. The organic layer was washed with water followed by brine, dried over anhydrous Na₂SO₄, and concentrated to afford the crude product. The crude product was purified by column chromatography (silica gel eluted with 3% methanol in dichloromethane) to afford compound JVM 64 as a white solid (yield: 62%).

$^1$H NMR (CDCl$_3$, 400 MHz): δ 6.22 (s, 2H), 5.82 (t, J=8 Hz, 1H), 5.50 (s, 1H), 4.90 (d, J=12.4 Hz, 1H), 4.81 (d, J=12.4 Hz, 1H), 3.85 (t, 9.6 Hz, 1H), 2.95 (s, 1H), 2.85 (d, J=9.2 Hz, 1H), 2.48-2.15 (m, 8H), 1.70-1.53 (m, 6H), 1.13 (t, J=12.4 Hz, 1H); $^{13}$C NMR (CDCl$_3$, 100 MHz): δ 169.1, 163.1, 157.4, 149.9, 138.5, 133.3, 132.7, 120.2, 80.7, 70.1, 62.9, 59.7, 42.4, 36.2, 25.6, 24.3, 23.7, 17.8, 13.5 ppm.

Example 6. JVM 66

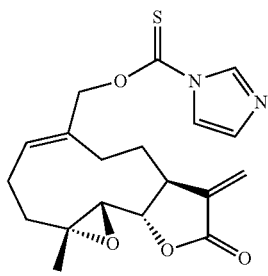 [SMILES: C=C1C(=O)O[C@H]2[C@H]1CC/C(COC(=S)n1ccnc1)=C\CC[C@@]1(C)O[C@@H]21]

To a stirred solution of MMB (50 mg, 0.19 mmol) in chloroform (2 mL), thiocarbonyldiimidazole (33.8 mg, 0.19 mmol) was added at ambient temperature. The reaction was maintained for 1 hour at ambient temperature. Upon completion as determined by TLC, water was added and the aqueous mixture was extracted with dichloromethane. The organic layer was dried over anhydrous Na₂SO₄ and concentrated to afford the crude product. The crude product was purified by column chromatography (silica gel eluted with a gradient of 3-8% methanol in dichloromethane) to afford compound JVM 66 as an off-white solid (yield: 60%) and compound JVM 66A as a white solid (yield: 15%).

$^1$H NMR (CDCl$_3$, 400 MHz): δ 8.11 (s, 1H), 7.38 (s, 1H), 7.07 (s, 1H), 6.22 (s, 1H), 5.52 (s, 2H), 5.14 (s, 1H), 4.30 (s, 1H), 3.78 (t, J=8.8 Hz, 1H), 3.16 (s, 1H), 2.94 (d, J=8.8 Hz, 1H), 2.47 (q, J=17.2 Hz, 2H), 2.3-2.18 (m, 3H), 1.77-1.66 (m, 2H), 1.39 (s, 3H), 1.32-1.23 (m, 1H); $^{13}$C NMR (CDCl$_3$, 100 MHz): δ 168.9, 165.1, 143.8, 138.7, 135.2, 131.0, 119.8, 116.4, 115.6, 79.4, 63.0, 59.8, 53.3, 45.1, 37.4, 29.8, 28.2, 24.7, 17.8 ppm.

Example 7. JVM 67

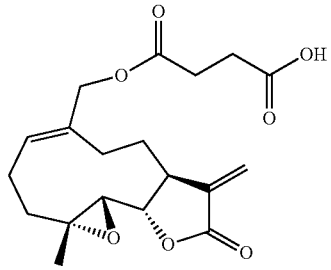 [SMILES: C=C1C(=O)O[C@H]2[C@H]1CC/C(COC(=O)CCC(=O)O)=C\CC[C@@]1(C)O[C@@H]21]

To a reaction mixture of MMB (200 mg, 0.76 mmol) and triethylamine (76.7 mg, 0.76 mmol) in dichloromethane (5 mL), succinic anhydride (76 mg, 0.76 mmol) was added at ambient temperature. The resulting reaction mixture was stirred for 48 hours. Upon completion as determined by TLC, the reaction mixture was concentrated under reduced pressure to afford the crude product. The crude product was purified by column chromatography (silica gel eluted with a gradient of 3-5% methanol in dichloromethane) to afford compound JVM 67 as a white solid (yield: 90%).

$^1$H NMR (DMSO-d$_6$, 400 MHz): δ 12.25 (s, 1H), 6.05 (d, J=2.8 Hz, 1H), 5.64-5.57 (m, 2H), 4.64 (d, J=12.4 Hz, 1H), 4.42 (d, J=12.8 Hz, 1H), 4.12 (t, J=9.6 Hz, 1H), 2.99 (t, J=3 Hz, 1H), 2.85 (d, J=9.6 Hz, 1H), 2.30-2.04 (m, 10H), 1.66 (t, J=11.6 Hz, 1H), 1.47 (s, 3H), 0.96 (t, J=11.6 Hz, 1H); $^{13}$C NMR (DMSO-d$_6$, 100 MHz): δ 173.8, 172.4, 169.8, 140.0, 135.3, 129.5, 119.7, 110.0, 81.0, 66.9, 63.0, 60.3, 42.2, 36.7, 29.1, 25.0, 24.2, 23.6, 17.9 ppm.

Example 8. JVM 88

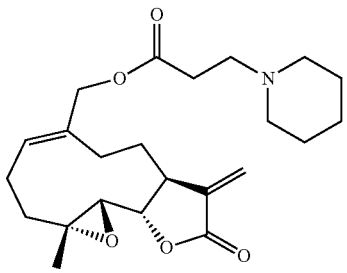 [SMILES: C=C1C(=O)O[C@H]2[C@H]1CC/C(COC(=O)CCN1CCCCC1)=C\CC[C@@]1(C)O[C@@H]21]

To a stirred solution of MMB (50 mg, 0.19 mmol) in dichloromethane (2 mL), was added 1-ethyl-3-(3-dimethylaminopropyl)carbodiimide (EDC, 43.93 mg, 0.23 mmol), triethylamine (48.4 mg, 0.48 mmol), dimethylaminopyridine (DMAP, 2.3 mg, 0.019 mmol) and 1-piperidylpropionic acid (29.8 mg, 0.19 mmol) at 0° C. The reaction mixture was stirred at ambient temperature for 24 hours. Upon completion, water was added and the mixture was extracted with dichloromethane. The organic layer was washed with water followed by brine, dried over anhydrous $Na_2SO_4$, and concentrated to afford the crude product. The crude product was purified by column chromatography (silica gel eluted with 2% methanol in dichloromethane) to afford compound JVM 88 as a white solid (yield: 62%).

$^1$H NMR ($CDCl_3$, 400 MHz): δ 6.23 (d, J=3.6 Hz, 1H), 5.65 (t, J=8 Hz, 1H), 5.52 (d, J=3.2 Hz, 1H), 4.69 (d, J=12.4 Hz, 1H), 4.42 (d, J=12.4 Hz, 1H), 3.84 (t, J=9.2 Hz, 1H), 2.85-2.81 (m, 2H), 2.65-2.62 (m, 2H), 2.52-2.48 (m, 2H), 2.42-2.12 (m, 10H), 1.63-1.52 (m, 8H), 1.41 (d, J=4.4 Hz, 2H), 1.10 (t, J=12 Hz, 1H); $^{13}$C NMR ($CDCl_3$, 100 MHz): δ 172.4, 169.4, 138.8, 135.0, 130.5, 120.4, 81.1, 66.6, 63.4, 60.0, 54.4, 54.3, 42.7, 36.7, 32.3, 25.9, 25.8, 24.4, 24.2, 23.9, 18.1 ppm.

Example 9. JVM 96

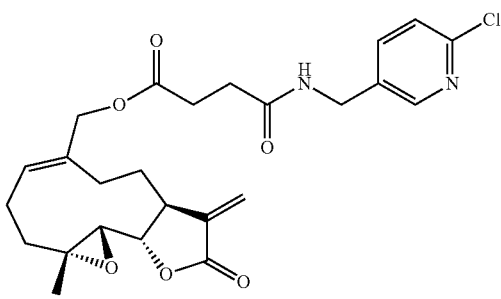 [SMILES: C=C1C(=O)O[C@H]2[C@H]1CC/C(COC(=O)CCC(=O)NCc1ccc(Cl)nc1)=C\CC[C@@]1(C)O[C@@H]21]

To a reaction mixture of MMB carboxylic acid (JVM 67), (50 mg, 0.14 mmol), EDC (40.26 mg, 0.21 mmol), N-hydroxybenzotriazole (HOBt, 28.35 mg, 0.21 mmol), and triethylamine (42.42 mg, 0.42 mmol) in dichloromethane (2 mL) was added 3-aminomethyl-6-chloropyridine (19.96 mg, 0.14 mmol) at 0° C. and the reaction mixture was stirred at ambient temperature for 16 hours. Upon completion as determined by TLC, water was added and the mixture extracted with dichloromethane. The organic layer was dried and concentrated to afford the crude compound. The crude product was further purified by column chromatography (silica gel using 3% methanol in dichloromethane) to afford JVM 96 as pure product as white solid (yield 75%).

$^1$H NMR ($CDCl_3$, 400 MHz): δ 8.28 (s, 1H), 7.61 (d, J=8.4 Hz, 1H), 7.29 (d, J=8.4 Hz, 1H), 6.22 (d, J=3.2 Hz, 1H), 6.07 (s, 1H), 5.68 (t, J=7.2 Hz, 1H), 5.55 (s, 1H), 4.65 (d, J=12.4 Hz, 1H), 4.49 (d, J=12.8 Hz, 1H), 4.42 (d, J=5.6 Hz, 2H), 3.85 (t, J=9.6 Hz, 1H), 2.95 (t, J=8.8 Hz, 1H), 2.85 (d, J=9.6 Hz, 1H), 2.68 (t, J=6 Hz, 2H), 2.52-2.11 (m, 7H), 1.67-1.62 (m, 2H), 1.53 (s, 3H), 1.12 (t, J=11.6 Hz, 1H); $^{13}$C NMR ($CDCl_3$, 100 MHz): δ 172.8, 171.5, 169.6, 150.7, 148.9, 138.9, 138.6, 134.8, 133.1, 130.8, 124.4, 120.4, 81.2, 67.2, 63.3, 60.1, 42.7, 40.5, 36.7, 30.7, 29.3, 25.8, 24.6, 23.9, 18.1 ppm.

Example 10. JVM 2-16

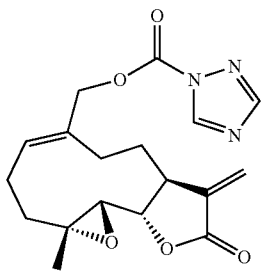 [SMILES: C=C1C(=O)O[C@H]2[C@H]1CC/C(COC(=O)n1cncn1)=C\CC[C@@]1(C)O[C@@H]21]

To a stirred solution of MMB (50 mg, 0.18 mmol) in dichloromethane, carbonylditriazole (46.5 mg, 0.28 mmol) was added at ambient temperature. The reaction mixture was stirred at ambient temperature for 10 minutes. Upon completion, water was added and the mixture extracted with dichloromethane, dried over $Na_2SO_4$ and concentrated under reduced pressure to afford pure product JVM 2-16 as white solid (yield: 85%).

$^1$H NMR ($CDCl_3$, 400 MHz): δ 8.83 (s, 1H), 8.06 (s, 1H), 6.26 (d, J=3.6 Hz, 1H), 5.92 (t, J=8.4 Hz, 1H), 5.55 (d, J=3.2 Hz, 1H), 5.08 (d, J=11.6 Hz, 1H), 4.90 (d, J=12 Hz, 1H), 3.89 (t, J=9.6 Hz, 1H), 2.91 (m, 2H), 2.56-2.17 (m, 6H), 1.84-1.72 (m, 1H), 1.55 (s, 3H), 1.17 (t, J=12.4 Hz, 1H); $^{13}$C NMR ($CDCl_3$, 100 MHz): δ 169.2, 154.0, 147.7, 145.8, 138.6, 134.4, 133.3, 120.6, 80.9, 71.5, 63.3, 59.9, 42.7, 36.5, 25.7, 24.3, 24.1, 18.1 ppm.

Example 11. JVM 2-26

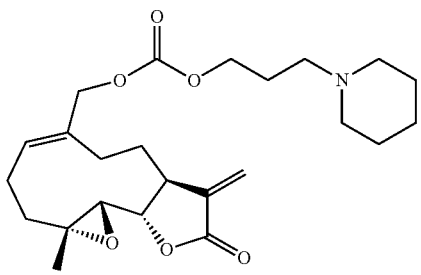 [SMILES: C=C1C(=O)O[C@H]2[C@H]1CC/C(COC(=O)OCCCN1CCCCC1)=C\CC[C@@]1(C)O[C@@H]21]

To a stirred solution of MMB (50 mg, 0.18 mmol) in dichloromethane (2 mL), carbonylditriazole (46.5 mg, 0.28 mmol) was added at ambient temperature. The reaction mixture was stirred for 10 minutes and piperidine-1-propanol (40 mg, 0.28 mmol) was added, and the reaction mixture was maintained at ambient temperature for 30 minutes. Upon completed as determined by TLC, water was added and the mixture extracted with dichloromethane. The organic layer was dried over Na$_2$SO$_4$ and concentrated to afford a crude product. The crude compound was purified by column chromatography (silica gel eluted with 3% methanol in dichloromethane) to afford pure product JVM 2-26, as a white solid (yield: 81%).

$^1$H NMR (CDCl$_3$, 400 MHz): δ 6.24 (d, J=3.6 Hz, 1H), 5.74 (t, J=7.6 Hz, 1H), 5.55 (d, J=3.2 Hz, 1H), 4.65 (d, J=12 Hz, 1H), 4.55 (d, J=12 Hz, 1H), 4.19 (t, J=6 Hz, 2H), 3.86 (t, J=8.8 Hz, 1H), 2.88-2.82 (m, 2H), 2.46-2.13 (m, 12H), 1.92 (s, 2H), 1.70-1.64 (m, 5H), 1.53 (s, 3H), 1.45 (s, 2H), 1.13 (t, J=11.6 Hz, 1H); $^{13}$C NMR (CDCl$_3$, 100 MHz): δ 169.5, 155.0, 138.7, 134.5, 131.7, 120.4, 81.1, 70.3, 66.8, 63.4, 60.0, 55.5, 54.5, 42.7, 36.6, 25.9, 25.5, 24.5, 24.1, 24.1, 23.9, 18.1 ppm.

Example 12. JVM 2-31

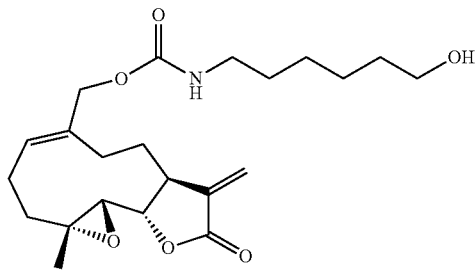 [SMILES: C=C1C(=O)O[C@H]2[C@H]1CC/C(COC(=O)NCCCCCCO)=C\CC[C@@]1(C)O[C@@H]21]

To a stirred solution of MMB (50 mg, 0.18 mmol) in dichloromethane at ambient temperature, was added carbonylditriazole (46.5 mg, 0.28 mmol). The reaction mixture was stirred for 10 minutes. 6-Amino-1-hexanol (32.7 mg, 0.28 mmol) was then added and the reaction was maintained for 30 minutes at ambient temperature. Upon completion of the reaction, as determined by TLC, water was added and the mixture extracted with dichloromethane. The organic layer was dried over anhydrous Na$_2$SO$_4$ and concentrated to afford the crude product. The crude compound was purified by column chromatography (silica gel eluted with 3% methanol in dichloromethane) to afford the pure product, JVM 2-31, as a colorless oil (yield: 85%).

$^1$H NMR (CDCl$_3$, 400 MHz): δ 6.28 (d, J=3.6 Hz, 1H), 5.73 (t, J=8 Hz, 1H), 5.59 (d, J=3.2 Hz, 1H), 4.68-4.63 (m, 2H), 4.51 (d, J=12.4 Hz, 1H), 3.90 (t, J=9.2 Hz, 2H), 3.68 (t, J=6 Hz, 2H), 3.21 (d, J=6.4 Hz, 2H), 2.98-2.88 (m, 2H), 2.46-2.16 (m, 6H), 1.71-1.51 (m, 8H), 1.45-1.36 (m, 4H), 1.16 (t, d, J=11.6 Hz, 1H) ppm; $^{13}$C NMR (CDCl$_3$, 100 MHz): δ 169.6, 156.3, 138.9, 135.7, 130.3, 120.3, 81.2, 67.2, 63.4, 62.8, 60.1, 42.7, 41.0, 36.7, 32.6, 30.0, 26.5, 25.9, 25.4, 24.7, 23.9, 18.1 ppm.

Example 13. JVM 2-35

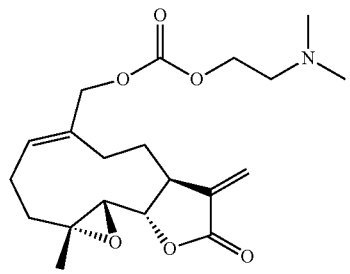 [SMILES: C=C1C(=O)O[C@H]2[C@H]1CC/C(COC(=O)OCCN(C)C)=C\CC[C@@]1(C)O[C@@H]21]

To a stirred solution of MMB (50 mg, 0.18 mmol) in dichloromethane, carbonylditriazole (46.5 mg, 0.28 mmol) was added at ambient temperature. The reaction mixture was stirred for 10 minutes. N,N-dimethylethanolamine (24.9 mg, 0.28 mmol) was then added and the reaction was maintained for 30 minutes at ambient temperature. Upon completion as determined by TLC, water was added and the mixture extracted with dichloromethane. The organic layer was dried over Na$_2$SO$_4$ and concentrated to afford the crude product. The crude compound was purified by column chromatography (silica gel eluted with 4% methanol in dichloromethane) to afford the pure product, JVM 2-35 as a white solid (yield: 81%).

$^1$H NMR (CDCl$_3$, 400 MHz) δ 6.24 (d, J=3.6 Hz, 1H), 5.74 (t, J=8.4 Hz, 1H), 5.55 (d, J=3.2 Hz, 1H), 4.65 (d, J=12 Hz, 1H), 4.56 (d, J=12.4 Hz, 1H), 4.24 (s, 2H), 3.85 (t, J=9.6 Hz, 1H), 2.84 (d, J=9.2 Hz, 2H), 2.62 (s, 2H), 2.47-2.12 (m, 12H), 1.72-1.60 (m, 1H), 1.53 (s, 3H), 1.12 (t, J=11.6 Hz, 1H); $^{13}$C NMR (CDCl$_3$, 100 MHz): δ 169.5, 155.1, 138.7, 134.5, 131.6, 120.5, 81.1, 70.4, 65.4, 63.4, 60.0, 57.6, 45.6, 42.7, 36.6, 25.8, 24.4, 23.9, 18.1 ppm.

Example 14. JVM 2-40

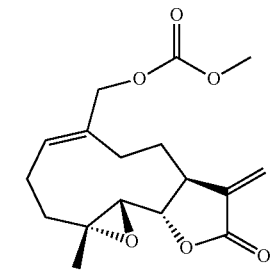 [SMILES: C=C1C(=O)O[C@H]2[C@H]1CC/C(COC(=O)OC)=C\CC[C@@]1(C)O[C@@H]21]

To a stirred solution of MMB (50 mg, 0.18 mmol) in methanol (2 mL), carbonylditriazole (46.5 mg, 0.28 mmol) was added at ambient temperature. The reaction mixture was stirred at same temperature for 1 hour. Upon completion as determined by TLC, the reaction mixture was concentrated under reduced pressure and the crude compound was purified by column chromatography (silica gel eluted with 2% methanol in dichloromethane) to afford pure product, JVM 2-40, as a white solid (yield: 80%).

$^1$H NMR (CDCl$_3$, 400 MHz): δ 6.24 (s, 1H), 5.72 (s, 1H), 5.53 (s, 1H), 4.65 (d, t, J=11.6 Hz, 1H), 4.56 (d, J=12 Hz, 1H), 3.85 (t, J=9.6 Hz, 1H), 3.77 (s, 3H), 2.83 (d, J=9.6 Hz, 2H), 2.44-2.13 (m, 6H), 1.66 (t, J=11.6 Hz, 1H), 1.52 (s, 3H), 1.12 (t, J=11.6 Hz, 1H); $^{13}$C NMR (CDCl$_3$, 100 MHz):

δ 169.4, 155.7, 138.7, 134.5, 131.6, 120.4, 81.1, 70.4, 63.4, 60.0, 55.1, 42.7, 36.6, 25.8, 24.4, 23.9, 18.1 ppm.

Example 15. JVM 2-41

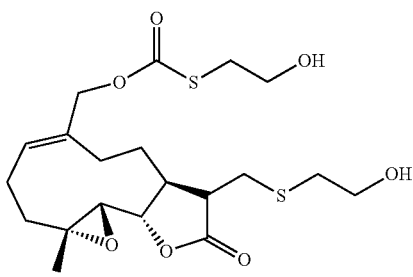

To a stirred solution of MMB (50 mg, 0.18 mmol) in dichloromethane, was added carbonylditriazole (46.5 mg, 0.28 mmol). The reaction mixture was stirred at room temperature for 10 minutes, and mercaptoethanol (21.84 mg, 0.28 mmol) was added. The reaction was maintained for 30 minutes. Upon completion as determined by TLC, water was added and the mixture extracted with dichloromethane. The organic layer was dried over $Na_2SO_4$ and concentrated to afford the crude product. The crude compound was purified by column chromatography (silica gel eluted with 4% methanol in dichloromethane) to afford the pure product, JVM 2-41, as an oil (yield: 65%).

$^1$H NMR (CDCl$_3$, 400 MHz): δ 5.11 (t, J=8 Hz, 1H), 5.02 (d, J=12 Hz, 1H), 4.62 (d, J=12 Hz, 1H), 3.90-3.76 (m, 4H), 3.07-3.02 (m, 3H), 2.84-2.74 (m, 3H), 2.61-2.57 (m, 1H), 2.47-2.12 (m, 7H), 1.99 (s, 4H), 1.63-1.57 (m, 1H), 1.53 (s, 3H), 1.11 (t, J=12.4 Hz, 1H); $^{13}$C NMR (CDCl$_3$, 100 MHz): δ 175.9, 171.6, 134.7, 131.3, 81.2, 70.0, 63.3, 61.8, 60.9, 60.0, 46.8, 42.7, 36.8, 36.6, 34.0, 29.7, 26.7, 24.2, 23.8, 18.0 ppm.

Example 16. JVM 2-49

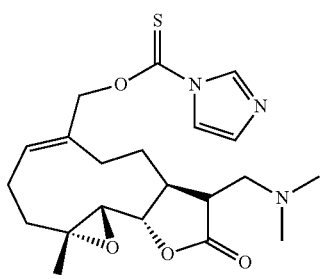

To the stirred solution of MMB (70 mg, 0.27 mmol) in dichloromethane, dimethylamine (14.40 mg, 0.32 mmol) in methanol was added the reaction mixture was maintained under ambient conditions for 2 hours. Upon completion, the reaction mixture was concentrated to remove solvent. The crude reaction mixture dissolved in dichloromethane and added the thiocarbonyldiimidazole (72 mg, 0.41 mmol). The reaction mixture was maintained at ambient temperature for 3 hours. Upon completion, the reaction mixture was concentrated and purified by column chromatography (silica gel eluted with 3% methanol in dichloromethane) to afford pure product.

$^1$H NMR (CDCl$_3$, 400 MHz): δ 8.12 (s, 1H), 7.38 (s, 1H), 7.07 (s, 1H), 5.51 (s, 1H), 5.19 (s, 1H), 4.32 (t, J=8 Hz, 1H), 3.80 (t, J=8 Hz, 1H), 2.99-2.03 (m, 17H), 1.6 (s, 1H), 1.41 (s, 3H), 1.29-1.23 (m, 1H); $^{13}$C NMR (CDCl$_3$, 100 MHz): δ 176.5, 165.4, 144.2, 135.5, 131.1, 116.8, 115.9, 79.7, 63.4, 60.0, 57.8, 53.8, 45.8, 45.3, 37.8, 30.0, 28.3, 26.1, 21.1, 18.0 ppm.

Example 17. Antileukemic Activity of Various MMB Derivatives

Derivatives were screened for antileukemic activity against AML cells in culture (See FIGS. 1-7). Compounds JVM 64, JVM 66, JVM 2-26, and JVM 2-49 (Examples 5, 6, 11, and 16, respectively) were the most active compounds against AML 052308 cells in culture and were more potent than MMB. JVM 66 (a thiocarbamate derivative of MMB, Example 6) was the most active molecule of this group with an $LC_{50}$ value of 2.6 μM, and was about 6-fold more cytotoxic than MMB ($LC_{50}$=16 μM); JVM 66 was also 3-fold more potent than parthenolide ($LC_{50}$=7.6 μM). The derivatives JVM 2-26, JVM 2-49, and JVM 64 (Examples 11, 16, and 5, respectively) exhibited similar cytotoxicity to parthenolide ($LC_{50}$=5, 5.2, 7.4 μM) and were 3-fold more cytotoxic than MMB against AML 052308 cells. JVM 61 (Example 4), JVM 59 (Example 3), and JVM 74 showed almost equal cytotoxicity to MMB, while JVM 57 (Example 2) and JVM 58 were less active than MMB. Compound JVM 88 (Example 8) was screened for antileukemic activity against the M9 ENL cell line, and against the AML 123009 and AML 100510 primary isolates, exhibiting good antileukemic activity compared to MMB in these cellular assays.

Figure 10:
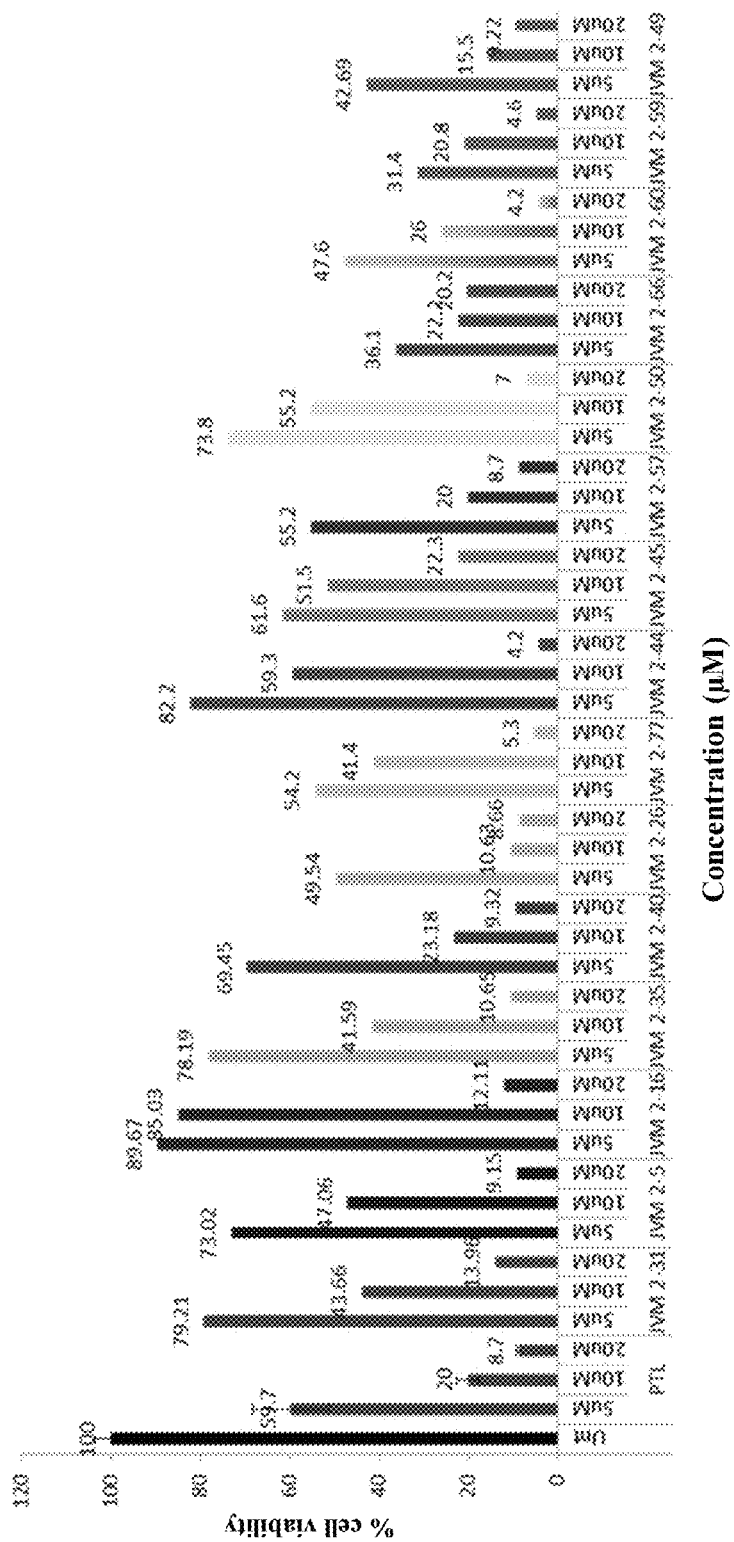
FIG. 10 shows a graph demonstrating the anti-leukemic activity of carbamate and carbonate derivatives of melampomagnolide B against M9 ENL cells.
Figure 11:
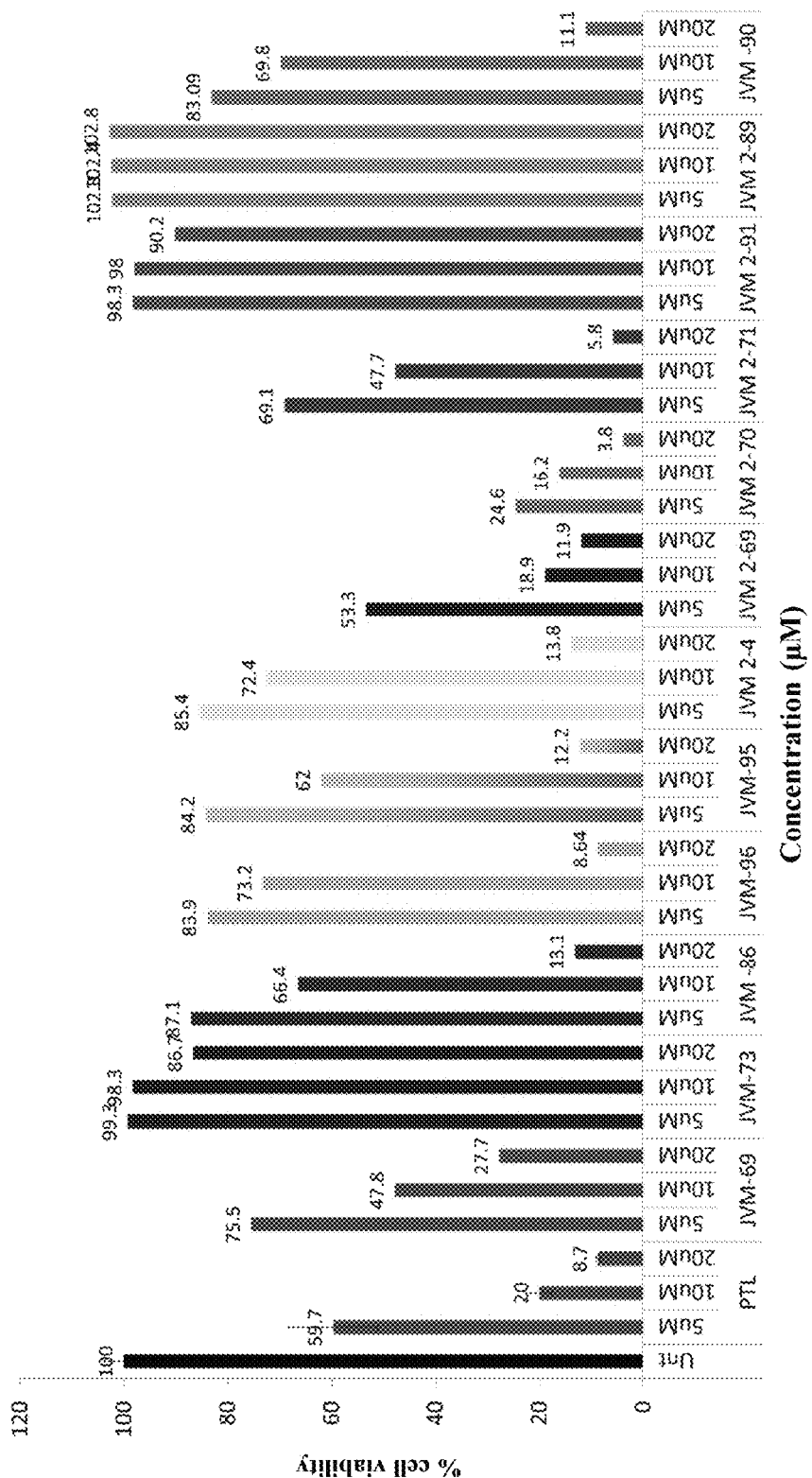
FIG. 11 shows a graph demonstrating the anti-leukemic activity of succinic amide derivatives of melampomagnolide B against M9 ENL cells.

Carbamate and carbonate derivatives of MMB were also screened for activity against M9 ENL cells at concentrations of 5, 10 and 20 μM (FIG. 10). JVM 2-66, JVM 2-60, JVM 2-59, and JVM 2-49 reduced cell viability by greater than 50% at the lowest concentration tested. Additionally, succinic amide derivatives of MMB were screened for activity against M9 ENL cells at concentrations of 5, 10 and 20 μM (FIG. 11). JVM 2-70 reduced cell viability by greater than 50% at the lowest concentration tested.

Example 18. In Vitro Growth Inhibition and Cytotoxicity

The compounds disclosed herein were also screened for anticancer activity against a panel of 60 human tumor cell lines. The compounds were first screened at a single concentration of $10^{-5}$ M. Compounds which showed more than 60% growth inhibition in at least eight human cancer cell lines from the panel were selected for a complete dose-response study at five concentrations: $10^{-4}$ M, $10^{-5}$ M, $10^{-6}$ M, $10^{-7}$ M, and $10^{-8}$ M. From the initial single dose screening, 16 compounds were selected for a five-dose screening: JVM 2-13 (Table 3), JVM 2-26 (Table 4), JVM 2-31 (Table 5), JVM 2-35 (Table 6), JVM 2-40 (Table 7), JVM 2-44 (Table 8), JVM 2-50 (Table 9), JVM 2-57 (Table 10), JVM 2-66 (Table 11), JVM 2-70 (Table 12), JVM-57 (6d) (Table 13), JVM-59 (6b) (Table 14), JVM-61 (6c) (Table 15), JVM-64 (6e) (Table 16), JVM-66 (Table 17), and JVM-96 (Table 18).

Example 19. Anti-Cancer Activity of Carbamate Derivatives of Melampomagnolide B (MMB)

Figure 8:
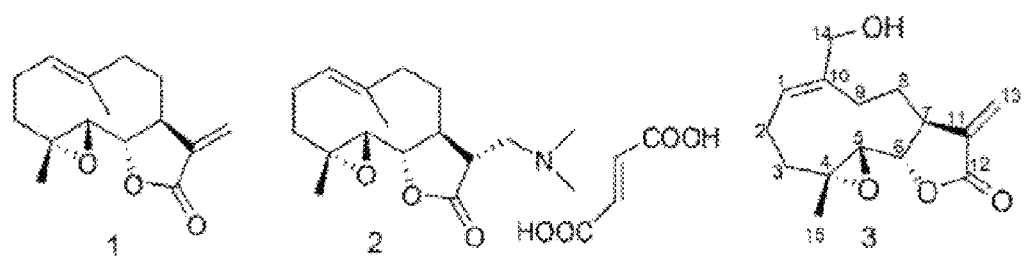
FIG. 8 shows structures of PTL (1), DMAPT fumarate (2) and MMB (3).

Parthenolide (PTL; 1, FIG. 8), a sesquiterpene lactone isolated from the medicinal herb Feverfew (*Tanacetum*

*parthenium*), has been widely reported in the literature as an anticancer agent that is effective against both hematological and solid tumors.[1,2] PTL and its analogs promote apoptosis by inhibiting the activity of the NF-κB transcription factor complex, and thereby down-regulates anti-apoptotic genes under NF-κB control.[3] Recent studies also demonstrate that PTL induces robust apoptosis of primary acute myeloid leukemia (AML) stem cells in culture.[4,5] AML is a clonal malignancy of the hematopoietic system characterized by accumulation of immature cell populations in the bone marrow or peripheral blood,[6] and is the most common type of leukemia in adults but has the lowest survival rate of all leukemias.[7]

More recently, we have shown that PTL and PTL analogs also selectively induce almost complete glutathione depletion and severe cell death in CD34+ AML cells,[8] but exhibit significantly less toxicity in normal CD34+ cells. PTL analogs perturb glutathione homeostasis by a multifactorial mechanism, including inhibition of key glutathione metabolic enzymes (GCLC and GPX1), and direct depletion of glutathione. Thus, primitive leukemia cells are uniquely sensitive to agents that target aberrant glutathione metabolism, an intrinsic property of primary human AML cells.

PTL is a major source for several novel anti-leukemic compounds arising from our research program over the past decade. The two best examples are dimethylaminoparthenolide (DMAPT; 2, FIG. 8) and melampomagnolide B (MMB; 3, FIG. 8). MMB is a melampolide originally isolated from *Magnolia grandiflora*.[9] MMB can be synthesized from commercially available PTL via $SeO_2$/tBuOOH oxidation.[10,11] Both of the above compounds 2 and 3 have been identified as new antileukemic sesquiterpenes with properties similar to PTL.[11,12] DMAPT is currently in Phase 1 clinical studies for evaluation as a treatment for acute myeloid leukemia cell (AML).[12]

More importantly, from a drug design point of view, MMB is a more intriguing molecule than either PTL or DMAPT because of the presence of the primary hydroxyl group at C-14, which can be structurally modified to improve potency, water solubility, bio-availability and tissue targeting of the molecule.

In the current study, we have prepared a series of novel carbamate analogs of MMB. These compounds were initially designed as potential prodrugs of MMB. However, we have found that on examining the anticancer activity of these compounds, several of the molecules exhibited significant growth inhibition properties in a panel of sixty human cancer cell lines. Two of these compounds exhibited $GI_{50}$ values of ≤10 μM against the majority of the human cancer cell lines in the panel.

Carbamate analogs of MMB were prepared by reaction of the p-nitrophenyloxycarbonyl ester of MMB[13] with a variety of primary and secondary heterocyclic amines containing pyrrolidine, morpholine, piperidine, imidazole, triazole and pyridine moieties, to afford carbamate products 6a-6g[14] with generally improved water-solubility (Scheme 4, Table 1) compared to MMB. The key p-nitrophenyloxycarbonyl ester of MMB was prepared by the reaction of MMB with p-nitrophenylchloroformate in the presence of triethylamine. All conjugation reactions were carried out at ambient temperature in dichloromethane. We have reported previously that the reaction of sesquiterpenes containing an exocyclic double bond attached to the 13-position of the 5-membered lactone ring with primary and secondary amines leads to the facile formation of Michael addition products.[15] However, under the reaction conditions employed in Scheme 4, the rate of O-carbamoylation appears to be much faster than the rate of C-13 Michael addition, and only in a few cases, with amines such as 2-morpholinoethylamine, 2-piperidinoethylamine and 3-aminopropylimidazole, were Michael addition byproducts observed (usually in low yields of 5-10%), due likely to the high nucleophilicity of these amines.

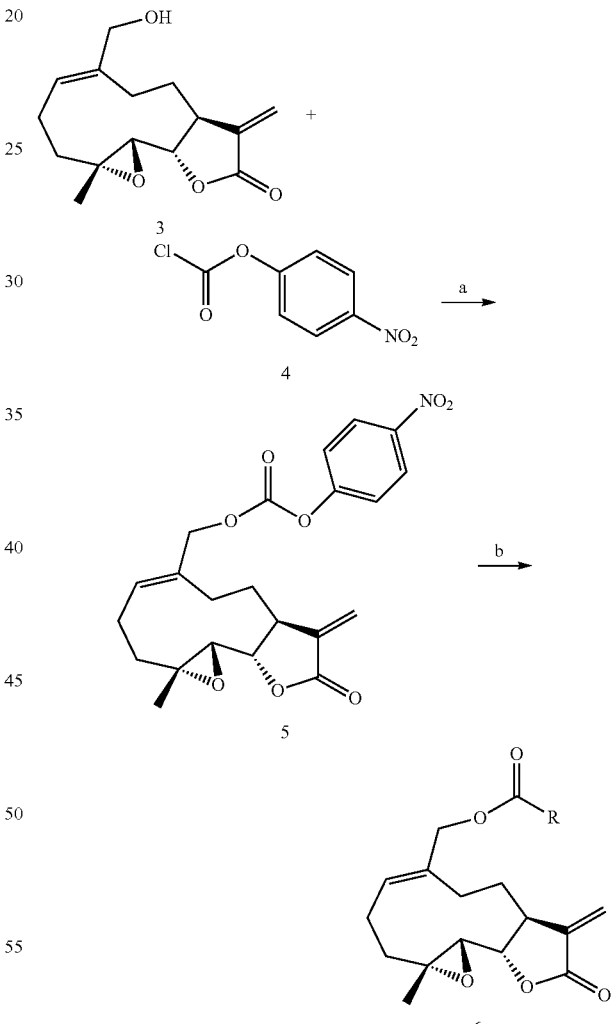

Scheme 4. Synthesis of carbamoylated MMB analogs 6a-6g: Reagents and conditions: (a) $CH_2Cl_2$, triethylamine, rt, 24 h; (b) $CH_2Cl_2$, heterocyclic amines, rt, 5-12 h.

All compounds were purified by column chromatography (silica gel; methanol/dichloromethane) to afford pure compounds in 50-75% yield. The synthesized compounds were fully characterized by $^1H$ NMR, $^{13}C$ NMR and high resolution mass spectral analysis.[14]

TABLE 1

Structures, reaction conditions, yields, and melting points for carbamate analogs of melampomagnolide B

| Amine | Product | Yield (%) | Time (h) | Mp (° C.) |
|---|---|---|---|---|
| 4,4-difluoropiperidine | 6a | 50 | 12 | 150 |
| 2-(pyrrolidin-1-yl)ethanamine | (structure) | 67 | 12 | 50 |
| 2-(pyridin-2-yl)ethanamine | 6c | 72 | 8 | 150 |
| 2-morpholinoethanamine | 6d | 65 | 6 | 80 |

TABLE 1-continued

Structures, reaction conditions, yields, and melting points for carbamate analogs of melampomagnolide B

| Amine | Product | Yield (%) | Time (h) | Mp (° C.) |
|---|---|---|---|---|
| (structure of amine for 6e) | 6e | 70 | 8 | 107 |
| (structure of amine for 6f) | 6f | 75 | 5 | 70 |
| (structure of amine for 6g) | 6g | 68 | 8 | 60 |

The above carbamate analogs were evaluated for growth inhibition properties against a panel of 60 human cancer cell lines derived from nine human cancer cell types, grouped into disease sub-panels that represent leukemia, lung, colon, central nervous system (CNS), melanoma, renal, ovary, breast, and prostate cancer cells. Growth inhibitory ($GI_{50}$) effects were measured as a function of the variation of optical density as a percentage of control.[16,17] Initial screening assays were carried out at a single concentration of 10 µM. Five analogs, 6a-6e, were identified as hits based on their ability to inhibit by 60% the growth of at least 8 of the 60 tumor cell lines in the panel. These five analogs were then evaluated in 5-dose assays over the concentration range $10^4$-$10^8$ µM, and their $GI_{50}$ values against the tumor cell lines in the panel determined (Table 2). Two analogs, 6a and 6e, were identified as lead compounds and generally exhibited improved growth inhibition against all human tumor cell lines when compared to PTL (1) and DMAPT (2), with the exception of the leukemia cell line subpanel; in these cell lines, the $GI_{50}$ values for DMAPT compared very favorably with those for both 6a and 6e. Compound 6a exhibited potency against leukemia cell line CCRF-CEM, melanoma cell line MDA-MB-435 and breast cancer cell line MDA-MB-468 in the nanomolar range with $GI_{50}$ values of 680, 460 and 570 nM, respectively. Compound 6e was found to possess potent anti-leukemic activity against leukemia cell line CCRF-CEM, non-small cell lung cancer cell line HOP-92 and renal cancer cell line RXF 393 with $GI_{50}$ values of 620, 650 and 900 nM, respectively, (Table 2).

Compounds 6a and 6e also exhibited significant growth inhibition against the following sub-panels of human cancer cell lines: non-small cell lung cancer ($GI_{50}$ values 0.65-1.45 µM); colon cancer ($GI_{50}$ values 1.12-2.06 µM); melanoma ($GI_{50}$ values 0.46-2.84 µM); renal cancer ($GI_{50}$ values 0.90-2.60 µM); and breast cancer ($GI_{50}$ values 0.57-3.07 µM) (Table 2).

We have determined the hydrolytic stability of the above five carbamate derivatives in human plasma and have shown that compounds 6b-6e have half-lives in the range 100-180 min, while compound 6a has a much longer half-life of 8 h in human plasma. Thus, we consider compounds 6b-6d to be anticancer agents that are also metabolized by plasma esterases to the active parent compound MMB, while compound 6a would be considered a more potent anticancer agent than MMB that is likely not metabolized to MMB in vivo.

The above results are interesting for a number of reasons: first, the antileukemic activities of 6a and 6e against the sub-panel of human leukemia cells indicates that these carbamate analogs of MMB are more potent than the parent compound. Second, the potent growth inhibition of human solid tumor cell lines by 6a and 6e is the first report of such activities for MMB analogs.

Third, these interesting results indicate that structural modification of the MMB molecule through appropriate carbamoylation of the primary hydroxyl group can lead to an improvement in the anticancer properties of MMB.

Figure 9:
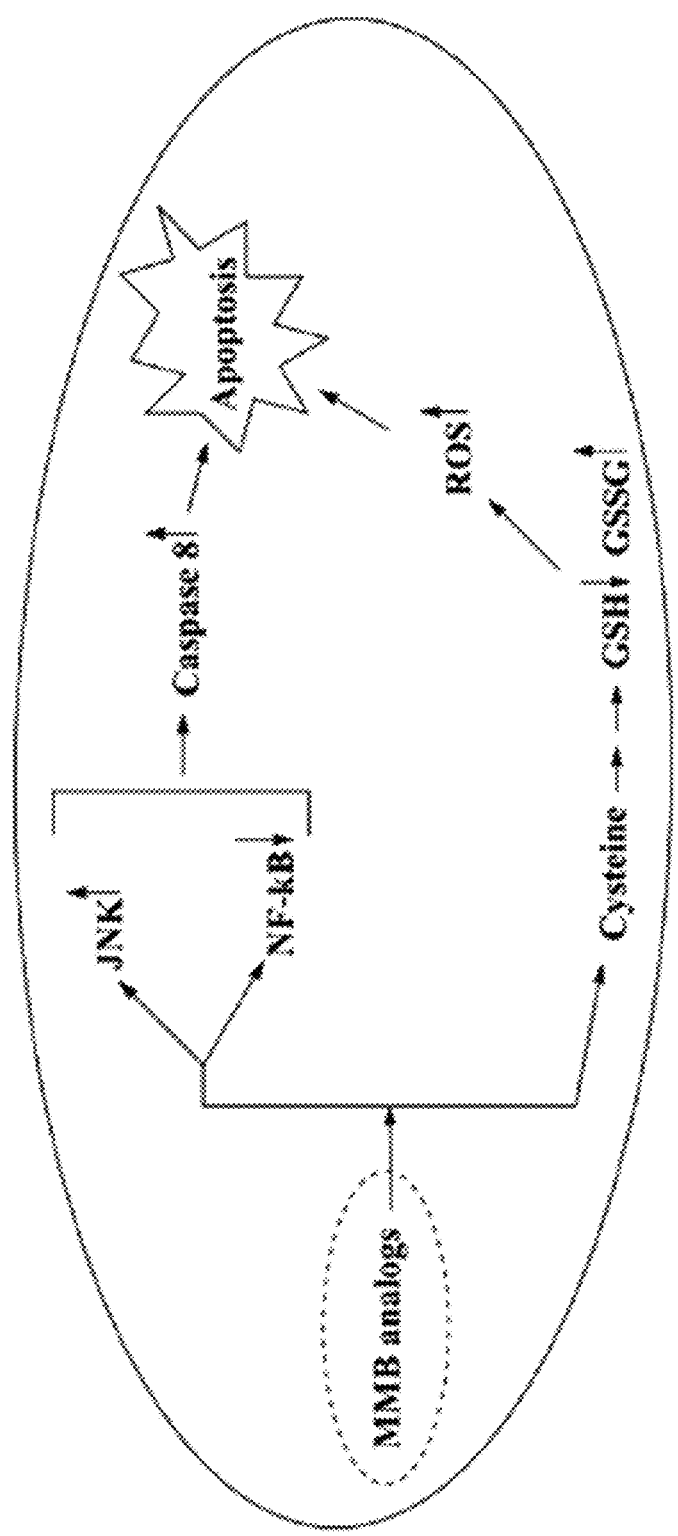
FIG. 9 shows the cytotoxic mechanism of action of MMB analogs.

The above MMB analogs, like PTL and DMAPT, are inhibitors of the NFκB pathway, activators of the nuclear kinase JNK, and selectively deplete glutathione levels in hematopoietic cancer stem cells, leading to an increase in reactive oxygen species (ROS) and subsequent apoptosis (FIG. 9).[4,8,11] We have recently shown that hematopoietic cancer stem cells have lower levels of reduced glutathione (GSH) and increased levels of oxidized glutathione (GSSG) when compared to normal stem cells, and are thus more vulnerable to agents such PTL and MMB and its analogs that induce oxidative stress through generation of ROS.[11] Specifically, PTL and MMB analogs inhibit several crucial enzymes in the glutathione pathway (i.e., GCLC and GPX1) leading to severe depletion of cellular glutathione and resulting in oxidative stress and apoptosis.

In summary, we have reported on a series of novel carbamate derivatives of MMB derived from heterocyclic and heteroaromatic amines. Among these derivatives, compounds 6a and 6e have been identified as potent anticancer agents with growth inhibition activities in the nanomolar range against a variety of hematological and solid tumor cell lines. Analogs 6a and 6e exhibit promising anti-leukemic activity against human leukemia cell line CCRF-CEM with $GI_{50}$ values of 680 and 620 nM, respectively. Compound 6a also exhibits $GI_{50}$ values of 460 and 570 nM against MDA-MB-435 melanoma and MDA-MB-468 breast cancer cell lines, respectively, and 6e has $GI_{50}$ values of 650 and 900 nM against HOP-92 non-small cell lung and RXF 393 renal cancer cell lines, respectively. Further structure-activity relationship studies will focus on the structural optimization of these interesting lead analogs and on the molecular basis for their mechanism of action.

TABLE 2

Growth inhibition ($GI_{50}$; μM)[b] data for PTL (1), DMAPT (2) and carbamoylated MMB analogs 6a-6e against a panel of human cancer cell lines

| Panel/cell line | 1a[a] $GI_{50}$ | 2a[a] $GI_{50}$ | 6a $GI_{50}$ | 6b $GI_{50}$ | 6c $GI_{50}$ | 6d $GI_{50}$ | 6e $GI_{50}$ |
|---|---|---|---|---|---|---|---|
| Leukemia | | | | | | | |
| CCRF-CEM | 7.94 | 1.99 | 0.68 | 2.49 | 2.65 | 3.03 | 0.62 |
| HL-60(TB) | 5.01 | 1.58 | 2.04 | 4.15 | ND | 3.59 | ND |
| K-562 | 19.9 | 2.51 | 3.45 | 3.26 | ND | 3.37 | ND |
| MOLT-4 | 15.8 | 3.16 | 2.05 | 3.48 | 5.54 | 5.00 | 2.32 |
| RPMI-8226 | 7.94 | 2.51 | 1.98 | 8.71 | 8.20 | 5.72 | 2.57 |
| SR | ND[c] | ND | 1.38 | 10.2 | 4.10 | 3.65 | 2.36 |
| Non-small cell lung cancer | | | | | | | |
| HOP-92 | 12.5 | 10.0 | 1.45 | 2.25 | 2.25 | 2.30 | 0.65 |
| NCI-H522 | 5.01 | 2.51 | 1.25 | 1.78 | 1.64 | 2.13 | 1.26 |
| Colon cancer | | | | | | | |
| COLO 205 | 15.8 | 31.6 | 2.06 | 4.78 | 3.54 | 8.89 | 1.79 |
| HCT-116 | 10.0 | 5.01 | 1.41 | 3.18 | 1.89 | 2.87 | 1.13 |
| SW-620 | 15.8 | 3.98 | 1.46 | 3.46 | 3.13 | 3.48 | 1.12 |
| CNS cancer | | | | | | | |
| SF-539 | 19.9 | 2.51 | 1.98 | 15.0 | 5.77 | 14.4 | 1.76 |
| SNB-75 | 50.1 | ND | 6.13 | 18.0 | 3.78 | 19.5 | 1.71 |
| Melanoma | | | | | | | |
| LOX IMVI | 7.94 | 10.0 | 2.23 | 7.88 | 4.96 | 4.84 | 1.95 |
| MALME-3M | 12.5 | ND | 1.90 | 4.18 | 7.52 | 6.12 | 2.32 |
| M14 | ND | 15.8 | 2.84 | 9.65 | 5.58 | 7.97 | 1.59 |
| MDA-MB-435 | ND | 7.94 | 0.46 | 6.56 | 6.01 | 5.89 | 2.24 |
| Ovarian cancer | | | | | | | |
| IGROV1 | 19.9 | 19.9 | 2.31 | 4.09 | 14.4 | 3.49 | 3.66 |
| OVCAR-3 | 19.9 | 12.5 | 1.69 | 8.41 | ND | 6.20 | ND |
| Renal cancer | | | | | | | |
| ACHN | ND | 15.8 | 1.79 | 3.80 | 2.75 | 3.74 | 1.75 |
| CAKI-1 | 10.0 | 12.5 | 2.03 | 6.86 | 2.88 | 4.31 | 1.99 |
| RXF 393 | 12.5 | 15.8 | 1.20 | 4.08 | 2.22 | 3.00 | 0.90 |
| TK-10 | ND | 3.16 | 2.60 | 3.11 | 3.78 | 3.93 | 2.51 |

TABLE 2-continued

Growth inhibition (GI$_{50}$; μM)[b] data for PTL (1), DMAPT (2) and carbamoylated MMB analogs 6a-6e against a panel of human cancer cell lines

| Panel/cell line | 1a[a] GI$_{50}$ | 2a[a] GI$_{50}$ | 6a GI$_{50}$ | 6b GI$_{50}$ | 6c GI$_{50}$ | 6d GI$_{50}$ | 6e GI$_{50}$ |
|---|---|---|---|---|---|---|---|
| Prostate cancer | | | | | | | |
| DU-145 | ND | 5.01 | 2.44 | 7.42 | 4.59 | 3.74 | 3.49 |
| Breast cancer | | | | | | | |
| MCF7 | 15.8 | 5.01 | 1.62 | 3.91 | 2.85 | 3.54 | 1.33 |
| BT-549 | ND | 5.01 | 2.69 | 4.75 | 2.60 | 4.99 | 1.47 |
| T-47D | ND | 39.8 | 3.07 | 4.86 | 6.19 | 6.32 | 2.23 |
| MDA-MB-468 | ND | ND | 0.57 | 2.30 | 3.22 | 3.26 | 1.29 |

GI$_{50}$ values < 1 μM are bolded.
[a]GI$_{50}$ values obtained from NCI database.
[b]GI$_{50}$, concentration of analog (μM) that halves cellular growth.
[c]ND not determined.

REFERENCES AND NOTES FOR EXAMPLE 19

1. Knight, D. W. *Nat. Prod. Rep.* 1995, 12, 271.
2. (a) Skalska, J.; Brookes, P. S.; Nadtochiy, S. M.; Hilchey, S. P.; Jordan, C. T.; Guzman, M. L.; Maggirwar, S. B.; Briehl, M. M.; Bernstein, S. H. *PLoS ONE* 2009, 4, e8115; (b) Shama, N.; Crooks, P. A. *Bioorg. Med. Chem. Lett.* 2008, 18, 3870; (c) Hewamana, S.; Alghazal, S.; Lin, T. T.; Clement, M.; Jenkins, C.; Guzman, M. L.; Jordan, C. T.; Neelakantan, S.; Crooks, P. A.; Burnett, A. K.; Pratt, G.; Fegan, C.; Rowntree, C.; Brennan, P.; Pepper, C. *Blood* 2008, 111, 4681; (d) Oka, D.; Nishimura, K.; Shiba, M.; Nakai, Y.; Arai, Y.; Nakayama, M.; Takayama, H.; Inoue, H.; Okuyama, A.; Nonomura, N. *Int. J. Cancer* 2007, 120, 2576.
3. (a) Bork, P. M.; Schmitz, M. L.; Kuhnt, M.; Escher, C.; Heinrich, M. *FEBS Lett.* 1997, 402, 85; (b) Wen, J.; You, K. R.; Lee, S. Y.; Song, C. H.; Kim, D. G. *J. Biol. Chem.* 2002, 277, 38954; (c) Hehner, S. P.; Heinrich, M.; Bork, P. M.; Vogt, M.; Ratter, F.; Lehmann, V.; Schulze-Osthoff, K.; Dröge, W.; Schmitz, M. L. *J. Biol. Chem.* 1998, 273, 1288; (d) Sweeney, C. J.; Li, L.; Shanmugam, R.; Bhat-Nakshatri, P. B.; Jayaprakasan, V.; Baldridge, L. A.; Gardner, T.; Smith, M.; Nakshatri, H.; Cheng, L. *Clin. Cancer Res.* 2004, 10, 5501; (e) Yip-Schneider, M. T.; Nakshatri, H.; Sweeney, C. J.; Marshall, M. S.; Wiebke, E. A.; Schmidt, C. M. *Mol. Cancer Ther.* 2005, 4, 587; (f) Nozaki, S.; Sledge, G. W.; Nakshatri, H. *Oncogene* 2001, 20, 2178.
4. Guzman, M. L.; Rossi, R. M.; Karnischky, L.; Li, X.; Peterson, D. R.; Howard, D. S.; Jordan, C. T. *Blood* 2005, 105, 4163.
5. (a) Guzman, M. L.; Jordan, C. T. *Expert Opin. Biol. Ther.* 2005, 5, 1147; (b) Dai, Y.; Guzman, M. L.; Chen, S.; Wang, L.; Yeung, S. K.; Pei, X. Y.; Dent, P.; Jordan, C. T.; Grant, S. *Br. J. Haematol.* 2010, 151, 70; (c) Kim, Y. R.; Eom, J. I.; Kim, S. J.; Jeung, H. K.; Cheong, J. W.; Kim, J. S.; Min, Y. H. *J. Pharmacol. Exp. Ther.* 2010, 335, 389.
6. Deschler, B.; Lubbert, M. *Cancer* 2006, 107, 2099.
7. (a) Estey, E.; Dohner, H. *Lancet* 2006, 368, 1894; (b) Lowenberg, B.; Suciu, S.; Archimbaud, E.; Haak, H.; Stryckmans, P.; De Cataldo, R.; Dekker, A. W.; Berneman, Z. N.; Thyss, A.; Van der Lelie, J.; Sonneveld, P.; Visani, G.; Fillet, G.; Hayat, M.; Hagemeijer, A.; Solbu, G.; Zittoun, R. *J. Clin. Oncol.* 1998, 16, 872; (c) Tazzari, P. L.; Cappellini, A.; Ricci, F.; Evangelisti, C.; Papa, V.; Grafone, T.; Martinelli, G.; Conte, R.; Cocco, L.; McCubrey, J. A.; Martelli, A. M. *Leukemia* 2007, 21, 427.
8. Pei, S.; Minhajuddin, M.; Callahan, K. P.; Balys, M.; Ashton, J. M.; Neering, S. J.; Lagadinou, E. D.; Corbett, C.; Ye, H.; Liesveld, J. L.; O'Dwyer, K. M.; Li, Z.; Shi, L.; Greninger, P.; Settleman, J.; Benes, C.; Hagen, F. K.; Munger, J.; Crooks, P. A.; Becker, M. W.; Jordan, C. T. *J. Biol. Chem.* 2013, 288, 33542.
9. El-Feraly, F. S. *Phytochemistry* 1984, 23, 2372.
10. Macias, F. A.; Galindo, J. C. G.; Massanet, G. M. *Phytochemistry* 1992, 31, 1969.
11. Shama, N.; ShanShan, P.; Fred, K. H.; Craig, T. J.; Peter, A. C. *Bioorg. Med. Chem.* 2011, 19, 1515.
12. Guzman, M. L.; Rossi, R. M.; Neelakantan, S.; Li, X.; Corbett, C. A.; Hassane, D. C.; Becker, M. W.; Bennett, J. M.; Sullivan, E.; Lachowicz, J. L.; Vaughan, A.; Sweeney, C. J.; Matthews, W.; Carroll, M.; Liesveld, J. L.; Crooks, P. A.; Jordan, C. T. *Blood* 2007, 110, 4427.
13. Synthetic procedure and analytical data for the p-nitrophenyloxycarbonyl ester of MMB (5): To the reaction mixture of MMB (100 mg, 0.378 mmol) and triethylamine (45.8 mg, 0.454 mmol) in dichloromethane (2 mL), p-nitrophenylchloroformate (76.3 mg, 0.378 mmol) was added at 0° C. The reaction mixture was stirred for 24 h at ambient temperature. When the reaction was completed (monitored by TLC), water was added to the reaction mixture and the aqueous mixture was extracted with dichloromethane. The organic layer was washed with water, followed by brine solution, dried over anhydrous Na2SO4 and concentrated to afford the crude product. The crude product was purified by column chromatography (silica gel, 2% methanol in dichloromethane) to afford compound 5 as a pale yellow solid. $^1$H NMR (CDCl3, 400 MHz): o 8.26 (d, J=9.6 Hz, 2H), 7.37 (d, J=9.8 Hz, 2H), 6.25 (s, 1H), 5.83 (t, J=8.4 Hz, 1H), 5.56 (s, 1H), 4.81 (d, J=12.8 Hz, 1H), 4.72 (d, J=12.4 Hz, 1H), 3.86 (m, 1H), 2.85 (m, 2H), 2.56 (m, 7H), 1.77 (m, 2H), 1.55 (s, 1H), 1.16 (t, J=13.2 Hz, 1H). $^{13}$C NMR (CDCl3, 100 MHz): o 169.1, 155.2, 152.2, 145.4, 138.6, 133.6, 132.8, 125.3, 121.5, 120.3, 80.8, 71.5, 63.1, 59.8, 42.7, 36.4, 25.6, 24.9, 23.9, 17.9 ppm.
14. General synthetic procedure and analytical data for carbamate derivatives of MMB: To the p-nitrophenyloxycarbonyl ester derivative of MMB (5) (70 mg, 0.16 mmol) in dichloromethane (2 mL), the appropriate amine (0.16 mmol) was added at 0° C. The reaction mixture was stirred for 18 h at ambient temperature. When the reaction was completed (monitored by TLC), water was added to the reaction mixture and the aqueous mixture was extracted with dichloromethane. The organic layer was washed with water, followed by brine solution, dried over anhydrous $Na_2SO_4$ and concentrated to afford the crude product. The crude product was purified by column chromatography (silica gel, 5% methanol in dichloromethane) to afford the carbamate analogs (6a-g) as white solids. ((1aR,7aS,10aS,10bS,E)-1a-methyl-8-methylene-9-oxo-1a,2,3,6,7,7a,8,9,10a,10b-decahydrooxireno[2',3':9,10]cyclodeca[1,2-b]furan-5-yl)methyl-4,4-difluoropiperidine-1-carboxylate (6a): $^1$H NMR (CDCl$_3$), 400 MHz): o 6.27 (d, J=2.8 Hz, 1H), 5.67 (t, J=8.4 Hz, 1H), 5.56 (s, 1H), 4.69 (d, J=12.4 Hz, 1H), 4.52 (d, J=12 Hz, 1H), 3.87 (t, J=9.6 Hz, 1H), 3.60 (br s, 4H), 2.87 (d, J=9.2 Hz, 2H), 2.50-2.16 (m, 6H), 1.96 (br s, 4H), 1.71 (t, J=10 Hz, 1H), 1.55 (s, 3H), 1.14 (t, J=12 Hz, 1H). $^{13}$C NMR (CDCl3, 100 MHz): o 169.4, 154.8, 138.7, 135.3, 129.9, 121.5, 120.5 (t, JCF=5.3 Hz, 1C), 81.1, 67.7, 63.4, 60.0, 42.7, 41.0, 36.7, 34.0, 25.8, 24.4, 23.9, 18.1 ppm. HRMS (ESI) m/z calcd for $C_{21}H_{28}F_2NO_5$ (M+H)$^+$ 412.1930. found 412.1933. ((1aR,7aS,10aS,10bS,E)-1a-methyl-8-methylene-9-oxo-1a,2,3,6,7,7a,8,9,10a,10b-decahydrooxireno[2',3':9,10]cyclodeca[1,2-b]furan-5-yl)methyl-(2-(pyrrolidin-1-yl)ethyl)carbamate (6b): $^1$H NMR (CDCl3, 400 MHz): o 6.22 (d, J=3.2 Hz, 1H), 5.65 (t, J=7 Hz, 1H), 5.55 (s, 1H), 4.62 (d, J=11.6 Hz, 1H), 4.47 (d, J=12.4 Hz, 1H), 3.82 (t, J=9.6 Hz, 1H), 3.35 (s, 2H), 2.90-2.83 (m, 2H), 2.70 (s, 4H), 2.42 (d, J=9.6 Hz, 2H), 2.38-2.13 (m, 7H) 1.84 (s, 4H), 1.66 (t, J=12 Hz, 1H), 1.52 (s, 3H), 1.13 (t, J=11.6 Hz, 1H). $^{13}$C NMR (CDCl$_3$, 100 MHz): δ 169.3, 156.1, 138.6, 135.3, 129.8, 120.1, 80.9, 67.0, 63.1, 59.8, 55.1, 53.8, 42.5, 38.9, 36.5, 25.6, 24.3, 23.6, 23.2, 17.8 ppm. HRMS (ESI) m/z calcd for $C_{22}H_{33}N_2O_5$ (M+H)$^+$ 405.2384. found 405.2390. ((1aR,7aS,10aS,10bS,E)-1a-methyl-8-methylene-9-oxo-1a,2,3,6,7,7a,8,9,10a,10b-decahydrooxireno[2',3':9,10]cyclodeca[1,2-b]furan-5-yl)methyl-(2-(pyridin-2-yl)ethyl)carbamate (6c): $^1$H NMR (CDCl$_3$, 400 MHz): δ 8.50 (s, 1H), 7.62 (t, J=7.2 Hz, 1H), 7.15 (d, J=7.6 Hz, 2H), 6.19 (s, 1H), 5.64 (t, J=8 Hz, 1H), 5.56-5.56 (m, 2H), 4.62 (d, J=12.4 Hz, 1H), 4.44 (d, J=12.8 Hz, 1H), 3.84 (t, J=9.2 Hz, 1H), 3.60 (d, J=6 Hz, 2H), 2.99-2.82 (m, 4H), 2.41-2.12 (m, 5H), 1.75 (s, 1H), 1.64 (d, J=10.4 Hz, 1H), 1.52 (s, 3H), 1.07 (t, J=13.6 Hz, 1H). $^{13}$C NMR (CDCl3, 100 MHz): o 169.3, 159.1, 156.0, 149.1, 138.6, 136.6, 135.5, 129.9, 123.4, 121.6, 120.2, 81.0, 67.0, 63.2, 59.8, 42.5, 40.1, 37.1, 36.6, 25.8, 24.4, 23.7, 17.9 ppm. HRMS (ESI) m/z calcd for $C_{23}H_{29}N_2O_5$ (M+H)$^+$ 413.2071. found 413.2073. ((1aR,7aS,10aS,10bS,E)-1a-methyl-8-methylene-9-oxo-1a,2,3,6,7,7a,8,9,10a,10b-decahydrooxireno[2',3':9,10]-cyclodeca[1,2-b]furan-5-yl)-methyl(2-morpholino ethyl) carbamate (6d): $^1$H NMR (CDCl$_3$, 400 MHz): δ 6.11 (d, J=3.6 Hz, 1H), 5.58 (t, J=8 Hz, 1H), 5.43 (d, J=2.8 Hz, 1H), 5.06 (s, 1H), 4.53 (d, J=12.4 Hz, 1H), 4.34 (d, J=12 Hz, 1H), 3.74 (t, J=8.8 Hz, 1H), 3.56 (s, 4H), 3.16 (t, J=5.2 Hz, 2H), 2.78-2.72 (m, 2H), 2.32 (s, 8H), 2.21-2.00 (m, 4H), 1.55 (t, J=10.4 Hz, 1H), 1.41 (s, 3H), 1.01 (t, J=12 Hz, 1H). $^{13}$C NMR (CDCl3, 100 MHz): δ 169.2, 155.9, 138.7, 135.4, 130.2, 120.0, 80.9, 67.0, 66.7, 63.1, 59.8, 57.2, 53.1, 42.5, 37.0, 36.5, 25.7, 24.4, 23.7, 17.8 ppm. HRMS (ESI) m/z calcd for $C_{22}H_{33}N_2O_6$ (M+H)$^+$ 421.2333. found 421.2331. ((1aR,7aS,10aS,10bS,E)-1a-methyl-8-methylene-9-oxo-1a,2,3,6,7,7a,8,9,10a,10b-decahydrooxireno[2',3':9,10]cyclodeca[1,2-b]furan-5-yl)methyl-(5-(methylthio)-1H-1,2,4-triazol-3-yl)carbamate (6e): $^1$H NMR (CDCl$_3$, 400 MHz): δ 6.22 (s, 2H), 5.82 (t, J=8 Hz, 1H), 5.50 (s, 1H), 4.90 (d, J=12.4 Hz, 1H), 4.81 (d, J=12.4 Hz, 1H), 3.85 (t, J=9.6 Hz, 1H), 2.95 (s, 1H), 2.85 (d, J=9.2 Hz, 1H), 2.48-2.15 (m, 8H), 1.70-1.53 (m, 6H), 1.13 (t, J=12.4 Hz, 1H) ppm. $^{13}$C NMR (CDCl$_3$, 100 MHz): δ 169.1, 163.1, 157.4, 149.9, 138.5, 133.3, 132.7, 120.2, 80.7, 70.1, 62.9, 59.7, 42.4, 36.2, 25.6, 24.3, 23.7, 17.8, 13.5 ppm. HRMS (ESI) m/z calcd for $C_{19}H_{25}N_4O_5S$ (M+H)$^+$ 421.1540. found 421.1524. ((1aR,7aS,10aS,10bS,E)-1a-methyl-8-methylene-9-oxo-1a,2,3,6,7,7a,8,9,10a,10b-decahydrooxireno[2',3':9,10]cyclodeca[1,2-b]furan-5-yl)methyl-(3-(1H-imidazol-1-yl)-propyl) carbamate (6f): $^1$H NMR (CDCl$_3$, 400 MHz): δ 7.56 (s, 1H), 7.09 (s, 1H), 6.95 (s, 1H), 6.26 (d, J=3.6 Hz, 1H), 5.69 (t, J=8 Hz, 1H), 5.56 (d, J=3.2 Hz, 1H), 4.85 (s, 1H), 4.64 (d, J=12.4 Hz, 1H), 4.51 (d, J=12.4 Hz, 1H), 4.04 (t, J=7.2 Hz, 2H), 3.88 (d, J=9.2 Hz, 1H), 3.21 (d, J=6 Hz, 2H), 2.93-2.85 (m, 2H), 2.47-2.16 (m, 7H), 2.03 (t, J=6.4 Hz, 1H) 1.70 (t, J=10.8 Hz, 1H), 1.55 (s, 3H), 1.15 (t, J=12.4 Hz, 1H). $^{13}$C NMR (CDCl3, 100 MHz): δ 169.5, 156.3, 138.9, 137.1, 135.3, 130.4, 129.6, 120.2, 118.8, 81.1, 67.3, 63.3, 60.0, 44.4, 42.7, 38.3, 36.7, 31.5, 25.8, 24.6, 23.8, 18.0 ppm. HRMS (ESI) m/z calcd for $C_{22}H_{30}N_3O_5$ (M+H)$^+$ 416.2180. found 416.2183. ((1aR,7aS,10aS,10bS,E)-1a-methyl-8-methylene-9-oxo-1a,2,3,6,7,7a,8,9,10a,10b-decahydrooxireno[2',3':9,10]-cyclodeca[1,2-b]furan-5-yl)methyl-(3-morpholinopropyl) carbamate (6g) $^1$H NMR (CDCl3, 400 MHz): δ 6.23 (s, 1H), 5.74 (s, 1H), 5.65 (t, J=8 Hz, 1H), 5.54 (s, 1H), 4.58 (d, J=12 Hz, 1H), 4.48 (d, J=16 Hz, 1H), 3.85 (t, J=9.2 Hz, 1H), 3.72 (s, 4H), 3.27 (s, 2H), 2.89-2.83 (m, 2H), 2.46-2.11 (m, 12H), 1.69 (t, J=12 Hz 3H), 1.52 (s, 3H), 1.11 (t, J=12 Hz, 1H). $^{13}$C NMR (CDCl$_3$, 100 MHz): δ 169.5, 156.3, 138.9, 135.7, 129.9, 120.4, 81.2, 67.0, 66.9, 63.4, 60.1, 57.4, 53.6, 42.7, 36.8, 25.9, 25.5, 24.6, 23.9, 18.1 ppm. HRMS (ESI) m/z calcd for $C_{23}H_{35}N_2O_6$ (M+H)$^+$ 435.2490. found 435.2482.

15. Neelakantan, S.; Shama, N.; Guzman, M. L.; Jordan, C. T.; Crooks, P. A. *Bioorg. Med. Chem. Lett.* 2009, 19, 4346.

16. Boyd, M. R.; Paull, K. D. *Drug Dev. Res.* 1995, 34, 91.

17. Acton, E. M.; Narayanan, V. L.; Risbood, P. A.; Shoemaker, R. H.; Vistica, D. T.; Boyd, M. R. *J. Med. Chem.* 1994, 37, 2185.

TABLE 3

NCI five dose result for JVM 2-13

| Panel/Cell | Time Zero | Ctrl | Mean Optical Densities | | | | | Percent Growth | | | | |
|---|---|---|---|---|---|---|---|---|---|---|---|---|
| | | | −8.0 | −7.0 | −6.0 | −5.0 | −4.0 | −8.0 | −7.0 | −6.0 | −5.0 | −4.0 |

| Leukemia | | | | | | | | | | | | |
|---|---|---|---|---|---|---|---|---|---|---|---|---|
| CCRF-CEM | 0.522 | 2.168 | 2.231 | 2.319 | 2.052 | 0.584 | 0.306 | 104 | 109 | 93 | 4 | −41 |
| HL-60(TB) | 1.473 | 3.000 | 2.840 | 3.095 | 3.103 | 1.511 | 0.827 | 90 | 106 | 107 | 2 | −44 |
| K-562 | 0.204 | 1.321 | 1.323 | 1.268 | 1.246 | 0.196 | 0.119 | 100 | 95 | 93 | −4 | −42 |
| MOLT-4 | 0.650 | 1.937 | 1.938 | 2.138 | 1.868 | 0.739 | 0.331 | 100 | 116 | 95 | 7 | −49 |
| SR | 0.388 | 1.416 | 1.600 | 1.364 | 1.160 | 0.500 | 0205 | 118 | 95 | 75 | 11 | −47 |

| Non-Small Cell Lung Cancer | | | | | | | | | | | | |
|---|---|---|---|---|---|---|---|---|---|---|---|---|
| A549/ATCC | 0.339 | 1.916 | 1.837 | 1.878 | 1.826 | 1.679 | 0.167 | 95 | 98 | 94 | 85 | −51 |
| HOP-62 | 0.830 | 2.237 | 2.043 | 2.163 | 2.109 | 2069 | 0.190 | 86 | 95 | 91 | 88 | −77 |
| HOP-92 | 0.903 | 1.477 | 1.374 | 1.339 | 1.255 | 0.928 | 0.157 | 82 | 76 | 61 | 4 | −83 |
| NCI-H226 | 1084 | 2.589 | 2.572 | 2.523 | 2482 | 1.866 | 0.716 | 99 | 96 | 93 | 52 | −34 |
| NC I-H 23 | 0609 | 1.871 | 1.841 | 1.868 | 1.915 | 1.330 | 0.158 | 98 | 100 | 104 | 57 | −74 |
| NCI-H322M | 0.787 | 1.705 | 1.754 | 1.814 | 1.760 | 1.650 | 0.085 | 105 | 112 | 106 | 94 | −89 |
| NCI-H460 | 0.278 | 2.870 | 2.913 | 2.870 | 2.858 | 2.479 | 0.094 | 102 | 100 | 100 | 85 | −66 |
| NC I-H 522 | 0.886 | 2.041 | 2.030 | 2100 | 1.536 | 0290 | 0.313 | 99 | 105 | 56 | −67 | −65 |

| Colon Cancer | | | | | | | | | | | | |
|---|---|---|---|---|---|---|---|---|---|---|---|---|
| COLO 205 | 0.478 | 1.829 | 1.727 | 1.846 | 1.694 | 0.156 | 0.118 | 92 | 101 | 90 | −67 | −75 |
| HCC-2998 | 0.667 | 2.060 | 2.049 | 2.134 | 2.115 | 2.003 | 0.156 | 99 | 105 | 104 | 96 | −77 |
| HCT-116 | 0.307 | 2.533 | 2.413 | 2.486 | 2.183 | 0.428 | 0.025 | 95 | 96 | 84 | 5 | −92 |
| HCT-15 | 0.365 | 2.588 | 2.390 | 2.482 | 2.329 | 0.585 | 0.091 | 91 | 95 | 88 | 10 | −75 |
| HT29 | 0.241 | 1.276 | 1.278 | 1.279 | 1.322 | 0.343 | 0.060 | 100 | 100 | 104 | 10 | −75 |
| KM12 | 0.396 | 2 229 | 2 340 | 2.334 | 2.243 | 1.776 | 0.066 | 106 | 106 | 101 | 75 | −83 |
| SW-620 | 0.365 | 2.850 | 2.845 | 2.795 | 2.426 | 0.545 | 0.094 | 100 | 96 | 83 | 7 | −74 |

| CNS Cancer | | | | | | | | | | | | |
|---|---|---|---|---|---|---|---|---|---|---|---|---|
| SF-268 | 0.553 | 1.947 | 1.909 | 1.998 | 1.890 | 1 241 | 0.121 | 97 | 104 | 96 | 49 | −78 |
| SF-295 | 0.825 | 3.013 | 2 805 | 2.910 | 2.925 | 2.883 | 1.518 | 90 | 95 | 96 | 94 | 32 |
| SF-539 | 0.584 | 1.973 | 1.866 | 1.842 | 1.853 | 0.726 | 0.131 | 92 | 91 | 91 | 10 | −78 |
| SNB-19 | 0.636 | 2.182 | 2.148 | 2.128 | 2.116 | 1.957 | 0.182 | 98 | 97 | 96 | 85 | −71 |
| SNB-75 | 0767 | 1.519 | 1.328 | 1.334 | 1.316 | 1.161 | 0.028 | 75 | 75 | 73 | 52 | −96 |
| U251 | 0487 | 2.142 | 2.111 | 2.089 | 2.042 | 2.026 | 0.077 | 98 | 97 | 94 | 93 | −84 |

| Melanoma | | | | | | | | | | | | |
|---|---|---|---|---|---|---|---|---|---|---|---|---|
| LOX IMVI | 0.447 | 2.582 | 2.627 | 2.553 | 2462 | 1.540 | 0.073 | 102 | 99 | 94 | 51 | −84 |
| MALME-3M | 0.447 | 0.721 | 0.729 | 0.718 | 0.630 | 0.295 | 0.194 | 103 | 99 | 67 | −34 | −57 |
| M14 | 0.555 | 2.098 | 1.961 | 2.029 | 1.953 | 1.199 | 0.100 | 91 | 96 | 91 | 42 | −82 |
| MDA-MB-435 | 0.539 | 2.535 | 2.426 | 2.479 | 2282 | 1.073 | 0.039 | 95 | 97 | 87 | 27 | −93 |
| SK-MEL-2 | 1.239 | 2.246 | 2.280 | 2.373 | 2.372 | 2.123 | 0.302 | 103 | 113 | 113 | 88 | −76 |
| SK-MEL-28 | 0.552 | 1.525 | 1.505 | 1.524 | 1.429 | 0.685 | 0.106 | 98 | 100 | 90 | 14 | −81 |
| 8K-MEL-5 | 0.756 | 3.167 | 3.160 | 3.194 | 3.138 | 2.812 | 0.066 | 100 | 101 | 99 | 85 | −91 |
| UACC-257 | 1.097 | 2.320 | 2.243 | 2.227 | 2.154 | 1.516 | 0.150 | 94 | 92 | 86 | 34 | −86 |
| UACC-62 | 0.531 | 2 451 | 2.361 | 2.353 | 2.227 | 1.156 | 0.078 | 95 | 95 | 88 | 33 | −85 |

| Ovarian Cancer | | | | | | | | | | | | |
|---|---|---|---|---|---|---|---|---|---|---|---|---|
| IGROVI | 0.706 | 2.023 | 2.090 | 2.105 | 2.042 | 1.136 | 0295 | 105 | 106 | 101 | 33 | −58 |
| OVCAR-3 | 0.500 | 1.587 | 1.670 | 1.646 | 1.427 | 0.467 | 0.018 | 108 | 105 | 85 | −7 | −97 |
| OVCAR-5 | 0.744 | 1.531 | 1.408 | 1.430 | 1.389 | 1.165 | 0.105 | 84 | 87 | 82 | 53 | −86 |
| OVCAR-8 | 0.473 | 2.159 | 2.153 | 2.116 | 2.034 | 1.016 | 0.118 | 100 | 97 | 93 | 32 | −75 |
| NCI/ADR-RES | 0.594 | 2.034 | 2.079 | 2.128 | 2.073 | 1.956 | 0.659 | 103 | 107 | 103 | 95 | 4 |
| SK-OV-3 | 0.993 | 1.866 | 1.793 | 1.891 | 1.842 | 1.843 | 0497 | 92 | 103 | 97 | 97 | −50 |

| Renal Cancer | | | | | | | | | | | | |
|---|---|---|---|---|---|---|---|---|---|---|---|---|
| 786-0 | 0.540 | 2.168 | 1.944 | 1.992 | 2.001 | 0.917 | 0.138 | 86 | 89 | 90 | 23 | −74 |
| A498 | 1.702 | 2.460 | 2.255 | 2.193 | 2.243 | 2.163 | 0.135 | 73 | 65 | 71 | 61 | −92 |
| ACHN | 0.483 | 2.100 | 2.009 | 2.049 | 1.830 | 0.610 | 0097 | 94 | 97 | 83 | 8 | −80 |
| CAKI-1 | 0.661 | 2.943 | 2.695 | 2.769 | 2.490 | 1.205 | 0.014 | 89 | 92 | 80 | 24 | −98 |
| RXF 393 | 1.123 | 1.717 | 1.703 | 1.633 | 1.573 | 1 A79 | 0.175 | 98 | 86 | 76 | −4 | −84 |
| SN12C | 0.530 | 2.022 | 1.979 | 1.930 | 1.903 | 0.811 | 0.155 | 97 | 94 | 92 | 19 | −71 |
| TK-10 | 1.092 | 2.327 | 2.388 | 2.362 | 2.186 | 1.148 | 0.066 | 105 | 103 | 89 | 5 | −94 |
| UO-31 | 0.743 | 1.980 | 1.869 | 1.874 | 1.755 | 1.004 | 0.140 | 91 | 91 | 82 | 21 | −81 |

| Prostate Cancer | | | | | | | | | | | | |
|---|---|---|---|---|---|---|---|---|---|---|---|---|
| PC-3 | 0.611 | 1.933 | 1.891 | 1.885 | 1.860 | 1.665 | 0.167 | 97 | 96 | 94 | 80 | −73 |
| DU-145 | 0.516 | 1.901 | 2.040 | 2.014 | 1.912 | 0.892 | 0.018 | 110 | 108 | 101 | 27 | −97 |

TABLE 3-continued

| | | | Breast Cancer | | | | | | | | |
|---|---|---|---|---|---|---|---|---|---|---|---|
| MCF7 | 0.359 | 1.982 | 1.764 | 1.843 | 1.695 | 0.421 | 0.130 | 87 | 91 | 82 | 4 | −64 |
| MDA-MB-231/ATCC | 0.700 | 1.532 | 1.592 | 1.522 | 1.454 | 1.006 | 0.150 | 107 | 99 | 91 | 37 | −79 |
| HS 57BT | 1.189 | 2.174 | 2.098 | 2.042 | 2.065 | 1.917 | 0.996 | 92 | 87 | 89 | 74 | −16 |
| 81-549 | 1.266 | 2.258 | 2.089 | 2.143 | 2.151 | 1.606 | 0.051 | 83 | 88 | 89 | 34 | −96 |
| T-47D | 0.738 | 1.731 | 1.550 | 1.613 | 1.490 | 0.810 | 0.260 | 82 | 88 | 76 | 7 | −65 |
| MDA-MB-468 | 0.774 | 1.390 | 1.385 | 1.360 | 1.174 | 0.504 | 0.247 | 99 | 95 | 65 | −35 | −68 |

| NCI five dose result for JVM 2-13 | | | |
|---|---|---|---|
| Panel/Cell | $GI_{50}$ | TGI | $LC_{50}$ |
| Leukemia | | | |
| CCRF-CEM | 3.03E−6 | 1.21E−5 | >1.00E−4 |
| HL-60(TB) | 3.50E−6 | 1.13E−5 | >1.00E−4 |
| K-562 | 2.79E−6 | 9.11E−6 | >1.00E−4 |
| MOLT-4 | 322E−6 | 1.33E−5 | >1.00E−4 |
| SR | 246E−6 | 1.54E−5 | >1.00E−4 |
| Non-Small Cell LungCancer | | | |
| A549/ATCC | 1.81E−5 | 4.22E−5 | 9.85E−5 |
| HOP-62 | 1.70E−5 | 341E−5 | 6.85E−5 |
| HOP-92 | 1.58E−6 | 1.12E−5 | 4.21E−5 |
| NCI-H226 | 1.05E−5 | 4.02E−5 | >1.00E−4 |
| NC I-H 23 | 1.13E−5 | 2.72E−5 | 6.55E−5 |
| NCI-H322M | 1.74E−5 | 126E−5 | 6.11E−5 |
| NCI-H460 | 170E−5 | 3.65E−5 | 7.81E−5 |
| NC I-H 522 | 1.12E−6 | 2.86E−6 | 7.25E−6 |
| Colon Cancer | | | |
| COLO 205 | 1.79E−6 | 1.73E−6 | 7.75E−6 |
| HCC-2998 | 1.85E−5 | 3.60E−5 | 7.01E−5 |
| HCT-116 | 2.72E−6 | 1.14E−5 | 3.70E−5 |
| HCT-15 | 3.08E−6 | 1.31E−5 | 5.07E−5 |
| HT29 | 3.76E−6 | 1.30E−5 | 5.04E−5 |
| KM12 | 1.44E−5 | 2.98E−5 | 6.16E−5 |
| SW-620 | 2.72E−6 | 1.23E−5 | 5.03E−5 |
| CNS Cancer | | | |
| SF-268 | 9.67E−6 | 2.44E−5 | 6.02E−5 |
| SF-295 | 5.08E−5 | >1.00E−4 | >1.00E−4 |
| SF-539 | 3.23E−6 | 1.31E−5 | 4.84E−5 |
| SNB-19 | 1.68E−5 | 1.51E−5 | 7.31E−5 |
| SNB-75 | 1.04E−5 | 2.256E−5 | 4.88E−5 |
| U251 | 1.75E−5 | 1.35E−5 | 6.41E−5 |
| Melanoma | | | |
| LOX IMVI | 1.02E−5 | 2.39E−5 | 5.62E−5 |
| MALME-3M | 1.47E−6 | 4.60E−6 | 5.06E−5 |
| M14 | 6.78E−6 | a 17E−5 | 5.51E−5 |
| MDA-MB-435 | 4.13E−6 | 1.67E−5 | 4.38E−5 |
| SK-MEL-2 | 1.70E−5 | 3.44E−5 | 6.97E−5 |
| SK-MEL-28 | 3.35E−5 | 1.40E−5 | 4.72E−5 |
| 8K-MEL-5 | 1.58E−5 | 3.04E−5 | 5.83E−5 |
| UACC-257 | 4.99E−6 | 1.92E−5 | 4.99E−5 |
| UACC-62 | 4.86E−6 | 1.89E−5 | 5.01E−5 |
| Ovarian Cancer | | | |
| IGROVI | 5.59E−6 | 2.29E−5 | 8.12E−5 |
| OVCAR-3 | 2.42E−6 | 8.46E−6 | 3.04E−5 |
| OVCAR-5 | 1.06E−5 | 2.42E−5 | 5.52E−5 |
| OVCAR-8 | 5.07E−6 | 2.00E−5 | 5.84E−5 |
| NCI/ADR-RES | 3.12E−5 | >1.00E−4 | >1.00E−4 |
| SK-OV-3 | 2.10E−5 | 4.58E−5 | >1.00E−4 |
| Renal Cancer | | | |
| 786-0 | 3.95E−6 | 1.73E−5 | 5.62E−5 |
| A498 | 1.18E−5 | 2.50E−5 | 5.31E−5 |
| ACHN | 2.76E−6 | 1.23E−5 | 4.56E−5 |
| CAKI-1 | 3.43E−6 | 1.57E−5 | 4.04E−5 |
| RXF 393 | 2.11E−6 | 8.93E−6 | 3.73E−5 |
| SN12C | 3.75E−6 | 1.62E−5 | 5.85E−5 |
| TK-10 | 2.88E−6 | 1.11E−5 | 3.58E−5 |
| UO-31 | 3.34E−6 | 1.61E−5 | 4.95E−5 |

TABLE 3-continued

|  | Prostate Cancer | | |
| --- | --- | --- | --- |
| PC-3 | 1.57E−5 | 3.33E−5 | 7.09E−5 |
| DU-145 | 4.89E−6 | 1.66E−5 | 4.20E−5 |
|  | Breast Cancer | | |
| MCF7 | 2.58E−6 | 1.14E−5 | 6.25E−5 |
| MDA-MB-231/ATCC | 5.69E−6 | 2.08E−5 | 5.65E−5 |
| HS 57BT | 1.84E−5 | 6.60E−5 | >1.00E−4 |
| 81-549 | 5.18E−6 | 1.83E−5 | 4.43E−5 |
| T-47D | 2.38E−6 | 1.26E−5 | 6.24E−5 |
| MDA-MB-468 | 1.41E−6 | 4.47E−6 | 2.85E−5 |

TABLE 4

NCI five dose result for JVM 2-26

| Panel/Cell | Time | | Mean Optical Densities (Log10 Concentration) | | | | | Percent Growth (Log10 Concentration) | | | | |
| --- | --- | --- | --- | --- | --- | --- | --- | --- | --- | --- | --- | --- |
|  | Zero | Ctrl | −8.0 | −7.0 | −6.0 | −5.0 | −4.0 | −8.0 | −7.0 | −6.0 | −5.0 | −4.0 |
| Leukemia | | | | | | | | | | | | |
| CCRF-CEM | 0.539 | 1.748 | 1.686 | 1.649 | 1.443 | 0.410 | 0.235 | 95 | 92 | 75 | −24 | −56 |
| HL-60(TB) | 0.667 | 2.381 | 2.263 | 2.109 | 1.912 | 0.599 | 0.332 | 93 | 64 | 73 | −10 | −50 |
| K-562 | 0.612 | 2.207 | 2.211 | 2.139 | 2.097 | 0.760 | 0.355 | 100 | 96. | 93 | 9 | −42 |
| MOLT-4 | 0.957 | 2.229 | 2.288 | 2.258 | 2.136 | 1.246 | 0.475 | 105 | 102 | 93 | 23 | −50 |
| SR | 0.252 | 1.050 | 0.953 | 0.928 | 0.843 | 0.256 | 0.116 | 88 | 65 | 74 | . | −54 |
| Non-Small Cell Lung Cancer | | | | | | | | | | | | |
| A549/ATCC | 0.398 | 1.497 | 1.453 | 1.467 | 1.491 | 1.286 | 0.091 | 96 | 97 | 99 | 81 | −77 |
| HOP-62 | 0.830 | 1.813 | 1.752 | 1.708 | 1.694 | 1.639 | 0.071 | 94 | 69 | 88 | 82 | −91 |
| HOP-92 | 0.944 | 1.476 | 1.438 | 1.423 | 1.343 | 0.841 | 0.098 | 93 | 90 | 75 | −11 | −90 |
| NCI-H226 | 0.851 | 2 268 | 2.184 | 2.140 | 2.093 | 1.268 | 0.352 | 94 | 91 | 88 | 29 | −59 |
| NC I-H 23 | 0.672 | 1 999 | 1.901 | 1.960 | 1.972 | 1.537 | 0.174 | 93 | 97 | 98 | 65 | −74 |
| NCI-H322M | 0.888 | 2.208 | 2.081 | 2.043 | 1.991 | 1.858 | 0.654 | 90 | 67 | 84 | 73 | −26 |
| NCI-H460 | 0.386 | 3.181 | 3.242 | 3.224 | 3.159 | 2.718 | 0.129 | 102 | 102 | 99 | 83 | −67 |
| NC I-H 522 | 1.103 | 2.123 | 2.106 | 2.032 | 1.626 | 0.334 | 0.298 | 98 | 91 | 71 | −70 | −73 |
| Colon Cancer | | | | | | | | | | | | |
| COLO 205 | 0.527 | 1.454 | 1.469 | 1.433 | 1.335 | 0.136 | 0.066 | 102 | 96 | 87 | −74 | −88 |
| HCC-2998 | 0.568 | 1.899 | 1.844 | 1.873 | 1.954 | 1.571 | 0.082 | 96 | 96 | 104 | 75 | −86 |
| HCT-116 | 0.207 | 1.669 | 1.643 | 1.603 | 1.406 | 0.167 | −0.029 | 98 | 95 | 82 | −20 | −100 |
| HCT-15 | 0.284 | 2.300 | 2.209 | 2.064 | 1.676 | 0.334 | 0.029 | 96 | BB | 79 | 2 | −90 |
| KM12 | 0.508 | 2.616 | 2.500 | 2494 | 2.562 | 2.222 | 0.089 | 95 | 94 | 97 | 81 | −83 |
| SW-620 | 0.314 | 2.517 | 2.504 | 2.413 | 2.064 | 0.299 | 0.051 | 99 | 95 | 79 | −5 | −84 |
| CNS Cancer | | | | | | | | | | | | |
| SF-268 | 0.564 | 1.900 | 1.808 | 1.751 | 1.634 | 1.071 | 0.095 | 93 | 69 | 95 | 38 | −83 |
| SF-295 | 0.641 | 2.700 | 2.549 | 2.430 | 2.496 | 2.236 | 0.193 | 93 | 67 | 90 | 77 | −70 |
| SF-539 | 0.954 | 2.543 | 2.413 | 2.323 | 2.2134 | 0.903 | 0.062 | 92 | 136 | 84 | −5 | −94 |
| SNB-19 | 0.705 | 2.275 | 2.158 | 2.202 | 2.093 | 1.816 | 0.069 | 93 | 95 | 88 | 71 | −90 |
| SNB-75 | 0.763 | 1.468 | 1.350 | 1.245 | 1.226 | 0.958 | −0.035 | 83 | 613. | 66 | 28 | −100 |
| U251 | 0.597 | 1.953 | 1.891 | 1.908 | 1.944 | 1.805 | 0.088 | 95 | 97 | 99 | 89 | −85 |
| Melanoma | | | | | | | | | | | | |
| LOX IMVI | 0.316 | 2.170 | 2.021 | 2.035 | 2.042 | 0.441 | 0.027 | 92 | 93 | 93 | 7 | −91 |
| M14 | 0.452 | 1.609 | 1.588 | 1.520 | 1.479 | 0.714 | 0.020 | 98 | 92 | 89 | 23 | −96 |
| MDA-MB-435 | 0.554 | 2 487 | 2.440 | 2.244 | 2.167 | 0.809 | 0.030 | 98 | 67 | 83 | 13 | −95 |
| SK-MEL-2 | 1.069 | 2 062 | 2.070 | 2.097 | 2.046 | 1 639 | 0.145 | 101 | 104 | 98 | 57 | −86 |
| SK-MEL-28 | 0.627 | 1.704 | 1.682 | 1.616 | 1.563 | 0.867 | 0.028 | 98 | 92 | 22 | −96 | |
| 8K-MEL-5 | 0.621 | 2.527 | 2.429 | 2.443 | 2.363 | 1.650 | 0.003 | 95 | 96 | 92 | 54 | −100 |
| UACC-257 | 1.042 | 2.075 | 1.979 | 1.942 | 1.969 | 1.405 | 0.063 | 91 | 67 | 90 | 35 | −94 |
| UACC-62 | 0.774 | 2.950 | 2.844 | 2.834 | 2.676 | 1.778 | 0.025 | 95 | 95 | 87 | 46 | −97 |
| Ovarian Cancer | | | | | | | | | | | | |
| IGROVI | 0.763 | 2.283 | 2.288 | 2.256 | 2.315 | 1.765 | 0.264 | 100 | 96 | 102 | 66 | −65 |
| OVCAR-3 | 0.513 | 1.577 | 1.556 | 1.533 | 1.370 | 0.390 | −0.020 | 98 | 96 | 80 | −24 | −100 |
| OVCAR-4 | 0.665 | 1.453 | 1.419 | 1.320 | 1.226 | 0.715 | 0.069 | 96 | 63 | 71 | 6 | −90 |
| OVCAR-5 | 0.693 | 1.438 | 1.394 | 1.299 | 1.289 | 1.070 | 0.058 | 94 | 81 | 80 | 51 | −92 |

TABLE 4-continued

| | | | | | | | | | | | | |
|---|---|---|---|---|---|---|---|---|---|---|---|---|
| OVCAR-8 | 0.632 | 2.168 | 2.112 | 2.137 | 2.124 | 1.429 | 0.074 | 96 | 98 | 97 | 52 | −88 |
| NCI/ADR-RES | 0.494 | 1.777 | 1.700 | 1.714 | 1.720 | 1.489 | 0.298 | 94 | 95 | 96 | 78 | −40 |
| SK-OV-3 | 0.933 | 1.639 | 1.592 | 1.676 | 1.603 | 1.566 | 0.624 | 93 | 105 | 95 | 90 | −33 |
| Renal Cancer | | | | | | | | | | | | |
| 786-0 | 0.506 | 1.850 | 1.789 | 1.678 | 1.577 | 0.565 | 0.047 | 95 | 87 | 80 | 4 | −91 |
| A498 | 1.386 | 2.262 | 2.138 | 2.235 | 2.0613 | 1.827 | 0.016 | 86 | 97 | 78 | 50 | −99 |
| ACHN | 0.448 | 1.772 | 1.778 | 1.693 | 1.491 | 0.412 | 0.036 | 100 | 94 | 79 | −8 | −92 |
| CAKI-1 | 0.613 | 2.647 | 2.446 | 2.311 | 2.067 | 0.781 | −0.029 | 90 | 83 | 71 | 8 | −100 |
| RXF 393 | 0.735 | 1.328 | 1.310 | 1.307 | 1.227 | 0.694 | 0.079 | 97 | 96 | 83 | −6 | −89 |
| SN12C | 0.945 | 3.124 | 3.094 | 3.117 | 3.027 | 1.954 | 0.157 | 99 | 100 | 96 | 46 | −83 |
| TK-10 | 0.971 | 2.151 | 2.050 | 2.057 | 1.905 | 0.818 | −0.003 | 92 | 92 | 79 | −16 | −100 |
| UO-31 | 0.831 | 2.274 | 2.040 | 2.053 | 1.908 | 0.956 | 0.171 | 84 | 65 | 75 | 9 | −79 |
| Prostate Cancer | | | | | | | | | | | | |
| PC-3 | 0.671 | 1.511 | 1.458 | 1.449 | 1.416 | 1.228 | 0.075 | 94 | 93 | 89 | 66 | −89 |
| DU -145 | 0.354 | 1.511 | 1.483 | 1.478 | 1.394 | 0.478 | −0.005 | 98 | 97 | 90 | 11 | −100 |
| Breast Cancer | | | | | | | | | | | | |
| MCF7 | 0.349 | 1.939 | 1.799 | 1.738 | 1.575 | 0.386 | 0.099 | 91 | 67 | 77 | 2 | −72 |
| MDA-MB-231/ATCC | 0.612 | 1.405 | 1.427 | 1.382 | 1.309 | 0.783 | 0.113 | 103 | 97 | 88 | 22 | −82 |
| HS 57BT | 1.009 | 2.130 | 2.052 | 2.029 | 1.977 | 1.392 | 0.550 | 93 | 91 | 86 | 34 | −46 |
| 81-549 | 0.820 | 1.698 | 1.633 | 1.565 | 1.506 | 1.007 | −0.018 | 93 | 85 | 78 | 21 | −100 |
| T-47D | 0.857 | 1.527 | 1467 | 1.401 | 1.420 | 0.786 | 0.246 | 91 | 81 | 84 | −8 | −71 |
| MDA-MB-468 | 0.681 | 1.231 | 1.202 | 1.161 | 0.898 | 0.345 | 0.130 | 95 | 87 | 39 | −49 | −81 |

| | NCI five dose result for JVM 2-26 | | |
|---|---|---|---|
| Panel/Cell | GI50 | TGI | LC50 |
| Leukemia | | | |
| CCRF-CEM | 1.78E−6 | 5.72E−6 | 6.35E−5 |
| HL-60(TB) | 1.88E−6 | 7.53E−6 | 9.87E−5 |
| K-562 | 3.27E−6 | 1.52E−5 | >1.00E−4 |
| MOLT-4 | 4.07E−6 | 1.04E−5 | 9.87E−5 |
| SR | 2.12E−6 | 1.02E−5 | 8.39E−5 |
| Non-Small Cell Lung Cancer | | | |
| A549/ATCC | 1.57E−5 | 1.24E−5 | 6.72E−5 |
| HOP-62 | 1.53E−5 | 1.98E−5 | 5.77E−5 |
| HOP-92 | 1.96E−5 | 7.47E−6 | 3.14E−5 |
| NCI-H226 | 4.43E−6 | 2.16E−0 | 7.98E−5 |
| NC I-H 23 | 1.28E−5 | 2.94E−5 | 6.71E−5 |
| NCI-H322M | 1.72E−5 | 5.44E−5 | >1.00E−4 |
| NCI-H460 | 1.67E−5 | 3.60E−5 | 7.75E−5 |
| NC I-H 522 | 1.41E−6 | 3.20E−6 | 7.24E−6 |
| Colon Cancer | | | |
| COLO 205 | 1.70E−6 | 3.47E−6 | 7.07E−6 |
| HCC-2998 | 1.44E−5 | 1.94E−5 | 6.01E−5 |
| HCT-116 | 2.07E−6 | 6.42E−6 | 2.39E−5 |
| HCT-15 | 2.39E−6 | 1.06E−5 | 3.70E−5 |
| KM12 | 1.55E−5 | 3.13E−5 | 6.33E−5 |
| SW-620 | 2.23E−6 | 8.74E−6 | 3.73E−5 |
| CNS Cancer | | | |
| SF-268 | 6.14E−6 | 2.06E−5 | 5.32E−5 |
| SF-295 | 1.54E−5 | 3.35E−5 | 7.32E−5 |
| SF-539 | 2.39E−6 | 8.70E−6 | 3.21E−5 |
| SNB-19 | 1.35E−5 | 2.75E−5 | 5.63E−5 |
| SNB-75 | 2.59E−6 | 1.65E−5 | 4.06E−5 |
| U251 | 1.67E−5 | 3.24E−5 | 6.27E−5 |
| Melanoma | | | |
| LOX IMVI | 3.15E−6 | 1.17E−5 | 3.78E−5 |
| M14 | 3.85E−6 | 1.55E−5 | 4.11E−5 |
| MDA-MB-435 | 2.99E−6 | 1.32E−5 | 3.85E−5 |
| SK-MEL-2 | 1.12E−5 | 2.51E−5 | 5.58E−5 |
| SK-MEL-28 | 3.83E−6 | 1.55E−5 | 4.10E−5 |
| 8K-MEL-5 | 1.06E−5 | 2.25E−5 | 4.76E−5 |
| UACC-257 | 5.34E−6 | 1.87E−5 | 4.56E−5 |
| UACC-62 | 8.05E−6 | 1.10E−5 | 4.71E−5 |

TABLE 4-continued

|  | Ovarian Cancer | | |
|---|---|---|---|
| IGROVI | 1.32E-5 | 3.17E-5 | 7.63E-5 |
| OVCAR-3 | 1.96E-6 | 5.88E-6 | 2.20E-5 |
| OVCAR-4 | 2.13E-6 | 1.16E-5 | 3.86E-5 |
| OVCAR-5 | 1.01E-5 | 2.27E-5 | 5.09E-5 |
| OVCAR-8 | 1.03E-5 | 1.35E-5 | 5.33E-5 |
| NCI/ADR-RES | 1.72E-5 | 4.58E-5 | >1.00E-4 |
| SK-OV-3 | 2.10E-5 | 5.37E-5 | >1.00E-4 |
|  | Renal Cancer | | |
| 786-0 | 2.48E-6 | 1.11E-5 | 3.73E-5 |
| A498 | 1.01E-5 | 2.18E-5 | 4.70E-5 |
| ACHN | 2.14E-6 | 8.06E-6 | 3.15E-5 |
| CAKI-1 | 2.19E-6 | 1.19E-5 | 3.45E-5 |
| RXF 393 | 2.35E-6 | 8.65E-6 | 3.40E-5 |
| SN12C | 8.41E-6 | 2.27E-5 | 5.52E-5 |
| TK-10 | 2.03E-6 | 6.82E-6 | 2.55E-5 |
| UO-31 | 2.36E-6 | 1.25E-5 | 4.63E-5 |
|  | Prostate Cancer | | |
| PC-3 | 1.27E-5 | 1.67E-5 | 5.62E-5 |
| DU-145 | 3.19E6 | 1.25E-5 | 3.53E-5 |
|  | Breast Cancer | | |
| MCF7 | 2.30E-6 | 1.07E-5 | 5.08E-5 |
| MDA-MB-231/ATCC | 3.73E-6 | 1.62E-5 | 4.94E-5 |
| HS 57BT | 4.96E-6 | 2.68E-5 | >1.00E-4 |
| 81-549 | 3.12E-6 | 1.50E-5 | 3.87E-5 |
| T-47D | 2.34E-6 | 8.12E-6 | 4.59E-5 |
| MDA-MB-468 | 6.01E-7 | 2.78E-6 | 1.05E-5 |

TABLE 5

NCI five dose result for JVM 2-31

| Panel/Cell | Time Zero | Ctrl | Mean Optical Densities Log10 Concentration | | | | | Percent Growth Log10 Concentration | | | | |
|---|---|---|---|---|---|---|---|---|---|---|---|---|
|  |  |  | -8.0 | -7.0 | -6.0 | -5.0 | -4.0 | -8.0 | -7.0 | -6.0 | -5.0 | -4.0 |
| Leukemia | | | | | | | | | | | | |
| CCRF-CEM | 0.539 | 1.748 | 1.802 | 1.830 | 1.614 | 0.555 | 0.295 | 104 | 107 | 89 | 1 | -45 |
| HL-60(TB) | 0.667 | 2.381 | 2.637 | 2.496 | 2.430 | 0.816 | 0.342 | 115 | 107 | 103 | 9 | -49 |
| K-562 | 0.612 | 2.207 | 2.235 | 2.409 | 2.217 | 1.057 | 0.412 | 102 | 113 | 101 | 28 | -33 |
| MOLT-4 | 0.957 | 2.229 | 2.223 | 2.230 | 2.241 | 1.350 | 0.558 | 99 | 100 | 101 | 31 | -42 |
| SR | 0.252 | 1.050 | 0.994 | 1.023 | 0.659 | 0.300 | 0.144 | 93 | 97 | 76 | 6 | -43 |
| Non-Small Cell Lung Cancer | | | | | | | | | | | | |
| A549/ATCC | 0.398 | 1.497 | 1.505 | 1.563 | 1.539 | 1.309 | 0.160 | 101 | 106 | 104 | 83 | -60 |
| HOP-62 | 0.830 | 1.813 | 1.711 | 1.724 | 1.762 | 1.768 | 0.335 | 90 | 91 | 95 | 95 | -60 |
| HOP-92 | 0.944 | 1.476 | 1.421 | 1.431 | 1.421 | 0.944 | 0.138 | 90 | 92 | 90 | . | -85 |
| NCI-H226 | 0.851 | 2 268 | 2.157 | 2.103 | 2.064 | 1.326 | 0.381 | 92 | 88 | 87 | 34 | -55 |
| NC I-H 23 | 0.672 | 1.999 | 1.998 | 2.023 | 2.010 | 1.571 | 0.205 | 100 | 102 | 101 | 68 | -70 |
| NCI-H322M | 0.888 | 2.208 | 2.242 | 2.246 | 2.312 | 2.308 | 0.837 | 103 | 103 | UM | 108 | -6 |
| NCI-H460 | 0.386 | 3.181 | 3.221 | 3.238 | 3.176 | 2.859 | 0.246 | 101 | 102 | 100 | 88 | -36 |
| NC I-H 522 | 1.103 | 2.123 | 2.143 | 2.131 | 1.956 | 0.408 | 0.405 | 102 | 101 | 84 | -63 | -63 |
| Colon Cancer | | | | | | | | | | | | |
| COLO 205 | 0.527 | 1.454 | 1.414 | 1.523 | 1.465 | 0.399 | 0.132 | 96 | 107 | 101 | -24 | -75 |
| HCC-2998 | 0.568 | 1.899 | 2.026 | 1.980 | 2.024 | 1.665 | 0.087 | 110 | 106 | 109 | 82 | -85 |
| HCT-116 | 0.207 | 1.669 | 1.600 | 1.654 | 1.471 | 0.271 | 0.005 | 98 | 99 | 86 | 4 | -98 |
| HCT-15 | 0.284 | 2.300 | 2.078 | 2.096 | 1.893 | 0.422 | 0.071 | 89 | 90 | 80 | 7 | -75 |
| HT29 | 0.508 | 2.616 | 2.631 | 2.692 | 2.664 | 2.465 | 0.198 | 101 | 104 | 102 | 93 | -61 |
| SW-620 | 0.314 | 2.517 | 2.491 | 2.473 | 2.220 | 0.495 | 0.130 | 99 | 98 | 87 | 8 | -59 |
| CNS Cancer | | | | | | | | | | | | |
| SF-268 | 0.564 | 1.900 | 1.910 | 1.938 | 1 932 | 1.183 | 0.996 | 101 | 103 | 102 | 46 | -65 |
| SF-295 | 0.641 | 2.700 | 2.265 | 2.501 | 2.446 | 2.133 | 0.265 | 84 | 90 | BB | 72 | -59 |
| SF-539 | 0.954 | 2.543 | 2.355 | 2.422 | 2.315 | 0.884 | 0.933 | 88 | 92 | 66 | -7 | -86 |
| SNB-19 | 0.705 | 2.275 | 2.234 | 2.194 | 2.205 | 1.848 | 0.496 | 97 | 95 | 96 | 73 | -30 |
| SNB-75 | 0.763 | 1.468 | 1.239 | 1.316 | 1.266 | 1.064 | 0.016 | 68 | 78 | 74 | 43 | -98 |
| U251 | 0.597 | 1.953 | 1.976 | 2.015 | 2.009 | 1.853 | 0.091 | 102 | 105 | 104 | 93 | -85 |

TABLE 5-continued

| Melanoma | | | | | | | | | | | | |
|---|---|---|---|---|---|---|---|---|---|---|---|---|
| LOX IMVI | 0.316 | 2.170 | 2.138 | 2.173 | 2.075 | 0.529 | 0.041 | 98 | 100 | 95 | 11 | −87 |
| M14 | 0.452 | 1.609 | 1.504 | 1.593 | 1.512 | 0.775 | 0.052 | 91 | 99 | 92 | 28 | −88 |
| MDA-MB-435 | 0.554 | 2.487 | 2.305 | 2.439 | 2.307 | 1.095 | 0.201 | 91 | 98 | 91 | 28 | −64 |
| SK-MEL-2 | 1.069 | 2.062 | 2.096 | 2.163 | 2.123 | 1.795 | 0.298 | 103 | 110 | 106 | 73 | −72 |
| SK-MEL-28 | 0.627 | 1.704 | 1.615 | 1.679 | 1.617 | 0.987 | 0.020 | 92 | 98 | 92 | 33 | −97 |
| 8K-MEL-5 | 0.621 | 2.527 | 2.424 | 2.413 | 2.337 | 1.420 | 0.106 | 95 | 94 | 90 | 42 | −83 |
| UACC-257 | 1.042 | 2.075 | 2.096 | 2.114 | 2.022 | 1.531 | 0.281 | 102 | 104 | 95 | 47 | −73 |
| UACC-62 | 0.774 | 2.950 | 2.869 | 2.871 | 2.778 | 1.676 | 0.122 | 96 | 96 | 92 | 41 | −84 |
| Ovarian Cancer | | | | | | | | | | | | |
| IGROVI | 0.763 | 2.283 | 2.430 | 2.485 | 2.525 | 2.074 | 0.275 | 110 | 113 | 116 | 86 | −64 |
| OVCAR-3 | 0.513 | 1.577 | 1.627 | 1.692 | 1.543 | 0.606 | 0.016 | 105 | 111 | 97 | 9 | −97 |
| OVCAR-4 | 0.665 | 1.453 | 1.339 | 1.395 | 1.332 | 0.880 | 0.215 | 86 | 93 | 85 | 27 | −68 |
| OVCAR-5 | 0.693 | 1.438 | 1.319 | 1.378 | 1.384 | 1.205 | 0.150 | 84 | 92 | 93 | 69 | −78 |
| OVCAR-8 | 0.632 | 2.168 | 2.205 | 2.238 | 2.177 | 1.419 | 0.230 | 102 | 105 | 101 | 51 | −64 |
| NCI/ADR-RES | 0.494 | 1.777 | 1.786 | 1.789 | 1.754 | 1.635 | 0.521 | 101 | 101 | 98 | 89 | 2 |
| SK-OV-3 | 0.933 | 1.639 | 1.622 | 1.623 | 1.675 | 1.701 | 0.746 | 98 | 98 | 105 | 109 | −20 |
| Renal Cancer | | | | | | | | | | | | |
| 786-0 | 0.506 | 1.850 | 1.700 | 1.769 | 1.649 | 0.659 | 0.079 | 89 | 94 | 85 | 11 | −84 |
| A498 | 1.386 | 2.262 | 2.180 | 2.227 | 2.256 | 1.961 | 0.093 | 91 | 96 | 99 | 66 | −93 |
| ACHN | 0.448 | 1.772 | 1.698 | 1.752 | 1.625 | 0.607 | 0.103 | 94 | 99 | 89 | 12 | −77 |
| CAKI-1 | 0.613 | 2.647 | 2.337 | 2.416 | 2.262 | 1.084 | 0.013 | 85 | 89 | 81 | 23 | −98 |
| RXF 393 | 0.735 | 1.328 | 1.279 | 1.286 | 1.063 | 0.731 | 0.130 | 92 | 93 | 55 | −1 | −82 |
| SN12C | 0.945 | 3.124 | 3.034 | 3.024 | 3.039 | 2.082 | 0.293 | 96 | 95 | 96 | 52 | −69 |
| TK-10 | 0.971 | 2.151 | 2.076 | 2.098 | 2.003 | 0.959 | 0.054 | 94 | 95 | 87 | −1 | −94 |
| UO-31 | 0.831 | 2.274 | 2.212 | 2.276 | 2.301 | 1.331 | 0.236 | 96 | 100 | 102 | 35 | −72 |
| Prostate Cancer | | | | | | | | | | | | |
| PC-3 | 0.671 | 1.511 | 1.427 | 1.447 | 1.482 | 1.243 | 0.146 | 90 | 92 | 96 | 68 | −78 |
| DU-145 | 0.354 | 1.511 | 1.499 | 1.578 | 1.419 | 0.559 | 0.015 | 99 | 106 | 92 | 18 | −96 |
| Breast Cancer | | | | | | | | | | | | |
| MCF7 | 0.349 | 1.405 | 1.366 | 1.343 | 1.300 | 0.879 | 0.147 | 95 | 92 | 67 | 34 | −76 |
| MDA-MB-231/ATCC | 0.612 | 2.130 | 2.070 | 2.049 | 2.039 | 1.520 | 0.976 | 95 | 93 | 92 | 46 | −3 |
| HS 57BT | 1.009 | 1.698 | 1.559 | 1.636 | 1.512 | 1.086 | 0.036 | 84 | 93 | 79 | 30 | −96 |
| 81-549 | 0.820 | 1.527 | 1.419 | 1.495 | 1.472 | 0.858 | 0.403 | 84 | 95 | 92 | | −53 |
| T-47D | 0.857 | 1.748 | 1.802 | 1.830 | 1.614 | 0.555 | 0.295 | 104 | 107 | 89 | 1 | −45 |
| MDA-MB-468 | 0.681 | 1.231 | 1.193 | 1.178 | 0.957 | 0.547 | 0.173 | 93 | 90 | 50 | −20 | −75 |

| NCI five dose result for JVM 2-31 | | | |
|---|---|---|---|
| Panel/Cell | GI50 | TGI | LC50 |
| Leukemia | | | |
| CCRF-CEM | 2.78E−6 | 1.07E−5 | >1.00E−4 |
| HL-60(TB) | 3.64E−6 | 1.42E−5 | >1.00E−4 |
| K-562 | 4.96E−6 | 2.88E−5 | >1.00E−4 |
| MOLT-4 | 5.33E−6 | 2.66E−5 | >1.00E−4 |
| SR | 2.35E−6 | 1.33E−5 | >1.00E−4 |
| Non-Small Cell Lung Cancer | | | |
| A549/ATCC | 1.70E−5 | 3.80E−5 | 8.52E−5 |
| HOP-62 | 1.96E−5 | 4.12E−5 | 8.67E−5 |
| HOP-92 | 2.77E−6 | 9.99E−6 | 3.85E−5 |
| NCI-H226 | 4.92E−6 | 2.39E−5 | 8.72E−5 |
| NC I-H 23 | 1.35E−5 | 3.11E−5 | 7.20E−5 |
| NCI-H322M | 3.22E−5 | 8.90E−5 | >1.00E−4 |
| NCI-H460 | 2.03E−5 | 5.12E−5 | >1.00E−4 |
| NC I-H 522 | 1.70E−6 | 3.72E−6 | 8.15E−6 |
| Colon Cancer | | | |
| COLO 205 | 2.56E−6 | 6.39E−6 | 3.20E−5 |
| HCC-2998 | 1.56E−5 | 3.11E−5 | 6.19E−5 |
| HCT-116 | 2.78E−6 | 1.10E−5 | 3.40E−5 |
| HCT-15 | 2.56E−6 | 1.21E−5 | 4.95E−5 |
| HT29 | 1.90E−5 | 4.01E−5 | 8.48E−5 |
| SW-620 | 2.93E−6 | 1.33E−5 | 7.40E−5 |
| CNS Cancer | | | |
| SF-268 | 8.59E−6 | 2.60E−5 | 7.30E−5 |
| SF-295 | 1.48E−5 | 3.57E−5 | 8.58E−5 |
| SF-539 | 2.42E−6 | 8.33E−6 | 3.48E−5 |

TABLE 5-continued

|  |  |  |  |
|---|---|---|---|
| SNB-19 | 1.67E−5 | 5.13E−5 | >1.00E−4 |
| SNB-75 | 5.84E−6 | 2.01E−5 | 4.56E−5 |
| U251 | 1.74E−5 | 3.33E−5 | 6.37E−5 |
| Melanoma | | | |
| LOX IMVI | 3.45E−6 | 1.31E−5 | 4.21E−5 |
| M14 | 4.50E−6 | 1.74E−5 | 4.67E−5 |
| MDA-MB-435 | 4.45E−6 | 2.02E−5 | 7.09E−5 |
| SK-MEL-2 | 1.44E−5 | 3.19E−5 | 7.04E−5 |
| SK-MEL-28 | 5.21E−6 | 1.81E−5 | 4.37E−5 |
| 8K-MEL-5 | 6.80E−6 | 2.17E−5 | 5.45E−5 |
| UACC-257 | 8.79E−6 | 2.47E−5 | 6.43E−5 |
| UACC-62 | 6.78E−6 | 2.14E−5 | 5.34E−5 |
| Ovarian Cancer | | | |
| IGROVI | 1.74E−5 | 3.75E−5 | 8.07E−5 |
| OVCAR-3 | 3.40E−6 | 1.21E−5 | 3.60E−5 |
| OVCAR-4 | 4.01E−6 | 1.94E−5 | 6.51E−5 |
| OVCAR-5 | 1.34E−5 | 2.93E−5 | 6.41E−5 |
| OVCAR-8 | 1.02E−5 | 2.79E−5 | 7.60E−5 |
| NCI/ADR-RES | 2.81E−5 | >1.00E−4 | >1.00E−4 |
| SK-OV-3 | 2.86E−5 | 6.99E−5 | >1.00E−4 |
| Renal Cancer | | | |
| 786-0 | 2.99E−6 | 1.31E−5 | 4.37E−5 |
| A498 | 1.25E−5 | 2.59E−5 | 5.34E−5 |
| ACHN | 3.21E−6 | 1.36E−5 | 4.96E−5 |
| CAKI-1 | 3.44E−6 | 1.55E−5 | 4.02E−5 |
| RXF 393 | 1.24E−5 | 9.75E−6 | 4.02E−5 |
| SN12C | 1.04E−5 | 2.70E−5 | 6.97E−5 |
| TK-10 | 2.64E−6 | 9.68E−6 | 3.33E−5 |
| UO-31 | 5.91E−6 | 2.12E−5 | 6.26E−5 |
| Prostate Cancer | | | |
| PC-3 | 1.33E−5 | 2.92E−5 | 6.41E−5 |
| DU-145 | 3.68E−6 | 1.43E−5 | 3.94E−5 |
| Breast Cancer | | | |
| MCF7 | 4.92E−6 | 1.20E−5 | 7.63E−5 |
| MDA-MB-231/ATCC | 8.01E−6 | 2.03E−5 | 5.79E−5 |
| HS 57BT | 3.92E−6 | 8.57E−5 | >1.00E−4 |
| 81-549 | 2.86E−6 | 1.74E−5 | 4.34E−5 |
| T-47D | 2.78E−6 | 1.00E−5 | 8.79E−5 |
| MDA-MB-468 | 1.01E−6 | 5.23E−6 | 3.57E−5 |

TABLE 6

NCI five dose result for JVM 2-35

| | | | Log10 Concentration | | | | | | | | | |
|---|---|---|---|---|---|---|---|---|---|---|---|---|
| | Time | | Mean Optical Densities | | | | | Percent Growth | | | | |
| Panel/Cell | Zero | Ctrl | −8.0 | −7.0 | −6.0 | −5.0 | −4.0 | −8.0 | −7.0 | −6.0 | −5.0 | −4.0 |
| Leukemia | | | | | | | | | | | | |
| CCRF-CEM | 0.539 | 1.630 | 1.548 | 1.564 | 1.427 | 0.454 | 0.300 | 93 | 96 | 81 | −16 | −44 |
| HL-60(TB) | 0.667 | 2.232 | 2.130 | 1.962 | 1.798 | 0.551 | 0.320 | 94 | 83 | 72 | −17 | −52 |
| K-562 | 0.612 | 1.972 | 1.989 | 1.912 | 2.065 | 1.026 | 0.408 | 101 | 96 | 107 | 30 | −33 |
| MOLT-4 | 0.957 | 2.230 | 2.258 | 2.283 | 2.130 | 1.405 | 0.485 | 102 | 104 | 92 | 35 | −49 |
| SR | 0.252 | 0.960 | 0.822 | 0.797 | 0.779 | 0.281 | 0.139 | 80 | 77 | 74 | 4 | −45 |
| Non-Small Cell Lung Cancer | | | | | | | | | | | | |
| A549/ATCC | 0.398 | 1.393 | 1.307 | 1.339 | 1.348 | 1.226 | 0.109 | 91 | 95 | 95 | 83 | −73 |
| HOP-62 | 0.830 | 1.799 | 1.753 | 1.718 | 1.653 | 1.630 | 0.766 | 95 | 92 | 85 | 83 | −8 |
| HOP-92 | 0.944 | 1.450 | 1.443 | 1.414 | 1.386 | 0.947 | 0.089 | 98 | 93 | 87 | | −91 |
| NCI-H226 | 0.851 | 2.238 | 2.136 | 2.112 | 2.084 | 1.663 | 0.381 | 93 | 91 | 89 | 58 | −55 |
| NC I-H 23 | 0.672 | 1.987 | 1.906 | 1.963 | 1.946 | 1.688 | 0.300 | 94 | 98 | 97 | 77 | −55 |
| NCI-H322M | 0.888 | 2.082 | 1.956 | 2.049 | 1.974 | 1.896 | 0.998 | 89 | 97 | 91 | 84 | 9 |
| NCI-H460 | 0.386 | 3.144 | 3.161 | 3.152 | 3.099 | 2.859 | 0.249 | 101 | 100 | 98 | 90 | −35 |
| NC I-H 522 | 1.103 | 2.486 | 2.312 | 2.342 | 2.099 | 0.525 | 0.351 | 87 | 90 | 72 | −52 | −68 |

TABLE 6-continued

| | | | | Colon Cancer | | | | | | | | |
|---|---|---|---|---|---|---|---|---|---|---|---|---|
| COLO 205 | 0.527 | 1.449 | 1.445 | 1.460 | 1.385 | 0.352 | 0.023 | 100 | 101 | 93 | −33 | −96 |
| HCC-2998 | 0.568 | 1.916 | 1.857 | 1.918 | 1.966 | 1.694 | 0.085 | 96 | 100 | 104 | 84 | −85 |
| HCT-116 | 0.207 | 1.707 | 1.683 | 1.521 | 1.449 | 0.292 | −0.009 | 98 | 88 | 83 | 6 | −100 |
| HCT-15 | 0.284 | 2167 | 2.081 | 2.020 | 1.829 | 0.469 | 0.049 | 95 | 92 | 82 | 10 | −83 |
| HT29 | 0.508 | 2.469 | 2.424 | 2.446 | 2.432 | 2.283 | 0.361 | 98 | 99 | 98 | 91 | −29 |
| SW-620 | 0.314 | 2.371 | 2.343 | 2.315 | 2.190 | 0.658 | 0.069 | 99 | 97 | 91 | 17 | −78 |
| | | | | CNS Cancer | | | | | | | | |
| SF-268 | 0.564 | 1.874 | 1.784 | 1.769 | 1.770 | 1.336 | 0.166 | 93 | 92 | 92 | 59 | −71 |
| SF-295 | 0.641 | 2.579 | 2.418 | 2.357 | 2.384 | 2.187 | 0.717 | 92 | 89 | 90 | 80 | 4 |
| SF-539 | 0.954 | 2.493 | 2.480 | 2.357 | 2.410 | 1.239 | 0.070 | 99 | 91 | 95 | 19 | −93 |
| SNB-19 | 0.705 | 2.102 | 2.032 | 2.005 | 1.958 | 1.765 | 0.565 | 95 | 93 | 90 | 76 | −20 |
| SNB-75 | 0.763 | 1.416 | 1.258 | 1.204 | 1.170 | 1.055 | 0.080 | 76 | 68 | 62 | 45 | 90 |
| U251 | 0.597 | 1.888 | 1.785 | 1.787 | 1.847 | 1.811 | 0.302 | 92 | 92 | 97 | 94 | −49 |
| | | | | Melanoma | | | | | | | | |
| LOX IMVI | 0.316 | 2.113 | 2.065 | 2.033 | 2.054 | 0.876 | 0.036 | 97 | 96 | 97 | 31 | −09 |
| M14 | 0.452 | 1.594 | 1.558 | 1.469 | 1.410 | 0.730 | 0.052 | 97 | 89 | 84 | 24 | −88 |
| MDA-MB-435 | 0.554 | 2.261 | 2.215 | 2.095 | 2.095 | 0.960 | 0.066 | 97 | 90 | 90 | 24 | −88 |
| SK-MEL-2 | 1.069 | 2.082 | 2.145 | 2.174 | 2.024 | 1.819 | 0.447 | 106 | 109 | 94 | 74 | −58 |
| SK-MEL-28 | 0.627 | 1.722 | 1.662 | 1.659 | 1.561 | 0.949 | 0.084 | 95 | 94 | 85 | 29 | −87 |
| 8K-MEL-5 | 0.621 | 2.466 | 2.433 | 2.450 | 2.306 | 1.712 | 0.061 | 98 | 99 | 91 | 59 | −90 |
| UACC-257 | 1.042 | 1.970 | 1.907 | 1.838 | 1.896 | 1.519 | 0.153 | 93 | 86 | 92 | 51 | −85 |
| UACC-62 | 0.774 | 2.793 | 2.714 | 2.670 | 2.501 | 1.590 | 0.041 | 96 | 94 | 86 | 40 | −95 |
| | | | | Ovarian Cancer | | | | | | | | |
| IGROVI | 0.763 | 2.217 | 2.225 | 2.222 | 2.237 | 1.946 | 0.419 | 101 | 100 | 101 | 81 | −45 |
| OVCAR-3 | 0.513 | 1.558 | 1.533 | 1.620 | 1.531 | 0.578 | 0.018 | 98 | 106 | 97 | 6 | −96 |
| OVCAR-4 | 0.665 | 1.394 | 1.365 | 1.296 | 1.282 | 0.923 | 0.027 | 96 | 87 | 85 | 35 | −96 |
| OVCAR-5 | 0.693 | 1.435 | 1.333 | 1.309 | 1.290 | 1.199 | 0.082 | 86 | 83 | 80 | 68 | −88 |
| OVCAR-8 | 0.632 | 2.030 | 2.052 | 2.055 | 2.077 | 1.543 | 0.303 | 102 | 102 | 103 | 65 | −52 |
| NCI/ADR-RES | 0.494 | 1.711 | 1.681 | 1.722 | 1.747 | 1.517 | 0.462 | 97 | 101 | 103 | 84 | −7 |
| SK-OV-3 | 0.933 | 1.619 | 1.629 | 1.628 | 1.612 | 1.590 | 0.856 | 102 | 101 | 99 | 96 | −8 |
| | | | | Renal Cancer | | | | | | | | |
| 786-0 | 0.506 | 1.875 | 1.798 | 1.730 | 1.637 | 0.623 | 0.032 | 94 | 89 | 83 | 9 | −94 |
| A498 | 1.386 | 2.331 | 2.140 | 2.266 | 2.138 | 2.044 | 0.149 | 80 | 93 | 80 | 70 | −89 |
| ACHN | 0.448 | 1.659 | 1.692 | 1.638 | 1.524 | 0.608 | 0.044 | 103 | 98 | 89 | 13 | −90 |
| CAKI-1 | 0.613 | 2.386 | 2.258 | 2.133 | 1.978 | 1.036 | 0.006 | 93 | 86 | 77 | 24 | −99 |
| RXF 393 | 0.735 | 1.268 | 1.260 | 1.286 | 1.206 | 0.805 | 0.130 | 98 | 103 | 88 | 13 | −82 |
| SN12C | 0.945 | 3.005 | 2.884 | 2.883 | 2.872 | 2.236 | 0.549 | 94 | 94 | 94 | 63 | −42 |
| TK-10 | 0.971 | 2.101 | 2.121 | 2.123 | 2.041 | 1.189 | 0.110 | 102 | 102 | 95 | 19 | −89 |
| UO-31 | 0.831 | 2.168 | 1.952 | 1.961 | 1.949 | 1.269 | 0.098 | 84 | 85 | 84 | 33 | −88 |
| | | | | Prostate Cancer | | | | | | | | |
| PC-3 | 0.671 | 1.474 | 1.431 | 1.406 | 1.360 | 1.248 | 0.144 | 95 | 91 | 86 | 72 | −79 |
| DU-145 | 0.354 | 1.471 | 1.483 | 1.468 | 1.427 | 0.501 | 0.013 | 101 | 100 | 96 | 13 | −96 |
| | | | | Breast Cancer | | | | | | | | |
| MCF7 | 0.349 | 1.810 | 1.684 | 1.595 | 1.599 | 0.482 | 0.106 | 91 | 85 | 86 | 9 | −70 |
| MDA-MB-231/ATCC | 0.612 | 1.319 | 1.328 | 1.313 | 1.241 | 0.883 | 0.131 | 101 | 99 | 89 | 38 | −79 |
| HS 57BT | 1.009 | 2.051 | 1.969 | 1.982 | 1.905 | 1.640 | 0.830 | 92 | 93 | 86 | 61 | −18 |
| 81-549 | 0.820 | 1.746 | 1.699 | 1.599 | 1.576 | 1.193 | 0.014 | 95 | 84 | 82 | 40 | −98 |
| T-47D | 0.857 | 1.560 | 1.620 | 1.537 | 1.478 | 0.905 | 0.283 | 108 | 97 | 88 | 7 | −67 |
| MDA-MB-468 | 0.681 | 1.233 | 1.208 | 1.195 | 1.013 | 0.666 | 0.203 | 95 | 93 | 60 | −2 | −70 |

| NCI five dose result for JVM 2-35 | | | |
|---|---|---|---|
| Panel/Cell | GI50 | TGI | LC50 |
| Leukemia | | | |
| CCRF-CEM | 2.10E−6 | 6.137E−6 | >1.00E−4 |
| HL-60(TB) | 1.77E−6 | 6.40E−6 | 8.70E−5 |
| K-562 | 5.55E−6 | 3.00E−5 | >1.00E−4 |
| MOLT-4 | 5.50E−6 | 2.61E−5 | >1.00E−4 |
| SR | 2.22E−6 | 1.21E−5 | >1.00E−4 |
| Non-Small Cell Lung Cancer | | | |
| A549/ATCC | 1.63E−5 | 3.42E−5 | 7.16E−5 |
| HOP-62 | 2.29E−5 | 8.21E−5 | >1.00E−4 |
| HOP-92 | 2.69E−6 | 1.01E−5 | 3.58E−5 |
| NCI-H226 | 1.19E−5 | 3.27E−5 | 8.99E−5 |
| NC I-H 23 | 1.60E−5 | 3.82E−5 | 9.10E−5 |

TABLE 6-continued

|  |  |  |  |
|---|---|---|---|
| NCI-H322M | 2.87E−5 | >1.00E−4 | >1.00E−4 |
| NCI-H460 | 2.07E−5 | 5.21E−5 | >1.00E−4 |
| NC I-H 522 | 1.50E−6 | 3.79E−6 | 9.57E−6 |
| Colon Cancer | | | |
| COLO 205 | 2.19E−6 | 5.46E−6 | 1.86E−5 |
| HCC-2998 | 1.58E−5 | 3.13E−5 | 6.19E−5 |
| HCT-116 | 2.66E−6 | 1.13E−5 | 3.36E−5 |
| HCT-15 | 2.78E−6 | 1.28E−5 | 4 43E−5 |
| HT29 | 2.18E−5 | 5.72E−5 | >1.00E−4 |
| SW-620 | 3.58E−6 | 1.50E−5 | 5.06E−5 |
| CNS Cancer | | | |
| SF-268 | 1.17E−5 | 2.85E−5 | 6 93E−5 |
| SF-295 | 2.47E−5 | >1.00E−4 | >1.00E−4 |
| SF-539 | 3.86E−6 | 1.47E−5 | 4.13E−5 |
| SNB-19 | 1.86E−5 | 6.20E−5 | >1.00E−4 |
| SNB-75 | 4.96E−6 | 2.15E−5 | 5.07E−5 |
| U251 | 2.03E−5 | 4.52E−5 | >1.00E−4 |
| Melanoma | | | |
| LOX IMVI | 5.16E−6 | 1.82E−5 | 4.75E−5 |
| M14 | 3.71E−6 | 1.64E−5 | 4.56E−5 |
| MDA-MB-435 | 4.03E−6 | 1.63E−5 | 4.57E−5 |
| SK-MEL-2 | 1.52E−5 | 3.63E−5 | 8.66E−5 |
| SK-MEL-28 | 4.27E−6 | 1.79E−5 | 4.83E−5 |
| 8K-MEL-5 | 1.15E−5 | 2.49E−5 | 5.38E−5 |
| UACC-257 | 1.02E−5 | 2.38E−5 | 5.52E−5 |
| UACC-62 | 6.13E−6 | 1.99E−5 | 4.66E−5 |
| Ovarian Cancer | | | |
| IGROVI | 1.77E−5 | 4.40E−5 | >1.00E−4 |
| OVCAR-3 | 3.31E−6 | 1.15E−5 | 3.53E−5 |
| OVCAR-4 | 5.04E−6 | 1.86E−5 | 4 46E−5 |
| OVCAR-5 | 1.31E−5 | 2.73E−5 | 5.70E−5 |
| OVCAR-8 | 1 35E−5 | 3.60E−5 | 9 60E−5 |
| NCI/ADR-RES | 2.37E−5 | 8.46E−5 | >1.00E−4 |
| SK-OV-3 | 2.75E−5 | 8.33E−5 | >1.00E−4 |
| Renal Cancer | | | |
| 786-0 | 2.75E−6 | 1.21E−5 | 3.73E−5 |
| A498 | 1.33E−5 | 2.74E−5 | 5.66E−5 |
| ACHN | 3.26E−6 | 1.34E−5 | 4.09E−5 |
| CAKI-1 | 3.22E−6 | 1.56E−5 | 3.99E−5 |
| RXF 393 | 3.23E−6 | 1.37E−5 | 4.58E−5 |
| SN12C | 1.32E−5 | 3.97E−5 | >1.00E4 |
| TK-10 | 3.92E−6 | 1.51E−5 | 4.38E−5 |
| UO-31 | 4.58E−6 | 1.86E−5 | 4.83E−5 |
| Prostate Cancer | | | |
| PC-3 | 1.40E−5 | 3.00E−5 | 6.45E−5 |
| DU-145 | 3.59E−6 | 1.32E−5 | 3.77E−5 |
| Breast Cancer | | | |
| MCF7 | 2.92E−6 | 1.30E−5 | 5.63E−5 |
| MDA-MB-231/ATCC | 5.86E−6 | 2.13E−5 | 5.69E−5 |
| HS 57BT | 1.36E−5 | 5.93E−5 | >1.00E−4 |
| 81-549 | 5.82E−6 | 1.95E−5 | 4.48E−5 |
| T-47D | 2.95E−6 | 1.24E−5 | 5.88E−5 |
| MDA-MB-468 | 1.46E−6 | 9.20E−6 | 5.04E−5 |

TABLE 7

NCI five dose result for JVM 2-40

| | | | Log10 Concentration | | | | | | | | | |
|---|---|---|---|---|---|---|---|---|---|---|---|---|
| | Time | | Mean Optical Densities | | | | | Percent Growth | | | | |
| Panel/Cell | Zero | Ctrl | −8.0 | −7.0 | −6.0 | −5.0 | −4.0 | −8.0 | −7.0 | −6.0 | −5.0 | −4.0 |

| Leukemia | | | | | | | | | | | | |
|---|---|---|---|---|---|---|---|---|---|---|---|---|
| CCRF-CEM | 0.539 | 1.823 | 1.728 | 1 762 | 1.363 | 0.442 | 0.268 | 93 | 95 | 64 | −18 | −50 |
| HL-60(TB) | 0.667 | 2.208 | 2.161 | 2.075 | 1.717 | 0.590 | 0.300 | 97 | 91 | 68 | −12 | −55 |
| K-562 | 0.612 | 2.135 | 2.155 | 2.127 | 2.082 | 0.930 | 0.424 | 101 | 99 | 97 | 21 | −31 |
| MOLT-4 | 0.957 | 2205 | 2.270 | 2.254 | 2.110 | 1.240 | 0.531 | 105 | 104 | 92 | 23 | −45 |
| SR | 0.252 | 0.944 | 0.874 | 0.837 | 0.769 | 0.280 | 0.156 | 90 | 85 | 75 | 4 | −38 |

| Non-Small Cell Lung Cancer | | | | | | | | | | | | |
|---|---|---|---|---|---|---|---|---|---|---|---|---|
| A549/ATCC | 0.398 | 1.494 | 1.424 | 1.372 | 1.467 | 1.152 | 0.072 | 94 | 89 | 98 | 69 | −82 |
| HOP-62 | 0.830 | 1.828 | 1.766 | 1.748 | 1.694 | 1.608 | 0.139 | 94 | 92 | 87 | 78 | −83 |
| HOP-92 | 0.944 | 1.454 | 1.416 | 1.402 | 1.374 | 0.858 | 0.066 | 93 | 90 | 84 | −9 | −93 |
| NCI-H226 | 0.851 | 2.222 | 2.140 | 2.110 | 2.043 | 1.447 | 0.378 | 94 | 92 | 87 | 43 | −56 |
| NC I-H 23 | 0.672 | 2.005 | 1.929 | 1.936 | 1.985 | 1.526 | 0.279 | 94 | 95 | 98 | 64 | −59 |
| NCI-H322M | 0.888 | 2.102 | 1.959 | 2.003 | 2.016 | 1.822 | 0.822 | 88 | 92 | 93 | 77 | −7 |
| NCI-H460 | 0.386 | 3.129 | 3.179 | 3.148 | 3.076 | 2.588 | 0.168 | 102 | 101 | 98 | 80 | −56 |
| NC I-H 522 | 1.103 | 2.131 | 1.983 | 1.985 | 1.660 | 0.199 | 0.244 | 86 | 86 | 54 | −82 | −78 |

| Colon Cancer | | | | | | | | | | | | |
|---|---|---|---|---|---|---|---|---|---|---|---|---|
| COLO 205 | 0.527 | 1.415 | 1.402 | 1.419 | 1.321 | 0.409 | 0.044 | 98 | 100 | 89 | −22 | −92 |
| HCC-2998 | 0.568 | 1.820 | 1.761 | 1 802 | 1.865 | 1.483 | 0.056 | 95 | 99 | 104 | 73 | −90 |
| HCT-116 | 0.207 | 1.676 | 1.650 | 1.533 | 1.304 | 0.271 | −0.014 | 98 | 90 | 75 | 4 | −100 |
| HCT-15 | 0.284 | 2.118 | 2.106 | 1.967 | 1.701 | 0.240 | 0.028 | 99 | 92 | 77 | −16 | −90 |
| HT29 | 0.508 | 2.581 | 2.504 | 2.506 | 2.553 | 2.223 | 0.122 | 96 | 96 | 99 | 83 | −76 |
| SW-620 | 0.314 | 2.411 | 2.410 | 2.425 | 1.921 | 0.443 | 0.073 | 100 | 101 | 77 | 6 | −77 |

| CNS Cancer | | | | | | | | | | | | |
|---|---|---|---|---|---|---|---|---|---|---|---|---|
| SF-268 | 0.564 | 1.956 | 1.868 | 1.665 | 1.831 | 1.173 | 0.148 | 94 | 93 | 91 | 44 | −74 |
| SF-295 | 0.641 | 2.913 | 2.468 | 2.356 | 2.453 | 1.999 | 0.097 | 92 | 87 | 92 | 69 | −85 |
| SF-539 | 0.954 | 2.439 | 2.312 | 2.230 | 2.264 | 0.904 | 0.075 | 91 | 86 | 88 | −5 | −92 |
| SNB-19 | 0.705 | 2.099 | 2.021 | 2.029 | 1.929 | 1.682 | 0.102 | 94 | 95 | 88 | 70 | −86 |
| SNB-75 | 0.763 | 1.447 | 1.321 | 1.226 | 1.189 | 0.993 | 0.005 | 82 | 68 | 62 | 34 | −99 |
| U251 | 0.597 | 1.931 | 1.855 | 1.881 | 1.854 | 1.810 | 0.009 | 94 | 96 | 94 | 91 | −98 |

| Melanoma | | | | | | | | | | | | |
|---|---|---|---|---|---|---|---|---|---|---|---|---|
| LOX IMVI | 0.316 | 2.003 | 1.955 | 1.938 | 1.898 | 0.509 | 0.047 | 97 | 96 | 94 | 11 | −85 |
| M14 | 0.452 | 1.565 | 1.517 | 1.391 | 1.3313 | 0.623 | 0.048 | 96 | 84 | 80 | 16 | −89 |
| MDA-MB-435 | 0.554 | 2.352 | 2.283 | 2.156 | 2.102 | 0.943 | 0.140 | 96 | 89 | 86 | 22 | −75 |
| SK-MEL-2 | 1.069 | 2.007 | 2.038 | 2.032 | 1.946 | 1.568 | 0.214 | 103 | 103 | 93 | 53 | −80 |
| SK-MEL-28 | 0.627 | 1.655 | 1 676 | 1.618 | 1.490 | 0.863 | 0.869 | 102 | 96 | 84 | 23 | −89 |
| 8K-MEL-5 | 0.621 | 2.422 | 2.393 | 2.324 | 2.230 | 1.425 | 0.064 | 98 | 95 | 89 | 45 | −90 |
| UACC-257 | 1.042 | 2.094 | 1.987 | 1.924 | 1.909 | 1.420 | 0.079 | 90 | 84 | 82 | 36 | −92 |
| UACC-62 | 0.774 | 2.751 | 2.637 | 2.646 | 2.515 | 1.537 | 0.041 | 94 | 95 | 88 | 39 | −95 |

| Ovarian Cancer | | | | | | | | | | | | |
|---|---|---|---|---|---|---|---|---|---|---|---|---|
| IGROVI | 0.763 | 2.185 | 2.223 | 2.242 | 2.317 | 1.910 | 0.311 | 103 | 104 | 109 | 81 | −59 |
| OVCAR-3 | 0.513 | 1.632 | 1.624 | 1.637 | 1.502 | 0.499 | −0.003 | 99 | 100 | 88 | −3 | −100 |
| OVCAR-4 | 0.665 | 1.334 | 1.377 | 1.302 | 1.264 | 0.848 | 0.213 | 99 | 89 | 83 | 25 | −68 |
| OVCAR-5 | 0.693 | 1.438 | 1.381 | 1 326 | 1.303 | 0.976 | 0.050 | 92 | 85 | 82 | 38 | −93 |
| OVCAR-8 | 0.632 | 1.996 | 1.976 | 1.944 | 2.032 | 1.266 | 0.180 | 99 | 96 | 103 | 46 | −72 |
| NCI/ADR-RES | 0.494 | 1.652 | 1.657 | 1.645 | 1.663 | 1370 | 0.328 | 100 | 99 | 101 | 76 | −34 |
| SK-OV-3 | 0.933 | 1.619 | 1 609 | 1.627 | 1.560 | 1.566 | 0.684 | 99 | 101 | 91 | 92 | −27 |

| Renal Cancer | | | | | | | | | | | | |
|---|---|---|---|---|---|---|---|---|---|---|---|---|
| 786-0 | 0.506 | 2.042 | 1.999 | 1.920 | 1.807 | 0.777 | 0.032 | 97 | 92 | 85 | 18 | −94 |
| A498 | 1.386 | 2.307 | 2.276 | 2.231 | 2.100 | 1.902 | 0.033 | 97 | 92 | 77 | 56 | −98 |
| ACHN | 0.448 | 1.678 | 1.713 | 1.668 | 1.502 | 0.411 | 0.043 | 103 | 99 | 86 | −8 | −91 |
| CAKI-1 | 0.613 | 2.436 | 2.316 | 2.194 | 1.944 | 1.005 | −0.802 | 93 | 87 | 73 | 21 | −100 |
| RXF 393 | 0.735 | 1.252 | 1.240 | 1.255 | 1.089 | 0.636 | 0.101 | 98 | 100 | 68 | −13 | −86 |
| SN12C | 0.945 | 2.949 | 2.894 | 2.925 | 2.819 | 1.729 | 0.274 | 97 | 99 | 94 | 39 | −71 |
| TK-10 | 0.971 | 2.021 | 1.963 | 2.003 | 1.854 | 1.008 | −0.816 | 94 | 98 | 84 | 3 | −100 |
| UO-31 | 0.831 | 2.171 | 1.980 | 2.014 | 1.968 | 1.046 | 0.085 | 86 | 88 | 85 | 16 | −90 |

| Prostate Cancer | | | | | | | | | | | | |
|---|---|---|---|---|---|---|---|---|---|---|---|---|
| PC-3 | 0.671 | 1.522 | 1.482 | 1.459 | 1.456 | 1.194 | 0.117 | 95 | 93 | 92 | 61 | −83 |
| DU-145 | 0.354 | 1.463 | 1.523 | 1.517 | 1.311 | 0.545 | 0.002 | 105 | 105 | 86 | 17 | −99 |

TABLE 7-continued

| Breast Cancer | | | | | | | | | | | | |
|---|---|---|---|---|---|---|---|---|---|---|---|---|
| MCF7 | 0.349 | 1.833 | 1.676 | 1.552 | 1.447 | 0.455 | 0.088 | 89 | 81 | 74 | 7 | −75 |
| MDA-MB-231/ATCC | 0.612 | 1.313 | 1.306 | 1.302 | 1.179 | 0.785 | 0.081 | 99 | 98 | 81 | 25 | −87 |
| HS 57BT | 1.009 | 2.100 | 2.054 | 2.071 | 1.990 | 1.344 | 0.794 | 96 | 97 | 90 | 31 | −21 |
| 81-549 | 0.820 | 1.643 | 1.597 | 1.518 | 1.574 | 1.123 | 0.008 | 94 | 85 | 92 | 37 | −99 |
| T-47D | 0.857 | 1.497 | 1.454 | 1.451 | 1.3137 | 0.902 | 0.297 | 93 | 93 | 83 | 7 | −65 |
| MDA-MB-468 | 0.681 | 1.176 | 1.147 | 1.122 | 0.867 | 0.414 | 0.155 | 94 | 89 | 38 | −39 | −77 |

| NCI five dose result for JVM 2-40 | | | |
|---|---|---|---|
| Panel/Cell | GI50 | TGI | LC50 |
| Leukemia | | | |
| CCRF-CEM | 1.49E−6 | 6.04E−6 | 9.80E−5 |
| HL-60(TB) | 1.69E−6 | 7.15E−6 | 7.63E−5 |
| K-562 | 4.12E−6 | 2.53E−5 | >1.00E−4 |
| MOLT-4 | 4.05E−6 | 2.17E−5 | >1.00E−4 |
| SR | 2.24E−6 | 1.25E−5 | >1.00E−4 |
| Non-Small Cell Lung Cancer | | | |
| A549/ATCC | 1.33E−5 | 2.86E−5 | 6.13E−5 |
| HOP-62 | 1.49E−5 | 3.04E−5 | 6.22E−5 |
| HOP-92 | 2.33E−6 | 7.99E−6 | 3.07E−5 |
| NCI-H226 | 7.07E−6 | 2.74E−5 | 8.77E−5 |
| NC I-H 23 | 1.30E−5 | 3.33E−5 | 8.52E−5 |
| NCI-H322M | 2.09E−5 | 8.15E−5 | >1.00E−4 |
| NCI-H460 | 1.67E−5 | 3_86E−5 | 8.97E−5 |
| NC I-H 522 | 1.07E−6 | 2.50E−6 | 5.82E−6 |
| Colon Cancer | | | |
| COLO 205 | 2.25E−6 | 6.29E−0 | 2.50E−5 |
| HCC-2998 | 1.38E−5 | 2.80E−5 | 5.68E−5 |
| HCT-116 | 2.24E−6 | 1.10E−5 | 3.32E−5 |
| HCT-15 | 1.96E−6 | 6.78E−6 | 2.89E−5 |
| HT29 | 1.61E−5 | 3.32E−5 | 6.86E−5 |
| SW-620 | 2.39E−6 | 1.19E−5 | 4.74E−5 |
| CNS Cancer | | | |
| SF-268 | 7.36E−6 | 2.36E−5 | 6.28E−5 |
| SF-295 | 1.32E−5 | 2.80E−5 | 5.93E−5 |
| SF-539 | 2.56E−6 | 8.79E−6 | 3.27E−5 |
| SNB-19 | 1.35E−5 | 2.82E−5 | 5.91E−5 |
| SNB-75 | 2.69E−6 | 1.79E−5 | 4.25E−5 |
| U251 | 1.64E−5 | 3.02E−5 | 5.55E−5 |
| Melanoma | | | |
| LOX IMVI | 3.40E−6 | 1.31E−5 | 4.33E−5 |
| M14 | 2.91E−6 | 1.41E−5 | 4.22E−5 |
| MDA-MB-435 | 3.63E−6 | 1.68E−5 | 5.54E−5 |
| SK-MEL-2 | 1.06E−5 | 2.51E−5 | 5.95E−5 |
| SK-MEL-28 | 3.59E−6 | 1.60E−5 | 4.48E−5 |
| 8K-MEL-5 | 7.58E−6 | 2.15E−5 | 5.06E−5 |
| UACC-257 | 4.98E−6 | 1.90E−5 | 4.67E−5 |
| UACC-62 | 593E−6 | 1.95E−5 | 4.62E−5 |
| Ovarian Cancer | | | |
| IGROVI | 1.66E−5 | 3.77E−5 | 8.58E−5 |
| OVCAR-3 | 2.63E−6 | 9.31E−6 | 3.06E−5 |
| OVCAR-4 | 3.76E−6 | 1.87E−5 | 6.41E−5 |
| OVCAR-5 | 5.31E−6 | 1.95E−5 | 4.70E−5 |
| OVCAR-8 | 8.95E−6 | 2.47E−5 | 6.56E−5 |
| NCI/ADR-RES | 1.72E−5 | 4.92E−5 | >1.00E−4 |
| SK-OV-3 | 2.27E−5 | 5.97E−5 | >1.00E−4 |
| Renal Cancer | | | |
| 786-0 | 3.29E−6 | 1.44E−5 | 4.85E−5 |
| A498 | 1.09E−5 | 2.31E−5 | 4.90E−5 |
| ACHN | 2.40E−6 | 8.17E−6 | 3.22E−5 |
| CAKI-1 | 2.79E−6 | 1.50E−5 | 3.88E−5 |
| RXF 393 | 1.68E−6 | 6.85E−6 | 3.17E−5 |
| SN12C | 6.31E−6 | 2.26E−5 | 6.44E−5 |
| TK-10 | 2.65E−6 | 1.08E−5 | 3.29E−5 |
| UO-31 | 3.21E−6 | 1.42E−5 | 4.21E−5 |

TABLE 7-continued

| | | | | |
|---|---|---|---|---|
| | Prostate Cancer | | | |
| | PC-3 | 1.20E−5 | 2.67E−5 | 5.94E−5 |
| | DU-145 | 3.35E−6 | 1.40E−5 | 3.77E−5 |
| | Breast Cancer | | | |
| | MCF7 | 2.28E−6 | 1.22E−5 | 4.98E−5 |
| | MDA-MB-231/ATCC | 3.54E−6 | 1.66E5 | 4.67E5 |
| | HS 57BT | 4.72E−6 | 3.89E−5 | >1.00E−4 |
| | 81-549 | 5.74E−6 | 1.87E−5 | 4.35E−5 |
| | T-47D | 2.70E−6 | 1.25E−5 | 6.13E−5 |
| | MDA-MB-468 | 5.74E−7 | 3.09E−6 | 1.92E−5 |

TABLE 8

NCI five dose result for JVM 2-44

| | Time | | Mean Optical Densities | | | | | Percent Growth | | | | |
|---|---|---|---|---|---|---|---|---|---|---|---|---|
| | | | | Log10 Concentration | | | | | | | | |
| Panel/Cell | Zero | Ctrl | −8.0 | −7.0 | −6.0 | −5.0 | −4.0 | −8.0 | −7.0 | −6.0 | −5.0 | −4.0 |
| Leukemia | | | | | | | | | | | | |
| CCRF-CEM | 0.522 | 2.393 | 2.265 | 2.250 | 2.185 | 0.689 | 0.393 | 93 | 92 | 89 | 9 | −25 |
| HL-60(TB) | 1.473 | 2.782 | 2.812 | 2.607 | 2.594 | 1.432 | 0.925 | 102 | 87 | B6 | −3 | −37 |
| K-562 | 0.204 | 1.116 | 1.141 | 1.030 | 1.109 | 0.394 | 0.152 | 103 | 91 | 99 | 21 | −25 |
| MOLT-4 | 0.650 | 1.823 | 1.889 | 1.794 | 1.734 | 1.062 | 0.453 | 106 | 98 | 92 | 35 | −30 |
| SR | 0.388 | 1.310 | 1.227 | 1.224 | 1.105 | 0.534 | 0.332 | 91 | 91 | 78 | 16 | −14 |
| Non-Small Cell Lung Cancer | | | | | | | | | | | | |
| A549/ATCC | 0.339 | 1.794 | 1.778 | 1.802 | 1.748 | 1.536 | 0.267 | 99 | 101 | 97 | 82 | −21 |
| HOP-62 | 0.830 | 2.250 | 2.193 | 2.046 | 2.174 | 2.007 | 0.936 | 96 | 86 | 95 | 83 | 7 |
| HOP-92 | 0.903 | 1.417 | 1.394 | 1.345 | 1.307 | 0.995 | 0.116 | 95 | 86 | 79 | 18 | −87 |
| NCI-H226 | 1.084 | 2.622 | 2.561 | 2.533 | 2.540 | 2.002 | 0.601 | 96 | 94 | 95 | 60 | −45 |
| NCI-H23 | 0.609 | 1.872 | 1.849 | 1.838 | 1.872 | 1.347 | 0.244 | 98 | 97 | 100 | 58 | −60 |
| NCI-H322M | 0.787 | 1.710 | 1.649 | 1.624 | 1.650 | 1.434 | 0.569 | 93 | 91 | 93 | 70 | −25 |
| NCI-H460 | 0.278 | 2.798 | 2.830 | 2.825 | 2.741 | 2.401 | 0.202 | 101 | 101 | 98 | 84 | −28 |
| NCI-H522 | 0.886 | 2.020 | 1.900 | 1.925 | 1.747 | 0.338 | 0.194 | 89 | 92 | 76 | −62 | −78 |
| Colon Cancer | | | | | | | | | | | | |
| COLO 205 | 0.478 | 1.778 | 1.784 | 1.715 | 1.790 | 0.767 | 0.159 | 100 | 95 | 101 | 22 | −67 |
| HCC-2998 | 0.667 | 2.809 | 1.968 | 1.999 | 2.049 | 1.871 | 0.178 | 97 | 99 | 103 | 90 | −73 |
| HCT-116 | 0.307 | 2.263 | 2.298 | 2.250 | 2.231 | 0.598 | 0.061 | 102 | 99 | 98 | 15 | −80 |
| HCT-15 | 0.365 | 2.556 | 2.435 | 2.370 | 2.210 | 0.643 | 0.108 | 94 | 92 | 84 | 13 | −71 |
| HT29 | 0.241 | 1.155 | 1.216 | 1.248 | 1.268 | 0.502 | 0.873 | 107 | 110 | 112 | 28 | −70 |
| KM12 | 0.396 | 2.171 | 2.117 | 2.151 | 2.184 | 1.680 | 0.105 | 97 | 99 | 101 | 72 | −74 |
| SW-620 | 0.365 | 2.749 | 2.698 | 2.683 | 2.599 | 0.753 | 0.080 | 98 | 97 | 94 | 16 | −78 |
| CNS Cancer | | | | | | | | | | | | |
| SF-268 | 0.553 | 1.862 | 1.843 | 1.839 | 1.625 | 1.432 | 0.188 | 99 | 9B | 97 | 67 | −66 |
| SF-295 | 0.825 | 2.997 | 2.920 | 2.707 | 2.913 | 2.724 | 1.767 | 96 | 87 | 96 | 87 | 43 |
| SF-539 | 0.584 | 1.953 | 1.915 | 1.799 | 1.761 | 1.049 | 0.121 | 97 | 89 | 87 | 34 | −79 |
| SNB-19 | 0.636 | 2.191 | 2.149 | 2.075 | 2.030 | 1.860 | 0.513 | 97 | 93 | 90 | 79 | −19 |
| SNB-75 | 0.767 | 1.507 | 1.343 | 1.274 | 1.330 | 1.112 | 0.183 | 78 | 68 | 76 | 47 | −76 |
| U251 | 0.487 | 2.044 | 2.013 | 2.003 | 2.002 | 1.893 | 0.206 | 98 | 97 | 97 | 90 | −58 |
| Melanoma | | | | | | | | | | | | |
| LOX IMVI | 0.447 | 2.542 | 2.424 | 2.419 | 2452 | 1.794 | 0.051 | 94 | 94 | 96 | 64 | −89 |
| MALME-3M | 0.447 | 0.708 | 0.702 | 0.680 | 0.705 | 0.461 | 0.168 | 98 | 89 | 99 | 5 | −63 |
| M14 | 0.555 | 1.968 | 1.953 | 1.848 | 1.877 | 1.229 | 0.178 | 99 | 91 | 94 | 48 | −68 |
| MDA-MB-435 | 0.539 | 2.359 | 2.396 | 2.240 | 2.253 | 1.343 | 0.109 | 102 | 93 | 94 | 44 | −80 |
| SK-MEL-2 | 1.239 | 2.100 | 2.082 | 2.037 | 2.148 | 1.984 | 0.382 | 98 | 93 | 106 | 87 | −69 |
| SK-MEL-28 | 0.552 | 1.492 | 1.458 | 1.424 | 1.424 | 0.950 | 0.108 | 96 | 93 | 93 | 42 | −80 |
| 8K-MEL-5 | 0.756 | 3.194 | 3.116 | 3.182 | 3.118 | 2.878 | 0.067 | 97 | 100 | 97 | 87 | −91 |
| UACC-257 | 1.097 | 2.228 | 2.160 | 2.135 | 2.046 | 1.662 | 0.150 | 94 | 92 | 84 | 50 | −86 |
| UACC-62 | 0.531 | 2.355 | 2.369 | 2.330 | 2.153 | 1.284 | 0.089 | 101 | 99 | 89 | 41 | −83 |
| Ovarian Cancer | | | | | | | | | | | | |
| IGROVI | 0.706 | 1.825 | 1.866 | 1.888 | 1.902 | 1.363 | 0.249 | 104 | 106 | 107 | 59 | −65 |
| OVCAR-3 | 0.500 | 1.526 | 1.551 | 1.594 | 1.396 | 0.743 | 0.031 | 102 | 107 | 87 | 24 | −94 |
| OVCAR-5 | 0.744 | 1.477 | 1.415 | 1.404 | 1.400 | 1.240 | 0.201 | 91 | 90 | 89 | 68 | −73 |
| OVCAR-8 | 0.473 | 2.831 | 2.052 | 2.055 | 1.997 | 1.385 | 0.184 | 101 | 102 | 98 | 59 | −61 |

TABLE 8-continued

| | | | | | | | | | | | | |
|---|---|---|---|---|---|---|---|---|---|---|---|---|
| NCI/ADR-RES | 0.594 | 2.895 | 2.060 | 2.049 | 2.094 | 1.819 | 0.606 | 98 | 97 | 100 | 82 | 1 |
| SK-OV-3 | 0.993 | 1.886 | 1.885 | 1.808 | 1.892 | 1.852 | 1.032 | 100 | 91 | 101 | 96 | 4 |

Renal Cancer

| | | | | | | | | | | | | |
|---|---|---|---|---|---|---|---|---|---|---|---|---|
| 786-0 | 0.540 | 2.173 | 2.113 | 2.022 | 2.074 | 1.194 | 0.194 | 96 | 91 | 94 | 40 | −64 |
| A498 | 1.702 | 2.586 | 2.357 | 2.301 | 2.296 | 2.150 | 0.967 | 74 | 68 | 67 | 51 | −43 |
| ACHN | 0.483 | 1.990 | 2.010 | 1.961 | 1.883 | 0.773 | 0.112 | 101 | 9B | 93 | 19 | −77 |
| CAKI-1 | 0.661 | 2.953 | 2.814 | 2.649 | 2.593 | 1.287 | 0.032 | 94 | 87 | 84 | 27 | −95 |
| RXF 393 | 1.123 | 1.719 | 1.646 | 1.692 | 1.644 | 1.871 | 0.329 | 88 | 96 | 87 | −5 | −71 |
| SN12C | 0.530 | 1.978 | 1.940 | 1.898 | 1.835 | 0.932 | 0.189 | 97 | 94 | 90 | 28 | −64 |
| TK-10 | 1.092 | 2.260 | 2.185 | 2.198 | 2.166 | 1.338 | 0.069 | 94 | 95 | 92 | 21 | −94 |
| UO-31 | 0.743 | 2.000 | 1.731 | 1.737 | 1.744 | 0.983 | 0.127 | 79 | 79 | 80 | 19 | −83 |

Prostate Cancer

| | | | | | | | | | | | | |
|---|---|---|---|---|---|---|---|---|---|---|---|---|
| PC-3 | 0.611 | 1.876 | 1.916 | 1.899 | 1.917 | 1.854 | 0.340 | 103 | 102 | 103 | 98 | −44 |
| DU-145 | 0.516 | 1.858 | 1.839 | 1.845 | 1.844 | 0.750 | 0.835 | 99 | 99 | 99 | 17 | −93 |

Breast Cancer

| | | | | | | | | | | | | |
|---|---|---|---|---|---|---|---|---|---|---|---|---|
| MCF7 | 0.359 | 1.932 | 1.767 | 1.666 | 1.725 | 0.561 | 0.116 | 89 | 83 | 87 | 13 | −68 |
| MDA-MB-231/ATCC | 0.700 | 1.569 | 1.619 | 1.568 | 1.525 | 1.153 | 0.200 | 106 | 106 | 95 | 52 | −72 |
| HS 57BT | 1.189 | 2.200 | 2.099 | 2 057 | 2.096 | 1 827 | 1.235 | 90 | 86 | 90 | 63 | 5 |
| 81-549 | 1.266 | 2.125 | 2.028 | 1.951 | 1.985 | 1.522 | 0.180 | 89 | 80 | 84 | 30 | −86 |
| T-47D | 0.738 | 1.646 | 1.664 | 1.593 | 1.660 | 0.946 | 0.323 | 102 | 94 | 102 | 23 | −56 |
| MDA-MB-468 | 0.774 | 1.354 | 1.328 | 1.377 | 1.156 | 0.737 | 0.228 | 95 | 104 | 66 | −5 | −71 |

| NCI five dose result for JVM 2-44 | | | |
|---|---|---|---|
| Panel/Cell | GI50 | TGI | LC50 |
| Leukemia | | | |
| CCRF-CEM | 3.06E−6 | 1.84E−5 | <1.00E−4 |
| HL-60(TB) | 2.53E−6 | 9.30E−6 | <1.00E−4 |
| K-562 | 4.25E−6 | 2.82E−5 | <1.00E−4 |
| MOLT-4 | 5.49E−6 | 3.43E−5 | <1.00E−4 |
| SR | 2.81E−6 | 3.33E−5 | <1.00E−4 |
| Non-Small Cell Lung Cancer | | | |
| A549/ATCC | 2.05E−5 | 6.23E−5 | <1.00E−4 |
| HOP-62 | 2.73E−5 | <1.00E−4 | <1.00E−4 |
| HOP-92 | 2.95E−6 | 1.48E−5 | 4.43E−5 |
| NCI-H226 | 1.24E−5 | 3.73E−5 | <1.00E−4 |
| NCI-H23 | 1.18E−5 | 3.12E−5 | 8.24E−5 |
| NCI-H322M | 1.62E−5 | 5.44E−5 | <1.00E−4 |
| NCI-H460 | 2.03E−5 | 5.67E−5 | <1.00E−4 |
| NCI-H522 | 1.54E−6 | 3.55E−5 | 8.20E−6 |
| Colon Cancer | | | |
| COLO 205 | 4.44E−6 | 1.76E−5 | 6.48E−5 |
| HCC-2998 | 1.75E−5 | 3.55E−5 | 7.19E−5 |
| HCT-116 | 3.79E−6 | 1.43E−5 | 4.80E−5 |
| HCT-15 | 3.01E−6 | 1.42E−5 | 5.66E−5 |
| HT29 | 5.54E−6 | 1.95E−5 | 6.20E−5 |
| KM12 | 1.42E−5 | 3.13E−5 | 6.89E−5 |
| SW-620 | 3.67E−6 | 1.49E−5 | 5.83E−5 |
| CNS Cancer | | | |
| SF-268 | 1.35E−5 | 3.19E−5 | 7.57E−5 |
| SF-295 | 7.07E−5 | >1.00E−4 | >1.00E−4 |
| SF-539 | 5.01E−6 | 1.99E−5 | 5.51E−5 |
| SNB-19 | 1.96E−5 | 6.35E−5 | >1.00E−4 |
| SNB-75 | 7.65E−6 | 2.40E−5 | 6.12E−5 |
| U251 | 1.87E−5 | 4.08E−5 | 8.87E−5 |
| Melanoma | | | |
| LOX IMVI | 1.24E−5 | 2.63E−5 | 5.59E−5 |
| MALME-3M | 3.33E−6 | 1.20E−5 | 6.54E−5 |
| M14 | 8.89E−6 | 2.58E−5 | 6.99E−5 |
| MDA-MB-435 | 7.64E−6 | 2.27E−5 | 5.75E−5 |
| SK-MEL-2 | 1.72E−5 | 3.60E−5 | 7.53E−5 |
| SK-MEL-28 | 7.03E−6 | 2.21E−5 | 5.65E−5 |
| 8K-MEL-5 | 1.61E−5 | 3.06E−5 | 5.87E−5 |
| UACC-257 | 9.93E−6 | 2.32E−5 | 5.41E−5 |
| UACC-62 | 6.56E−6 | 2.14E−5 | 5.41E−5 |

TABLE 8-continued

|  | Ovarian Cancer | | |
|---|---|---|---|
| IGROVI | 1.11E−5 | 2.99E−5 | 7.60E−5 |
| OVCAR-3 | 3.86E−6 | 1.59E−5 | 4.23E−5 |
| OVCAR-5 | 1.34E−5 | 3.03E−5 | 6.86E−5 |
| OVCAR-8 | 1.11E−5 | 3.06E−5 | 8.06E−5 |
| NCI/ADR-RES | 2.46E−5 | >1.00E−4 | >1.00E−4 |
| SK-OV-3 | 3.18E−5 | >1.00E−4 | >1.00E−4 |
|  | Renal Cancer | | |
| 786-0 | 6.53E−6 | 2.42E−5 | 7.23E−5 |
| A498 | 1.02E−5 | 3.47E−5 | >1.00E−4 |
| ACHN | 3.83E−6 | 1.59E−5 | 5.26E−5 |
| CAKI-1 | 4.00E−6 | 1.67E−5 | 4.28E−5 |
| RXF 393 | 2.55E−6 | 8.91E−6 | 4.86E−5 |
| SN12C | 4 40E−6 | 2.80E−5 | 6.97E−5 |
| TK-10 | 3.91E−6 | 1.53E−5 | 4.16E−5 |
| UO-31 | 3.08E−6 | 1.54E−5 | 4.76E−5 |
|  | Prostate Cancer | | |
| PC-3 | 2.18E−5 | 4.89E−5 | >1.00E−4 |
| DU-145 | 3.98E−6 | 1.44E−5 | 4.87E−5 |
|  | Breast Cancer | | |
| MCF7 | 3.14E−6 | 1.44E−5 | 6.01E−5 |
| MDA-MB-231/ATCC | 1.04E−5 | 2.64E−5 | 6.70E−5 |
| HS 57BT | 1.67E−5 | >1.00E−4 | >1.00E−4 |
| 81-549 | 4.21E−6 | 1.81E−5 | 4.90E−5 |
| T-47D | 4.52E−6 | 1.94E−5 | 8.23E−5 |
| MDA-MB-468 | 1.87E−6 | 8.56E−6 | 4.87E−5 |

TABLE 9

NCI five dose result for JVM 2-50

| Panel/Cell | Time Zero | Ctrl | Mean Optical Densities Log10 Concentration | | | | | Percent Growth Log10 Concentration | | | | | GI50 | TGI | LC50 |
|---|---|---|---|---|---|---|---|---|---|---|---|---|---|---|---|
|  |  |  | −8.0 | −7.0 | −6.0 | −5.0 | −4.0 | −8.0 | −7.0 | −6.0 | −5.0 | −4.0 |  |  |  |
|  | Leukemia | | | | | | | | | | | | | | |
| CCRF-CEM | 0.458 | 2.041 | 2.004 | 2.068 | 1.773 | 0.467 | 0.256 | 98 | 102 | 83 | 1 | −44 | 2.52E−6 | 1.03E−5 | >1.00E−4 |
| HL-60(TB) | 1.062 | 3.014 | 3.130 | 3.166 | 3.231 | 1.245 | 0.557 | 106 | 109 | 111 | 9 | −48 | 3.99E−6 | 146E−5 | >1.00E−4 |
| K-562 | 0.164 | 1.071 | 1.247 | 1.159 | 1.074 | 0.376 | 0.123 | 119 | 110 | 100 | 23 | −25 | 4.51E−6 | 3.02E−5 | >1.00E−4 |
| MOLT-4 | 0.736 | 2.441 | 2.549 | 2.662 | 2.500 | 1.469 | 0.452 | 106 | 114 | 103 | 43 | −39 | 7.65E−6 | 3.368−5 | >1.00E−4 |
| RPMI-8226 | 1.080 | 2.466 | 2.435 | 2.420 | 2.369 | 1.531 | 0.554 | 98 | 97 | 93 | 33 | −49 | 5.14E−6 | 2.51E−5 | >1.00E−4 |
| SR | 0.462 | 1.926 | 1.919 | 1.922 | 1.798 | 0.728 | 0.326 | 100 | 100 | 91 | 18 | −30 | 3.67E−6 | 240E−5 | >1.00E−4 |
|  | Non-Small Cell Lung Cancer | | | | | | | | | | | | | | |
| A549/ATCC | 0.464 | 2.347 | 2.272 | 2.200 | 2.278 | 2.223 | 0.221 | 96 | 92 | 96 | 93 | 3 | 3.02E−5 | >1.00E−4 | >1.00E−4 |
| HOP-62 | 0.764 | 2.176 | 2.006 | 2.035 | 2.059 | 2.011 | 0.890 | 88 | 90 | 92 | 88 | 9 | 3.04E−5 | >1.00E−4 | >1.00E−4 |
| HOP-92 | 1.261 | 1.863 | 1.802 | 1.792 | 1.625 | 1.341 | 0.155 | 90 | 86 | 94 | 13 | −88 | 3.49E−6 | 1.35E−5 | 4.23E−5 |
| NCI-H226 | 1.048 | 2.573 | 2.467 | 2.508 | 2.439 | 2.071 | 0.664 | 93 | 96 | 91 | 67 | −37 | 1.46E−5 | 4.43E−5 | >1.00E−4 |
| NC I-H 23 | 0.701 | 2.013 | 1.990 | 2.045 | 2.012 | 1.579 | 0.329 | 98 | 102 | 100 | 67 | −53 | 1.38E−5 | 3.61E−5 | 9.43E−5 |
| NCI-H322M | 0.835 | 1.954 | 2.013 | 2.055 | 2.011 | 2.059 | 1.196 | 105 | 109 | 105 | 109 | 32 | 5.88E−5 | >1.00E−4 | >1.00E−4 |
| NCI-H460 | 0.321 | 3.278 | 3.287 | 3.272 | 3.220 | 3.209 | 0.560 | 100 | 100 | 98 | 98 | 8 | 3.40E−5 | >1.00E−4 | >1.00E−4 |
| NCI-H522 | 1.088 | 2.382 | 2.351 | 2.431 | 2.342 | 0.479 | 0.333 | 98 | 104 | 97 | −56 | −69 | 2.03E−6 | 4.30E−6 | 9.13E−6 |
|  | Colon Cancer | | | | | | | | | | | | | | |
| COLO 205 | 0.512 | 1.688 | 1.640 | 1.756 | 1.785 | 0.761 | 0.104 | 96 | 106 | 108 | 21 | −80 | 4.87E−6 | 1.62E−5 | 5.07E−5 |
| HCC-2998 | 0.753 | 2.226 | 2.203 | 2.310 | 2 309 | 2.293 | 0.230 | 98 | 106 | 136 | 105 | −70 | 2.06E−5 | 3.99E−5 | 7.72E−5 |
| HCT-116 | 0.241 | 2.134 | 1.995 | 2.068 | 1.940 | 0.534 | 0.061 | 93 | 96 | 90 | 15 | −75 | 3.43E−6 | 1.48E−5 | 5.32E−5 |
| HCT-15 | 0.420 | 2.719 | 2.560 | 2.614 | 2.584 | 0799 | 0.122 | 93 | 95 | 94 | 16 | −71 | 3.70E−6 | 1.54E−5 | 5.75E−5 |
| HT29 | 0.313 | 1.673 | 1.657 | 1.729 | 1.789 | 1.091 | 0.167 | 99 | 104 | 109 | 57 | −47 | 1.17E−5 | 3.55E−5 | 1.00E−4 |
| SW-620 | 0.382 | 2.199 | 2.241 | 2.275 | 2.226 | 2.065 | 0.109 | 102 | 104 | 101 | 93 | −71 | 1.82E−5 | 3.67E−5 | 7.40E−5 |
|  | CNS Cancer | | | | | | | | | | | | | | |
| SF-268 | 0.664 | 2.092 | 2.077 | 2.060 | 2.096 | 1.955 | 0.329 | 99 | 99 | 100 | 90 | −51 | 1.93E−5 | 4.38E−5 | 9.91E−5 |
| SF-295 | 0.791 | 3.033 | 2.773 | 2.819 | 2.918 | 2.865 | 1.767 | 88 | 90 | 95 | 92 | 44 | 7.37E−5 | 1.06E−4 | >1.00E−4 |
| SF-539 | 1.057 | 2.897 | 2.809 | 2.801 | 2.764 | 2.059 | 0.160 | 95 | 95 | 93 | 54 | −85 | 1.08E−5 | 2.46E−5 | 5.62E−5 |
| SNB-19 | 0.702 | 2.347 | 2.337 | 2.235 | 2.261 | 2.088 | 1.018 | 99 | 93 | 95 | 84 | 19 | 3.26E−5 | >1.00E−4 | >1.00E−4 |

TABLE 9-continued

NCI five dose result for JVM 2-50

| Panel/Cell | Time Zero | Ctrl | Mean Optical Densities | | | | | Percent Growth | | | | | GI50 | TGI | LC50 |
|---|---|---|---|---|---|---|---|---|---|---|---|---|---|---|---|
| | | | −8.0 | −7.0 | −6.0 | −5.0 | −4.0 | −8.0 | −7.0 | −6.0 | −5.0 | −4.0 | | | |
| SNB-75 | 1.019 | 1.900 | 1.633 | 1.713 | 1.719 | 1.617 | 0.815 | 70 | 79 | 79 | 68 | −20 | 1.60E-5 | 5.92E-5 | >1.00E-4 |
| U251 | 0.618 | 2.493 | 2.428 | 2.408 | 2.331 | 2.379 | 0.458 | 97 | 95 | 91 | 94 | −26 | 2.33E-5 | 6.08E-5 | >1.00E-4 |
| Melanoma | | | | | | | | | | | | | | | |
| LOX IMVI | 0.548 | 2.843 | 2.845 | 2.887 | 2.791 | 2.093 | 0.067 | 100 | 102 | 98 | 67 | −88 | 1.29E-5 | 2.72E-5 | 5.71E-5 |
| MALME-3M | 0891 | 1.174 | 1.209 | 1.225 | 1.223 | 0.970 | 0.230 | 107 | 111 | 110 | 58 | −67 | 1.15E-5 | 2.91E-5 | 7.33E-5 |
| M14 | 0429 | 1.914 | 1.774 | 1.864 | 1.795 | 1.257 | 0.184 | 91 | 97 | 92 | 56 | −57 | 1.12E-5 | 3.11E-5 | 8.83E-5 |
| MDA-MB-435 | 0.580 | 2.663 | 2.480 | 2.577 | 2.477 | 1.413 | 0.091 | 91 | 96 | 91 | 40 | −84 | 6.37E-6 | 2.10E-5 | 5.20E-5 |
| SK-MEL-2 | 0.921 | 1.582 | 1.622 | 1.689 | 1.679 | 1.500 | 0.428 | 106 | 116 | 115 | 83 | −54 | 1.85E-5 | 4.18E-5 | 944E-5 |
| SK-MEL-28 | 0.748 | 2.193 | 2.127 | 2.249 | 2.176 | 1.449 | 0.292 | 95 | 104 | 99 | 48 | −61 | 9.33E-6 | 2.77E-5 | 7.94E-5 |
| 8K-MEL-5 | 0.749 | 3.114 | 3.160 | 3.112 | 3.122 | 2.744 | 0.494 | 102 | 100 | 100 | 84 | −34 | 1.95E-5 | 5.15E-5 | >1.00E-4 |
| UACC-257 | 0.950 | 2.114 | 2.052 | 2.662 | 1.934 | 1.458 | 0.257 | 95 | 90 | 65 | 44 | −73 | 7.00E-6 | 2.37E-5 | 6.35E-5 |
| UACC-62 | 1.123 | 3.071 | 2.937 | 2.935 | 3.005 | 2.326 | 0.178 | 93 | 93 | 97 | 62 | −84 | 1.20E-5 | 2.65E-5 | 5.83E-5 |
| Ovarian Cancer | | | | | | | | | | | | | | | |
| IGROVI | 0.500 | 1.624 | 1.563 | 1.687 | 1.722 | 1.056 | 0.321 | 95 | 106 | 109 | 49 | −36 | 9.79E-6 | 1.80E-5 | >1.00E-4 |
| OVCAR-3 | 0.539 | 1.818 | 1.857 | 1.900 | 1.654 | 1.047 | 0.037 | 103 | 106 | 103 | 40 | −93 | 6.27E-6 | 1.99E-5 | 4.73E-5 |
| OVCAR-5 | 0.629 | 1.690 | 1.578 | 1.598 | 1.528 | 1.348 | 0.288 | 89 | 91 | 85 | 68 | −54 | 1.40E-5 | 1.59E-5 | 9.24E-5 |
| OVCAR-8 | 0553 | 2.273 | 2.238 | 2.198 | 2.219 | 1.615 | 0.415 | 98 | 96 | 97 | 62 | −25 | 1.37E-5 | 5.15E-5 | >1.00E-4 |
| NCI/ADR-RES | 0.588 | 1.976 | 2.086 | 2.149 | 2.061 | 2.040 | 0.814 | 108 | 113 | 106 | 105 | 16 | 4.15E-5 | >1.00E-4 | >1.00E-4 |
| SK-OV-3 | 0.843 | 1.738 | 1.864 | 1.766 | 1.769 | 1.789 | 1.047 | 92 | 103 | 103 | 106 | 23 | 4.70E-5 | >1.00E-4 | >1.00E-4 |
| Renal Cancer | | | | | | | | | | | | | | | |
| 786-0 | 0.295 | 2.473 | 2.295 | 2.416 | 2.419 | 1.699 | 0.158 | 91 | 97 | 97 | 59 | −74 | 1.17E-5 | 2.78E-5 | 6.64E-5 |
| A498 | 1.172 | 1.902 | 1.716 | 1.670 | 1.613 | 1.593 | 0.883 | 74 | 68 | 60 | 58 | −25 | 1.24E-5 | 5.01E-5 | >1.00E-4 |
| ACHN | 0.458 | 2.153 | 2.087 | 2.176 | 2.144 | 1.182 | 0.166 | 96 | 101 | 99 | 43 | 84 | 7.44E-6 | 2.52E-5 | 7.11E-5 |
| CAKI-1 | 0.812 | 3.058 | 2.804 | 2.859 | 2.770 | 1.895 | 0.285 | 89 | 91 | 87 | 48 | −65 | 8.99E-6 | 2.67E-5 | 7.38E-5 |
| RXF 393 | 0.730 | 1.486 | 1.421 | 1.436 | 1.473 | 0.882 | 0.234 | 91 | 93 | 98 | 20 | −68 | 4.14E-6 | 1.69E-5 | 6.25E-5 |
| SN12C | 0.737 | 2.770 | 2.640 | 2.591 | 2.595 | 2.222 | 0.649 | 94 | 91 | 31 | 73 | −12 | 1.86E-5 | 7.22E-5 | >1.00E-4 |
| TK-10 | 1.011 | 1.853 | 1.852 | 1.662 | 1.933 | 1.473 | 0.090 | 100 | 103 | 110 | 55 | −91 | 1.08E-5 | 236E-5 | 5.23E-5 |
| UO-31 | 0.844 | 2107 | 2.041 | 2.093 | 2.060 | 1.694 | 0.296 | 95 | 99 | 96 | 67 | −65 | 1.35E-5 | 3.23E-5 | 7.71E-5 |
| Prostate Cancer | | | | | | | | | | | | | | | |
| PC-3 | 0.632 | 2.247 | 2.209 | 2.141 | 2.193 | 2.149 | 0.500 | 98 | 93 | 97 | 94 | −21 | 2.41E-5 | 6.57E-5 | >1.00E-4 |
| DU-145 | 0.442 | 1.790 | 1.896 | 1.902 | 1.689 | 1.245 | 0.035 | 108 | 106 | 107 | 60 | −92 | 1.16E-5 | 2.47E-5 | 5.28E-5 |
| Breast Cancer | | | | | | | | | | | | | | | |
| MCF7 | 0.461 | 2.392 | 2.132 | 2.176 | 2.091 | 0.761 | 0.189 | 87 | 89 | 84 | 16 | −59 | 3.16E-6 | 1.61E-5 | 7.55E-5 |
| MDA-MB-231/ATCC | 0.769 | 1841 | 1.840 | 1.749 | 1.828 | 1.450 | 0.263 | 100 | 91 | 99 | 63 | −66 | 1.27E-5 | 1.10E-5 | 7.55E-5 |
| HS 578T | 0.962 | 2.180 | 2.078 | 2.036 | 2.067 | 1.962 | 1.232 | 92 | 88 | 91 | 82 | 22 | 3.43E-5 | >1.00E-4 | >1.00E-4 |
| BT-549 | 0.866 | 1.736 | 1.604 | 1.659 | 1.585 | 1.046 | 0.078 | 85 | 91 | 83 | 21 | −91 | 3.26E-6 | 1.53E-5 | 4.29E-5 |
| T-47D | 1.033 | 2.130 | 2.011 | 2.060 | 2.013 | 1.213 | 0.474 | 89 | 95 | 69 | 16 | −54 | 3.46E-6 | 1.71E-5 | 8.74E-5 |
| MDA-MB-468 | 0.768 | 1.419 | 1.407 | 1.358 | 1.205 | 0.674 | 0.255 | 98 | 91 | 67 | −12 | −67 | 1.64E-6 | 7.01E-6 | 4.91E-5 |

TABLE 10

NCI five dose result for JVM 2-57

| Panel/Cell | Time Zero | Ctrl | Mean Optical Densities | | | | | Percent Growth | | | | | GI50 | TGI | LC50 |
|---|---|---|---|---|---|---|---|---|---|---|---|---|---|---|---|
| | | | −8.0 | −7.0 | −6.0 | −5.0 | −4.0 | −8.0 | −7.0 | −6.0 | −5.0 | −4.0 | | | |
| Leukemia | | | | | | | | | | | | | | | |
| CCRF-CEM | 0.458 | 1.876 | 1.831 | 1.771 | 1.289 | 0.327 | 0.216 | 97 | 93 | 59 | −29 | −53 | 1.25E-6 | 4.69E-6 | 7.63E-5 |
| HL-60(TB) | 1.062 | 2.916 | 2.849 | 2.751 | 2.613 | 0.950 | 0.478 | 96 | 91 | 84 | −11 | −55 | 2.28E-6 | 7.73E-6 | 7.72E-5 |
| K-562 | 0.164 | 0.918 | 0.910 | 3.859 | 0.861 | 0.284 | 0.939 | 99 | 92 | 92 | 16 | −16 | 3.58E-6 | 3.20E-5 | >1.00E-4 |
| MOLT-4 | 0.736 | 2.356 | 2.315 | 2194 | 2.316 | 0.869 | 0.446 | 97 | 90 | 98 | 8 | −39 | 3.40E-6 | 1.49E-5 | >1.00E-4 |
| RPMI-8226 | 1.080 | 2.427 | 2.447 | 2.340 | 2.253 | 1.170 | 0.512 | 101 | 94 | 87 | 7 | −53 | 2.89E-6 | 1.30E-5 | 9.03E-5 |
| SR | 0.462 | 1.909 | 1.920 | 1.857 | 1.573 | 0.520 | 0.253 | 101 | 96 | 77 | 4 | −45 | 2.33E-6 | 1.21E-5 | >1.00E-4 |
| Non-Small Cell Lung Cancer | | | | | | | | | | | | | | | |
| A549/ATCC | 0.464 | 2.271 | 2.270 | 2.245 | 2.178 | 1.746 | 0.056 | 100 | 99 | 95 | 71 | −88 | 1.35E-5 | 2.80E-5 | 5.77E-5 |
| HOP-62 | 0.764 | 2.149 | 2.087 | 1.951 | 2044 | 1.768 | 0.110 | 95 | 86 | 92 | 72 | −86 | 1.39E-5 | 2.87E-5 | 5.95E-5 |

TABLE 10-continued

NCI five dose result for JVM 2-57

| | Time | | Mean Optical Densities (Log10 Concentration) | | | | | Percent Growth (Log10 Concentration) | | | | | | | |
|---|---|---|---|---|---|---|---|---|---|---|---|---|---|---|---|
| Panel/Cell | Zero | Ctrl | −8.0 | −7.0 | −6.0 | −5.0 | −4.0 | −8.0 | −7.0 | −6.0 | −5.0 | −4.0 | GI50 | TGI | LC50 |
| HOP-92 | 1.261 | 1.941 | 1.792 | 1.788 | 1.740 | 1.143 | 0.061 | 92 | 91 | 83 | −9 | −95 | 2.26E−6 | 7.90E−6 | 2.97E−5 |
| NCI-H226 | 1.048 | 2.621 | 2.502 | 2.644 | 2.403 | 1.816 | 0.506 | 92 | 101 | 86 | 49 | −52 | 9.29E−6 | 3.06E−5 | 9.61E−5 |
| NCI-H 3 | 0.701 | 2.022 | 1.945 | 1.959 | 1.917 | 1.101 | 0.227 | 94 | 95 | 92 | 30 | −68 | 4.79E−6 | 2.04E−5 | 6.61E−5 |
| NCI-H322M | 0.835 | 1.912 | 1.888 | 1.853 | 1.864 | 1.675 | 0.693 | 98 | 94 | 97 | 78 | −17 | 1.97E−5 | 6.62E−5 | >1.00E−4 |
| NCI-H460 | 0.321 | 3.194 | 3.274 | 3.281 | 3.230 | 2.548 | 0.111 | 103 | 103 | 101 | 78 | −65 | 1.56E−5 | 3.49E−5 | 7.80E−5 |
| NCI-H522 | 1.088 | 2.392 | 2.252 | 2.218 | 1.969 | 0.293 | 0.279 | 89 | 87 | 68 | −73 | −74 | 1.33E−6 | 3.02E−6 | 6.85E−6 |
| Colon Cancer | | | | | | | | | | | | | | | |
| COLO 205 | 0.512 | 1.745 | 1.780 | 1.707 | 1.685 | 0.470 | 0.033 | 103 | 97 | 95 | −8 | −94 | 2.73E−6 | 8.33E−6 | 3.08E−5 |
| HCC-2998 | 0.753 | 2.226 | 2.143 | 2.692 | 2.328 | 1.716 | 0.145 | 94 | 91 | 107 | 65 | −81 | 1.27E−5 | 2.80E−5 | 6.16E−5 |
| HCT-116 | 0.241 | 1.936 | 1.972 | 1.810 | 1.730 | 0.294 | 0.005 | 102 | 93 | 88 | 3 | −98 | 2.80E−6 | 1.07E−5 | 3.36E−5 |
| HCT-15 | 0.420 | 2.699 | 2.653 | 2.638 | 2.289 | 0.520 | 0.071 | 98 | 97 | 82 | 4 | −83 | 2.58E−6 | 1.12E−5 | 4.18E−5 |
| HT29 | 0.313 | 1.618 | 1.628 | 1.570 | 1.673 | 0.590 | 0.085 | 101 | 96 | 104 | 21 | −73 | 4.50E−6 | 1.68E−5 | 5.70E−5 |
| KM12 | 0.382 | 2.260 | 2.227 | 2.211 | 2.240 | 1.757 | 0.032 | 98 | 97 | 99 | 73 | −92 | 1.38E−5 | 2.78E−5 | 5.59E−5 |
| SW-620 | 0.259 | 2.533 | 2.482 | 2.513 | 1.744 | 0.386 | 0.052 | 98 | 99 | 65 | 6 | −80 | 1.80E−6 | 1.16E−5 | 4.47E−5 |
| CNS Cancer | | | | | | | | | | | | | | | |
| SF-268 | 0.664 | 2.133 | 2.011 | 1.981 | 2.017 | 1.627 | 0.182 | 92 | 90 | 92 | 66 | −73 | 1.30E−5 | 2.98E−5 | 6.86E−5 |
| SF-295 | 0.791 | 3.004 | 2.929 | 2.779 | 2.849 | 2.467 | 0.555 | 97 | 90 | 93 | 76 | −30 | 1.75E−5 | 5.21E−5 | >1.00E−4 |
| SF-539 | 1.057 | 2.929 | 2.864 | 2.756 | 2.703 | 1.478 | 0.084 | 97 | 91 | 88 | 22 | −92 | 3.80E−6 | 1.57E−5 | 4.29E−5 |
| SNB-19 | 0.702 | 2.228 | 2.144 | 2.149 | 2.112 | 1.834 | 0.437 | 94 | 95 | 92 | 74 | −38 | 1.64E−5 | 4.59E−5 | >1.00E−4 |
| SNB-75 | 1.019 | 1.932 | 1.780 | 1.713 | 1.730 | 1.519 | 0.599 | 83 | 76 | 78 | 55 | −41 | 1.12E−5 | 3.72E−5 | >1.00E−4 |
| U251 | 0.618 | 2.380 | 2.366 | 2.323 | 2.231 | 2.049 | −0.003 | 99 | 97 | 92 | 81 | −100 | 1.49E−5 | 2.81E−5 | 5.30E−5 |
| Melanoma | | | | | | | | | | | | | | | |
| LOX IMVI | 0.548 | 2.845 | 2.760 | 2.719 | 2.657 | 1.037 | 0.050 | 96 | 95 | 92 | 21 | −91 | 3.92E−6 | 1.55E−5 | 4.32E−5 |
| MALME-3M | 0.691 | 1.194 | 1.171 | 1.168 | 1.166 | 0.818 | 0.164 | 95 | 95 | 94 | 25 | −76 | 4.38E−6 | 1.77E−5 | 5.50E−5 |
| M14 | 0.429 | 1.806 | 1.795 | 1.660 | 1.629 | 0.795 | 0.145 | 99 | 89 | 87 | 27 | −66 | 4.10E−6 | 1.93E−5 | 6.67E−5 |
| MDA-MB-435 | 0.580 | 2.715 | 2.683 | 2.570 | 2.531 | 1.268 | 0.109 | 99 | 93 | 91 | 32 | −81 | 5.01E−6 | 1.92E−5 | 5.31E−5 |
| SK-MEL-2 | 0.921 | 1.538 | 1.516 | 1.532 | 1.531 | 1.246 | 0.279 | 96 | 99 | 99 | 53 | −70 | 1.05E−5 | 2.69E−5 | 6.90E−5 |
| SK-MEL-28 | 0.748 | 2.190 | 2.163 | 2.054 | 2.057 | 1.099 | 0 154 | 98 | 91 | 91 | 24 | −79 | 4.11E−6 | 1.72E−5 | 5.20E−5 |
| 8K-MEL-5 | 0.749 | 3.184 | 3.179 | 3.134 | 3.104 | 2.103 | 0.200 | 100 | 98 | 97 | 56 | −73 | 1.11E−5 | 2.70E−5 | 6.60E−5 |
| UACC-257 | 0.950 | 2.049 | 1.982 | 1.985 | 1.755 | 1.213 | 0.088 | 94 | 94 | 73 | 24 | −91 | 2.96E−6 | 1.62E−5 | 4.41E−5 |
| UACC-62 | 1.123 | 2.979 | 2.972 | 2.967 | 2.727 | 1.773 | 0.160 | 100 | 99 | 86 | 35 | −86 | 5.11E−6 | 1.95E−5 | 5.05E−5 |
| Ovarian Cancer | | | | | | | | | | | | | | | |
| IGROVI | 0.500 | 1.597 | 1.598 | 1.611 | 1.620 | 0 587 | 0 213 | 100 | 101 | 102 | 8 | −57 | 3.58E−6 | 1.32E−5 | 7.70E−5 |
| OVCAR-3 | 0.539 | 1.826 | 1.810 | 1.831 | 1.646 | 0.633 | 0.002 | 99 | 100 | 86 | 7 | −100 | 2.87E−6 | 1.17E−5 | 3.43E−5 |
| OVCAR-5 | 0.629 | 1.593 | 1.526 | 1.440 | 1.460 | 0.861 | 0.060 | 93 | 84 | 86 | 24 | −90 | 3.82E−6 | 1.62E−5 | 4.43E−5 |
| OVCAR-8 | 0.553 | 2.237 | 2.242 | 2.240 | 2.109 | 1.063 | 0.134 | 100 | 160 | 92 | 30 | −76 | 4.82E−6 | 1.93E−5 | 5.72E−5 |
| NCI/ADR-RES | 0.588 | 2.030 | 1.959 | 2.043 | 2.017 | 1.458 | 0.428 | 95 | 101 | 99 | 60 | −27 | 1.31E−5 | 4.89E−5 | >1.00E−4 |
| SK-OV-3 | 0.843 | 1.709 | 1.721 | 1.625 | 1.753 | 1.632 | 0.620 | 101 | 90 | 105 | 91 | −26 | 2.24E−5 | 5.96E−5 | >1.00E−4 |
| Renal Cancer | | | | | | | | | | | | | | | |
| 786-0 | 0.595 | 2.440 | 2.364 | 2.253 | 2.306 | 1.287 | 0.070 | 96 | 90 | 93 | 38 | −88 | 5.94E−6 | 1.99E−5 | 4.96E−5 |
| A498 | 1.172 | 1.903 | 1.691 | 1.687 | 1.653 | 1.409 | 0.123 | 71 | 70 | 66 | 32 | −90 | 2.97E−6 | 1.84E−5 | 4.74E−5 |
| ACHN | 0.458 | 2.108 | 2.078 | 1.995 | 1.851 | 0.572 | 0.080 | 98 | 93 | 84 | 7 | −83 | 2.78E−6 | 1.19E−5 | 4.33E−5 |
| CAKI-1 | 0.812 | 3.093 | 2.993 | 2.838 | 2.674 | 1.050 | 0.026 | 96 | 89 | 82 | 10 | −97 | 2.78E−6 | 1.25E−5 | 3.66E−5 |
| RXF 393 | 0.730 | 1.446 | 1.437 | 1.497 | 1.270 | 0.714 | 0.173 | 99 | 107 | 75 | −2 | −76 | 2.12E−6 | 9.35E−6 | 4.41E−5 |
| SN12C | 0.737 | 2.702 | 2.626 | 2.648 | 2.560 | 1.288 | 0.300 | 96 | 97 | 93 | 28 | −59 | 4.57E−6 | 2.09E−5 | 7.81E−5 |
| TK-10 | 1.011 | 1.775 | 1.726 | 1.758 | 1.744 | 0.963 | 0.053 | 94 | 98 | 96 | −5 | −95 | 2.86E−6 | 8.97E−6 | 3.18E−5 |
| UO-31 | 0.844 | 2.031 | 1.847 | 1.892 | 1.812 | 0.922 | 0.059 | 84 | 88 | 82 | 7 | −93 | 2.63E−6 | 1.16E−5 | 3.69E−5 |
| Prostate Cancer | | | | | | | | | | | | | | | |
| PC-3 | 0.632 | 2.370 | 2.330 | 2.327 | 2.303 | 1.797 | 0.188 | 98 | 97 | 96 | 67 | −70 | 1.33E−5 | 3.08E−5 | 7.11E−5 |
| DU-145 | 0.442 | 1.776 | 1.831 | 1.812 | 1.679 | 0.691 | 0.014 | 104 | 103 | 93 | 19 | −97 | 3.78E−6 | 1.45E−5 | 3.93E−5 |
| Breast Cancer | | | | | | | | | | | | | | | |
| MCF7 | 0.461 | 2.313 | 2.197 | 2.093 | 2.001 | 0.527 | 0.114 | 94 | 88 | 83 | 4 | −75 | 2.61E−6 | 1.11E−5 | 4.77E−5 |
| MDA-MB-231/ATCC | 0.769 | 1.837 | 1.902 | 1.722 | 1.690 | 1.096 | 0.178 | 106 | 89 | 86 | 31 | −77 | 4.48E−6 | 1.93E−5 | 5.62E−5 |
| HS 578T | 0.962 | 2.162 | 2.053 | 2.070 | 2.006 | 1.747 | 1.050 | 91 | 92 | 87 | 65 | 7 | 1.84E−5 | >1.00E−4 | >1.00E−4 |
| BT-549 | 0.866 | 1.999 | 2.056 | 1.839 | 1.710 | 0.865 | 0.035 | 105 | 86 | 74 | | −96 | 2.13E−6 | 9.96E−6 | 3.31E−5 |
| T-47D | 1.033 | 1.950 | 1.897 | 1.819 | 1.775 | 0.995 | 0.204 | 94 | 86 | 81 | −4 | −80 | 2.32E−6 | 9.04E−6 | 4.02E−5 |
| MDA-MB-468 | 0.768 | 1.447 | 1.447 | 1.441 | 1.159 | 0.633 | 0.273 | 100 | 99 | 58 | −18 | −65 | 1.26E−6 | 5.83E−6 | 4.90E−5 |

TABLE 11

NCI five dose result for JVM 2-66

| | Time | | Mean Optical Densities | | | | | | Percent Growth | | | | | | |
|---|---|---|---|---|---|---|---|---|---|---|---|---|---|---|---|---|
| | | | | | Log10 Concentration | | | | | | | | | | |
| Panel/Cell | Zero | Ctrl | −8.0 | −7.0 | −6.0 | −5.0 | −4.0 | −8.0 | −7.0 | −6.0 | −5.0 | −4.0 | GI50 | TGI | LC50 |
| Leukemia | | | | | | | | | | | | | | | |
| CCRF-CEM | 0.458 | 1.932 | 1.881 | 1.885 | 1.058 | 0.295 | 0.216 | 97 | 97 | 41 | −36 | −53 | 6.82E-7 | 3.41E-6 | 6.76E-5 |
| HL-60(TB) | 1.062 | 2.871 | 2.813 | 2.575 | 2.482 | 0.920 | 0.538 | 97 | 84 | 79 | −13 | −49 | 2.04E-6 | 7.15E-6 | >1.00E-4 |
| K-562 | 0.164 | 0.893 | 0.920 | 0.856 | 0.842 | 0.259 | 0.147 | 104 | 95 | 93 | 13 | −10 | 3.45E-6 | 3.61E-5 | >1.00E-4 |
| MOLT-4 | 0.736 | 2.281 | 2.195 | 2.043 | 2.050 | 0.535 | 0.447 | 94 | 85 | 85 | −27 | −39 | 2.05E-6 | 5.71E-6 | >1.00E-4 |
| RPMI-8226 | 1.080 | 2.543 | 2.510 | 2.503 | 2.272 | 0.811 | 0.583 | 98 | 97 | 81 | −25 | −46 | 1.98E-6 | 5.83E-6 | >1.00E-4 |
| SR | 0.462 | 1.851 | 1.768 | 1.677 | 1.292 | 0.417 | 0.288 | 94 | 87 | 60 | −10 | −38 | 1.38E-6 | 7.24E-6 | >1.00E-4 |
| Non-Small Cell Lung Cancer | | | | | | | | | | | | | | | |
| A549/ATCC | 0.464 | 2.188 | 2.148 | 2.143 | 2.072 | 1.450 | 0.124 | 98 | 97 | 93 | 57 | −73 | 1.13E-5 | 2.74E-5 | 6.62E-5 |
| HOP-62 | 0.764 | 2.310 | 2.322 | 2.168 | 2.202 | 1.861 | 0.099 | 101 | 92 | 93 | 71 | −87 | 1.36E-5 | 2.81E-5 | 5.83E-5 |
| HOP-92 | 1.261 | 1.968 | 1.932 | 1.908 | 1.748 | 0.657 | 0.070 | 95 | 92 | 69 | −48 | −94 | 1.45E-6 | 3.89E-6 | 1.11E-5 |
| NCI-H226 | 1.048 | 2.504 | 2.527 | 2.354 | 2.313 | 0.533 | 0.301 | 102 | 90 | 87 | −49 | −71 | 1.87E-5 | 4.35E-5 | 1.09E-5 |
| NCI-H23 | 0.701 | 1.883 | 1.802 | 1.835 | 1.766 | 0.654 | 0.210 | 93 | 96 | 98 | −7 | −70 | 2.59E-6 | 8.51E-6 | 4.82E-5 |
| NCI-H322M | 0.835 | 1.887 | 1.846 | 1.879 | 1.911 | 1.553 | 0.066 | 96 | 99 | 102 | 68 | −92 | 1.30E-5 | 2.66E-5 | 5.46E-5 |
| NCI-H460 | 0.321 | 3.213 | 3.228 | 3.232 | 3.184 | 2.250 | 0.100 | 100 | 101 | 99 | 67 | −69 | 1.33E-5 | 3.10E-5 | 7.26E-5 |
| NCI-H522 | 1.088 | 2.354 | 2.243 | 2.256 | 1.898 | 0.202 | 0.215 | 91 | 92 | 64 | −81 | −80 | 1.25E-6 | 2.75E-6 | 6.08E-6 |
| Colon Cancer | | | | | | | | | | | | | | | |
| COLO 205 | 0.512 | 1.806 | 1.838 | 1.752 | 1.822 | 0.195 | 0.036 | 102 | 96 | 101 | −62 | −93 | 2.06E-6 | 4.17E-6 | 8.44E-6 |
| HCC-2998 | 0.753 | 2.081 | 2.029 | 1.966 | 2.092 | 1.243 | 0.173 | 96 | 91 | 101 | 37 | −77 | 6.24E-6 | 2.11E-5 | 5.79E-5 |
| HCT-116 | 0.241 | 1.981 | 1.963 | 1.858 | 1.459 | 0.085 | −0.001 | 99 | 93 | 70 | −65 | −100 | 1.41E-6 | 3.30E-6 | 7.75E-6 |
| HCT-15 | 0.420 | 2.553 | 2.551 | 2.426 | 1.919 | 0.210 | 0.058 | 100 | 94 | 70 | −50 | −86 | 1.47E-6 | 3.84E-6 | 1.00E-5 |
| HT29 | 0.313 | 1.578 | 1.538 | 1.592 | 1.599 | 0.338 | 0.051 | 97 | 101 | 102 | 2 | −84 | 3.30E-6 | 1.05E-5 | 4.03E-5 |
| KM12 | 0.382 | 2.216 | 2.269 | 2.164 | 2.194 | 1.234 | 0.059 | 103 | 97 | 99 | 46 | −85 | 8.55E-6 | 2.26E-5 | 5.45E-5 |
| SW-620 | 0.259 | 2.368 | 2.345 | 2.311 | 1.678 | 0.161 | 0.037 | 99 | 97 | 67 | −38 | −86 | 1.46E-6 | 4.37E-6 | 1.79E-5 |
| CNS Cancer | | | | | | | | | | | | | | | |
| SF-268 | 0.664 | 2.085 | 2.021 | 1.988 | 2.018 | 1.436 | 0.104 | 95 | 93 | 95 | 54 | −84 | 1.07E-5 | 2.47E-5 | 5.65E-5 |
| SF-295 | 0.791 | 2.935 | 2.831 | 2.738 | 2.746 | 2.132 | 0.035 | 95 | 91 | 91 | 63 | −96 | 1.20E-5 | 2.49E-5 | 5.15E-5 |
| SF-539 | 1.057 | 2.809 | 2.734 | 2.547 | 2.643 | 0.568 | 0.132 | 96 | 85 | 90 | −46 | −88 | 1.98E-6 | 459E-6 | 1.23E-5 |
| SNB-19 | 0.702 | 2.108 | 2.006 | 1.980 | 1.956 | 1.627 | 0.145 | 93 | 91 | 89 | 66 | −79 | 1 28E-5 | 2.84E-5 | 6 27E-5 |
| SNB-75 | 1.019 | 2.025 | 1.894 | 1.774 | 1.815 | 1.443 | 0.056 | 87 | 75 | 79 | 42 | −95 | 6.13E-6 | 2.03E-5 | 4.72E-5 |
| U251 | 0.618 | 2.376 | 2.306 | 2.313 | 2.236 | 1.903 | 0.008 | 96 | 96 | 92 | 73 | −99 | 136E-5 | 2.66E-5 | 5.21E-5 |
| Melanoma | | | | | | | | | | | | | | | |
| LOX IMVI | 0.548 | 2.661 | 2.575 | 2.515 | 2.496 | 0.390 | 0.062 | 96 | 93 | 92 | −29 | −89 | 2.23E-6 | 5.77E-6 | 2.25E-5 |
| MALME-3M | 0.691 | 1.242 | 1.236 | 1.191 | 1.155 | 0.421 | 0.196 | 99 | 91 | 84 | −39 | −72 | 1.90E-6 | 4.82E-6 | 2.16E-5 |
| M14 | 0.429 | 1.830 | 1.771 | 1.653 | 1.621 | 0.535 | 0.063 | 96 | 87 | 85 | 8 | −85 | 284E-6 | 121E-5 | 4.17E-5 |
| MDA-MB-435 | 0.580 | 2.886 | 2.844 | 2.672 | 1.263 | 1.034 | 0.281 | 98 | 91 | 30 | 20 | −52 | 4.64E-7 | 1.89E-5 | 9.51E-5 |
| SK-MEL-2 | 0.921 | 1.538 | 1.540 | 1.533 | 1.526 | 0.876 | 0.145 | 100 | 99 | 98 | −5 | −84 | 2.93E-6 | 8.95E-6 | 3.70E-5 |
| SK-MEL-28 | 0.748 | 2.072 | 2.096 | 1.986 | 1.971 | 0.645 | 0.123 | 102 | 94 | 92 | −14 | −84 | 2.51E-6 | 7.42E-6 | 3.30E-5 |
| 8K-MEL-5 | 0.749 | 2.949 | 2.935 | 2.928 | 2.745 | 1.202 | 0.031 | 99 | 99 | 91 | 21 | −96 | 3.81E-6 | 1.50E-5 | 4.03E-5 |
| UACC-257 | 0.950 | 2.089 | 2.023 | 2.043 | 1.648 | 0.959 | 0.099 | 94 | 96 | 79 | 1 | −90 | 2.34E-6 | 1.02E-5 | 3.65E-5 |
| UACC-62 | 1.123 | 2.887 | 2.830 | 2.780 | 2.638 | 0.848 | 0.064 | 97 | 94 | 86 | −24 | −94 | 2.11E-6 | 6.00E-6 | 2.32E-5 |
| Ovarian Cancer | | | | | | | | | | | | | | | |
| IGROVI | 0.500 | 1.595 | 1.671 | 1.656 | 1.450 | 0.430 | 0.198 | 107 | 106 | 87 | −14 | −60 | 2.31E-6 | 7.26E-6 | 5.97E-5 |
| OVCAR-3 | 0.539 | 1.852 | 1.872 | 1.793 | 1.593 | 0.258 | 0.006 | 101 | 95 | 80 | −52 | −99 | 1.69E-6 | 4.03E-6 | 9.62E-6 |
| OVCAR-5 | 0.629 | 1.500 | 1.467 | 1.413 | 1.488 | 0.814 | 0.106 | 96 | 90 | 99 | 21 | −83 | 4.25E-6 | 1.60E-5 | 4.81E-5 |
| OVCAR-8 | 0.553 | 2.226 | 2.189 | 2.156 | 2.075 | 0.559 | 0.080 | 98 | 96 | 91 | | −86 | 2.83E-6 | 1.01E-5 | 3.85E-5 |
| NCI/ADR-RES | 0.588 | 1.877 | 1.880 | 1.859 | 1.871 | 0.981 | 0.205 | 100 | 99 | 99 | 30 | −65 | 5.22E-6 | 2.08E-5 | 6.95E-5 |
| SK-OV-3 | 0.843 | 1.835 | 1.831 | 1.760 | 1.837 | 1.688 | 0.145 | 100 | 92 | 100 | 85 | −83 | 1.62E-5 | 3.22E-5 | 6.38E-5 |
| Renal Cancer | | | | | | | | | | | | | | | |
| 786-0 | 0.595 | 2.491 | 2.435 | 2.314 | 2.351 | 0.921 | 0.115 | 97 | 91 | 93 | 17 | −81 | 3.67E-6 | 1.50E-5 | 4.86E-5 |
| A498 | 1.172 | 1.824 | 1.718 | 1.647 | 1.601 | 1.022 | 0.078 | 84 | 73 | 66 | −13 | −93 | 1.59E-6 | 6.87E-6 | 2.89E-5 |
| ACHN | 0.458 | 1.966 | 2.005 | 1.859 | 1.593 | 0.346 | 0.079 | 103 | 93 | 75 | −25 | −83 | 1.79E-6 | 5.68E-6 | 2.74E-5 |
| CAKI-1 | 0.812 | 3.200 | 3.140 | 2.988 | 2.767 | 0.635 | 0.028 | 97 | 91 | 82 | −22 | −97 | 2.03E-6 | 6.16E-6 | 2.38E-5 |
| RXF 393 | 0.730 | 1.449 | 1.447 | 1.416 | 1.178 | 0.057 | 0.060 | 100 | 95 | 62 | −92 | −92 | 1.20E-6 | 2.53E-6 | 5.33E-6 |
| SN12C | 0.737 | 2.599 | 2.571 | 2.493 | 2.339 | 0.794 | 0.081 | 98 | 94 | 86 | 3 | −89 | 2.72E-6 | 1.06E-5 | 3.77E-5 |
| TK-10 | 1.011 | 1.814 | 1.766 | 1.776 | 1.827 | 0.780 | 0.042 | 94 | 95 | 102 | −23 | −96 | 2.60E-6 | 6.55E-6 | 2.35E-5 |
| UO-31 | 0.844 | 2.071 | 1.827 | 1.893 | 1.875 | 0.590 | 0.105 | 80 | 86 | 84 | −30 | −88 | 1.99E-6 | 5.44E-6 | 2.22E-5 |
| Prostate Cancer | | | | | | | | | | | | | | | |
| PC-3 | 0.632 | 2.456 | 2.474 | 2.437 | 2.409 | 1.628 | 0.072 | 101 | 99 | 97 | 55 | −89 | 1.08E-5 | 2.41E-5 | 5.38E-5 |
| DU-145 | 0.442 | 1.803 | 1.825 | 1.796 | 1.618 | 0.410 | −0.005 | 102 | 100 | 86 | −7 | −100 | 2.44E-6 | 8.35E-6 | 2.89E-5 |

TABLE 11-continued

NCI five dose result for JVM 2-66

| Panel/Cell | Time Zero | Ctrl | Mean Optical Densities | | | | | Percent Growth | | | | | GI50 | TGI | LC50 |
|---|---|---|---|---|---|---|---|---|---|---|---|---|---|---|---|
| | | | -8.0 | -7.0 | -6.0 | -5.0 | -4.0 | -8.0 | -7.0 | -6.0 | -5.0 | -4.0 | | | |
| Breast Cancer | | | | | | | | | | | | | | | |
| MCF7 | 0.461 | 2.239 | 2.045 | 1.935 | 1.736 | 0.313 | 0.117 | 89 | 83 | 72 | -32 | -75 | 1.62E-6 | 4.91E-6 | 2.64E-5 |
| MDA-MB-231/ATCC | 0.769 | 1.644 | 1 651 | 1.578 | 1.464 | 0.634 | 0.123 | 101 | 92 | 79 | -18 | -84 | 2.01E-6 | 6.59E-6 | 3.07E-5 |
| HS 578T | 0.962 | 2.131 | 2049 | 2.851 | 2.000 | 1 652 | 0.861 | 93 | 93 | 89 | 59 | -10 | 1.35E-5 | 7.06E-5 | >1.00E4 |
| BT-549 | 0.866 | 1.956 | 1.951 | 1.934 | 1.877 | 0.807 | 0.011 | 100 | 98 | 93 | -7 | -99 | 2.69E-6 | 8.54E-6 | 2.95E-5 |
| T-47D | 1.033 | 2.597 | 2.492 | 2.352 | 2.373 | 1.229 | 0.564 | 93 | 84 | 86 | 13 | -45 | 3.07E-6 | 1.64E-5 | >1.00E4 |
| MDA-MB-468 | 0.768 | 1.381 | 1.307 | 1.357 | 0.986 | 0.397 | 0.191 | 88 | 96 | 36 | -48 | -75 | 5.78E-7 | 2.65E-6 | 1.15E-5 |

TABLE 12

NCI five dose result for JVM 2-70

| Panel/Cell | Time Zero | Ctrl | Mean Optical Densities | | | | | Percent Growth | | | | | GI50 | TGI | LC50 |
|---|---|---|---|---|---|---|---|---|---|---|---|---|---|---|---|
| | | | -8.0 | -7.0 | -6.0 | -5.0 | -4.0 | -8.0 | -7.0 | -6.0 | -5.0 | -4.0 | | | |
| Leukemia | | | | | | | | | | | | | | | |
| CCRF-CEM | 0.458 | 1.991 | 1.967 | 1.872 | 1.440 | 0.314 | 0.204 | 98 | 92 | 64 | -32 | -56 | 1.40E-6 | 4.68E-6 | 5.86E-5 |
| HL-60(TB) | 1.062 | 2.937 | 3.121 | 3.144 | 3.165 | 0.933 | 0.431 | 110 | 111 | 112 | -12 | -59 | 3.16E-6 | 7.96E-6 | 6.31E-5 |
| K-562 | 0.164 | 1.667 | 1.146 | 1.152 | 0.981 | 0.229 | 0.103 | 109 | 109 | 90 | 7 | -38 | 3.06E-6 | 1.45E-5 | >1.00E-4 |
| MOLT-4 | 0.736 | 2.189 | 2.329 | 2.467 | 2.400 | 0.670 | 0.378 | 110 | 119 | 115 | -9 | -49 | 3.33E-6 | 8.45E-6 | >1.00E-4 |
| RPMI-8226 | 1.080 | 2.752 | 2.761 | 2.716 | 2.689 | 1.545 | 0.714 | 101 | 98 | 96 | 28 | -34 | 4.74E-6 | 2.82E-5 | >1.00E-4 |
| SR | 0.462 | 1.777 | 1.789 | 1.801 | 1.561 | 0.545 | 0.287 | 101 | 102 | 84 | 6 | -38 | 2.72E-6 | 1.39E-5 | >1.00E-4 |
| Non-Small Cell Lung Cancer | | | | | | | | | | | | | | | |
| A549/ATCC | 0.464 | 2.222 | 2.167 | 2.157 | 2.095 | 1.860 | 0.151 | 97 | 96 | 93 | 79 | -68 | 1.58E-5 | 3.47E-5 | 7.59E-5 |
| HOP-62 | 0.764 | 2.343 | 2.129 | 2.220 | 2.208 | 1.996 | 0.242 | 86 | 92 | 91 | 78 | -68 | 1.55E-5 | 3.41E-5 | 7.49E-5 |
| HOP-92 | 1.261 | 1.952 | 1.860 | 1.832 | 1.754 | 1.281 | 0.109 | 87 | 83 | 71 | 3 | -91 | 2.05E-6 | 1.07E-5 | 3.64E-5 |
| NCI-H226 | 1.048 | 2.509 | 2.392 | 2.407 | 2.321 | 1.326 | 0.427 | 92 | 93 | 87 | 19 | -59 | 3.51E-6 | 1.75E-5 | 7.61E-5 |
| NCI-H23 | 0.701 | 2.003 | 1.937 | 2.015 | 1.926 | 1.129 | 0.213 | 95 | 101 | 94 | 33 | -70 | 5.24E-6 | 2.09E-5 | 6.43E-5 |
| NCI-H322M | 0.835 | 1.947 | 1.972 | 2.038 | 1.964 | 1.873 | 0.144 | 102 | 108 | 102 | 93 | -83 | 1.76E-5 | 3.39E-5 | 6.51E-5 |
| NCI-H460 | 0.321 | 3.804 | 3.299 | 3.327 | 3.274 | 2.631 | 0.140 | 100 | 101 | 99 | 77 | -57 | 1.60E-5 | 3.76E-5 | 8.94E-5 |
| NCI-H522 | 1.088 | 2.503 | 2.409 | 2.444 | 2.214 | 0.141 | 0.316 | 93 | 96 | 80 | -87 | -71 | 1.50E-6 | 3.00E-6 | 5.99E-6 |
| Colon Cancer | | | | | | | | | | | | | | | |
| COLO 205 | 0.512 | 1.898 | 1.813 | 1.990 | 1.951 | 0.456 | 0.059 | 94 | 107 | 104 | -11 | -88 | 2.94E-6 | 8.03E-6 | 3.19E-5 |
| HCC-2998 | 0.753 | 2.198 | 2.283 | 2.246 | 2.339 | 1.599 | 0.153 | 106 | 103 | 110 | 59 | -80 | 1.15E-5 | 2.65E-5 | 6.10E-5 |
| HCT-116 | 0.241 | 2.008 | 1.855 | 1.914 | 1.631 | 0.129 | 0.018 | 91 | 95 | 79 | -46 | -93 | 1.69E-6 | 4.25E-6 | 1.19E-5 |
| HCT-15 | 0.420 | 2.691 | 2.468 | 2.462 | 2.096 | 0.298 | 0.127 | 90 | 91 | 74 | -29 | -70 | 1.70E-6 | 5.22E-6 | 3.26E-5 |
| HT29 | 0.313 | 1.686 | 1.677 | 1.767 | 1.728 | 0.575 | 0.040 | 99 | 106 | 103 | 19 | -87 | 4.28E-6 | 1.51E-5 | 4.45E-5 |
| KM12 | 0.382 | 2.246 | 2.275 | 2.288 | 2.213 | 1.543 | 0.050 | 102 | 102 | 98 | 62 | -87 | 1.21E-5 | 2.61E-5 | 5.66E-5 |
| SW-620 | 0.259 | 2.356 | 2.332 | 2.290 | 1.911 | 0.270 | 0.053 | 99 | 97 | 79 | 1 | -80 | 2.33E-6 | 1.02E-5 | 4.26E-5 |
| CNS Cancer | | | | | | | | | | | | | | | |
| SF-268 | 0.664 | 2.091 | 2.089 | 2.101 | 1.996 | 1.617 | 0.184 | 100 | 101 | 93 | 67 | -72 | 1.32E-5 | 3.02E-5 | 6.91E-5 |
| SF-295 | 0.791 | 2.940 | 2.695 | 2.791 | 2.789 | 2.387 | 0.224 | 89 | 93 | 93 | 74 | -72 | 1.47E-5 | 3.23E-5 | 7.10E-5 |
| SF-539 | 1.057 | 2.915 | 2.762 | 2.868 | 2.760 | 0.842 | 0.101 | 93 | 97 | 92 | -20 | -90 | 2.35E-6 | 6.58E-6 | 2.65E-5 |
| SNB-19 | 0.702 | 2.232 | 2.160 | 2.168 | 2.160 | 1.812 | 0.139 | 95 | 96 | 95 | 73 | -80 | 1.40E-5 | 2.98E-5 | 6.34E-5 |
| SNB-75 | 1.019 | 1.978 | 1.711 | 1.798 | 1.782 | 1.568 | 0.157 | 72 | 81 | 80 | 57 | -85 | 1.12E-5 | 2.53E-5 | 5.70E-5 |
| U251 | 0.618 | 2.355 | 2.270 | 2.263 | 2.336 | 2.186 | 0.059 | 95 | 95 | 99 | 90 | -90 | 1.67E-5 | 3.16E-5 | 5.97E-5 |
| Melanoma | | | | | | | | | | | | | | | |
| LOX IMVI | 0.548 | 2.740 | 2.654 | 2.654 | 2.547 | 0.628 | 0.089 | 96 | 96 | 91 | 4 | -84 | 2.95E-6 | 1.10E-5 | 4.10E-5 |
| MALME-3M | 0.691 | 1.218 | 1.252 | 1.259 | 1.211 | 0 657 | 0.230 | 106 | 108 | 99 | -5 | -67 | 2.95E-6 | 8.96E-5 | 5.36E-5 |
| M14 | 0.429 | 1.840 | 1.707 | 1.757 | 1.613 | 0 722 | 0.080 | 91 | 94 | 84 | 21 | -81 | 3.44E-6 | 1.60E-5 | 4.93E-5 |
| MDA-MB-435 | 0.580 | 2.847 | 2.592 | 2.731 | 2.610 | 1.301 | 0.185 | 89 | 95 | 90 | 32 | -72 | 4.84E-6 | 2.03E-5 | 6.19E-5 |
| SK-MEL-2 | 0.921 | 1.582 | 1.622 | 1.661 | 1.633 | 1.368 | 0.165 | 106 | 112 | 108 | 68 | -82 | 1.31E-5 | 2.83E-5 | 6.10E-5 |
| SK-MEL-28 | 0.748 | 2.158 | 2.003 | 2.163 | 2.085 | 0.800 | 0.156 | 89 | 100 | 95 | 4 | -79 | 3.10E-6 | 1.11E-5 | 4.45E-5 |
| 8K-MEL-5 | 0.749 | 3.047 | 2.994 | 3.025 | 2.949 | 1.721 | 0.049 | 98 | 99 | 96 | 42 | -93 | 7.17E-6 | 2.05E-5 | 4.78E-5 |
| UACC-257 | 0.950 | 2.056 | 1.955 | 1.973 | 1.866 | 1 209 | 0.134 | 91 | 92 | 83 | 23 | -86 | 3.57E-6 | 1.64E-5 | 4.70E-5 |
| UACC-62 | 1.123 | 3.045 | 2.993 | 2.925 | 2.883 | 1.760 | 0.152 | 97 | 94 | 92 | 33 | -87 | 5.15E-6 | 1.89E-5 | 4.95E-5 |

TABLE 12-continued

NCI five dose result for JVM 2-70

| Panel/Cell | Time | | Mean Optical Densities | | | | | Percent Growth | | | | | GI50 | TGI | LC50 |
|---|---|---|---|---|---|---|---|---|---|---|---|---|---|---|---|
| | Zero | Ctrl | −8.0 | −7.0 | −6.0 | −5.0 | −4.0 | −8.0 | −7.0 | −6.0 | −5.0 | −4.0 | | | |

Log10 Concentration

Ovarian Cancer

| IGROVI | 0.500 | 1.662 | 1.771 | 1.874 | 1.709 | 0.721 | 0.241 | 109 | 118 | 104 | 19 | −52 | 4.32E−6 | 1.85E−5 | 9.40E−5 |
| OVCAR-3 | 0.539 | 1.887 | 2.008 | 1.956 | 1.724 | 0.528 | 0.024 | 109 | 105 | 88 | −2 | −96 | 2.846−6 | 9.47E−6 | 3.25E−5 |
| OVCAR-5 | 0.629 | 1.544 | 1.411 | 1.424 | 1.424 | 1.004 | 0.067 | 86 | 87 | 87 | 41 | −89 | 6.36E−6 | 2.06E−5 | 4.99E−5 |
| OVCAR-8 | 0.553 | 2.249 | 2.148 | 2.159 | 2.070 | 0.801 | 0.069 | 94 | 95 | 89 | 15 | −88 | 3.37E−6 | 1.39E−5 | 4.29E−5 |
| NCI/ADR-RES | 0.588 | 1.967 | 1.894 | 2.028 | 1.947 | 1.466 | 0.282 | 95 | 104 | 99 | 64 | −52 | 1.31E−5 | 3.55E−5 | 9.60E−5 |
| SK-OV-3 | 0.843 | 1.865 | 1.788 | 1.877 | 1856 | 1.811 | 0.762 | 92 | 101 | 99 | 95 | −10 | 2.68E−5 | 8.06E−5 | >1.00E−4 |

Renal Cancer

| 786-0 | 0.595 | 2.436 | 2.245 | 2.392 | 2.429 | 1.318 | 0.133 | 90 | 98 | 100 | 39 | −78 | 6.64E−6 | 2.17E−5 | 5.80E−5 |
| A498 | 1.172 | 1.899 | 1.595 | 1.565 | 1.656 | 1.381 | 0.100 | 58 | 54 | 67 | 29 | −92 | 2.77E−6 | 1.73E−5 | 4.52E−5 |
| ACHN | 0.458 | 2.029 | 1.995 | 2.057 | 1.797 | 0.488 | 0.095 | 98 | 102 | 85 | 2 | −79 | 2.64E−6 | 1.05E−5 | 4.35E−5 |
| CAKI-1 | 0.812 | 3.151 | 2.908 | 3.025 | 2.861 | 0.917 | 0.057 | 90 | 95 | 88 | 4 | −93 | 2.83E−6 | 1.11E−5 | 3.62E−5 |
| RXF 393 | 0.730 | 1.435 | 1.467 | 1.443 | 1.369 | 0.337 | 0.091 | 105 | 101 | 91 | −54 | −88 | 1 91E−6 | 4 24E−6 | 9.41E−6 |
| SN12C | 0.737 | 2.753 | 2.684 | 2.604 | 2.602 | 1.344 | 0.133 | 97 | 93 | 92 | 30 | −82 | 4.80E−6 | 1.86E−5 | 5.19E−5 |
| TK-10 | 1.011 | 1.837 | 1.809 | 1.868 | 1.908 | 1.089 | 0.033 | 97 | 106 | 109 | 9 | −97 | 3.90E−6 | 1.23E−5 | 3.63E−5 |
| UO-31 | 0.843 | 2.881 | 2.027 | 2.008 | 1.937 | 1.077 | 0.138 | 96 | 94 | 88 | 19 | −84 | 3.56E−6 | 1.53E−5 | 4.69E−5 |

Prostate Cancer

| PC-3 | 0.632 | 2.357 | 2.260 | 2.238 | 2.257 | 1.768 | 0.176 | 94 | 93 | 94 | 66 | −72 | 1.30E−5 | 3.00E−5 | 6.91E−5 |
| DU-145 | 0.442 | 1.829 | 1.928 | 1.908 | 1.757 | 0.797 | 0.051 | 107 | 106 | 95 | 26 | −89 | 4.44E−6 | 1.68E−5 | 4.59E−5 |

Breast Cancer

| MCF7 | 0.461 | 2.290 | 1.973 | 2.075 | 1.817 | 0.543 | 0.171 | 83 | 88 | 74 | 4 | −63 | 2.22E−6 | 1.16E−5 | 6.41E−5 |
| MDA-MB-231/ATCC | 0.769 | 1.804 | 1.854 | 1.775 | 1.821 | 1.194 | 0.116 | 105 | 97 | 102 | 41 | −85 | 7.13E−6 | 2.12E−5 | 5.28E−5 |
| HS 578T | 0.962 | 2.176 | 2.076 | 2.077 | 2.005 | 1.809 | 1.034 | 92 | 92 | 86 | 70 | 6 | 2.04E−5 | >1.00E−4 | >1.00E−4 |
| BT-549 | 0.866 | 1.731 | 1.565 | 1.613 | 1.480 | 0.781 | 0.037 | 81 | 86 | 71 | −10 | −96 | 1.82E−6 | 7.55E−6 | 2.93E−5 |
| T-47D | 1.033 | 2.668 | 2.432 | 2.575 | 2.564 | 1.596 | 0.536 | 86 | 94 | 94 | 34 | −48 | 5.45E−6 | 2.61E−5 | >1.00E−4 |
| MDA-MB-468 | 0.768 | 1.406 | 1.331 | 1.352 | 1.100 | 0.514 | 0.241 | 88 | 92 | 52 | −33 | −69 | 1.06E−6 | 4.06E−6 | 2.98E−5 |

TABLE 13

NCI five dose result for JVM-57

| Panel/Cell | Time | | Mean Optical Densities | | | | | Percent Growth | | | | | GI50 | TGI | LC50 |
|---|---|---|---|---|---|---|---|---|---|---|---|---|---|---|---|
| | Zero | Ctrl | −8.0 | −7.0 | −6.0 | −5.0 | −4.0 | −8.0 | −7.0 | −6.0 | −5.0 | −4.0 | | | |

Log10 Concentration

Leukemia

| CCRF-CEM | 0.645 | 2.416 | 2.380 | 2.358 | 2.306 | 0.695 | 0.375 | 98 | 97 | 94 | 3 | −42 | 3.03E−6 | 1.16E−5 | 1.09E−4 |
| HL-60(TB) | 0.952 | 3.038 | 3.038 | 3.062 | 2.926 | 1.248 | 0.430 | 100 | 101 | 95 | 14 | −55 | 3.59E−6 | 1.61E−5 | 8.51E−5 |
| K-562 | 0.196 | 1.555 | 1.549 | 1.539 | 1.424 | 0.385 | 0.164 | 100 | 99 | 90 | 14 | −16 | 3.37E−6 | 2.88E−5 | >1.00E−4 |
| MOLT-4 | 0.598 | 2.160 | 2.266 | 2.265 | 2.235 | 1.011 | 0.316 | 107 | 107 | 105 | 26 | −47 | 5.00E−6 | 2.29E−5 | >1.00E−4 |
| RPMI-8226 | 1.212 | 2.701 | 2.704 | 2.657 | 2.684 | 1.724 | 0.638 | 100 | 97 | 99 | 34 | −47 | 5.72E−6 | 2.63E−5 | >1.00E−4 |
| SR | 0.640 | 2.052 | 1.924 | 2.073 | 1.873 | 0.936 | 0.438 | 91 | 101 | 87 | 21 | −32 | 3.65E−6 | 2.51E−5 | >1.00E−4 |

Non-Small Cell Lung Cancer

| A549/ATCC | 0.383 | 1.974 | 1.844 | 1.890 | 1.896 | 1.817 | 0.414 | 92 | 95 | 95 | 90 | 2 | 2.85E−5 | >1.00E−4 | >1.00E−4 |
| HOP-62 | 0.694 | 1.596 | 1.658 | 1.697 | 1.868 | 1.831 | 0.362 | 107 | 111 | 130 | 126 | −48 | 2.74E−5 | 5.30E−5 | >1.00E−4 |
| HOP-92 | 1.344 | 1.817 | 1.130 | 1.834 | 1.731 | 1.268 | 0.140 | 82 | 104 | 82 | −6 | −90 | 2.30E−6 | 8.61E−6 | 3.37E−5 |
| NCI-H226 | 1.086 | 1.864 | 1.734 | 1.772 | 1.727 | 1.671 | 1.361 | 83 | 88 | 82 | 75 | 35 | 4.27E−5 | >1.00E−4 | >1.00E−4 |
| NCI-H23 | 0.839 | 2.393 | 2.388 | 2.451 | 2.443 | 2.042 | 0.234 | 100 | 104 | 103 | 77 | −60 | 1.58E−5 | 3.65E−5 | 8 43E−5 |
| NCI-H322M | 0.824 | 2.012 | 2.045 | 2.006 | 1.981 | 1.896 | 1.071 | 103 | 99 | 97 | 90 | 21 | 3.79E−5 | >1.00E−4 | >1.00E−4 |
| NCI-H460 | 0.361 | 3.180 | 3.240 | 3.186 | 3.162 | 2.975 | 0.340 | 102 | 100 | 99 | 93 | −6 | 2.71E−5 | 8.73E−5 | >1.00E−4 |
| NCI-H522 | 0.699 | 1.868 | 1.805 | 1.860 | 1.719 | 0.517 | 0.184 | 95 | 99 | 87 | −26 | −74 | 2.13E−6 | 5.88E−6 | 3.18E−5 |

Colon Cancer

| COLO 205 | 0.601 | 3.020 | 3.085 | 3.071 | 3.157 | 1.738 | 0.202 | 103 | 102 | 106 | 47 | −66 | 8.89E−6 | 2.59E−5 | 7.16E−5 |
| HCC-2998 | 0.936 | 3.069 | 3.126 | 3.148 | 3.126 | 3.113 | 0.235 | 103 | 104 | 103 | 102 | −75 | 1.97E−5 | 3.77E−5 | 7.23E−5 |

TABLE 13-continued

NCI five dose result for JVM-57

| | Time | | Mean Optical Densities | | | | | Percent Growth | | | | | | | |
|---|---|---|---|---|---|---|---|---|---|---|---|---|---|---|---|
| | | | | | Log10 Concentration | | | | | | | | | | |
| Panel/Cell | Zero | Ctrl | −8.0 | −7.0 | −6.0 | −5.0 | −4.0 | −8.0 | −7.0 | −6.0 | −5.0 | −4.0 | GI50 | TGI | LC50 |
| HCT-116 | 0.214 | 1.663 | 1.681 | 1.662 | 1.517 | 0.254 | 0.029 | 101 | 100 | 98 | 3 | −87 | 2.87E−6 | 1.07E−5 | 3.89E−5 |
| HCT-15 | 0.373 | 2.246 | 2.232 | 2.135 | 2.139 | 1.345 | 0.206 | 99 | 94 | 94 | 52 | −45 | 1.05E−5 | 3.44E−5 | >1.00E−4 |
| HT29 | 0.298 | 1.591 | 1.622 | 1.693 | 1.717 | 0.853 | 0.079 | 102 | 108 | 110 | 43 | −74 | 7.83E−6 | 2.33E−5 | 6.27E−5 |
| KM12 | 0.699 | 2.886 | 2.933 | 3.012 | 2.883 | 2.784 | 0.612 | 102 | 106 | 100 | 95 | −12 | 2.63E−5 | 7.66E−5 | >1.00E−4 |
| SW-620 | 0.304 | 1.945 | 1.919 | 1.918 | 1.885 | 0.082 | 0.109 | 98 | 98 | 96 | 11 | −64 | 3.48E−6 | 1.39E−5 | 6.48E−5 |
| | | | | | | | CNS Cancer | | | | | | | | |
| SF-268 | 0.543 | 1.776 | 1.818 | 1.779 | 1.798 | 1.466 | 0.112 | 103 | 100 | 102 | 75 | −79 | 1.45E−5 | 3.05E−5 | 6.44E−5 |
| SF-295 | 0.971 | 2.941 | 2.887 | 2.852 | 2.916 | 2.904 | 1.956 | 97 | 95 | 99 | 98 | 50 | >1.00E−4 | >1.00E−4 | >1.00E−4 |
| SF-539 | 1.018 | 2.786 | 2.669 | 2.699 | 2.716 | 2.384 | 0.058 | 93 | 95 | 96 | 77 | −94 | 1.44E−5 | 2.82E−5 | 5.52E−5 |
| SNB-19 | 0.728 | 2.274 | 2.227 | 2.195 | 2.175 | 2.084 | 1.196 | 97 | 95 | 94 | 88 | 30 | 4.53E−5 | >1.00E−4 | >1.00E−4 |
| SNB-75 | 0.899 | 1.693 | 1.538 | 1.446 | 1.514 | 1.445 | 0.933 | 80 | 69 | 77 | 69 | 4 | 1.95E−5 | >1.00E−4 | >1 00E−4 |
| U251 | 0.749 | 2.599 | 2.508 | 2.436 | 2.491 | 2.060 | 1.217 | 95 | 91 | 94 | 92 | 25 | 4.29E−5 | >1.00E−4 | >1.00E−4 |
| | | | | | | | Melanoma | | | | | | | | |
| LOX IMVI | 0.374 | 2.397 | 2.443 | 2.388 | 2.329 | 0.951 | 0.044 | 102 | 100 | 97 | 29 | −88 | 4.84E−6 | 1.75E−5 | 4.70E−5 |
| MALME-3M | 0.712 | 1.292 | 1.292 | 1.243 | 1.277 | 0.928 | 0.202 | 100 | 91 | 97 | 37 | −72 | 6.12E−6 | 2.19E−5 | 6.32E−5 |
| M14 | 0.497 | 1.783 | 1.782 | 1.805 | 1.735 | 1.075 | 0.106 | 100 | 102 | 96 | 45 | −79 | 7.97E−6 | 2.31E−5 | 5.85E−5 |
| MDA-MB-435 | 0.622 | 2.552 | 2.485 | 2.527 | 2.519 | 1.308 | 0.199 | 97 | 99 | 98 | 36 | −68 | 5.89E−6 | 2.20E−5 | 6.69E−5 |
| SK-MEL-2 | 0.987 | 2.000 | 2.125 | 2.158 | 2.113 | 1.668 | 0.234 | 112 | 116 | 111 | 67 | −76 | 1.32E−5 | 2.94E−5 | 6.55E−5 |
| SK-MEL-28 | 0.500 | 1.560 | 1.498 | 1.482 | 1.498 | 1.064 | −0.008 | 94 | 93 | 94 | 53 | −100 | 1.05E−5 | 2.22E−5 | 4.72E−5 |
| 8K-MEL-5 | 0.836 | 2.755 | 2.582 | 2.655 | 2.592 | 2.125 | 0.012 | 91 | 95 | 91 | 67 | −99 | 1.27E−5 | 2.54E−5 | 5.09E−5 |
| UACC-62 | 0.981 | 2.982 | 3.004 | 2.862 | 2.667 | 2.202 | 0.079 | 101 | 94 | 94 | 61 | −92 | 1.18E−5 | 2.51E−5 | 5.32E−5 |
| | | | | | | | Ovarian Cancer | | | | | | | | |
| IGROVI | 0.521 | 1.390 | 1.475 | 1.392 | 1.330 | 0.640 | 0.160 | 110 | 100 | 93 | 14 | −69 | 3.49E−6 | 1.46E−5 | 5.86E−5 |
| OVCAR-3 | 0.855 | 2.267 | 2.385 | 2.391 | 2.278 | 1.373 | 0.019 | 109 | 109 | 101 | 37 | −98 | 6.20E−6 | 1.87E−5 | 4.41E−5 |
| OVCAR-4 | 0.622 | 1.454 | 1.424 | 1.407 | 1.344 | 1.042 | 0.157 | 96 | 94 | 87 | 50 | −75 | 1.01E−5 | 2.53E−5 | 6.34E−5 |
| OVCAR-5 | 0.688 | 1.530 | 1.497 | 1.540 | 1.441 | 1.347 | 0.241 | 95 | 101 | 89 | 78 | −65 | 1.57E−5 | 3.52E−5 | 7.85E−5 |
| OVCAR-8 | 0.526 | 2.247 | 2.246 | 2.248 | 2.203 | 1.577 | 0.279 | 100 | 100 | 97 | 61 | −47 | 1.27E−5 | 3.68E−5 | >1.00E−4 |
| NCI/ADR-RES | 0.735 | 2.260 | 2.305 | 2.349 | 2.343 | 2.225 | 1.213 | 103 | 106 | 105 | 98 | 31 | 5.23E−5 | >1.00E−4 | >1.00E−4 |
| SK-OV-3 | 0.731 | 2.189 | 2.283 | 2.254 | 2.364 | 2.259 | 1.094 | 105 | 104 | 112 | 105 | 25 | 4.85E−5 | >1.00E−4 | >1.00E−4 |
| | | | | | | | Renal Cancer | | | | | | | | |
| 786-0 | 0.831 | 2.694 | 2.780 | 2.797 | 2.737 | 1.909 | 0.153 | 105 | 106 | 102 | 58 | −82 | 1.14E−5 | 2.60E−5 | 5.94E−5 |
| A498 | 1.638 | 2.554 | 2.470 | 2.457 | 2.397 | 2.377 | 1.212 | 91 | 89 | 83 | 81 | −26 | 1.94E−5 | 5.70E−5 | >1.00E−4 |
| ACHN | 0.370 | 1.366 | 1.383 | 1.389 | 1.325 | 0.529 | 0.052 | 102 | 102 | 96 | 16 | −86 | 3.74E−6 | 1.43E−5 | 4.43E−5 |
| CAKI-1 | 0.957 | 2.648 | 2.548 | 2.527 | 2.502 | 1.400 | 0.198 | 94 | 93 | 91 | 26 | −79 | 4.31E−6 | 1.77E−5 | 5.27E−5 |
| RXF 393 | 0.937 | 1.711 | 1.625 | 1.647 | 1.626 | 0.993 | 0.130 | 89 | 92 | 89 | 7 | −86 | 3.00E−6 | 1.19E−5 | 4.10E−5 |
| SN12C | 0.609 | 2.739 | 2.672 | 2.621 | 2.652 | 2.299 | 0.441 | 97 | 94 | 96 | 79 | −28 | 1.88E−5 | 5.52E−5 | >1.00E−4 |
| TK-10 | 0.710 | 1.374 | 1.381 | 1.357 | 1.372 | 0.817 | 0.029 | 101 | 97 | 100 | 16 | −96 | 3.93E−6 | 1.39E−5 | 3.89E−5 |
| UO-31 | 0.749 | 2.149 | 2.024 | 2.065 | 2.024 | 1.507 | 0.095 | 91 | 94 | 91 | 54 | −87 | 1.07E−5 | 2.41E−5 | 5.45E−5 |
| | | | | | | | Prostate Cancer | | | | | | | | |
| PC-3 | 0.575 | 2.086 | 2.021 | 2.012 | 2.030 | 1.797 | 0.234 | 96 | 95 | 96 | 81 | −59 | 1.66E−5 | 3.78E−5 | 8.58E−5 |
| DU-145 | 0.418 | 1.688 | 1.791 | 1.763 | 1.668 | 0.596 | 0.006 | 108 | 106 | 98 | 14 | −99 | 3.74E−6 | 1.33E−5 | 3.70E−5 |
| | | | | | | | Breast Cancer | | | | | | | | |
| MCF7 | 0.260 | 1.688 | 1.630 | 1.535 | 1.601 | 0.060 | 0.067 | 96 | 89 | 94 | 14 | −74 | 3.54E−6 | 1.44E−5 | 5.31E−5 |
| MDA-MB-231/ATCC | 0.760 | 1.921 | 1.982 | 1.898 | 1.916 | 1.577 | 0.163 | 105 | 98 | 100 | 70 | −79 | 1.37E−5 | 2.97E−5 | 6.43E−5 |
| HS 578T | 1.209 | 2.350 | 2.253 | 2.244 | 2.238 | 1.982 | 1.313 | 91 | 91 | 90 | 68 | 9 | 2.01E−5 | >1.00E−4 | >1.00E−4 |
| BT-549 | 0.984 | 2.075 | 2.108 | 2.064 | 2.073 | 1.295 | 0.150 | 103 | 99 | 100 | 28 | −85 | 4.99E−6 | 1.76E−5 | 4.93E−5 |
| T-47D | 0.661 | 1.157 | 1.830 | 1.790 | 1.763 | 1.072 | 0.232 | 107 | 103 | 101 | 37 | −65 | 6.32E−6 | 2.32E−5 | 7.15E−5 |
| MDA-MB-468 | 0.972 | 2.079 | 1.933 | 1.948 | 1.953 | 1.120 | 0.304 | 87 | 88 | 89 | 13 | −69 | 3.26E−6 | 1.46E−5 | 5.91E−5 |

TABLE 14

NCI five dose result for JVM-59

| | Time | | Mean Optical Densities | | | | | Log10 Concentration | | | | | | | |
| | | | | | | | | | Percent Growth | | | | | | |
| Panel/Cell | Zero | Ctrl | -8.0 | -7.0 | -6.0 | -5.0 | -4.0 | -8.0 | -7.0 | -6.0 | -5.0 | -4.0 | GI50 | TGI | LC50 |
|---|---|---|---|---|---|---|---|---|---|---|---|---|---|---|---|
| | | | | | | | Leukemia | | | | | | | | |
| CCRF-CEM | 0.645 | 2.318 | 2.250 | 2.275 | 2.069 | 0.622 | 0.252 | 96 | 97 | 85 | -4 | -61 | 2.49E-6 | 9.12E-6 | 6.43E-5 |
| HL-60(TB) | 0.952 | 3.120 | 2.860 | 3.030 | 3.005 | 1.437 | 0.352 | 88 | 96 | 95 | 22 | -63 | 4.15E-6 | 1.83E-5 | 7.03E-5 |
| K-562 | 0.196 | 1.577 | 1.397 | 1.284 | 1.419 | 0.381 | 0.125 | 87 | 79 | 89 | 13 | -36 | 3.26E-6 | 1.86E-5 | >1.00E-4 |
| MOLT-4 | 0.598 | 2.259 | 2.251 | 2.119 | 2.074 | 0.883 | 0.279 | 100 | 92 | 89 | 17 | -53 | 3.48E-6 | 1.75E-5 | 8.97E-5 |
| RPMI-8226 | 1.212 | 2.598 | 2.650 | 2.574 | 2.551 | 1.864 | 0.591 | 184 | 98 | 97 | 47 | -51 | 8.71E-6 | 3.01E-5 | 9.71E-5 |
| SR | 0.640 | 2.036 | 1.954 | 1.945 | 1.916 | 1.351 | 0.418 | 94 | 93 | 91 | 51 | -35 | 1.02E-5 | 3.93E-5 | >1.00E-4 |
| | | | | | | | Non-Small Cell Lung Cancer | | | | | | | | |
| A549/ATCC | 0.383 | 2.052 | 2.037 | 2.033 | 1.904 | 1.895 | 0.378 | 99 | 99 | 91 | 91 | -1 | 2.76E-5 | 9.65E-5 | >1.00E-4 |
| HOP-62 | 0.694 | 1.533 | 1.436 | 1.438 | 1.458 | 1.912 | 0.083 | 88 | 89 | 91 | 97 | -88 | 1.80E-5 | 3.35E-5 | 6.23E-5 |
| HOP-92 | 1.344 | 1.791 | 1.709 | 1.713 | 1.713 | 1.215 | 0.148 | 82 | 83 | 83 | -10 | -89 | 2.25E-6 | 7.86E-6 | 3.23E-5 |
| NCI-H226 | 1.086 | 1.814 | 1.773 | 1.675 | 1.743 | 1.661 | 1.276 | 94 | 81 | 90 | 79 | 28 | 3.53E-5 | >1.00E-4 | >1.00E-4 |
| NCI-H23 | 0.839 | 2.403 | 2.272 | 2.285 | 2.366 | 2.109 | 0.305 | 92 | 92 | 96 | 81 | -64 | 1.64E-5 | 3.63E-5 | 8.04E-5 |
| NCI-H322M | 0.824 | 1.949 | 1.876 | 1.947 | 1.987 | 1.910 | 1.308 | 94 | 100 | 103 | 96 | 43 | 7.39E-5 | >1.00E-4 | >1.00E-4 |
| NCI-H460 | 0.361 | 3.154 | 3.229 | 3.255 | 3.208 | 3.097 | 0.217 | 103 | 104 | 102 | 98 | -40 | 2.23E-5 | 5.14E-5 | >1.00E-4 |
| NCI-H522 | 0.699 | 1.864 | 1.628 | 1.672 | 1.605 | 0.470 | 0234 | 80 | 83 | 76 | -33 | -67 | 1.78E-6 | 5.05E-6 | 3.22E-5 |
| | | | | | | | Colon Cancer | | | | | | | | |
| COLO 205 | 0.601 | 2.894 | 2.842 | 2.868 | 2.905 | 1.202 | 0.058 | 98 | 99 | 100 | 26 | -90 | 4.78E-6 | 1.68E-5 | 4.50E-5 |
| HCC-2998 | 0.936 | 2.992 | 2.839 | 2.934 | 3.147 | 3.030 | 0.181 | 93 | 97 | 106 | 102 | -81 | 1.92E-5 | 3.61E-5 | 6.79E-5 |
| HCT-116 | 0.214 | 1.649 | 1.540 | 1.568 | 1.499 | 0.369 | 0.014 | 92 | 94 | 90 | 11 | -94 | 3.18E-6 | 1.27E-5 | 3.82E-5 |
| HCT-15 | 0.373 | 2.266 | 2.195 | 2.216 | 2.110 | 1.620 | 0.169 | 96 | 97 | 92 | 66 | -55 | 1.35E-5 | 3.51E-5 | 9.12E-5 |
| HT29 | 0.298 | 1.592 | 1.562 | 1.601 | 1.580 | 1.064 | 0.072 | 98 | 101 | 99 | 59 | -76 | 1.17E-5 | 2.74E-5 | 6.44E-5 |
| KM12 | 0.699 | 2.963 | 2.866 | 2.851 | 2.920 | 2.745 | 0.584 | 96 | 95 | 96 | 90 | -17 | 2.39E-5 | 7.00E-5 | >1.00E-4 |
| SW-620 | 0.304 | 1.845 | 1.827 | 1.832 | 1.738 | 0.509 | 0.059 | 99 | 99 | 93 | 13 | -81 | 3.46E-6 | 1.38E-5 | 4.72E-5 |
| | | | | | | | CNS Cancer | | | | | | | | |
| SF-268 | 0.543 | 1.788 | 1.731 | 1.767 | 1.758 | 1.507 | 0.081 | 95 | 98 | 96 | 77 | -85 | 1.47E-5 | 3.00E-5 | 6.08E-5 |
| SF-295 | 0.971 | 2.968 | 2.884 | 2.877 | 2.893 | 2.804 | 1.592 | 96 | 95 | 96 | 92 | 31 | 4.88E-5 | >1.00E-4 | >1.00E-4 |
| SF-539 | 1.018 | 2.680 | 2.628 | 2.612 | 2.652 | 2.372 | 0.022 | 97 | 96 | 96 | 81 | -98 | 1.50E-5 | 2.85E-5 | 5.41E-5 |
| SNB-19 | 0.728 | 2.112 | 2.090 | 1.992 | 2.082 | 1.934 | 1.268 | 98 | 91 | 96 | 87 | 39 | 5.91E-5 | >1.00E-4 | >1.00E-4 |
| SNB-75 | 0.899 | 1.697 | 1.541 | 1.638 | 1.557 | 1.456 | 0.829 | 80 | 93 | 82 | 70 | -8 | 1.80E-5 | 7.93E-5 | >1.00E-4 |
| U251 | 0.749 | 2.696 | 2.617 | 2.600 | 2.587 | 2.487 | 0.728 | 96 | 95 | 94 | 89 | -3 | 2.67E-5 | 9.31E-5 | >1.00E-4 |
| | | | | | | | Melanoma | | | | | | | | |
| LOX IMVI | 0.374 | 2.424 | 2.317 | 2.281 | 2.345 | 1.290 | 0.089 | 95 | 93 | 96 | 45 | -76 | 7.88E-6 | 2.34E-5 | 6.06E-5 |
| MALME-3M | 0.712 | 1.262 | 1.212 | 1.224 | 1.271 | 0.814 | 0.187 | 91 | 93 | 102 | 18 | -74 | 4.18E-6 | 1.59E-5 | 5.52E-5 |
| M14 | 0.497 | 1.786 | 1.707 | 1.684 | 1.655 | 1.134 | 0.096 | 94 | 92 | 90 | 49 | -81 | 9.65E-6 | 2.40E-5 | 581E-5 |
| MDA-MB-435 | 0.622 | 2.459 | 2.472 | 2.446 | 2.352 | 1.358 | 0.102 | 101 | 99 | 94 | 40 | -84 | 6.56E-6 | 2.11E-5 | 5.34E-5 |
| SK-MEL-2 | 0.688 | 1.978 | 1.968 | 1.961 | 2.027 | 1.703 | 0.163 | 99 | 96 | 105 | 72 | -81 | 1.40E-5 | 2.95E-5 | 6.24E-5 |
| SK-MEL-28 | 0.526 | 1.553 | 1.545 | 1.596 | 1.544 | 1.177 | 0.023 | 99 | 104 | 99 | 64 | -95 | 1.23E-5 | 2.53E-5 | 5.20E-5 |
| 8K-MEL-5 | 0.735 | 2.634 | 2.605 | 2.501 | 2.552 | 2.352 | 0.027 | 98 | 93 | 95 | 84 | -97 | 1.55E-5 | 2.92E-5 | 5.51E-5 |
| UACC-62 | 0.731 | 2.836 | 2.786 | 2.826 | 2.723 | 2.280 | 0.092 | 97 | 99 | 94 | 70 | -91 | 1.33E-5 | 2.73E-5 | 5.58E-5 |
| | | | | | | | Ovarian Cancer | | | | | | | | |
| IGROVI | 0.521 | 1.353 | 1.406 | 1.328 | 1.372 | 0.661 | 0.192 | 106 | 97 | 102 | 17 | -63 | 4.09E-6 | 1.62E-5 | 6.85E-5 |
| OVCAR-3 | 0.855 | 2.276 | 2.289 | 2.278 | 2.310 | 1.505 | 0.018 | 101 | 100 | 102 | 46 | -98 | 8.41E-6 | 2.08E-5 | 4.64E-5 |
| OVCAR-4 | 0.622 | 1.418 | 1.361 | 1.360 | 1.323 | 1.039 | 0.118 | 93 | 93 | BB | 52 | -81 | 1.04E-5 | 2.47E-5 | 5.85E-5 |
| OVCAR-5 | 0.688 | 1.495 | 1.443 | 1.461 | 1.406 | 1.254 | 0.102 | 94 | 9B | 89 | 70 | -85 | 135E-5 | 2.83E-5 | 5.93E-5 |
| OVCAR-8 | 0.526 | 2.277 | 2.222 | 2.164 | 2.232 | 1.706 | 0.162 | 97 | 94 | 97 | 67 | -69 | 1.34E-5 | 3.11E-5 | 7.22E-5 |
| NCI/ADR-RES | 0.735 | 2.289 | 2.281 | 2.284 | 2.327 | 2.211 | 1.547 | 99 | 100 | 102 | 95 | 52 | >1.00E-4 | >1.00E-4 | >1.00E-4 |
| SK-OV-3 | 0.731 | 2.137 | 2.089 | 2.086 | 2.129 | 1.950 | 0.849 | 97 | 96 | 99 | 87 | 8 | 2.94E-5 | >1.00E-4 | >1.00E-4 |
| | | | | | | | Renal Cancer | | | | | | | | |
| 786-0 | 0.831 | 2.600 | 2.531 | 2.524 | 2 489 | 2.170 | 0.118 | 96 | 96 | 34 | 76 | -86 | 1.44E-5 | 2.94E-5 | 6.00E-5 |
| A498 | 1.638 | 2.499 | 2.513 | 2.415 | 2.393 | 2.468 | 0.767 | 102 | 96 | 88 | 96 | -53 | 2.04E-5 | 4.41E-5 | 9.52E-5 |
| ACHN | 0.370 | 1.318 | 1.342 | 1.300 | 1.244 | 0.555 | 0.011 | 103 | 98 | 92 | 19 | -97 | 3.80E-6 | 1.47E-5 | 3.94E-5 |
| CAKI-1 | 0.957 | 2.615 | 2.534 | 2.526 | 2.460 | 1.654 | 0.127 | 95 | 95 | 91 | 42 | -87 | 6.86E-6 | 2.12E-5 | 5.18E-5 |
| RXF 393 | 0.937 | 1.669 | 1.603 | 1.575 | 1.593 | 1.118 | 0.140 | 91 | 87 | 90 | 25 | -85 | 4.08E-6 | 1.68E-5 | 4.79E-5 |
| SN12C | 0.609 | 2.537 | 2.539 | 2.494 | 2.528 | 2.276 | 0.244 | 100 | 98 | 100 | 86 | -60 | 1.77E-5 | 3.90E-5 | 8.55E-5 |
| TK-10 | 0.710 | 1.455 | 1.404 | 1.344 | 1.324 | 0.834 | 0.046 | 93 | 85 | 82 | 17 | -94 | 3.11E-6 | 1.41E-5 | 4.02E-5 |
| UO-31 | 0.749 | 2.101 | 1.890 | 1.938 | 2.001 | 1.656 | 0.251 | 64 | 88 | 93 | 67 | -66 | 1.34E-5 | 3.18E-5 | 7.53E-5 |
| | | | | | | | Prostate Cancer | | | | | | | | |
| PC-3 | 0.575 | 2.180 | 2.050 | 2.077 | 2.029 | 1.862 | 0.151 | 92 | 94 | 91 | 80 | -74 | 1.57E-5 | 3.32E-5 | 7.01E-5 |
| DU-145 | 0.418 | 1.693 | 1.702 | 1.698 | 1.715 | 0.958 | 0.015 | 101 | 100 | 102 | 42 | -96 | 7.42E-6 | 2.02E-5 | 4.63E-5 |

TABLE 14-continued

NCI five dose result for JVM-59

| | Time | | Mean Optical Densities | | | | | Percent Growth | | | | | | |
| --- | --- | --- | --- | --- | --- | --- | --- | --- | --- | --- | --- | --- | --- | --- |
| | | | Log10 Concentration | | | | | | | | | | | |
| Panel/Cell | Zero | Ctrl | −8.0 | −7.0 | −6.0 | −5.0 | −4.0 | −8.0 | −7.0 | −6.0 | −5.0 | −4.0 | GI50 | TGI | LC50 |
| Breast Cancer | | | | | | | | | | | | | | | |
| MCF7 | 0.260 | 1.695 | 1.625 | 1.662 | 1.596 | 0.551 | 0.086 | 95 | 98 | 93 | 20 | −67 | 3.91E−6 | 1.71E−5 | 6.37E−5 |
| MDA-MB-231/ATCC | 0.760 | 1.769 | 1.824 | 1.810 | 1.821 | 1.569 | 0.117 | 105 | 104 | 105 | 80 | −85 | 1.52E−5 | 3.06E−5 | 6.16E−5 |
| HS 578T | 1.209 | 2.247 | 2.190 | 2.207 | 2.221 | 2.010 | 1.030 | 94 | 96 | 97 | 77 | −15 | 1.97E−5 | 6.90E−5 | >1.00E−4 |
| BT-549 | 0.984 | 2.061 | 1.928 | 2.004 | 1.932 | 1.327 | 0.065 | 88 | 95 | 88 | 32 | −93 | 4.75E−6 | 1.86E−5 | 4.50E−5 |
| T-47D | 0.661 | 1.609 | 1.581 | 1.567 | 1.607 | 0.919 | 0.207 | 97 | 96 | 100 | 27 | −69 | 4.86E−6 | 1.92E−5 | 6.38E−5 |
| MDA-MB-468 | 0.972 | 1.955 | 1.906 | 1.802 | 1.762 | 0.937 | 0.224 | 95 | 84 | 80 | −4 | −77 | 2.30E−6 | 9.06E−6 | 4.29E−5 |

TABLE 15

NCI five dose result for JVM-61

| | Time | | Mean Optical Densities | | | | | Percent Growth | | | | | | |
| --- | --- | --- | --- | --- | --- | --- | --- | --- | --- | --- | --- | --- | --- | --- |
| | | | Log10 Concentration | | | | | | | | | | | |
| Panel/Cell | Zero | Ctrl | −8.0 | −7.0 | −6.0 | −5.0 | −4.0 | −8.0 | −7.0 | −6.0 | −5.0 | −4.0 | GI50 | TGI | LC50 |
| Leukemia | | | | | | | | | | | | | | | |
| CCRF-CEM | 0.666 | 2.444 | 2.510 | 2.441 | 2.290 | 0.623 | 0.407 | 104 | 100 | 91 | −6 | −39 | 2.65E−6 | 8.59E−6 | >1.00E−4 |
| MOLT-4 | 0.920 | 2.884 | 3.000 | 3.009 | 2.987 | 1.528 | 0.483 | 106 | 106 | 105 | 31 | −47 | 5.54E−6 | 2.50E−5 | >1.00E−4 |
| RPMI-8226 | 1.575 | 3.067 | 3.100 | 3.071 | 3.063 | 2.251 | 1.076 | 102 | 100 | 100 | 45 | −32 | 8.20E−6 | 3.88E−5 | >1.00E−4 |
| SR | 0.811 | 2.566 | 2.547 | 2.574 | 2.472 | 1.193 | 0.536 | 99 | 100 | 95 | 22 | −34 | 4.10E−6 | 2.46E−5 | >1.00E−4 |
| Non-Small Cell Lung Cancer | | | | | | | | | | | | | | | |
| A549/ATCC | 0.365 | 2.018 | 1.939 | 1.516 | 1.605 | 1.419 | 0.167 | 95 | BB | 6.7 | 64 | −54 | 1.31E−5 | 3.47E−5 | 9.20E−5 |
| HOP-62 | 0.645 | 1.658 | 1.649 | 1.682 | 1.739 | 1.571 | 0.223 | 99 | 102 | 108 | 91 | −65 | 1.84E−5 | 3.83E−5 | 7.97E−5 |
| HOP-92 | 1.575 | 1.975 | 1.903 | 1.549 | 1.555 | 1.622 | 0.206 | 0.2 | 66 | 71 | 12 | −87 | 2.25E−6 | 1.31E−5 | 4.22E−5 |
| NCI-H226 | 0.811 | 1.837 | 1.778 | 1.756 | 1.747 | 1.525 | 0.310 | 94 | 92 | 91 | 70 | −62 | 1.41E−5 | 3.38E−5 | 8.13E−5 |
| NCI-H23 | 0.686 | 1.994 | 2.042 | 2.010 | 1.993 | 1.424 | 0.259 | 104 | 101 | 100 | 56 | −62 | 1.13E−5 | 2.99E−5 | 7.88E−5 |
| NCI-H322M | 0.723 | 1.947 | 2.025 | 1.988 | 2.003 | 1.789 | 0.593 | 106 | 103 | 105 | 87 | −18 | 2.25E−5 | 6.34E−5 | >1.00E4 |
| NCI-H460 | 0.285 | 2.805 | 2.914 | 2.640. | 2.865 | 2.028 | 0.139 | 104 | 102 | 102 | 69 | −51 | 1.44E−5 | 3.75E−5 | 9.74E−5 |
| NCI-H522 | 0.880 | 2.262 | 2.190 | 2.211 | 1.963 | 0.403 | 0.270 | 95 | 96 | 76 | −54 | −69 | 1.64E−6 | 3.90E−6 | 9.29E−6 |
| Colon Cancer | | | | | | | | | | | | | | | |
| COLO 205 | 0.583 | 2.505 | 2.579 | 2.668 | 2.624 | 0.649 | 0.124 | 104 | 108 | 107 | 3 | −79 | 3.54E−6 | 1.10E−5 | 4.46E−5 |
| HCC-2998 | 1.076 | 2.956 | 2.970 | 3.015 | 2.960 | 2.703 | 0.154 | 101 | 103 | 100 | 87 | −86 | 1.63E−5 | 3.18E−5 | 6.21E−5 |
| HCT-116 | 0.212 | 1.571 | 1.557 | 1.600 | 1.325 | 0.141 | 0.003 | 99 | 102 | 82 | −33 | −99 | 1.59E−6 | 5.12E−6 | 1.79E−5 |
| HCT-15 | 0.465 | 2.478 | 2.439 | 2.424 | 2.249 | 0.908 | 0.089 | 98 | 97 | 89 | 22 | −81 | 3.50E−6 | 1.54E−5 | 5.01E−5 |
| HT29 | 0.315 | 1.704 | 1.761 | 1.786 | 1.843 | 0.649 | 0.069 | 104 | 106 | 110 | 24 | −78 | 4.69E−6 | 1.72E−5 | 5.31E−5 |
| KM12 | 0.586 | 2.507 | 2.609 | 2.637 | 2.566 | 2.274 | 0.084 | 105 | 107 | 103 | 88 | −86 | 1.65E−5 | 3.21E−5 | 6.22E−5 |
| SW-620 | 0.308 | 1.873 | 2.017 | 1.954 | 1.752 | 0.419 | 0.091 | 109 | 105 | 92 | 7 | −70 | 3.13E5 | 1.23E−5 | 5.45E−5 |
| CNS Cancer | | | | | | | | | | | | | | | |
| SF-268 | 0.720 | 2.227 | 2.323 | 2.362 | 2.263 | 1.959 | 0.199 | 106 | 109 | 102 | 82 | −72 | 1.62E−5 | 3.40E−5 | 7.17E−5 |
| SF-539 | 0.810 | 2.461 | 2.461 | 2.410 | 2.395 | 1.398 | 0.008 | 103 | 97 | 96 | 36 | −99 | 5.77E−6 | 1.54E−5 | 4.32E−5 |
| SNB-19 | 0.798 | 2.328 | 2.278 | 2.215 | 2.234 | 2.137 | 0.839 | 97 | 93 | 94 | 88 | 3 | 2.77E−5 | 1.60E−4 | >1.00E4 |
| SNB-75 | 0.999 | 1.780 | 1.634 | 1.596 | 1.576 | 1.252 | 0.121 | 81 | 76 | 74 | 32 | −88 | 3.78E−6 | 1.86E−5 | 4.84E−5 |
| U251 | 0.400 | 1.987 | 1 939 | 1.850 | 1.870 | 1.434 | 0.043 | 97 | 91 | 93 | 65 | −89 | 1.25E−5 | 2.54E−5 | 5.56E−5 |
| Melanoma | | | | | | | | | | | | | | | |
| LOX IMVI | 0.459 | 2.550 | 2.531 | 2.602 | 2.457 | 1.087 | 0.117 | 99 | 102 | 96 | 30 | −75 | 4.96E−6 | 1.94E−5 | 5.82E−5 |
| MALME-3M | 0.661 | 1.307 | 1.395 | 1.305 | 1.276 | 0.943 | 0.283 | 114 | 100 | 95 | 44 | −57 | 7.52E−6 | 2.71E−5 | 8.49E−5 |
| M14 | 0.496 | 1.572 | 1.568 | 1.597 | 1.538 | 0.863 | 0.159 | 100 | 102 | 97 | 34 | −68 | 5.58E−6 | 2.16E−5 | 6.67E−5 |
| MDA-MB-435 | 0.548 | 2.381 | 2.328 | 2.271 | 2.265 | 1.237 | 0.230 | 97 | 94 | 94 | 38 | −58 | 6.01E−6 | 2.47E−5 | 8.24E−5 |
| SK-MEL-2 | 1.320 | 2.305 | 2.397 | 2.403 | 2.426 | 2.079 | 0.338 | 109 | 110 | 112 | 77 | −74 | 1.51E−5 | 3.23E−5 | 6.90E−5 |
| SK-MEL-28 | 0.490 | 1.475 | 1.517 | 1.451 | 1.435 | 0.807 | 0.036 | 104 | 96 | 96 | 32 | −93 | 5.25E−6 | 1.81E−5 | 4.55E−5 |
| 8K-MEL-5 | 0.753 | 2 896 | 2 815 | 2 783 | 2.819 | 1.815 | 0.042 | 96 | 95 | 96 | 50 | −94 | 9.78E−6 | 2.21E−5 | 4.91E−5 |
| UACC-257 | 0.666 | 1.567 | 1.538 | 1.494 | 1.415 | 0.964 | 0.128 | 97 | 92 | 83 | 33 | −81 | 4.59E−6 | 1.95E−5 | 5.37E−5 |
| UACC-62 | 0.896 | 2.579 | 2.586 | 2.449 | 2.392 | 1.573 | 0.086 | 100 | 92 | 89 | 40 | −90 | 6.29E−6 | 2.03E−5 | 4.90E−5 |
| Ovarian Cancer | | | | | | | | | | | | | | | |
| IGROVI | 0.747 | 2.434 | 2.528 | 2.505 | 2.465 | 1.955 | 0.270 | 106 | 104 | 102 | 72 | −64 | 1.44E−5 | 3.38E−5 | 7.89E−5 |
| OVCAR-4 | 0.782 | 1.404 | 1.425 | 1.379 | 1.400 | 1.041 | 0.274 | 103 | 96 | 99 | 42 | −65 | 7.17E−6 | 2.46E−5 | 7.23E−5 |

TABLE 15-continued

NCI five dose result for JVM-61

| | Time | | Mean Optical Densities | | | | | Percent Growth | | | | | | | |
|---|---|---|---|---|---|---|---|---|---|---|---|---|---|---|---|
| | | | | | Log10 Concentration | | | | | | | | | | |
| Panel/Cell | Zero | Ctrl | −8.0 | −7.0 | −6.0 | −5.0 | −4.0 | −8.0 | −7.0 | −6.0 | −5.0 | −4.0 | GI50 | TGI | LC50 |
| OVCAR-5 | 0.650 | 1.521 | 1.581 | 1.4913 | 1.485 | 1.096 | 0.036 | 107 | 97 | 96 | 51 | −94 | 1.02E−5 | 2.25E−5 | 4.95E−5 |
| OVCAR-8 | 0.330 | 1.507 | 1.603 | 1.504 | 1.454 | 0.620 | 0.109 | 108 | 100 | 96 | 25 | −67 | 4.39E−6 | 1.85E−5 | 6.51E−5 |
| NCI/ADR-RES | 0.644 | 2.153 | 2.231 | 2.242 | 2.251 | 1.926 | 0.450 | 105 | 106 | 106 | 85 | −30 | 2.01E−5 | 5.47E−5 | >1.00E−4 |
| SK-OV-3 | 0.792 | 2.022 | 2.099 | 2.109 | 2.060 | 1.857 | 0.784 | 106 | 187 | 103 | 87 | −1 | 2.62E−5 | 9.74E−5 | >1.00E−4 |
| | | | | | | | Renal Cancer | | | | | | | | |
| 786-0 | 0.594 | 2.319 | 2.345 | 2.329 | 2.252 | 0.853 | 0.040 | 101 | 101 | 96 | 15 | −93 | 3.70E−6 | 1.38E−5 | 3.98E−5 |
| A498 | 1.515 | 2 009 | 1.946 | 1.920 | 1.945 | 1.788 | 0.044 | 87 | B2 | 87 | 55 | −97 | 1.68E−5 | 2.51E−5 | 4.91E−5 |
| ACHN | 0.388 | 1.552 | 1.574 | 1.520 | 1.377 | 0.450 | 0.010 | 102 | 97 | 85 | 5 | −98 | 2.75E−6 | 1.13E−5 | 3.45E−5 |
| CAKI-1 | 0.668 | 2.591 | 2.571 | 2.446 | 2.351 | 0.783 | 0.116 | 99 | 93 | 88 | 6 | −83 | 2.88E−6 | 1.17E−5 | 4.28E−5 |
| RXF 393 | 0.880 | 1.652 | 1.659 | 1.569 | 1.464 | 0.892 | 0.199 | 101 | B9 | 76 | 2 | −77 | 2.22E−6 | 1.55E−5 | 4.50E−5 |
| SN12C | 0.631 | 2.302 | 2.219 | 2.172 | 2.151 | 1.317 | 0.191 | 95 | 92 | 91 | 41 | −70 | 6.61E−6 | 2.54E−5 | 6.63E−5 |
| TK-10 | 0.733 | 1.539 | 1.543 | 1.573 | 1.553 | 0.831 | 0.029 | 101 | 104 | 102 | 12 | −96 | 3.13E−6 | 1.29E−5 | 3.75E−5 |
| UO-31 | 0.739 | 2.172 | 2.069 | 2.073 | 2.016 | 1.319 | 0.097 | 93 | 93 | 89 | 40 | −87 | 6.38E−6 | 2.08E−5 | 5.13E−5 |
| | | | | | | | Prostate Cancer | | | | | | | | |
| PC-3 | 0.749 | 2.843 | 2.805 | 2.742 | 2.775 | 2.491 | 0.245 | 98 | 95 | 97 | 83 | −67 | 1.56E−5 | 3.57E−5 | 7.68E−5 |
| DU-145 | 0.436 | 1.926 | 1.953 | 2.043 | 1.886 | 0.820 | 0.057 | 102 | 108 | 97 | 26 | −87 | 4.59E−6 | 1.69E−5 | 4.70E−5 |
| | | | | | | | Breast Cancer | | | | | | | | |
| MCF7 | 0.290 | 1.706 | 1.581 | 1.5413 | 1.459 | 0.409 | 0.100 | 91 | B9 | 85 | 8 | −66 | 2.65E−6 | 1.30E−5 | 6.14E−5 |
| MDA-MB-231/ATCC | 0.842 | 2.028 | 2.062 | 2.029 | 1.976 | 1.533 | 0.120 | 103 | 100 | 96 | 58 | −86 | 1.14E−5 | 2.54E−5 | 5.64E−5 |
| HS 578T | 0.902 | 1.883 | 1.868 | 1.1367 | 1.823 | 1.179 | 0.677 | 98 | 96 | 94 | 28 | −25 | 4.66E−6 | 3.39E−5 | 1.00E−4 |
| BT-549 | 0.876 | 1.824 | 1.789 | 1.757 | 1.653 | 0.880 | 0.042 | 96 | 96 | 85 | . | −95 | 2.60E−6 | 1.01E−5 | 3.36E−5 |
| T-47D | 0.572 | 1.338 | 1.319 | 1.370 | 1.385 | 0.842 | 0.324 | 98 | 104 | 106 | 35 | −43 | 6.19E−6 | 2.50E−5 | >1.00E−4 |
| MDA-MB-468 | 0.884 | 2.026 | 1.964 | 1.898 | 1.831 | 1.091 | 0.301 | 95 | 89 | 83 | 18 | −66 | 3.22E−6 | 1.64E−5 | 6.45E−5 |

TABLE 16

NCI five dose result for JVM-64

| | Time | | Mean Optical Densities | | | | | Percent Growth | | | | | | | |
|---|---|---|---|---|---|---|---|---|---|---|---|---|---|---|---|
| | | | | | Log10 Concentration | | | | | | | | | | |
| Panel/Cell | Zero | Ctrl | −8.0 | −7.0 | −6.0 | −5.0 | −4.0 | −8.0 | −7.0 | −6.0 | −5.0 | −4.0 | GI50 | TGI | LC50 |
| | | | | | | | Leukemia | | | | | | | | |
| CCRF-CEM | 0.666 | 2.500 | 2.526 | 2.398 | 1.375 | 0.457 | 0.291 | 101 | 94 | 39 | −31 | −56 | 6.26E−7 | 3.56E−6 | 5.58E−5 |
| MOLT-4 | 0.920 | 2.854 | 2.936 | 2.974 | 2.666 | 0.736 | 0.445 | 104 | 106 | 90 | −20 | −52 | 2.32E−6 | 6.59E−6 | 8.85E−5 |
| RPMI-8226 | 1.575 | 3.083 | 3.099 | 3.081 | 2.970 | 1.398 | 0.858 | 101 | 100 | 93 | −11 | −46 | 2.57E−6 | 7.79E−6 | >1.00E−4 |
| SR | 0.811 | 2.552 | 2.524 | 2.598 | 2.354 | 0.888 | 0.408 | 98 | 103 | 139 | −15 | −50 | 2.36E−6 | 7.13E−6 | >1.00E−4 |
| | | | | | | | Non-Small Cell Lung Cancer | | | | | | | | |
| A549/ATCC | 0.365 | 1.890 | 1.860 | 1.836 | 1.781 | 0.731 | 0.160 | 98 | 96 | 93 | 24 | −56 | 4.19E−6 | 1.99E−5 | 8.35E−5 |
| HOP-62 | 0.645 | 1.593 | 1.694 | 1.655 | 1.616 | 1.002 | 0.192 | 111 | 106 | 102 | 38 | −70 | 6.45E−6 | 2.23E−5 | 6.49E−5 |
| HOP-92 | 1.575 | 1.951 | 1.878 | 1.855 | 1.749 | 1.072 | 0.157 | 78 | 72 | 45 | −32 | −90 | 6.55E−7 | 3.84E−6 | 2.04E−5 |
| NCI-H226 | 0.811 | 1.836 | 1.714 | 1.708 | 1.734 | 1.332 | 0.405 | 88 | 88 | 90 | 51 | −50 | 1.02E−5 | 3.19E−5 | 9.97E−5 |
| NCI-H23 | 0.686 | 2.050 | 2.123 | 2.098 | 1.917 | 0.833 | 0.262 | 105 | 103 | 90 | 11 | −62 | 3.21E−6 | 1.41E−5 | 6.36E−5 |
| NCI-H322M | 0.723 | 1.869 | 1.833 | 1.919 | 1.844 | 1.571 | 0.109 | 97 | 104 | 98 | 74 | −85 | 1.42E−5 | 2.92E−5 | 6.03E−5 |
| NCI-H460 | 0.285 | 2.898 | 2.935 | 2.865 | 2.852 | 0.769 | 0.148 | 101 | 99 | 98 | 19 | −48 | 4.03E−6 | 1.89E−5 | >1.00E−4 |
| NCI-H522 | 0.880 | 2.225 | 2.162 | 2.179 | 1.724 | 0.332 | 0.294 | 95 | 97 | 63 | −62 | −67 | 1.26E−6 | 3.17E−6 | 7.87E−6 |
| | | | | | | | Colon Cancer | | | | | | | | |
| COLO 205 | 0.583 | 2.416 | 2.551 | 2.626 | 2.261 | 0.164 | 0.110 | 107 | 111 | 92 | −72 | −81 | 1.79E−6 | 3.63E−6 | 7.35E−6 |
| HCC-2998 | 1.076 | 3.147 | 3.158 | 3.178 | 3.230 | 1.962 | 0.153 | 101 | 102 | 104 | 43 | −86 | 7.63E−6 | 2.15E−5 | 5.27E−5 |
| HCT-116 | 0.212 | 1.614 | 1.629 | 1.580 | 1.018 | 0.040 | 0.014 | 101 | 98 | 57 | −81 | −94 | 1.13E−6 | 2.60E−6 | 5.86E−6 |
| HCT-15 | 0.465 | 2.447 | 2.448 | 2.336 | 2.107 | 0 448 | 0.077 | 100 | 94 | 133 | −4 | −84 | 2 40E−6 | 9.05E−6 | 3.80E−5 |
| HT29 | 0.315 | 1.663 | 1.695 | 1.678 | 1.553 | 0.280 | 0.067 | 102 | 101 | 92 | −11 | −79 | 2.55E−6 | 7.77E−6 | 3.74E−5 |
| KM12 | 0.586 | 2.503 | 2.577 | 2.653 | 2.518 | 0.906 | 0.052 | 104 | 108 | 101 | 17 | −91 | 4.01E−6 | 1.43E−5 | 4.15E−5 |
| SW-620 | 0.308 | 1.978 | 1.960 | 1.955 | 1.239 | 0.129 | 0.077 | 99 | 99 | 56 | −58 | −75 | 1.12E−6 | 3.09E−6 | 8.49E−6 |
| | | | | | | | CNS Cancer | | | | | | | | |
| SF-268 | 0.720 | 2.295 | 2.331 | 2.313 | 2.243 | 0.958 | 0.179 | 102 | 101 | 97 | 15 | −75 | 3.73E−6 | 1.47E−5 | 5.26E−5 |
| SF-295 | 1.051 | 3.046 | 2.977 | 2.959 | 3.015 | 2.502 | 0.217 | 97 | 96 | 98 | 73 | −79 | 1.41E−5 | 3.01E−5 | 6.41E−5 |

TABLE 16-continued

NCI five dose result for JVM-64

| | Time | | Mean Optical Densities | | | | | Percent Growth | | | | | | | |
|---|---|---|---|---|---|---|---|---|---|---|---|---|---|---|---|
| | | | | | Log10 Concentration | | | | | | | | | | |
| Panel/Cell | Zero | Ctrl | −8.0 | −7.0 | −6.0 | −5.0 | −4.0 | −8.0 | −7.0 | −6.0 | −5.0 | −4.0 | GI50 | TGI | LC50 |
| SF-539 | 0.810 | 2.472 | 2.409 | 2.334 | 2.203 | 0.378 | 0.029 | 96 | 92 | 84 | −53 | −96 | 1.76E−6 | 4.08E−6 | 9.46E−6 |
| SNB-19 | 0.798 | 2.287 | 2.214 | 2.147 | 2.173 | 1.919 | 0.402 | 95 | 91 | 92 | 75 | −50 | 1.59E−5 | 4.00E−5 | >1.00E−4 |
| SNB-75 | 0.999 | 1.704 | 1.582 | 1.534 | 1.458 | 1.002 | 0.041 | 83 | 76 | 65 | . | −96 | 1.71E−6 | 1.01E−5 | 3.34E−5 |
| U251 | 0.400 | 1.952 | 1.919 | 1.820 | 1.773 | 0.705 | 0.085 | 98 | 92 | 68 | 20 | −79 | 3.62E−6 | 1.58E−5 | 5.10E−5 |
| Melanoma | | | | | | | | | | | | | | | |
| LOX IMVI | 0.459 | 2.674 | 2.831 | 2.697 | 2.346 | 0.293 | 0.081 | 98 | 101 | B5 | −36 | −82 | 1.95E−6 | 5.03E−6 | 1.98E−5 |
| MALME-3M | 0.661 | 1.276 | 1.302 | 1.267 | 1.189 | 0.582 | 0.302 | 104 | 99 | 66 | −12 | −54 | 2.32E−6 | 7.53E−6 | 7.88E−5 |
| M14 | 0.496 | 1.511 | 1.468 | 1.463 | 1.320 | 0.134 | 0.012 | 96 | 95 | 81 | −73 | −98 | 1.59E−6 | 3.36E−6 | 7.09E−6 |
| MDA-MB-435 | 0.548 | 2.425 | 2.361 | 2.414 | 2.140 | 0.468 | 0.246 | 97 | 99 | 65 | −15 | −55 | 2.24E−6 | 7.13E−6 | 7.48E−5 |
| SK-MEL-2 | 1.320 | 2.638 | 2.877 | 2.662 | 2.650 | 1.434 | 0.459 | 103 | 103 | 101 | 9 | −65 | 3.56E−6 | 1.31E−5 | 6.22E−5 |
| SK-MEL-28 | 0.490 | 1.498 | 1.500 | 1.461 | 1.315 | 0.308 | 0.061 | 100 | 96 | 82 | −37 | −88 | 1.85E−6 | 4.86E−6 | 1.79E−5 |
| 8K-MEL-5 | 0.753 | 2.989 | 2.856 | 2.829 | 2.761 | 0.967 | 0.044 | 94 | 93 | 90 | 10 | −94 | 3.13E−6 | 1.24E−5 | 3.75E−5 |
| UACC-257 | 0.666 | 1.485 | 1.499 | 1.424 | 1.237 | 0.535 | 0.135 | 102 | 93 | 70 | −20 | −80 | 1.66E−6 | 6.02E−6 | 3.19E−5 |
| UACC-62 | 0.896 | 2.629 | 2.567 | 2.521 | 2.171 | 0.523 | 0.097 | 96 | 94 | 74 | −42 | −89 | 1.60E−6 | 4.35E−6 | 1.50E−5 |
| Ovarian Cancer | | | | | | | | | | | | | | | |
| IGROVI | 0.747 | 2.293 | 2.380 | 2.378 | 2.268 | 0.941 | 0.228 | 106 | 105 | 98 | 13 | −70 | 3.66E−6 | 1.42E−5 | 5.78E−5 |
| OVCAR-4 | 0.782 | 1 364 | 1.300 | 1.302 | 1.209 | 0.946 | 0.234 | 89 | 89 | 73 | 28 | −70 | 3.28E−6 | 1.93E−5 | 6.24E−5 |
| OVCAR-5 | 0.650 | 1.571 | 1.546 | 1.498 | 1.471 | 0.479 | 0.073 | 97 | 92 | 69 | −26 | −89 | 2.18E−6 | 5.92E−6 | 2.40E−5 |
| OVCAR-8 | 0.330 | 1.484 | 1.526 | 1.478 | 1.290 | 0.405 | 0.090 | 104 | 99 | 83 | 6 | −73 | 2.71E−6 | 1.21E−5 | 5.16E−5 |
| NCI/ADR-RES | 0.644 | 2.189 | 2.231 | 2.281 | 2.260 | 1.833 | 0.771 | 103 | 106 | 105 | 77 | 8 | 2.47E−5 | >1.00E−4 | >1.00E−4 |
| SK-OV-3 | 0.792 | 2.032 | 2.024 | 2.111 | 2.068 | 1.498 | 0.429 | 99 | 106 | 103 | 57 | −46 | 1.17E−5 | 3.58E−5 | >1.00E−4 |
| Renal Cancer | | | | | | | | | | | | | | | |
| 786-0 | 0.594 | 2.278 | 2.249 | 2.282 | 2.016 | 0.164 | 0.040 | 98 | 100 | 84 | −72 | −93 | 1.66E−6 | 3.45E−6 | 7.20E−6 |
| A498 | 1.515 | 2.035 | 2.015 | 1.976 | 1.997 | 1.333 | 0.037 | 96 | 89 | 93 | −12 | −98 | 2.56E−6 | 7.67E−6 | 2.78E−5 |
| ACHN | 0.388 | 1.506 | 1.527 | 1.485 | 1.254 | 0.253 | 0.020 | 102 | 98 | 77 | −35 | −95 | 1.75E−6 | 4.89E−6 | 1.78E−5 |
| CAKI-1 | 0.668 | 2.539 | 2.484 | 2.515 | 2.121 | 0.570 | 0.152 | 97 | 99 | 78 | −15 | −77 | 1.99E−6 | 6.93E−6 | 3.66E−5 |
| RXF 393 | 0.880 | 1.618 | 1.586 | 1.557 | 1.235 | 0.196 | 0.209 | 96 | 92 | 48 | −78 | −76 | 9.06E−7 | 2.41E−6 | 6.02E−6 |
| SN12C | 0.631 | 2.409 | 2.206 | 2.267 | 2.252 | 0.871 | 0.138 | 89 | 92 | 91 | 2 | −78 | 2.90E−6 | 1.07E−5 | 4.46E−5 |
| TK-10 | 0.733 | 1.555 | 1.606 | 1.581 | 1.507 | 0.616 | 0.047 | 106 | 103 | 94 | −16 | −94 | 2.51E−6 | 7.16E−6 | 2.74E−5 |
| UO-31 | 0.739 | 2.161 | 2.021 | 1.997 | 1.831 | 0.638 | 0.133 | 90 | 88 | 77 | −14 | −82 | 1.98E−6 | 7.86E−6 | 3.40E−5 |
| Prostate Cancer | | | | | | | | | | | | | | | |
| PC-3 | 0.749 | 2.760 | 2.719 | 2.705 | 2.652 | 1.687 | 0.282 | 98 | 97 | 95 | 47 | −62 | 8.51E−6 | 2.68E−5 | 7.70E−5 |
| DU-145 | 0.436 | 1.844 | 1.958 | 1.954 | 1.757 | 0.622 | 0.003 | 108 | 108 | 94 | 13 | −99 | 3.49E−6 | 1.31E−5 | 3.84E−5 |
| Breast Cancer | | | | | | | | | | | | | | | |
| MCF7 | 0.290 | 1.740 | 1.598 | 1.580 | 1.117 | 0.308 | 0.118 | 90 | 89 | 57 | 1 | −59 | 1.33E−6 | 1.05E−5 | 7.02E−5 |
| MDA-MB-231/ATCC | 0.842 | 2.090 | 2.125 | 2.099 | 2.050 | 0.812 | 0.133 | 103 | 101 | 97 | −4 | −84 | 2.93E−6 | 9.22E−6 | 3.77E−5 |
| HS 578T | 0.902 | 1.910 | 1.824 | 1.834 | 1.759 | 0.855 | 0.651 | 91 | 92 | 65 | −5 | −28 | 2.44E−6 | 8.75E−6 | >1.00E−4 |
| BT-549 | 0.876 | 1.792 | 1.749 | 1.732 | 1.578 | 0.153 | 0.038 | 95 | 93 | 77 | −83 | −96 | 1.47E−6 | 3.83E−6 | 6.24E−6 |
| T-47D | 0.572 | 1.291 | 1.318 | 1.324 | 1.265 | 0.363 | 0.273 | 104 | 104 | 96 | −37 | −52 | 2.23E−6 | 5.31E−6 | 7.09E−5 |
| MDA-MB-468 | 0.884 | 1.989 | 1.958 | 1.860 | 1.562 | 0.533 | 0.265 | 97 | 88 | 61 | −40 | −70 | 1.29E−6 | 4.04E−6 | 2.18E−5 |

TABLE 17

NCI five dose result for JVM-66

| | Time | | Mean Optical Densities | | | | | Percent Growth | | | | | | | |
|---|---|---|---|---|---|---|---|---|---|---|---|---|---|---|---|
| | | | | | Log10 Concentration | | | | | | | | | | |
| Panel/Cell | Zero | Ctrl | −8.0 | −7.0 | −6.0 | −5.0 | −4.0 | −8.0 | −7.0 | −6.0 | −5.0 | −4.0 | GI50 | TGI | LC50 |
| Leukemia | | | | | | | | | | | | | | | |
| CCRF-CEM | 0.645 | 2.380 | 2.374 | 2.367 | 2.258 | 0.847 | 0.379 | 100 | 99 | 93 | 12 | −41 | 3.38E−6 | 1.66E−5 | >1.00E−4 |
| HL-60(TB) | 0.952 | 3.162 | 3.062 | 3.177 | 3.264 | 1.315 | 0.358 | 95 | 101 | 102 | 16 | −62 | 4.05E−6 | 1.62E−5 | 6.95E−5 |
| K-562 | 0.196 | 1.508 | 1.455 | 1.375 | 1.509 | 0.400 | 0.212 | 96 | 90 | 100 | 16 | 1 | 1.91E−5 | >1.00E−4 | >1.00E−4 |
| MOLT-4 | 0.598 | 2.301 | 2.286 | 2.336 | 2.307 | 1.242 | 0.403 | 99 | 102 | 100 | 38 | −33 | 6.38E−6 | 3.44E−5 | >1.00E−4 |
| RPMI-8226 | 1.212 | 2.660 | 2.706 | 2.710 | 2.694 | 1.986 | 0.836 | 103 | 103 | 102 | 53 | −31 | 1.10E−5 | 4.29E−5 | >1.00E−4 |
| SR | 0.640 | 2.155 | 2.105 | 2.089 | 2.127 | 1.204 | 0.471 | 97 | 96 | 98 | 37 | −26 | 6.17E−6 | 3.85E−5 | >1.00E−4 |

TABLE 17-continued

NCI five dose result for JVM-66

| Panel/Cell | Time Zero | Ctrl | Mean Optical Densities | | | | | Percent Growth | | | | | GI50 | TGI | LC50 |
|---|---|---|---|---|---|---|---|---|---|---|---|---|---|---|---|
| | | | −8.0 | −7.0 | −6.0 | −5.0 | −4.0 | −8.0 | −7.0 | −6.0 | −5.0 | −4.0 | | | |
| Non-Small Cell Lung Cancer | | | | | | | | | | | | | | | |
| A549/ATCC | 0.383 | 1.943 | 1.967 | 1.937 | 1.839 | 1.761 | 0.476 | 102 | 100 | 93 | 88 | 6 | 19.2E−5 | 1.06E−4 | >1.00E−4 |
| HOP-62 | 0.694 | 1.587 | 1.564 | 1.555 | 1.692 | 1.809 | 0.636 | 97 | 96 | 112 | 125 | −8 | 3.65E−5 | 8.656−5 | >1.00E−4 |
| HOP-92 | 1.344 | 1.864 | 1.818 | 1.779 | 1.769 | 1.571 | 0.563 | 31 | 84 | 82 | 44 | −58 | 6.83E−6 | 2.69E−5 | 8.32E−5 |
| NCI-H226 | 1.086 | 1.054 | 1.806 | 1.685 | 1.799 | 1.683 | 1.470 | 94 | 78 | 93 | 78 | 50 | 9.96E−5 | >1.00E−4 | >1.00E−4 |
| NCI-H23 | 0.839 | 2.355 | 2.245 | 2.304 | 2.364 | 1.941 | 0.664 | 93 | 97 | 101 | 73 | −21 | 1.35E−5 | 5.98E−5 | >1.00E−4 |
| NCI-H322M | 0.824 | 2.119 | 2.037 | 2.021 | 2.118 | 2.074 | 1.359 | 94 | 92 | 100 | 96 | 41 | 6.95E−5 | 1.06E−4 | >1.00E−4 |
| NCI-H460 | 0.361 | 3.179 | 3.255 | 3.307 | 3.251 | 3.071 | 0.302 | 103 | 105 | 103 | 96 | −16 | 1.57E−5 | 7.14E−5 | >1.00E−4 |
| NCI-H522 | 0.699 | 1.837 | 1.705 | 1.690 | 1.751 | 1.076 | 0.227 | 88 | 87 | 92 | 33 | −68 | 5.19E−6 | 2.13E−5 | 6.69E−5 |
| Colon Cancer | | | | | | | | | | | | | | | |
| COLO 205 | 0.601 | 3.035 | 2.919 | 2.947 | 3.032 | 2.127 | 0.123 | 95 | 96 | 100 | 63 | −80 | 1.23E−5 | 2.76E−5 | 6.19E−5 |
| HCC-2998 | 0.936 | 3.032 | 3.027 | 3.012 | 3.122 | 2.808 | 0.144 | 100 | 99 | 104 | 89 | −85 | 1.68E−5 | 1.26E−5 | 6.32E−5 |
| HCT-116 | 0.214 | 1.714 | 1.661 | 1.628 | 1.613 | 0.178 | 0.041 | 96 | 94 | 93 | −17 | −81 | 2.47E−6 | 7.03E−6 | 3.30E−5 |
| HCT-15 | 0.373 | 2.202 | 2.082 | 2.103 | 2.042 | 1.141 | 0.169 | 93 | 95 | 91 | 42 | −55 | 6.88E−6 | 2.71E−5 | 8.92E−5 |
| HT29 | 0.298 | 1.590 | 1.571 | 1.596 | 1.656 | 1.078 | 0.089 | 99 | 100 | 105 | 60 | −70 | 1.20E−5 | 2.90E−5 | 6.99E−5 |
| KM12 | 0.699 | 2.840 | 2.849 | 2.138 | 2.813 | 2.816 | 1.973 | 100 | 102 | 99 | 99 | 60 | >1.00E−4 | >1.00E−4 | >1.00E−4 |
| SW-620 | 0.304 | 1.960 | 1.917 | 1.948 | 1.855 | 0.803 | 0.123 | 97 | 99 | 94 | 30 | −60 | 4.86E−6 | 2.17E−5 | 7.83E−5 |
| CNS Cancer | | | | | | | | | | | | | | | |
| SF-268 | 0.543 | 1.807 | 1.753 | 1.795 | 1.779 | 1.615 | 0.449 | 96 | 99 | 98 | 85 | −17 | 2.19E−5 | 6.77E−5 | >1.00E−4 |
| SF-295 | 0.971 | 2.971 | 2.838 | 2.659 | 2.860 | 2.794 | 1.534 | 93 | 94 | 94 | 91 | 28 | 4.50E−5 | 1.06E−4 | >1.00E−4 |
| SF-539 | 1.018 | 2.698 | 2.627 | 2.615 | 2.638 | 2.465 | 0.244 | 96 | 95 | 96 | 86 | −76 | 1.67E−5 | 3.40E−5 | 6.91E−5 |
| SNB-19 | 0.728 | 2.299 | 2.188 | 2.199 | 2.180 | 2.029 | 1.327 | 93 | 94 | 92 | 83 | 38 | 5.43E−5 | >1.00E−4 | >1.00E−4 |
| SNB-75 | 0.899 | 1.846 | 1.651 | 1.692 | 1.695 | 1.586 | 1.228 | 79 | 84 | 84 | 72 | 35 | 3.93E−5 | >1.06E−4 | >1.00E−4 |
| U251 | 0.749 | 2.605 | 2.568 | 2.535 | 2.524 | 2.487 | 0.906 | 98 | 96 | 96 | 94 | 8 | 3.25E−5 | >1.00E−4 | >1.00E−4 |
| Melanoma | | | | | | | | | | | | | | | |
| LOX IMVI | 0.374 | 2.319 | 2.266 | 2.187 | 2.229 | 0 498 | 0.066 | 97 | 93 | 95 | 6 | −82 | 3.23E−6 | 1.18E−5 | 4.31E−5 |
| MALME-3M | 0.712 | 1.324 | 1.290 | 1.291 | 1.368 | 1.115 | 0.487 | 94 | 95 | 107 | 66 | −32 | 1.45E−5 | 4.74E−5 | >1.00E−4 |
| M14 | 0.497 | 1.845 | 1.764 | 1.762 | 1.733 | 1.332 | 0.220 | 94 | 94 | 92 | 62 | −56 | 1.26E−5 | 3.36E−5 | 8.92E−5 |
| MDA-MB-435 | 0.622 | 2.670 | 2.569 | 2.617 | 2.503 | 2.191 | 0.356 | 95 | 97 | 92 | 77 | −43 | 1.67E−5 | 4.38E−5 | >1.00E−4 |
| SK-MEL-2 | 0.987 | 1.974 | 2.002 | 1.953 | 1.969 | 1.760 | 0.452 | 103 | 96 | 99 | 78 | −54 | 1.64E−5 | 3.96E−5 | 9.30E−5 |
| SK-MEL-28 | 0.500 | 1.654 | 1.655 | 1.725 | 1.581 | 1.359 | 0.248 | 100 | 136 | 94 | 74 | −50 | 1.57E−5 | 3.95E−5 | 9.93E−5 |
| 8K-MEL-5 | 0.836 | 2.736 | 2.680 | 2.494 | 2.590 | 2.221 | 0.067 | 97 | 87 | 92 | 73 | −92 | 1.33E−5 | 2.77E−5 | 5.56E−5 |
| UACC-62 | 0.981 | 2.984 | 2.896 | 2.861 | 2.849 | 2.377 | 0.321 | 96 | 94 | 93 | 70 | −67 | 1.39E−5 | 3.23E−5 | 7.48E−5 |
| Ovarian Cancer | | | | | | | | | | | | | | | |
| IGROVI | 0.521 | 1.514 | 1.570 | 1.518 | 1.521 | 0.995 | 0.310 | 106 | 100 | 161 | 48 | −41 | 9.04E−6 | 347E−5 | >1.00E−4 |
| OVCAR-3 | 0.855 | 2.245 | 2.264 | 2.247 | 2.294 | 1.587 | 0.037 | 101 | 130 | 103 | 53 | −96 | 1.04E−5 | /26E−5 | 4.92E−5 |
| OVCAR-4 | 0.622 | 1.513 | 1.470 | 1.433 | 1.421 | 1.267 | 0.603 | 95 | 91 | 90 | 72 | −3 | 1.98E−5 | 9.09E−5 | >1.00E−4 |
| OVCAR-5 | 0.688 | 1.525 | 1.474 | 1.475 | 1.509 | 1.420 | 0.230 | 94 | 94 | 98 | 88 | −67 | 1.35E−5 | 176E−5 | 7.81E−5 |
| OVCAR-8 | 0.526 | 2.297 | 2.236 | 2.278 | 2.263 | 1.843 | 0.535 | 97 | 99 | 98 | 74 | 1 | 1.14E−5 | >1.00E−4 | >1.00E−4 |
| NCI/ADR-RES | 0.735 | 2.272 | 2.201 | 1.201 | 2.264 | 2.042 | 0.916 | 95 | 95 | 96 | 85 | 12 | 3.01E−5 | >1.00E−4 | >1.00E−4 |
| SK-OV-3 | 0.731 | 2.181 | 2.161 | 2.184 | 2.242 | 2.112 | 1.279 | 99 | 100 | 104 | 95 | 38 | 6.14E−5 | >1.00E−4 | >1.00E−4 |
| Renal Cancer | | | | | | | | | | | | | | | |
| 786-0 | 0.831 | 2.755 | 2.674 | 2.689 | 2.718 | 2.407 | 0.337 | 96 | 97 | 98 | 82 | −60 | 1.68E−5 | 3.79E−5 | 8.57E−5 |
| A498 | 1.638 | 2.518 | 2.499 | 2.445 | 2.489 | 2.479 | 1.286 | 98 | 92 | 97 | 95 | −21 | 1.45E−5 | 6.55E−5 | >1.00E−4 |
| ACHN | 0.370 | 1.340 | 1.293 | 1.255 | 1.370 | 0.748 | 0.048 | 95 | 91 | 103 | 39 | −87 | 6.73E−6 | 2.04E−5 | 5.07E−5 |
| CAKI-1 | 0.957 | 2.801 | 2.726 | 2.743 | 2.757 | 2.119 | 0.315 | 96 | 97 | 98 | 63 | −67 | 1.26E−5 | 3.05E−5 | 7.38E−5 |
| RXF 393 | 0.937 | 1.750 | 1.725 | 1.663 | 1.700 | 0.970 | 0.308 | 97 | 82 | 94 | 4 | −67 | 3.08E−6 | 1.14E−5 | 5.74E−5 |
| SN12C | 0.609 | 2.738 | 2.703 | 2.743 | 2.627 | 2.441 | 0.243 | 98 | 100 | 95 | 86 | −60 | 1.37E−5 | 1.88E−5 | 8.53E−5 |
| TK-10 | 0.710 | 1.422 | 1.350 | 1 363 | 1 359 | 1.088 | 0.131 | 90 | 92 | 91 | 53 | −82 | 1.05E−5 | 2.48E−5 | 5.82E−5 |
| UO-31 | 0.749 | 2.204 | 1.951 | 1.998 | 2.050 | 1.429 | 0.151 | 83 | 86 | 89 | 47 | −80 | 8.37E−6 | 2.34E−5 | 5.81E−5 |
| Prostate Cancer | | | | | | | | | | | | | | | |
| PC-3 | 0.575 | 2.155 | 2.155 | 2.072 | 2.089 | 1.926 | 0.470 | 100 | 95 | 96 | 85 | −18 | 1.20E−5 | 6.66E−5 | >1.00E−4 |
| DU-145 | 0.418 | 1.705 | 1.722 | 1.679 | 1.715 | 1.223 | 0.070 | 101 | 98 | 161 | 63 | −83 | 1.22E−5 | 2.69E−5 | 5.91E−5 |
| Breast Cancer | | | | | | | | | | | | | | | |
| MCF7 | 0.260 | 1.848 | 1.794 | 1.832 | 1.700 | 0.662 | 0.105 | 97 | 99 | 91 | 25 | −60 | 4.19E−6 | 1.98E−5 | 7.67E−5 |
| MDA-MB-231/ATCC | 0.760 | 1.877 | 1.947 | 1.880 | 1.849 | 1.646 | 0.245 | 106 | 100 | 97 | 79 | −68 | 1.58E−5 | 3.46E−5 | 7.57E−5 |
| HS 578T | 1.209 | 2.325 | 2.218 | 2.252 | 2.265 | 2.042 | 1.393 | 90 | 93 | 95 | 75 | 16 | 2.65E−5 | >1.00E−4 | >1.00E−4 |
| BT-549 | 0.984 | 2.104 | 2.059 | 2.030 | 2.089 | 1.801 | 0.840 | 96 | 93 | 99 | 73 | −15 | 1.83E−5 | 6.80E−5 | >1.00E−4 |

TABLE 17-continued

NCI five dose result for JVM-66

| Panel/Cell | Time | | Mean Optical Densities | | | | | Percent Growth | | | | | GI50 | TGI | LC50 |
|---|---|---|---|---|---|---|---|---|---|---|---|---|---|---|---|
| | Zero | Ctrl | −8.0 | −7.0 | −6.0 | −5.0 | −4.0 | −8.0 | −7.0 | −6.0 | −5.0 | −4.0 | | | |
| T-47D | 0.661 | 1.698 | 1.679 | 1.636 | 1.733 | 1.289 | 0.423 | 98 | 94 | 103 | 61 | −36 | 1.29E−5 | 4.24E−5 | >1 00E−4 |
| MDA-MB-468 | 0.972 | 2.032 | 1.966 | 1.875 | 1.887 | 1.187 | 0.735 | 94 | 85 | 86 | 20 | −24 | 3.55E−6 | 2.85E−5 | >1.00E−4 |

TABLE 18

NCI five dose result for JVM-96

| Panel/Cell | Time | | Mean Optical Densities | | | | | Percent Growth | | | | | GI50 | TGI | LC50 |
|---|---|---|---|---|---|---|---|---|---|---|---|---|---|---|---|
| | Zero | Ctrl | −8.0 | −7.0 | −6.0 | −5.0 | −4.0 | −8.0 | −7.0 | −6.0 | −5.0 | −4.0 | | | |
| Leukemia | | | | | | | | | | | | | | | |
| CCRF-CEM | 0.539 | 1.740 | 1.732 | 1.746 | 1.519 | 0.482 | 0.275 | 99 | 100 | 82 | −11 | −49 | 2.20E−6 | 7.66E−6 | >1.00E−4 |
| HL-60(TB) | 0.667 | 2.556 | 2.384 | 2.139 | 2.111 | 0.636 | 0.348 | 91 | 78 | 76 | −5 | −48 | 2.12E−6 | 8.75E−6 | >1.00E−4 |
| MOLT-4 | 0.612 | 2.163 | 2.117 | 2.234 | 2.324 | 1.144 | 0.462 | 97 | 105 | 110 | 34 | −25 | 6.22E−6 | 3.82E−5 | >1.00E−4 |
| RPMI-8226 | 0.957 | 2.219 | 2.290 | 2.302 | 2.148 | 1.243 | 0.495 | 106 | 107 | 94 | 23 | −48 | 4.16E−6 | 2.09E−5 | >1.00E−4 |
| SR | 0.252 | 1.042 | 0.919 | 0.963 | 0.859 | 0.347 | 0.164 | 84 | 90 | 77 | 12 | −35 | 2.59E−6 | 1.80E−5 | >1.00E−4 |
| Non-Small Cell Lung Cancer | | | | | | | | | | | | | | | |
| A549/ATCC | 0.398 | 1.375 | 1.295 | 1.309 | 1.417 | 1.214 | 0.134 | 92 | 93 | 104 | 83 | −66 | 1.67E−5 | 3.61E−5 | 7.78E−5 |
| HOP-62 | 0.830 | 1.790 | 1.738 | 1.724 | 1.766 | 1.741 | 0.389 | 95 | 93 | 98 | 95 | −53 | 2.01E−5 | 4.37E−5 | 9.52E−5 |
| HOP-92 | 0.944 | 1.514 | 1.473 | 1.477 | 1.458 | 0.924 | 0.068 | 93 | 93 | 90 | −2 | −93 | 2.72E−6 | 9.47E−6 | 3.37E−5 |
| NCI-H226 | 0.851 | 2.146 | 2.091 | 2.107 | 2.074 | 1.665 | 0.329 | 96 | 97 | 94 | 63 | −61 | 1.27E−5 | 3.20E−5 | 8.10E−5 |
| NCI-H23 | 0.672 | 1.930 | 1.881 | 1.965 | 1.973 | 1.722 | 0.383 | 96 | 103 | 103 | 83 | −43 | 1.84E−5 | 4.57E−5 | >1.00E−4 |
| NCI-H322M | 0.888 | 2.093 | 2.001 | 2.031 | 2.075 | 1.972 | 0.950 | 92 | 95 | 99 | 90 | 5 | 2.96E−5 | >1.00E−4 | >1.00E4 |
| NCI-H460 | 0.386 | 3.174 | 3.223 | 3.235 | 3.204 | 2.918 | 0.258 | 102 | 102 | 101 | 91 | −33 | 2.13E−5 | 5.39E−5 | >1.00E4 |
| NCI-H522 | 1.103 | 1.880 | 1.890 | 1.893 | 1.722 | 0.381 | 0.247 | 101 | 102 | 80 | −66 | −78 | 1.60E−6 | 3.54E−6 | 7.82E−6 |
| Colon Cancer | | | | | | | | | | | | | | | |
| COLO 205 | 0.527 | 1.425 | 1.506 | 1.466 | 1.449 | 0.539 | 0.054 | 109 | 105 | 103 | 1 | −90 | 3.30E−6 | 1.03E−5 | 3.66E−5 |
| HCC-2998 | 0.568 | 1.857 | 1.843 | 1.872 | 1.961 | 1.552 | 0.055 | 99 | 101 | 108 | 76 | −90 | 1.44E−5 | 2.87E−5 | 5.73E−5 |
| HCT-116 | 0.207 | 1.551 | 1.516 | 1.456 | 1.504 | 0.386 | −0.002 | 97 | 93 | 97 | 13 | −100 | 3.62E−6 | 1.31E−5 | 3.62E−5 |
| HCT-15 | 0.284 | 2.158 | 2.032 | 2.035 | 1.960 | 0.580 | 0.035 | 93 | 93 | 8.9 | 16 | −88 | 3.43E−6 | 1.42E−5 | 4.31E−5 |
| KM12 | 0.508 | 2.629 | 2.581 | 2.630 | 2.718 | 2.468 | 0.108 | 98 | 100 | 104 | 92 | −79 | 1.77E−5 | 3.46E−5 | 6.79E−5 |
| SW-620 | 0.314 | 2.531 | 2.517 | 2.499 | 2.502 | 0.810 | 0.105 | 99 | 99 | 99 | 22 | −67 | 4.35E−6 | 1.78E−5 | 6.49E−5 |
| CNS Cancer | | | | | | | | | | | | | | | |
| SF-268 | 0.564 | 1.919 | 1.878 | 1.896 | 1.883 | 1.275 | 0.966 | 97 | 98 | 97 | 52 | −71 | 1.05E−5 | 2.67E−5 | 6.76E−5 |
| SF-295 | 0.641 | 2.532 | 2.408 | 2.361 | 2.461 | 2.175 | 0.253 | 93 | 91 | 96 | 81 | −61 | 1.66E−5 | 3.74E−5 | 8.42E−5 |
| SF-539 | 0.954 | 2.492 | 2.432 | 2.264 | 2.398 | 1.079 | 0.124 | 96 | 85 | 94 | 8 | −87 | 3.25E−6 | 1.22E−5 | 4.08E−5 |
| SNB-19 | 0.705 | 2.241 | 2.136 | 2.176 | 2.059 | 1.818 | 0.401 | 93 | 96 | 88 | 72 | −43 | 1.56E−5 | 4.23E−5 | >1.00E−4 |
| SNB-75 | 0.763 | 1.519 | 1.369 | 1.282 | 1.275 | 1.073 | 0.043 | 80 | 69 | 68 | 41 | −94 | 4.59E−6 | 2.01E−5 | 4.70E−5 |
| U251 | 0.597 | 1.881 | 1.779 | 1.790 | 1.872 | 1.726 | 0.105 | 92 | 93 | 99 | 88 | −82 | 1.67E−5 | 3.28E−5 | 6.45E−5 |
| Melanoma | | | | | | | | | | | | | | | |
| LOX IMVI | 0.316 | 2.075 | 2.047 | 2.036 | 2.125 | 0.750 | 0.043 | 98 | 98 | 103 | 25 | −86 | 4.74E−6 | 1.67E−5 | 4.70E−5 |
| M14 | 0.452 | 1.526 | 1.501 | 1.433 | 1.464 | 0.833 | 0.062 | 98 | 91 | 96 | 35 | −86 | 5.75E−6 | 1.95E−5 | 5.03E−5 |
| MDA-MB-435 | 0.554 | 2.517 | 2.451 | 2.308 | 2.327 | 1.188 | 0.957 | 97 | 89 | 90 | 32 | −72 | 4.95E−6 | 2.04E−5 | 6.19E−5 |
| SK-MEL-2 | 1.069 | 1.923 | 1.836 | 1.852 | 1.894 | 1.557 | 0.261 | 90 | 92 | 97 | 57 | −76 | 1.13E−5 | 2.69E−5 | 6.41E−5 |
| SK-MEL-28 | 0.627 | 1.739 | 1.655 | 1.642 | 1.603 | 0.820 | 0.099 | 92 | 91 | 8.8. | 17 | −84 | 3.44E−6 | 1.48E−5 | 4.60E−5 |
| 8K-MEL-5 | 0.621 | 2.416 | 2.367 | 2.373 | 2.227 | 1.576 | 0.068 | 97 | 98 | 8.9 | 53 | −89 | 1.05E−5 | 2.37E−5 | 5.31E−5 |
| UACC-257 | 1.042 | 1.937 | 1.825 | 1.849 | 1.892 | 1.466 | 0.139 | 88 | 90 | 95 | 47 | −87 | 8.82E−6 | 2.26E−5 | 5.32E−5 |
| UACC-62 | 0.774 | 2.836 | 2.792 | 2.804 | 2.627 | 1.625 | 0.098 | 98 | 98 | 90 | 41 | −87 | 6.61E−6 | 2.09E−5 | 5.12E−5 |
| Ovarian Cancer | | | | | | | | | | | | | | | |
| IGROVI | 0.763 | 2.251 | 2.350 | 2.338 | 2.358 | 1.943 | 0.362 | 107 | 106 | 107 | 79 | −53 | 1.67E−5 | 3.99E−5 | 9.55E−5 |
| OVCAR-3 | 0.513 | 1.638 | 1.587 | 1.712 | 1.639 | 0.782 | 0.010 | 96 | 107 | 100 | 24 | −98 | 4.54E−6 | 1.57E−5 | 4.03E−5 |
| OVCAR-4 | 0.665 | 1.413 | 1.385 | 1.341 | 1.317 | 1.044 | 0.100 | 96 | 90 | 87 | 51 | −85 | 1.01E−5 | 2.36E−5 | 5.52E−5 |
| OVCAR-5 | 0.693 | 1.481 | 1.428 | 1.354 | 1.392 | 1.181 | 0.130 | 93 | 84 | 89 | 62 | −81 | 1.21E−5 | 2.71E−5 | 6.05E−5 |
| OVCAR-8 | 0.632 | 2.020 | 1.954 | 1.947 | 2.086 | 1.505 | 0.197 | 95 | 95 | 105 | 63 | −69 | 1.25E−5 | 3.00E−5 | 7.20E−5 |
| NCI/ADR-RES | 0.494 | 1.715 | 1.721 | 1.726 | 1.795 | 1.630 | 0.563 | 101 | 101 | 107 | 93 | 6 | 3.11E−5 | >1.00E−4 | >1.00E−4 |
| SK-OV-3 | 0.933 | 1.575 | 1.571 | 1.602 | 1.611 | 1.611 | 0.757 | 99 | 104 | 106 | 106 | −19 | 2.80E−5 | 7.05E−5 | >1.00E−4 |

TABLE 18-continued

NCI five dose result for JVM-96

| | Time | | Mean Optical Densities | | | | | Percent Growth | | | | | | | |
|---|---|---|---|---|---|---|---|---|---|---|---|---|---|---|---|
| | | | Log10 Concentration | | | | | | | | | | | | |
| Panel/Cell | Zero | Ctrl | −8.0 | −7.0 | −6.0 | −5.0 | −4.0 | −8.0 | −7.0 | −6.0 | −5.0 | −4.0 | GI50 | TGI | LC50 |
| Renal Cancer | | | | | | | | | | | | | | | |
| 786-0 | 0.506 | 1.660 | 1.777 | 1.750 | 1.781 | 0.856 | 0.045 | 94 | 92 | 94 | 26 | −91 | 4.43E-6 | 1.66E-5 | 4.44E-5 |
| A498 | 1.386 | 2.309 | 2.268 | 2.373 | 2.265 | 2.073 | 0.068 | 96 | 107 | 95 | 74 | −95 | 1.39E-5 | 2.75E-5 | 5.42E-5 |
| ACHN | 0.448 | 1.776 | 1.745 | 1.697 | 1.671 | 0.809 | 0.087 | 98 | 94 | 92 | 27 | −81 | 4.45E-6 | 1.79E-5 | 5.19E-5 |
| CAKI-1 | 0.613 | 2.568 | 2.423 | 2.280 | 2.317 | 1.414 | 0.045 | 93 | 85 | 87 | 41 | −93 | 6.37E-6 | 2.03E-5 | 4.79E-5 |
| RXF 393 | 0.735 | 1.273 | 1.235 | 1.272 | 1.236 | 0.817 | 0.147 | 93 | 100 | 93 | 15 | −80 | 3.57E-6 | 1.44E-5 | 4.84E-5 |
| SN12C | 0.945 | 3.077 | 3.003 | 3.075 | 2.961 | 2.211 | 0.581 | 97 | 100 | 95 | 59 | −39 | 1.25E-5 | 4.04E-5 | >1.00E-4 |
| TK-10 | 0.971 | 1.914 | 1.937 | 1.942 | 1.908 | 1.110 | 0.009 | 102 | 103 | 99 | 15 | −99 | 3.83E-6 | 1.35E-5 | 3.79-5 |
| UO-31 | 0.831 | 2.192 | 2.015 | 2.027 | 2.083 | 1.526 | 0.105 | 87 | 88 | 92 | 51 | −87 | 1.02E-5 | 2.34E-5 | 5.37E-5 |
| Prostate Cancer | | | | | | | | | | | | | | | |
| PC-3 | 0.671 | 1.469 | 1.391 | 1.408 | 1.414 | 1.293 | 0.218 | 90 | 92 | 93 | 78 | −68 | 1.56E-5 | 3.43E-5 | 7.57E-5 |
| DU-145 | 0.354 | 1.507 | 1.490 | 1.575 | 1.488 | 0.535 | 0.012 | 99 | 106 | 98 | 16 | −97 | 3.84E-6 | 1.39E-5 | 3.84E-5 |
| Breast Cancer | | | | | | | | | | | | | | | |
| MCF7 | 0.349 | 1.821 | 1.676 | 1.660 | 1.679 | 0.502 | 0.112 | 90 | 89 | 90 | 10 | −68 | 3.20E-6 | 1.36E-5 | 5.89E-5 |
| MDA-MB-231/ATCC | 0.612 | 1.382 | 1.359 | 1.355 | 1.313 | 0.914 | 0.160 | 97 | 96 | 91 | 39 | −74 | 6.19E-6 | 2.22E-5 | 6.15E-5 |
| HS 578T | 1.009 | 2.160 | 2.102 | 2.176 | 2.088 | 1.713 | 0.958 | 95 | 101 | 94 | 61 | −5 | 1.47E-5 | 6.37E-5 | >1.00E-4 |
| BT-549 | 0.820 | 1.560 | 1.576 | 1.576 | 1.511 | 1.060 | 0.022 | 102 | 139 | 93 | 32 | −97 | 5.14E-6 | 1.78E-5 | 4.31E-5 |
| T-47D | 0.857 | 1.577 | 1.578 | 1.574 | 1.536 | 0.953 | 0.245 | 100 | 100 | 94 | 13 | −71 | 3.52E-6 | 1.44E-5 | 5.59E-5 |
| MDA-MB-468 | 0.681 | 1.184 | 1.123 | 1.153 | 1.001 | 0.615 | 0.192 | 88 | 94 | 64 | −10 | −72 | 1.54E-6 | 7.38E-6 | 4.46E-5 |

What is claimed is:

1. A method for inhibiting growth of a cancer cell, the method comprising contacting the cancer cell with an amount of a compound comprising Formula (I) or (II), or a salt thereof, effective to inhibit growth of the cancer cell, the compound comprising Formula (I) or (II):

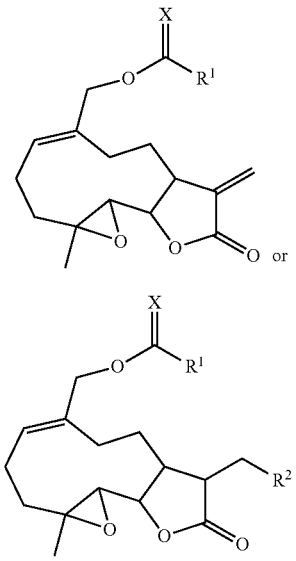

wherein:
X is O or S;
$R^1$ and $R^2$ are independently selected from the group consisting of —$OR^3$, —O-alkyl-$NR^3R^4$, —$SR^3$, —S-alkyl-$NR^3R^4$, alkyl-C(O)$NR^3R^4$, and -alkyl-$R^5$ or when X is S, $R^1$ is $NR^3R^4$;

$R^3$ is selected from the group consisting of hydrocarbyl, substituted hydrocarbyl, and $R^5$;

$R^4$ is selected from the group consisting of hydrogen, hydrocarbyl, and substituted hydrocarbyl;

$R^5$ is an optionally substituted nitrogen-containing heterocyclic ring;

one or more of $R^3$ and $R^4$ may form part of a ring or ring system chosen from the group consisting of heterocyclic, substituted heterocyclic, and combinations thereof; and when $R^4$ is hydrogen, $R^3$ is selected from the group consisting of alkyl, $R^5$, and substituted hydrocarbyl having at least one hydroxyl or $R^5$;

wherein the cancer cell is an acute myelogenous leukemia (AML) cancer cell or a solid tumor cell; and wherein the solid tumor cell is selected from the group consisting of non-small cell lung cancer, colon cancer, CNS cancer, melanoma, ovarian cancer, renal cancer, prostate cancer and breast cancer.

2. The method of claim 1, wherein $R^1$ and $R^2$ are selected from the group consisting of alkoxy, alkylamino, dialkylamino, dialkylaminoalkoxy, heterocyclylalkoxy, hydroxyalkylamino, heterocyclyamino, and heterocycylalkylamino.

3. The method of claim 2, wherein $R^1$ and $R^2$ are selected from the group consisting of methylamino, dimethylamino, hydroxyhexylamino, hydroxyethylamino, pyrrolyl, pyrrolidinyl, pyridinyl, piperdinyl, pyrazinyl, piperazinyl, pyrimidinyl, imidazolyl, triazolyl, hydroxypiperdinyl, difluoropiperdinyl, triazolylamino, methylthiotriazolylamino, morpholinyl, morpholinylethylamino, pyridinylmethylamino, piperdinylethylamino, pyridinylethylamino, morpholinylpropylamino, imidazolylpropylamino, methoxy, di methylaminoethoxy, piperdinylpropoxy, piperdinylethoxy, pyrrolidinylethoxy, morpholinylethyoxy, piperidinylethoxyhydroxyethylthio, and piperdinylethyl.

4. The method of claim 2, wherein $R^1$ and $R^2$ are independently selected from the group consisting of imidazolylpropylaminocarbonylethylcarbonyl, difluoropiperinylcarbonylethylcarbonyl, methylthiotriazolylaminocarbonylethylcarbonyl, chloropyridinylmethylaminocarbonylethylcarbonyl, methylpiperdinylcarbonylethylcarbonyl, and methylpiperazinylcarbonylethylcarbonyl.

5. The method of claim 1, wherein $R^1$ is $R^5$, and $R^2$ is dialkylamino.

6. The method of claim 1, wherein one or more $R^1$, $R^2$, $R^3$, $R^4$, or $R^5$ is substituted with at least one selected from the group consisting of methyl, ethyl, propyl, cyano, $C_1$-$C_3$-alkylamino, carboxyl, hydroxyl, trifluoromethyl, thio, alkylthio, and halogen.

7. The method of claim 1, wherein the cancer cell is in vivo or in vitro.

* * * * *

UNITED STATES PATENT AND TRADEMARK OFFICE
CERTIFICATE OF CORRECTION

PATENT NO. : 9,908,892 B2
APPLICATION NO. : 15/254849
DATED : March 6, 2018
INVENTOR(S) : Venumadhav Janganati et al.

It is certified that error appears in the above-identified patent and that said Letters Patent is hereby corrected as shown below:

On the Title Page

Item (73), add additional Assignee --UNIVERSITY OF ROCHESTER, Rochester, New York--.

Signed and Sealed this
Seventeenth Day of July, 2018

Andrei Iancu
*Director of the United States Patent and Trademark Office*